United States Patent
Maduskuie, Jr. et al.

(10) Patent No.: US 6,521,614 B1
(45) Date of Patent: *Feb. 18, 2003

(54) N-(AMIDINOPHENYL)CYCLOUREA ANALOGS AS FACTOR XA INHIBITORS

(75) Inventors: Thomas Peter Maduskuie, Jr., Wilmington, DE (US); Robert Anthony Galemmo, Jr., Collegeville, PA (US); Celia Dominguez, Newark, DE (US); Mimi Lifen Quan, Newark, DE (US); Karen Anita Rossi, Wilmington, DE (US); Petrus Fredericus Wilhelmus Stouten, Wilmington, DE (US); Jung-Hui Sun, Hockessin, DE (US); Brian Lloyd Wells, Wilmington, DE (US)

(73) Assignee: Bristol-Myers Squibb Pharma Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/305,561

(22) Filed: May 5, 1999

Related U.S. Application Data

(62) Division of application No. 08/838,246, filed on Apr. 16, 1997, now Pat. No. 5,925,635.
(60) Provisional application No. 60/042,532, filed on Apr. 1, 1997, and provisional application No. 60/015,684, filed on Apr. 17, 1996.

(51) Int. Cl.$^7$ .................. C07D 243/04; A61K 31/551; A61P 7/02
(52) U.S. Cl. ........................ 514/218; 540/531
(58) Field of Search .......................... 540/531; 514/218

(56) References Cited

PUBLICATIONS

Edmunds, J.J. et al, "Annual Reports Med. Chem.", 31, 1996, 51–60.*
Bennett, J.C. Editor, "Cecil Textbook of Medicine, 20th Edition, vol. 1", W.B. Saunders, Philadelphia, 1996, pp. 987–1003.*

* cited by examiner

Primary Examiner—Mukund J. Shah
Assistant Examiner—Thomas McKenzie
(74) Attorney, Agent, or Firm—David H. Vance

(57) ABSTRACT

The present application describes N-(amidinophenyl) cyclourea analogs of formula I:

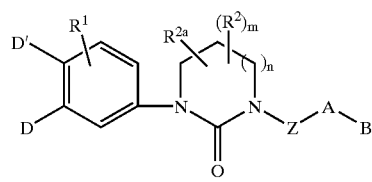

which are useful as inhibitors of factor Xa.

48 Claims, No Drawings

N-(AMIDINOPHENYL)CYCLOUREA ANALOGS AS FACTOR XA INHIBITORS

This application is a divisional of application Ser. No. 08/838,246, filed Apr. 16, 1997, now U.S. Pat. No. 5,925,635, and claims the benefit of U.S. Provisional Application No. 60/042,532, file Apr. 1, 1997, now abandoned, and U.S. Provisional Application No. 60/015,684, filed Apr. 17, 1997, now abandoned.

FIELD OF THE INVENTION

This invention relates generally to N-(amidinophenyl) cyclourea analogs which are inhibitors of factor Xa, pharmaceutical compositions containing the same, and methods of using the same as anticoagulant agents for treatment and prevention of thromboembolic disorders.

BACKGROUND OF THE INVENTION

Bovy et al, U.S. Pat. No. 5,430,043 describe phenyl amidines of the formula:

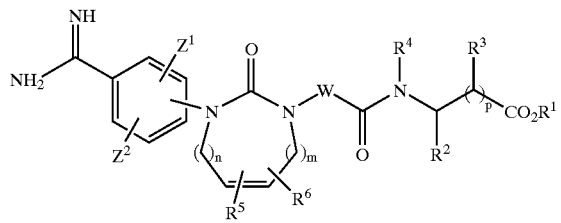

which are reported to be platelet aggregation inhibitors. However, no mention is made of inhibiting Factor Xa.

Himmelsbach et al, CA 2,105,934, address cyclic ureas of the formula:

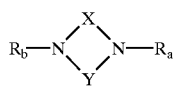

wherein, among the multitude of choices, X may be a carbonyl, Y may be an $C_{2-4}$ alkylene, $R_a$ may be A—B—C— and $R_b$ may be —D—E—F. Group F is selected from —$CO_2R$, phosphono, tetrazolyl, and $R_8CO$—O—$CHR_9$—O—CO—. The compounds described by the above formula are alleged to have aggregation inhibiting and/or fibrinogen binding properties. Factor Xa inhibiting is not discussed.

Lam et al, WO 94/19329, report cyclic carbonyls which may be cyclic ureas of the formula:

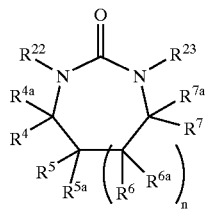

wherein at least one of $R^4$, $R^{4a}$, $R^7$, and $R^{7a}$ is other than hydrogen. Compounds of this sort are said to be useful as HIV protease inhibitors. N-(Amidinophenyl)cycloureas are not suggested as factor Xa inhibitors.

Currie et al, WO 96/36639, set forth amidine derivatives of the formula:

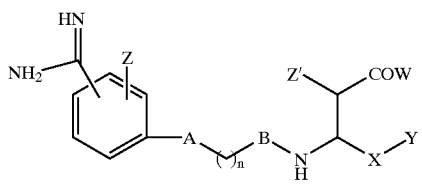

wherein A may be a 6-membered cyclic urea, which may be useful as anti-platelet aggregation inhibitors. However, Y is nitrate, nitrite, or a nitric oxide donating group. The present compounds, in contrast, do not contain the nitric oxide donating groups of WO 96/36639.

Klinger et al, WO 94/21607, illustrate heterocyclic compounds of the formula:

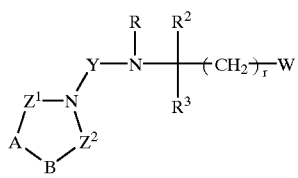

wherein, upon judicious selection of variables, $Z^1$ may be a carbonyl, A may be $NR^1$, $R^1$ may be an amidino-substituted phenyl, and B and $Z^2$ may each be $CH_2$. However, the present compounds do not include the right-side chain shown above. Mohan et al, WO 96/38421, describe N,N-di(arylmethyl)cyclic urea derivatives of the formula:

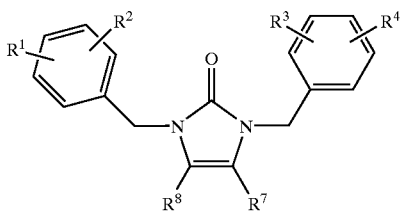

wherein $R^7$ and $R^8$ may combine to form a benzene ring and the double bond shown may be absent, which may be useful as Factor Xa inhibitors. These compounds are preferably bis-amidino substituted. However, the presently claimed compounds are neither bis-benzyl nor bis-amidino substituted.

Chakravarty et al, WO 95/03044, discuss benzimidazoles substituted with phenoxyphenylacetic acid dervatives of the formula:

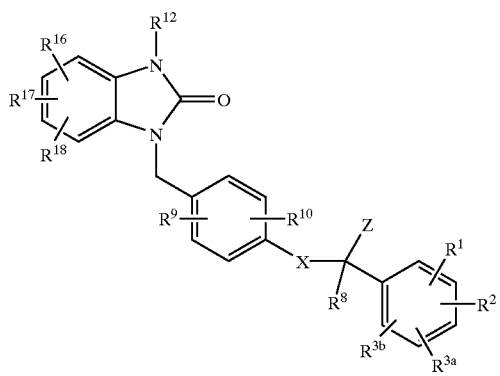

wherein $R^{12}$ may be a substituted aryl group. But, this reference does not consider amidino-phenyl groups. Furthermore, the present compounds do not contain the above variable Z, which is defined as a carbonyl, sulfonyl, or phosphoryl group.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation*. Thromb. Res. 1979, 15, 617–629), inhibition of factor Xa may be more efficient that inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel N-(amidinophenyl)cyclourea factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

I or pharmaceutically acceptable salt or prodrug forms thereof, wherein A, B, $R^1$, $R^2$, m and n are defined below, are effective factor Xa inhibitors.

DETAILED DESCRIPTION OF PREFERRED EMBODIMENTS

[1] Thus, in a first embodiment, the present invention provides novel compounds of formula I:

I or stereoisomers or pharmaceutically acceptable salt forms thereof, wherein;

one of D and D' is selected from CN, $C(=NR^{11})NR^{12}R^{13}$, $NHC(=NR^{11})NR^{12}R^{13}$, $NR^{12}CH(=NR^{11})$, $C(O)NR^{12}R^{13}$, and $(CH_2)_rNR^{12}R^{13}$ and the other is H;

$R^1$ is selected from H, $(CH_2)_rOR^3$, halo, $C_{1-4}$ alkyl, $(CH_2)_rNR^4R^{4'}$, $(CH_2)_rCO_2H$, $(CH_2)_rC(=O)R^4$, $(CH_2)_rNR^4C(=O)R^4$, $(CH_2)_rSO_2R^5$, and $(CH_2)_rNR^4SO_2R^5$;

$R^2$ is selected from H, =O, $C_{1-4}$ alkyl substituted with 0, 1, or 2 $R^7$, $C_{2-6}$ alkenyl substituted with 0, 1, or 2 $R^7$, $(CH_2)_rOR^3$, $(CH_2)_rC(O)R^4$, $(CH_2)_rOC(O)R^4$, $(CH_2)_rNR^3R^{3'}$, $(CH_2)_rNR^3C(O)R^4$, $(CH_2)_rSO_2R^5$, $(CH_2)_rNR^3SO_2R^5$, $C_{3-10}$ carbocyclic residue substituted with 0–2 $R^6$; and, 5–10 membered heterocyclic system containing from 1–3 heteroatoms selected from the group consisting of N, O, and S substituted with 0–2 $R^6$;

$R^{2a}$ is absent;

alternatively, $R^2$ and $R^{2a}$ may be present on adjacent carbon atoms and combine to form a benzene ring substituted with 0–2 $R^{10}$ or a 5–6 membered aromatic heterocycle containing 0–2 heteroatoms selected from the group consisting of N, O, and S and substituted with 0–2 $R^{10a}$;

$R^3$ and $R^{3'}$ are independently selected from H, $C_{1-4}$ alkyl, benzyl and phenyl;

$R^3$ and $R^{3'}$ may be taken together to form a 5 or 6 membered ring substituted with 0–2 $R^6$;

$R^4$ and $R^{4'}$ are independently selected from H, $OR^3$, $C_{1-4}$ alkyl, phenyl and $NR^3R^{3'}$;

$R^5$ is selected from $C_{1-4}$ alkyl, phenyl and $NR^3R^{3'}$;

Z is selected from a bond, $C_{1-4}$ alkylene, $(CH_2)_rO(CH_2)_r$, $(CH_2)_2NR^3(CH_2)_r$, $(CH_2)_rC(O)(CH_2)_r$, $(CH_2)_rC(O)O(CH_2)_r$, $(CH_2)_2OC(O)(CH_2)_r$, $(CH_2)_rC(O)NR^3(CH_2)_r$, $(CH_2)_2NR^3C(O)(CH_2)_r$, $(CH_2)_2OC(O)O(CH_2)_r$, $(CH_2)_2OC(O)NR^3(CH_2)_r$, $(CH_2)_2NR^3C(O)O(CH_2)_r$, $(CH_2)_2NR^3C(O)NR^3(CH_2)_r$, $(CH_2)_rS(O)_p(CH_2)_r$, $(CH_2)_r SO_2NR^3(CH_2)_r$, $(CH_2)_2NR^3SO_2(CH_2)_r$, and $(CH_2)_2NR^3SO_2NR^3(CH_2)_r$;

A is selected from:
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

B is selected from:
X—Y, $NR^3R^{3'}$, $C(O)NR^3R^{3'}$, $SO_2NR^3R^{3'}$, benzyl substituted with 0–2 $R^6$,
$C_{3-10}$ carbocyclic residue substituted with 0–2 $R^6$, and 5–10 membered heterocyclic system containing from 1–3 heteroatoms selected from the group consisting of N, O, and S substituted with 0–2 $R^6$;

X is selected from $C_{1-4}$ alkylene, —C(O)—, —C(O)$CR^3R^{3'}$—, —$CR^3R^{3'}$C(O)—, —C(O)O—, —C(O)OCR$^3$R$^{3'}$—, —CR$^3$R$^{3'}$C(O)O—, —OC(O)—, —OC(O)CR$^3$R$^{3'}$—, —CR$^3$R$^{3'}$OC(O)—, —S(O)$_p$—, —S(O)$_p$CR$^3$R$^{3'}$—, —CR$^3$R$^{3'}$S(O)$_p$—, —S(O)$_2$NR$^3$—, —NR$^3$S(O)$_2$—, —NR$^3$S(O)$_2$CR$^3$R$^{3'}$, —CR$^3$R$^{3'}$S(O)$_2$NR$^3$—, —NR$^3$S(O)$_2$NR$^3$—, —C(O)NR$^3$—, —NR$^3$C(O)—, —C(O)NR$^3$CR$^3$R$^{3'}$—, —NR$^3$C(O)CR$^3$R$^{3'}$—, —CR$^3$R$^{3'}$C(O)NR$^3$—, —CR$^3$R$^{3'}$NR$^3$C(O)—, —NR$^3$C(O)O—, —OC(O)NR$^3$—, —NR$^3$C(O)NR$^3$—, —NR$^3$—, —NR$^3$CR$^3$R$^{3'}$—, —CR$^3$R$^{3'}$NR$^3$—, O, —CR$^3$R$^{3'}$O—, —OCR$^3$R$^{3'}$—, S, —CR$^3$R$^{3'}$S—, and —SCR$^3$R$^{3'}$—;

Y is selected from:
C$_{1-4}$ alkyl substituted with 0–2 R$^6$
C$_{3-10}$ carbocyclic residue substituted with 0–2 R$^6$, and
5–10 membered heterocyclic system containing from 1–3 heteroatoms selected from the group consisting of N, O, and S substituted with 0–2 R$^6$;

R$^6$ is selected from H, OH, CF$_3$, (CH$_2$)$_n$OR$^3$, halo, C$_{1-4}$ alkyl, CN, NO$_2$, (CH$_2$)$_r$NR$^3$R$^{3'}$(CH$_2$)$_r$C(O)R$^3$, NR$^3$C(O)R$^{3'}$, NR$^3$C(O)NR$^3$R$^{3'}$, SO$_2$NR$^3$R$^{3'}$, NR$^3$SO$_2$NR$^3$R$^{3'}$, NR$^3$SO$_2$—C$_{1-4}$ alkyl, SO$_2$-phenyl, and NR$^3$SO$_2$R$^8$;

R$^7$ is selected from:
C$_{3-10}$ carbocyclic residue substituted with 0–2 R$^6$; and,
5–10 membered heterocyclic system containing from 1–3 heteroatoms selected from the group consisting of N, O, and S substituted with 0–2 R$^6$;

R$^8$ is selected from:
C$_{3-10}$ carbocyclic residue substituted with 0–2 R$^9$; and,
5–10 membered heterocyclic system containing from 1–3 heteroatoms selected from the group consisting of N, O, and S substituted with 0–2 R$^9$;

R$^9$ is selected from H, OH, (CH$_2$)$_n$OR$^3$, halo, C$_{1-4}$ alkyl, CN, NO$_2$, (CH$_2$)$_r$NR$^3$R$^{3'}$, (CH$_2$)$_r$C(O)R$^3$, NR$^3$C(O)R$^{3'}$, NR$^3$C(O)NR$^3$R$^{3'}$, SO$_2$NR$^3$R$^{3'}$, NR$^3$SO$_2$NR$^3$R$^{3'}$, and NR$^3$SO$_2$—C$_{1-4}$ alkyl;

R$^{10}$ is selected from H, OR$^3$, halo, C$_{1-4}$ alkyl, CN, NO$_2$, NR$^3$R$^{3'}$, NR$^3$C(O)R$^{3'}$, NR$^3$C(O)OR$^{3'}$, NR$^3$SO$_2$-phenyl, and NR$^3$SO$_2$—C$_{1-4}$ alkyl;

R$^{10a}$ if a substituent on nitrogen is selected from H and C$_{1-4}$ alkyl;

R$^{10a}$ if a substituent on carbon is selected from H, C$_{1-4}$ alkyl, NR$^3$R$^{3'}$, NR$^3$C(O)R$^{3'}$, NR$^3$C(O)OR$^{3'}$, NR$^3$SO$_2$-phenyl, and NR$^3$SO$_2$—C$_{1-4}$ alkyl;

R$^{11}$ is selected from H, OH, C$_{1-6}$ alkyl, C$_{1-6}$ alkylcarbonyl, C$_{1-6}$ alkoxy, C$_{1-4}$ alkoxycarbonyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl C$_{1-4}$ alkoxycarbonyl;

R$^{12}$ is selected from H, C$_{1-6}$ alkyl and (CH$_2$)$_n$-phenyl;
R$^{13}$ is selected from H, C$_{1-6}$ alkyl and (CH$_2$)$_n$-phenyl;
n is selected from 0, 1, 2, and 3;
m is selected from 0 and 1;
p is selected from 0, 1, and 2;
q is selected from 1, 2, 3, 4, and 5; and,
r is selected from 0, 1, and 2.

[2] In a preferred embodiment, the present invention provides compounds of formula I wherein:
is C(=NH)NH$_2$;
D' is H;
R$^1$ is selected from H, (CH$_2$)$_r$OR$^3$, halo, (CH$_2$)$_r$NR$^4$R$^{4'}$, (CH$_2$)$_r$CO$_2$H, (CH$_2$)$_r$C(=O)R$^4$, (CH$_2$)$_r$NR$^4$C(=O)R$^4$, (CH$_2$)$_r$SO$_2$R$^5$, and (CH$_2$)$_r$NHSO$_2$R$^5$;

R$^2$ is selected from H, =O, (CH$_2$)$_r$OR$^3$, (CH$_2$)$_r$C(O)R$^4$, (CH$_2$)$_r$OC(O)R$^4$, (CH$_2$)$_r$NR$^3$R$^{3'}$, (CH$_2$)$_r$NR$^3$C(O)R$^4$, (CH$_2$)$_r$SO$_2$R$^5$, (CH$_2$)$_r$NR$^3$SO$_2$R$^5$, C$_{3-10}$ carbocyclic residue substituted with 0–2 R$^6$; and, 5–10 membered heterocyclic system containing from 1–3 heteroatoms selected from the group consisting of N, O, and S substituted with 0–2 R$^6$;

R$^4$ and R$^{4'}$ are independently selected from H, OR$^3$, C$_{1-4}$ alkyl, and NR$^3$R$^{3'}$;

R$^5$ is selected from C$_{1-4}$ alkyl and NR$^3$R$^{3'}$;

Z is selected from a bond, C$_{1-4}$ alkylene, (CH$_2$)$_r$C(O)(CH$_2$)$_r$, (CH$_2$)$_r$C(O)NR$^3$(CH$_2$)$_r$, (CH$_2$)$_2$NR$^3$C(O)(CH$_2$)$_r$, (CH$_2$)$_2$OC(O)NR$^3$(CH$_2$)$_r$, (CH$_2$)$_2$NR$^3$C(O)O(CH$_2$)$_r$, (CH$_2$)$_2$NR$^3$C(O)NR$^3$(CH$_2$)$_r$, (CH$_2$)$_r$S(O)$_p$(CH$_2$)$_r$, (CH$_2$)$_r$SO$_2$NR$^3$(CH$_2$)$_r$, (CH$_2$)$_2$NR$^3$SO$_2$(CH$_2$)$_r$, and (CH$_2$)$_2$NR$^3$SO$_2$NR$^3$(CH$_2$)$_r$; and, X is selected from C$_{1-4}$ alkylene, —C(O)—, —C(O)CR$^3$R$^{3'}$—, —CR$^3$R$^{3'}$C(O)—, —C(O)O—, —C(O)OCR$^3$R$^{3'}$—, —CR$^3$R$^{3'}$C(O)O—, —OC(O)—, —OC(O)CR$^3$R$^{3'}$—, —CR$^3$R$^{3'}$OC(O)—, —S(O)$_p$—, —S(O)$_p$CR$^3$R$^{3'}$—, —CR$^3$R$^{3'}$S(O)$_p$—, —S(O)$_2$NR$^3$—, —C(O)NR$^3$—, —NR$^3$C(O)—, —NR$^3$C(O)O—, —OC(O)NR$^3$—, —NR$^3$C(O)NR$^3$—, —NR$^3$—, —NR$^3$CR$^3$R$^{3'}$—, —CR$^3$R$^{3'}$NR$^3$—, O, —CR$^3$R$^{3'}$O, and —OCR$^3$R$^{3'}$—,

[3] In a more preferred embodiment, the present invention provides compounds of formula I wherein:
R$^1$ is selected from H, OR$^3$, (CH$_2$)OR$^3$, halo, NR$^4$R$^{4'}$, (CH$_2$)NR$^4$R$^{4'}$, C(=O)R$^4$, (CH$_2$)C(=O)R$^4$, NHC(=O)R$^4$, (CH$_2$)NHC(=O)R$^4$, SO$_2$R$^5$, (CH$_2$)SO$_2$R$^5$, NHSO$_2$R$^5$, and (CH$_2$) NHSO$_2$R$^5$;

R$^2$ is selected from H, =O, OR$^3$, C(O)R$^4$, (CH$_2$)C(O)R$^4$, OC(O)R$^4$, NR$^4$R$^{4'}$, NR$^3$C(O)R$^4$, and NR$^4$SO$_2$R$^5$;

A is selected from:
C$_{5-6}$ carbocyclic residue substituted with 0–1 R$^6$, and
5–6 membered heterocyclic system containing from 1–2 heteroatoms selected from the group consisting of N and O substituted with 0–1 R$^6$;

B is selected from: Y, X—Y, and NR$^2$R$^{2a}$;

Y is selected from one of the following carbocyclic and heterocyclic systems which are substituted with 0–2 R$^{4a}$;
phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzoxazole, benzthiazole, indazole, benzisoxazole, benzisothiazole, isoindazole, and benzothiadiazole;

Y may also be selected from the following bicyclic heteroaryl ring systems:

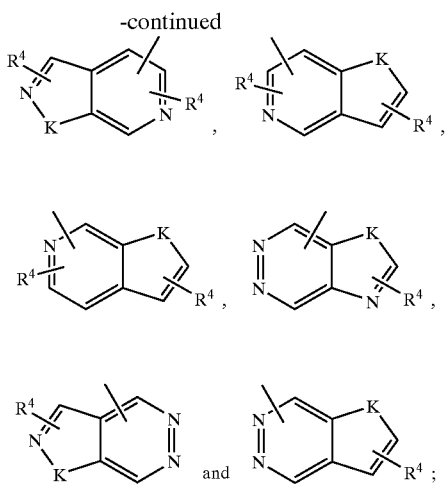

K is selected from O, S, NH, and N;

X is selected from —CH$_2$—, —C(O)—, —C(O)CHR$^3$—, —CHR$^3$C(O)—, —S(O)$_p$—, —S(O)$_p$CR$^3$R$^{3'}$—, —CHR$^3$S(O)$_p$—, —S(O)$_2$NR$^3$—, —C(O)NR$^3$—, —NR$^3$C(O)—, —NR$^3$—, —NR$^3$CHR$^3$—, and —CHR$_3$NR$^3$;

R$^6$ is selected from H, OH, CF$_3$, (CH$_2$)$_n$OR$^3$, halo, C$_{1-4}$ alkyl, CN, NO$_2$, (CH$_2$)$_r$NR$^3$R$^{3'}$,(CH$_2$)$_r$C(O)R$^3$, NR$^3$C(O)R$^{3'}$, SO$_2$NR$^3$R$^{3'}$, SO$_2$-phenyl, NR$^3$SO$_2$—C$_{1-4}$ alkyl, and NR$^3$SO$_2$R$^8$;

R$^8$ is selected from:

C$_{5-6}$ carbocyclic residue substituted with 0–2 R$^9$; and,

5–6 membered heterocyclic system containing from 1–3 heteroatoms selected from the group consisting of N, O, and S substituted with 0–2 R$^9$;

R$^9$ is selected from H, OH, (CH$_2$)$_n$OR$^3$, halo, C$_{1-4}$ alkyl, CN, NO$_2$, (CH$_2$)$_r$NR$^3$R$^{3'}$, (CH$_2$)$_r$C(O)R$^3$, NR$^3$C(O)R$^{3'}$, NR$^3$C(O)NR$^3$R$^{3'}$, SO$_2$NR$^3$R$^{3'}$, NR$^3$SO$_2$NR$^3$R$^{3'}$, and NR$^3$SO$_2$—C$_{1-4}$ alkyl; and, p is 2.

[4] In an even more preferred embodiment, the present invention provides compounds of formula I wherein:

Z is selected from a bond, C$_{1-4}$ alkylene, (CH$_2$)$_r$C(O)(CH$_2$)$_r$, (CH$_2$)$_r$C(O)NR$^3$(CH$_2$)$_r$, (CH$_2$)$_2$NR$^3$C(O)(CH$_2$)$_r$, (CH$_2$)$_2$NR$^3$C(O)NR$^3$(CH$_2$)$_r$, and (CH$_2$)$_r$S(CH$_2$)$_r$;

X is selected from —CH$_2$—, —C(O)—, —C(O)CHR$^3$—, —CHR$^3$C(O)—, —S(O)$_p$—, —S(O)$_p$CR$^3$R$^{3'}$—, —CHR$^3$S(O)$_p$—, —S(O)$_2$NR$^3$—, —C(O)NR$^3$—, and —NR$^3$C(O)—;

R$^6$ is selected from H, OH, CF$_3$, (CH$_2$)$_n$OR$^3$, halo, C$_{1-4}$ alkyl, CN, NO$_2$, (CH$_2$)$_r$NR$^3$R$^{3'}$(CH$_2$)$_r$C(O)R$^3$, NR$^3$C(O)R$^{3'}$, SO$_2$NR$^3$R$^{3'}$, SO$_2$-phenyl, and NR$^3$SO$_2$—C$_{1-4}$ alkyl;

m is 1; and, r is selected from 0 and 1.

[5] In a further preferred embodiment, the present invention provides compounds of formula I wherein:

R$^3$ and R$^{3'}$ are independently selected from H and C$_{1-4}$ alkyl;

Z is selected from a bond, C$_{1-4}$ alkylene, (CH$_2$)$_r$C(O)NR$^3$(CH$_2$)$_r$, (CH$_2$)$_2$NR$^3$C(O)(CH$_2$)$_r$, and (CH$_2$)$_2$NR$^3$C(O)NR$^3$(CH$_2$)$_r$;

A is selected from phenyl substituted with 0–1 R$^6$ and a 6 membered heterocyclic system containing 1 N and 0–1 O atoms and substituted with 0–1 R$^6$;

X is selected from —CH$_2$—, —S(O)$_p$—, —S(O)$_p$CR$^3$R$^{3'}$—, —S(O)$_2$NR$^3$—, —C(O)NR$^3$—, and;

Y is selected from phenyl, i-propyl, quinolynyl, thiadizolyl, benzothiadiazolyl, thiophenyl, pyridyl, cyclohexyl, and naphthyl, each of which is substituted with 0–2 R$^6$; and, n is selected from 0, 1, and 2.

[6] In an even further preferred embodiment, the present invention provides compounds of formula I wherein:

R$^3$ and R$^{3'}$ are independently selected from H and methyl;

Z is selected from a bond, CH$_2$, —CH$_2$CH$_2$—, —CH$_2$CH$_2$CH$_2$— and —CH$_2$CH$_2$CH$_2$CH$_2$—;

A is selected from phenyl substituted with 0–1 R$^6$, and piperidinyl substituted with 0–1 R$^6$; and, n is 2.

[7] In a particularly preferred embodiment, the present invention provides compounds selected from:

N-(3-amidinophenyl)-N'-((4-((2-sulphonamido)phenyl)phenyl)methyl)cycloheptylurea;

N-(3-amidinophenyl)-N'-(1-benzylpiperidin-4-yl)cycloheptylurea;

N-(3-amidinophenyl)-N'-(1-(picolin-2-yl)piperidin-4-yl)cycloheptylurea;

N-(3-amidinophenyl)-N'-(1-(picolin-3-yl)piperidin-4-yl)cycloheptylurea;

N-(3-amidinophenyl)-N'-(1-(picolin-4-yl)piperidin-4-yl)cycloheptylurea;

N-(3-amidinophenyl)-N'-(1-(a-phenethyl)piperidin-4-yl)cycloheptylurea;

N-(3-amidinophenyl)-N'-(1-((phenyl)methane)sulfonyl)-piperidin-4-yl)cycloheptylurea;

N-(3-amidinophenyl)-N'-(1-(phenyl)sulfonylpiperidin-4-yl)cycloheptylurea;

N-(3-amidinophenyl)-N'-(1-(quinolin-8-yl)sulfonylpiperidin-4-yl)cycloheptylurea;

N-(3-amidinophenyl)-N'-(1-(2-fluorophenyl)sulfonylpiperidin-4-yl)cycloheptylurea;

N-(3-amidinophenyl)-N'-(1-(4-acetamidophenyl)sulfonyl-piperidin-4-yl)cycloheptylurea;

N-(3-amidinophenyl)-N'-(1-(2-aminophenyl)sulfonylpiperidin-4-yl)cycloheptylurea;

N-(3-amidinophenyl)-N'-(1-(3-aminophenyl)sulfonylpiperidin-4-yl)cycloheptylurea;

N-(3-amidinophenyl)-N'-(1-(4-aminophenyl)sulfonylpiperidin-4-yl)cycloheptylurea;

N-(3-amidinophenyl)-N'-(1-((2-aminophenyl)methane)sulfonyl)-piperidin-4-yl)cycloheptylurea;

N-(3-amidinophenyl)-N'-(1-((2-acetamido-phenyl)methane)-sulfonylpiperidin-4-yl)cycloheptylurea;

N-(3-amidinophenyl)-N'-(1-((thiophen-2-yl)sulfonyl)piperidin-4-yl)cycloheptylurea;

N-(3-amidinophenyl)-N'-(1-((5-chlorothiophen-2-yl)sulfonyl)-piperidin-4-yl)cycloheptylurea;

N-(3-amidinophenyl)-N'-(1-((5-carbomethoxythiophen-2-yl)sulfonyl)piperidin-4-yl)cycloheptylurea;

N-(3-amidinophenyl)-N'-(1-((benzo-2,1,3-thiadiazo-4-yl)sulfonyl)piperidin-4-yl)cycloheptylurea;

N-(3-amidinophenyl)-N'-(1-((cyclohexyl)sulfamido)piperidin-4-yl)cycloheptylurea;

N-(3-amidinophenyl)-N'-(1-((isopropyl)sulfamido)piperidin-4-yl)cycloheptylurea;

N-(3-amidinophenyl)-N'-(1-((phenyl)sulfamido)piperidin-4-yl)cycloheptylurea;

N-(3-amidinophenyl)-N'-(1-((isopropyl)sulfonyl)piperidin-4-yl)cycloheptylurea;

N-(3-amidinophenyl)-N'-(1-((5-amino-4-methylthiazol-2-yl)sulfonyl)piperidin-4-yl)cycloheptylurea;

N-(3-amidinophenyl)-N'-(1-((5-acetamido-4-methylthiazol-2-yl)sulfonyl)piperidin-4-yl)cycloheptylurea;

N-(3-amidinophenyl)-N'-(1-(6-carbomethoxyphenyl-sulfonyl)piperidin-4-yl)cycloheptylurea;

N-(3-amidinophenyl)-N'-(2-pyridylmethyl)piperidin-4-yl)cycloheptylurea;

N-(3-amidinophenyl)-N'-(3-pyridylmethyl)piperidin-4-yl)cycloheptylurea;

N-(3-amidinophenyl)-N'-(4-pyridylmethyl)piperidin-4-yl)cycloheptylurea;

N-(3-amidinophenyl)-N'-(phenyl-N"-methylsulfamido)piperidin-4-yl)cycloheptylurea;

N-(3-amidinophenyl)-N'-((4-phenylsulfonylthiophen-2-yl)sulfonyl)-piperidin-4-yl)cycloheptylurea;

N-(3-amidinophenyl)-N'-(4-pyridylmethylsulfonyl)piperidin-4-yl)cycloheptylurea;

N-(3-amidinophenyl)-N'-(thiophen-2-ylsulfonyl)piperidin-4-yl)cycloheptylurea;

N-(3-amidinophenyl)-N'-(4-fluorobenzylsulfonyl)piperidin-4-yl)cycloheptylurea;

N-(3-amidinophenyl)-N'-(2-pyridylsulfonyl)piperidin-4-yl)cycloheptylurea;

N-(3-amidinophenyl)-N'-(2-trifluormethyl-phenylsulfonyl)piperidin-4-yl)cycloheptylurea;

N-(3-amidinophenyl)-N'-(2-phenylisopropylsulfonyl)piperidin-4-yl)cycloheptylurea;

N-(3-amidinophenyl)-N'-((1-((phenyl)-1,1-dimethyl)methane)sulfonyl)-piperidin-4-yl)cycloheptylurea;

N-(3-amidinophenyl)-N'-(methyl((phenyl-methane)carbamide)morpholin-3-yl))cycloheptylurea;

N-(3-amidinophenyl)-N'-(methyl((thiophen-2-yl)sulfonyl)morpholin-3-yl))cycloheptylurea;

N-(3-amidinophenyl)-N'-(methyl((phenyl-methane)sulfonyl)morpholin-3-yl))cycloheptylurea;

N-(3-amidinophenyl)-N'-((N-benzyl)piperidin-3-yl)cycloheptylurea;

N-(3-amidinophenyl)-N'-((N-(benzyl)sulfonyl)-piperidin-3-yl)cycloheptylurea;

N-(3-amidinophenyl)-N'-((N-(thiophen-2-yl)sulfonyl)piperidin-3-yl)cycloheptylurea;

N-(3-amidinophenyl)-N'-(4-(2-sulfonamido-phenyl)phenyl)cycloheptylurea;

N-(3-amidinophenyl)-N'-(5-(2-sulfonamido-phenyl)pyridin-2-yl)cycloheptylurea; and, N-(3-amidinophenyl)-N'-(methyl(4-(2-sulfonamidophenyl)phenyl))cycloheptylurea;

or stereoisomers or pharmaceutically acceptable salt forms thereof.

[8] In another preferred embodiment, the present invention provides compounds wherein:
  n is 2; and,
  $R^2$ and $R^{21}$ are on adjacent carbon atoms and combine to form a benzene ring substituted with 0–2 $R^{10}$ or a 5–6 membered aromatic heterocycle containing 0–2 heteroatoms selected from the group consisting of N, O, and S and substituted with 0–2 $R^{10a}$.

[9] In another more preferred embodiment, the present invention provides novel compounds of formula II:

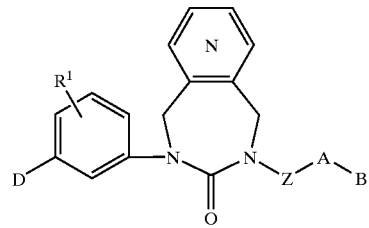

or stereoisomers or pharmaceutically acceptable salt forms thereof, wherein;
  ring N contains 0–2 N atoms and is substituted with 0–2 $R^{10}$; and,
  D is selected from CN, C(=NR$^{11}$)NR$^{12}$R$^{13}$, NHC(=NR$^{11}$)NR$^{12}$R$^{13}$, NR$^{12}$CH(=NR$^{11}$), C(O)NR$^{12}$R$^{13}$, and (CH$_2$)$_r$NR$^{12}$R$^{13}$.

[10] In another even more preferred embodiment, the present invention provides compounds of formula II wherein:
  D is C(=NH)NH$_2$;
  $R^1$ is selected from H, (CH$_2$)$_r$OR$^3$, halo, (CH$_2$)$_r$NR$^4$R$^{4'}$, (CH$_2$)$_r$CO$_2$H, (CH$_2$)$_r$C(=O)R$^4$, (CH$_2$)$_r$NR$^4$C(=O)R$^4$, (CH$_2$)$_r$SO$_2$R$^5$, and (CH$_2$)$_r$NHSO$_2$R$^5$;
  $R^4$ and $R^{4'}$ are independently selected from H, OR$^3$, C$_{1-4}$ alkyl, and NR$^3$R$^{3'}$;
  $R^5$ is selected from C$_{1-4}$ alkyl and NR$^3$R$^{3'}$;
  Z is selected from a bond, C$_{1-4}$ alkylene, (CH$_2$)$_r$C(O)(CH$_2$)$_r$, (CH$_2$)$_r$C(O)NR$^3$(CH$_2$)$_r$, (CH$_2$)$_2$NR$^3$C(O)(CH$_2$)$_r$, (CH$_2$)$_2$OC(O)NR$^3$(CH$_2$)$_r$, (CH$_2$)$_2$NR$^3$C(O)O(CH$_2$)$_r$, (CH$_2$)$_2$NR$^3$C(O)NR$^3$(CH$_2$)$_r$, (CH$_2$)$_r$S(O)$_p$(CH$_2$)$_r$, and (CH$_2$)$_r$SO$_2$NR$^3$(CH$_2$)$_r$; and,
  X is selected from C$_{1-4}$ alkylene, —CO(O), —C(O)CR$^3$R$^{3'}$—, —CR$^3$R$^{3'}$C(O)—, —C(O)O—, —C(O)OCR$^3$R$^{3'}$, —CR$^3$R$^{3'}$C(O)O—, —OC(O)—, —OC(O)CR$^3$R$^{3'}$—, —CR$^3$R$^{3'}$OC(O)—, —S(O)$_p$—, —S(O)$_p$CR$^3$R$^{3'}$—, —CR$^3$R$^{3'}$S(O)$_p$—, —C(O)NR$^3$—, —NR$^3$C(O)—, —NR$^3$C(O)O—, —OC(O)NR$^3$—, —NR$^3$C(O)NR$^3$—, —NR$^3$—, —NR$^3$CR$^3$R$^{3'}$—, —CR$^3$R$^{3'}$NR$^3$—, O, —CR$^3$R$^{3'}$O—, and —OCR$^3$R$^{3'}$—.

[11] In another further preferred embodiment, the present invention provides compounds of formula II, wherein:
  Z is selected from a bond, C$_{1-4}$ alkylene, C(O)NR$^3$(CH$_2$)$_r$, S(O)$_2$, S(O)$_2$CH$_2$, and (CH$_2$)$_r$SO$_2$NR$^3$(CH$_2$)$_r$;
  A is selected from phenyl substituted with 0–1 $R^6$ and 6 membered heterocyclic system containing 1 N and substituted with 0–1 $R^6$; and,
  X is selected from C$_{1-4}$ alkylene, —C(O)—, —C(O)CR$^3$R$^{3'}$—, —CR$^3$R$^{3'}$C(O)—, —S(O)$_p$—, —S(O)$_p$CR$^3$R$^{3'}$—, —C(O)NR$^3$—, and, —NR$^3$—.

[12] In another even further preferred embodiment, the present invention provides compounds selected from:

1,2,4,5-tetrahydro-2-((phenyl)methane)-sulfonyl)piperidin-4-yl)-4-(3-amidinophenyl)-3H-2,4-benzodiazepin-3-one;

1,2,4,5-tetrahydro-2-(thiopen-2-yl)-sulfonyl)piperidin-4-yl)-4-(3-amidinophenyl)-3H-2,4-benzodiazepin-3-one;

1,2,4,5-tetrahydro-2-((phenyl)methane)-sulfonyl)piperidin-4-yl)-4-(3-amidinophenyl)-7,8-dimethoxy-3H-2,4-benzodiazepin-3-one; and, 1,2,4,5-tetrahydro-2-(thiophen-2-yl)-sulfonyl)piperidin-4-yl)-4-(3-amidinophenyl)-7,8-dimethoxy-3H-2,4-benzodiazepin-3-one.

In a second embodiment, the present invention provides novel pharmaceutical compositions, comprising: a pharmaceutically acceptable carrier and a therapeutically effective amount of a compound of formula (I) or a pharmaceutically acceptable salt or prodrug form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt or prodrug form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, benzothiadiazolyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3- thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is C(=NR$^{11}$)NH$_2$, and R$^{11}$ is selected from OH, C$_{1-4}$ alkoxy, C$_{6-10}$ aryloxy, C$_{1-4}$ alkoxycarbonyl, C$_{6-10}$ aryloxycarbonyl, C$_{6-10}$ arylmethylcarbonyl, C$_{1-4}$ alkylcarbonyloxy C$_{1-4}$ alkoxycarbonyl, and C$_{6-10}$ arylcarbonyloxy C$_{1-4}$ alkoxycarbonyl. More preferred prodrugs are where R$^{11}$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

Synthesis

Compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. All the temperatures are reported herein in degrees Celsius.

The compounds of Formula 1 can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991).

Two general approaches can be used for the preparation of the cyclic ureas of this invention. The first involves bimolecular cyclizations to the cyclic urea, as outlined in Scheme I, the second uses the internal unimolecular cyclizations of Scheme II.

Scheme I:
Bimolecular cyclization routes to a cyclic urea precursor to Formula 1.

Route A

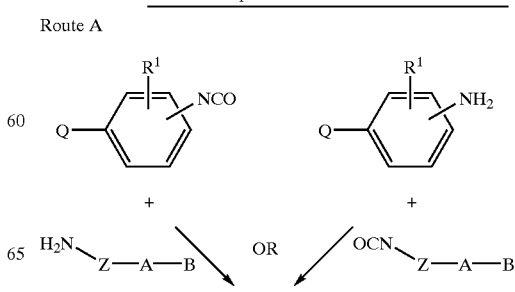

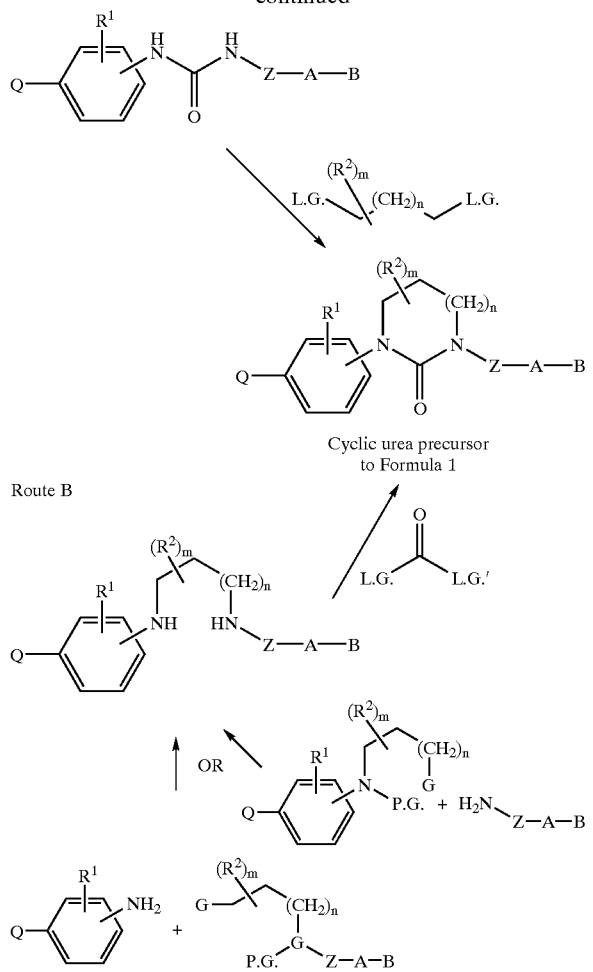

Route B

Cyclic urea precursor to Formula 1

Route A of Scheme I illustrates the bis-alkylation of an N,N'-disubstituted urea with an alkane substituted at both termini with an appropriate leaving group (L.G.), such as a halogen or sulfonate ester. The flexibility of this approach also allows for the bis-alkylation with an alkene or $R^2$-substituted alkane which is again substituted at both termini with an appropriate leaving group (L.G.). Such alkylation agents are either commercially available, e.g. 1,4-dibromobutane and its lower homologs, found in the literature, e.g. the isopropylidene ether of 1,4-diiodido-2,3-dihydroxybutane (Deluca and Magnus, *J. Chem. Soc.* (Perkin Trans. I), 2661(1991), and Hoye and Suhadolnik, *Tetrahedron*, 42 (11) 2855 (1986)), or can be prepared by a practitioner skilled in the art using standard chemical methods.

The N,N'-disubstituted urea can be generated from two primary amines, one of which must be a $Q,R^1$-substituted aniline wherein Q is a functional group from which an amidine could be readily generated such as nitrile; in some special cases Q may be tolerated as a mono- or di- acyl or carbamoyl protected amidine. The second primary amine, $H_2N$—Z—A—B, may be any amine deemed appropriate within the limits of Formula 1. This amine may be commercially available, e.g. 1-benzyl-4-aminopiperidine, found in the literature, e.g. 1-t-butoxycabonyl-4-aminopiperidine (Mach et al., *J. Med. Chem.*, 36(23), 3707 (1993)), or can be prepared by a practitioner skilled in the art utilizing standard chemical methods.

The two primary amines described above can be assembled to the desired N,N'-disubstituted urea by selecting one for transformation to the corresponding isocyanate in situ by stirring with phosgene or its equivalent such as trichloromethyl chloroformate or p-nitrophenylchloroformate in the presence of a trialkylamine base and a dry, aprotic solvent such as dimethylformamide, dioxane, benzene or a chlorinated alkane. The temperature of this reaction may be varied from −10° C. to the reflux point of the solvent (Takeda et al., *Tetrahedron Lett.*, 24(42) 4569 (1983), Cortez et al., *Synth. Commun.*, 21(2) 285 (1991)). Alternatively the desired isocyanate may be commercially available, such as 3-cyanophenyl isocyanate, in which case convenience dictates that this substrate be used. Conditions for direct reaction of a preformed isocyanate are similar to those described above with the caveat that the phosgene equivalent is necessary, and the trialkylamine base may be omitted (Shiau et al., *J. Heterocyclic Chem.*, 26, 595(1989)).

Ring formation in Route A is achieved by alkylation of the N,N'-disubstituted urea with the dihalogenated (Curtis, *Aust. J. Chem.*, 41 585 (1988), Htay et al., *Tetrahedron Lett.*, 79 (1976), Sulsky et al., *Synth. Commun.*, 19, 1871 (1989)) or disulfonated (Ayyana et al., *Chem. Ind.* (London), 599 (1988)) alkylating agent described above. Typically, the disubstituted urea is added at ambient temperature or lower to a mixture of at least two equivalents of strong base such as sodium hydride, potassium t-butoxide or an alkyl lithium in an appropriate anhydrous solvent such as tetrahydrofuran, dimethylformamide, t-butanol, toluene or dimethylsulfoxide. After deprotonation is complete, a solution of the alkylating agent in the selected solvent is added slowly to the disubstituted urea at ambient temperature or lower; when the addition is completed, the reaction may be continued at ambient temperature or lower or heated up to the reflux temperature of the solvent, depending upon the reactivity of the alkylating agent/disubstituted urea pair and the patience of the practitioner.

Route B of Scheme I illustrates use of an appropriately substituted diamine and phosgene or its equivalent to generate a cyclic urea precursor to Formula 1. The required diamine can be generated by two approaches. The first approach utilizes a $Q,R^1$-substituted aniline which is conjoined with an N-acyl or N-carbamoyl protected secondary amine where G is a halogen or sulfonate ester leaving group for a standard alkylation of the $Q,R^1$-substituted aniline or G could be an aldehyde suitable for reductive alkylation of the $Q,R^1$-substituted aniline. The second approach to diamine formation conjoins an N-acyl or N-carbamoyl protected N-alkylated $Q,R^1$-substituted aniline, where G is as described above, with primary amine $H_2N$—Z—A—B by a standard or reductive alkylation.

Both protected secondary amines are available by similar chemistry. The selected aniline or primary amine $H_2N$—Z—A—B is protected with a N-acyl or N-carbamoyl protecting group according to a method specified in Greene and Wuts; N-t-butoxy carbamoyl is useful for this application. This protected amine can then be cleanly mono-alkylated with one of the dihalogenated or disulfonylated alkylating agents recommended for Route A (Reed et al., *Tetrahedron Lett.*, 79(45) 5725 (1988)). Alternatively, the protected amine can be mono-alkylated with a protected halo alcohol. Both alkylations are readily achieved in anhydrous aprotic solvents such as toluene, tetrahydrofuran, dimethylformamide or dimethylsulfoxide at temperatures ranging from −78° C. to the reflux temperature of the selected solvent with a strong base such as sodium hydride, potassium t-butoxide or an alkyl lithium. In the case where G is a protected alcohol, the protecting group is removed and an aldehyde generated by Moffatt oxidation (Pfitzner and Moffatt, *J. Amer. Chem. Soc.*, 87 5661 (1965)) or through use of pyridinium chlorochromate (Corey and Suggs, *Tetrahedron Lett.*, 2647 (1975)) or pyridinium dichromate in dichloromethane (Coates and Corrigan, *Chem. Ind.* (London), 1594 (1969)).

The required diamine can then be prepared by stirring the alkylating agent with the primary amine component either neat or in an aprotic solvent such as toluene, tetrahydrofuran, dimethylformamide or dimethylsulfoxide. The temperature of this reaction may range from −78° C. to the reflux temperature of the selected solvent. A strong base such as sodium hydride, potassium t-butoxide or an alkyl lithium or a weaker trialkylamine base may be used, depending upon the reactivity of the two components. As an alternative, when G is an aldehyde, a reductive alkylation of the primary amine component is possible. The direct method involves the use of a borohydride reducing agent, most preferably sodium or lithium cyanoborohydride, in a mixture of aldehyde and amine components in an alcoholic solvent (Borch et al., *J. Amer. Chem. Soc.*, 93 2897 (1971)). A stepwise method involves generation of an intermediate imine/enamine by azeotropic removal of water from a heated mixture of aldehyde and primary amine component in a suitable solvent such as benzene at reflux temperature. The imine/enamine intermediate can then be isolated and reduced by palladium catalyst under an atmosphere of hydrogen gas at ambient pressure or higher or reduced by borohydride reagents under conditions similar to those preferred for the direct method. The required diamine is generated by removal of the protecting group according to a method recommended in Greene and Wuts.

The diamine formed above is reacted with phosgene or its equivalent such as trichloromethyl chloroformate or p-nitrophenylchloroformate in the presence of an excess of a trialkylamine base and a dry, aprotic solvent such as dimethylformamide, dioxane, toluene, benzene or a chlorinated alkane to form a cyclic urea precursor to Formula 1. The temperature of this reaction may be varied from −10° C. to the reflux point of the solvent.

Scheme II:
Unimolecular cyclization routes to cyclic urea precursors to Formula 1.

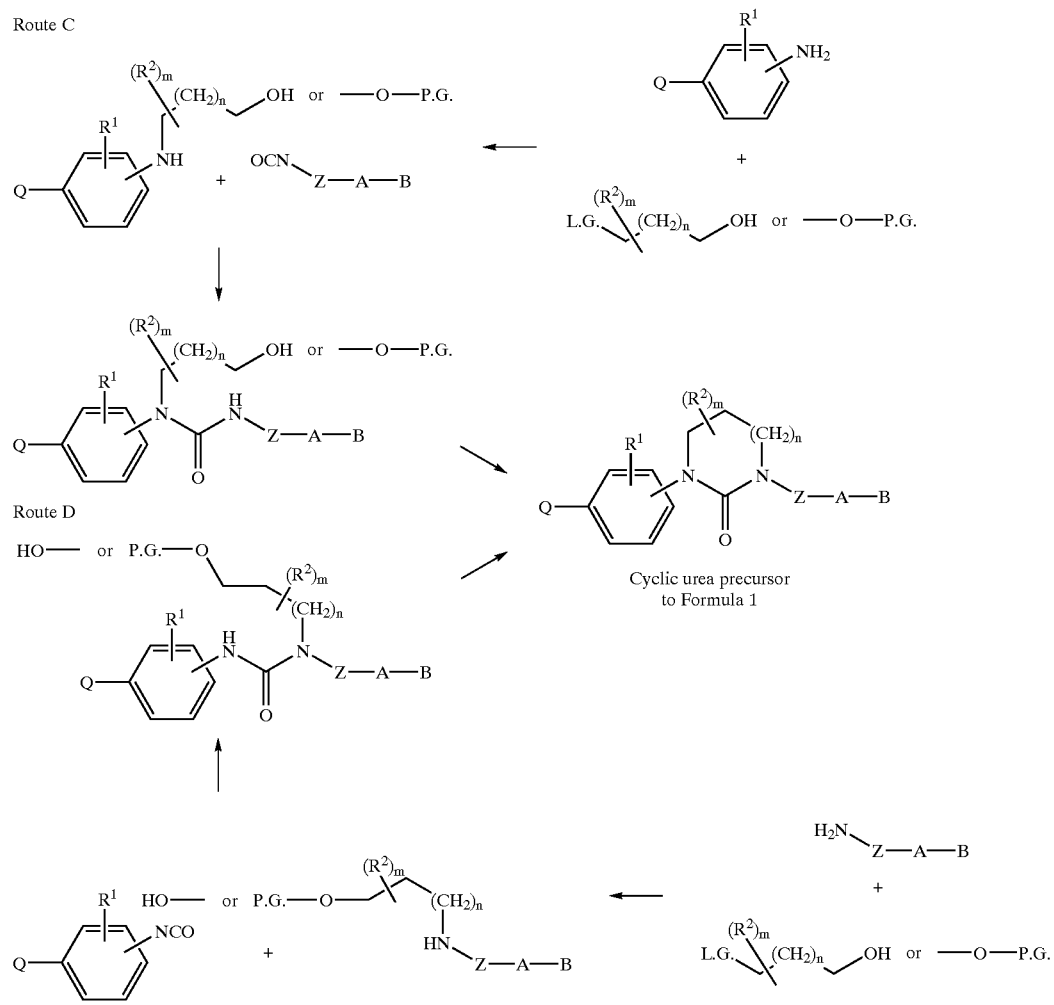

Two alternatives, Route C and Route D, for the preparation of precursors of Formula 1 by a unimolecular cyclization method are outlined in Scheme II. In Route C one begins by alkylating a Q,R[1]-substituted aniline with a halogenated alkylalcohol, such as 4-bromobutan-1-ol or its homologs, or a protected version of the same, such as the methoxymethyl ether of 4-bromobutan-1-ol, either neat or in an anhydrous solvent such as dimethylformamide, benzene, tetrahydrofuran, hexamethylphosphorotriamide, or dimethylsulfoxide. This reaction may be furthered by heating the mixture up to the reflux point of the solvent. Depending upon the reactivity of the substrate no base, or a strong base, such as sodium hydride, potassium t-butoxide or an alkyl lithium, or a weak base, such as potassium carbonate or a trialkylamine, may be necessary. The alkylation product is then reacted with an isocyanate OCN—Z—A—B generated from the amine $NH_2$—Z—A—B by the same method described above for Route A of Scheme I to give a product alcohol or protected alcohol which can be transformed to a halogenated or sulfonyl ester analog for cyclization to a cyclic urea precursor to Formula 1.

Following deprotection according to an appropriate method found in Greene and Wuts (if necessary), halogenation of the primary alcohol can be carried out with a variety of reagents such as neat thionyl chloride, triphenylphosphine in carbon tetrachloride (Lee and Downie, *Tetrahedron*, 23 359 (1967)), or triphenylphosphine with N-chloro- or N-bromosuccinimide in dimethylformamide. The alternative sulfonyl ester is also readily prepared from an appropriate sulfonyl chloride, such as the commercially available p-toluenesulfonyl chloride or methanesulfonyl chloride, in a variety of anhydrous aprotic solvents, such as pyridine, benzene, tetrahydrofuran or a chlorinated hydrocarbon, with or without cooling, and with or without a trialkylamine base.

Ring closure to a cyclic urea precursor to Formula 1 has been observed to occur spontaneously in some cases, but may be furthered in an anhydrous solvent such as dimethylformamide, benzene, tetrahydrofuran, hexamethylphosphorotriamide, or dimethylsulfoxide, by heating the mixture up to the reflux point of the solvent. Depending upon the reactivity of the substrate no base, or a strong base, such as sodium hydride, potassium t-butoxide or an alkyl lithium, or a weak base, such as potassium carbonate or a trialkylamine, may be necessary.

Route D of Scheme II may be advantageous over Route C for the availability of starting materials such as the commercially produced 1-benzyl-4-aminopiperidine for $NH_2$—Z—A—B component, 2-bromoethanol for the halo alcohol component, and 3-cyanophenyl isocyanate for the isocyanate component. In any respect, the chemistry described in Route C is applicable to an analogous reaction in Route D with modifications appropriate for the particular materials involved.

In Formula 1 the radical Z serves as a linking group interposed between the cyclic urea structure and radical A—B. For the purposes of this discussion it is recognized that there are variations of Z, that is where Z=a bond or $C_{1-4}$ alkylene or a portion of the defined linkage, that for synthetic purposes are best incorporated as a substituent of A. It is also assumed for the purpose of this discussion that the analog of A used throughout may contain an orthogonal protecting group, which is compatible with the chemistry suggested. Furthermore, this protecting group may be removed to reveal a substituent that can be used to generate a group X.

Scheme III:
Preparation of $H_2N$—Z—A, where Z = —$CH_2CH_2$—O— functional group.

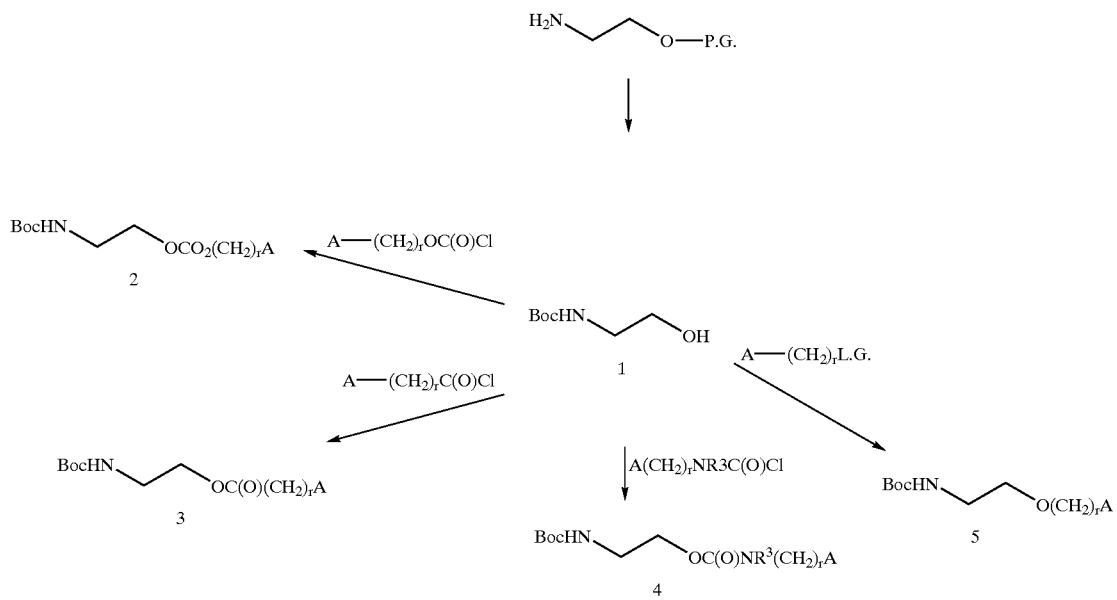

The preparation of Z outlined in Scheme III begins with the 0-protected derivative of 2-aminoethanol. The t-butyldimethylsilyl analog is recommended for this purpose and is know in the literature (see WO 9504277 and WO 9205186). However, a worker skilled in the art would recognize that the approaches discussed herein are not limited to this particular analog of 2-aminoethanol. O-Protected 2-aminoethanol can then be protected as the N-t-butoxycarbonyl analog and selectively O-deprotected according to procedures found in Greene and Wuts. The resulting 2—(N-t-butoxycarbamoyl)ethanol (1) can then be reacted with various analogs of A to give the desired group Z.

Product 2 is the result of reaction of the chlorocarbonate analog of A with 1 in a variety of aprotic solvents, such as a chlorocarbon, tetrahydrofuran, or pyridine, with or without a trialkylamine base at temperatures ranging from −78° to ambient temperature. The carbonyl chloride analog of A (A(CH$_2$)$_r$OC(O)Cl) is avaialable by reaction of an appropriate alcohol analog of A with phosgene or one of its equivilents in a variety of aprotic solvents, such as a chlorocarbon, tetrahydrofuran, or pyridine, with or without a trialkylamine base at temperatures ranging from −78° to ambient temperature.

Product 3 is prepared by reaction of the acid chloride of an appropriate acid analog of A with 1 in a variety of aprotic solvents, such as a chlorocarbon, tetrahydrofuran, or pyridine, with or without a trialkylamine base at temperatures ranging from −78° to ambient temperature. The acid chloride can be obtained by reaction of the acid analog of A with phosphorous oxychloride, phosphorous pentachloride, thionyl chloride or oxalyl chloride with or without a nonpolar aprotic solvent such as a chlorocarbon, benzene or toluene at temperatures ranging from 0° C. to the reflux point of the solvent or neat reagent.

Product 4 can be prepared by the reaction of a carbamoyl chloride analog of A with 1 in a variety of aprotic solvents, such as a chlorocarbon, tetrahydrofuran, or pyridine, with or without a trialkylamine base at temperatures ranging from −78° C. to ambient temperature. The carbamoyl chloride analog of A (A(CH$_2$)$_r$NR$^3$C(O)Cl) is avaialable by reaction of an appropriate amine analog of A with phosgene or one of its equivilents in a variety of aprotic solvents, such as a chlorocarbon, tetrahydrofuran, or pyridine, with or without a trialkylamine base at temperatures ranging from −78° C. to ambient temperature.

Product 5 is available by the reaction of an analog of A substituted with an appropriate leaving group with the alkoxide generated from 2 by treatment of 2 with a strong base such as sodium or potassium hydride or a thallium alkoxide in an aprotic solvent such as dimethylformamide, tetrahydrofuran or dimethylsulfoxide at a temperature ranging from 0 to 120° C. The leaving group of A is most conviently generated from an appropriate alcohol analog of A. The alcohol function can be used to prepare a sulfonate ester from a sulfonyl chloride in a cholorocarbon solvent with a trialkylamine base or in pyridine; alternatively the halogen can be generated from a variety of reagents, triphenyl phosphine and carbon tetrabromide, phosphorous pentabromide or chloride, and thionyl chloride, to name a few.

Scheme IV:
Preparation of H$_2$N—Z—A, where Z = —CH$_2$CH$_2$—NR$^3$— functional group.

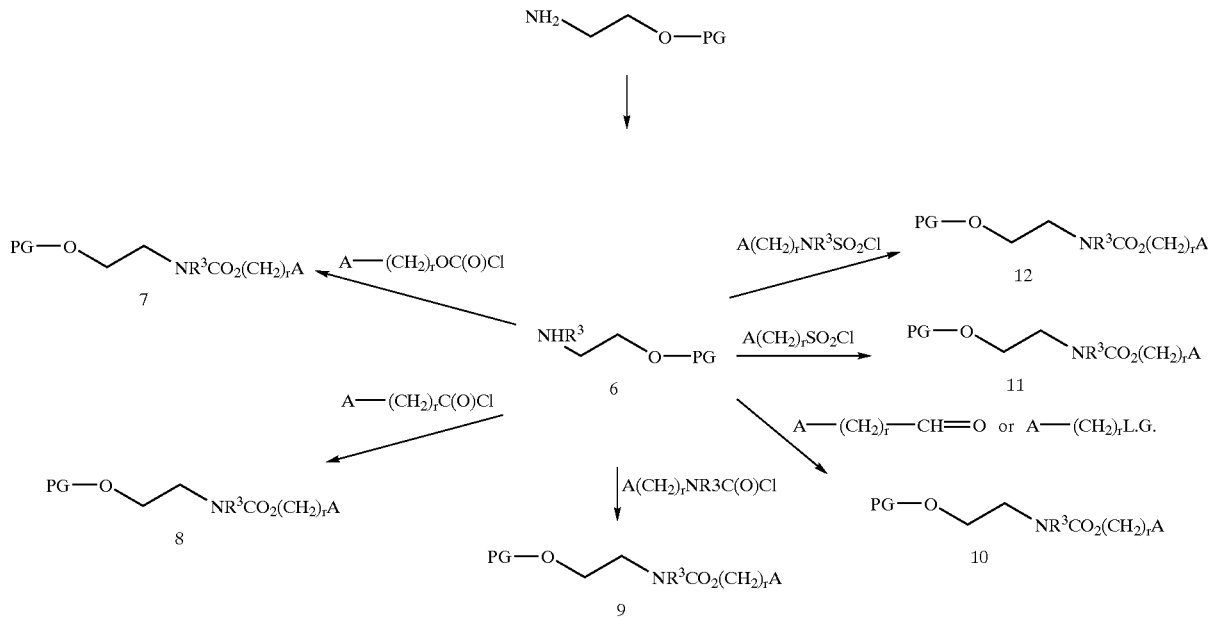

The series of analogs in Scheme IV can be prepared from the protected amino alcohol 6 to give products 7 to 12 by methods similar to some of those described for Scheme III. Compound 6 is prepared from 2-amino-(O-t-butyldimethylsilyl)ethanol by reductive amination of the primary amine by a variety of methods. The primary amine may be reacted with an aldehyde or ketone under dehydrating conditions to form an imine or enamine intermediate which is then reduced to the N-alkyl derivative using palladium catalyst under an atmosphere of hydrogen in an appropriate solvent. Alternatively, reductive alkylation can be effected by a mixture of the ketone or aldehyde and the amine with lithium or sodium cyanoborohydride in methanol or ethanol as solvent.

It is to be understood that products 7 to 12 need to have the terminal protected oxygen transformed to the primary amine either at this stage or after elaboration with group B. This can conveniently be achieved by deprotection of the primary alcohol. The alcohol function can then be used to prepare a sulfonate ester from a sulfonyl chloride in a chlorocarbon solvent with a trialkylamine base or in pyridine; alternatively a halogen can be generated from a variety of reagents, triphenyl phosphine and carbon tetrabromide, phosphorous pentabromide or chloride, and thionyl chloride, to name a few. The resulting leaving group is then displaced with a mixture of sodium azide in dimethylformamide at an elevated temperature to form the primary azide. The azide can then be reduced to the amine by catalytic hydrogenation in an alcoholic solvent with palladium catalyst under an atmosphere of hydrogen gas at pressures ranging from ambient to 65 psi; an alternative method for effecting this transformation involves refluxing the azide intermediate with triphenylphosphine in benzene or toluene and hydrolyzing the resulting intermediate with aqueous acid.

Product 7 of Scheme IV is the result of the reaction of the chlorocarbonate analog of A with 6 in a variety of aprotic solvents, such as a chlorocarbon, tetrahydrofuran, or pyridine, with or without a trialkylamine base at temperatures ranging from −78° C. to ambient temperature. Product 8 is prepared by the reaction of the acid chloride of an appropriate acid analog of A with 6 in a variety of aprotic solvents, such as a chlorocarbon, tetrahydrofuran, or pyridine, with or without a trialkylamine base at temperatures ranging from −78° C. to ambient temperature. Product 9 can be prepared by the reaction of a carbamoyl chloride analog of A with 6 in a variety of aprotic solvents, such as a chlorocarbon, tetrahydrofuran, or pyridine, with or without a trialkylamine base at temperatures ranging from −78° to ambient temperature.

Product 10 may be obtained from 7 by two routes, conventional alkylation or reductive alkylation. If 6 is a primary amine, then reductive alkylation is recommended. The primary amine 6 may be reacted with an aldehyde or ketone analog of A under dehydrating conditions to form an imine or enamine intermediate which is then reduced to the N-alkyl derivative using palladium catalyst under an atmosphere of hydrogen in an appropriate solvent. Alternatively, reductive alkylation can be effected by a mixture of the ketone or aldehyde and the amine with lithium or sodium cyanoborohydride in methanol or ethanol as solvent. The aldehyde or ketone analog of A is readily accessible from the appropriate alcohol by Swern, Moffat or Jones oxidation. In the case where 6 is a secondary amine product 10 is available by the reaction of an analog of A substituted with an appropriate leaving group with 7 in the presence of a weak base such as a trialkylamine or solid sodium or potassium carbonate in an aprotic solvent such as dimethylformamide, acetone, tetrahydrofuran or dimethylsulfoxide at a temperature ranging from 0° to 120° C.

Product 11 is prepared by the reaction of the sulfonyl chloride of an appropriate analog of A with 6 in a variety of aprotic solvents, such as a chlorocarbon, tetrahydrofuran, or pyridine, with or without a trialkylamine base at temperatures ranging from −78° to ambient temperature. The sulfonyl chloride analog of A is available via the sulfonic acid of A which can be prepared by heating a halogen analog of A in a aqueous sodium sulfite. The sulfonyl chloride of A can be prepared by reacting the sulfonic acid with phosphorous oxychloride, phosphorous pentachloride, thionyl chloride or oxalyl chloride with or without a non-polar aprotic solvent such as a chlorocarbon, benzene or toluene at temperatures ranging from 0° C. to the reflux point of the solvent or neat reagent. Product 12 is prepared by the reaction of the sulfamoyl chloride of an appropriate analog of A with 6 in a variety of aprotic solvents, such as a chlorocarbon, tetrahydrofuran, or pyridine, with or without a trialkylamine base at temperatures ranging from −78° C. to ambient temperature.

Scheme V:
Preparation of compounds of Formula 1 where Z =

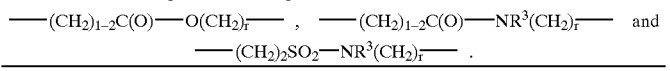

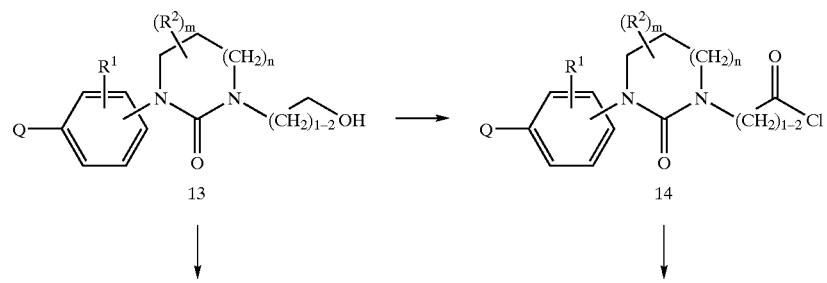

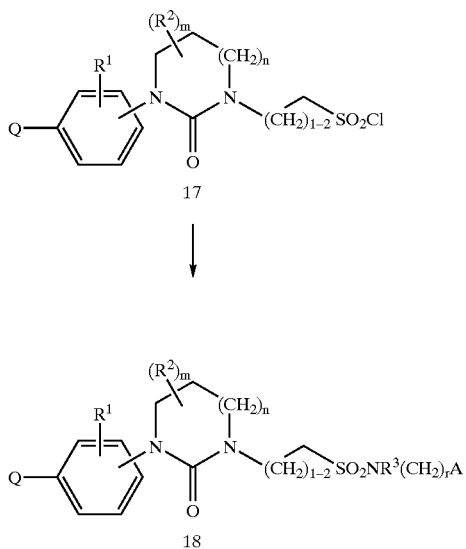

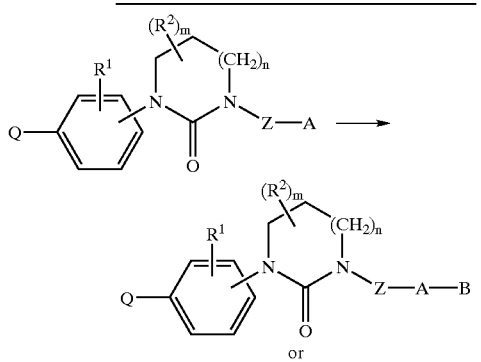

Scheme V outlines the preparation of variations of Z that are not readily prepared by the strategies in Schemes III and IV. Compound 13 is available by the routes developed in Schemes I and II by replacing the primary amine $NH_2ZAB$ with O-t-butyldimethylsilyl-2-aminoethanol or its propanol homolog. Jones oxidation of 13 gives corresponding carboxylic acid which is then transformed to the acid chloride 14 by one of the methods outlined in the preceding discussion. The ester 15 is prepared by reaction of 14 with an alcohol derivative of A under conditions similar to those detailed for the preparation of ester 2 in Scheme III. The amide 16 is available by the reaction of 14 with an amine derived from A under conditions similar to those used for the formation of amide 8 found in Scheme IV. The sulfonyl chloride 17 of Scheme V is prepared by the alcohol to halide to sulfonic acid to sulfonyl chloride route discussed for the sulfonyl analogs of Scheme IV. Reaction of 17 with an amine derivative of A under conditions used for the formation of 11 in Scheme IV gives the sulfonamide 18 of Scheme V.

Scheme VI:
Methods to incorporate B where B = X—Y.

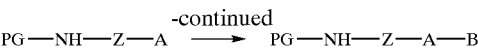

-continued

PG—NH—Z—A $\longrightarrow$ PG—NH—Z—A—B

In Scheme VI two approaches to the incorporation of group B are outlined; in each case it is assumed that the starting structures are suitably protected to accommodate the chemistry that follows. It is also understood that both approaches may not be equivilent and, for purposes of compatibility with the chemistry that follows, one approach may have certain advantages over the other. It is further assumed that groups A and B have been selected to be derivatives of A and B that contain functionality suitable for the chemistry contemplated. Groups A and B are available either through commercial sources, known in the literature or readily synthesized by the adaptation of standard procedures known to practioners skilled in the art of organic synthesis.

The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE 1

Preparation of Amide, Ester, Urea, Sulfonamide and Sulfamide linkages between A and B.

| Rxn. No. | if A contains: | then the reactive substituent of Y is: | to give the following product A-X-Y: |
|---|---|---|---|
| 1 | A-NHR$^3$ as a substituent | ClC(O)—Y | A-NR$^3$-C(O)—Y |
| 2 | a secondary NH as part of a ring or chain | ClC(O)—Y | A-C(O)—Y |

TABLE 1-continued

Preparation of Amide, Ester, Urea, Sulfonamide and Sulfamide linkages between A and B.

| Rxn. No. | if A contains: | then the reactive substituent of Y is: | to give the following product A-X-Y: |
|---|---|---|---|
| 3 | A-OH as a substituent | ClC(O)—Y | A-O—C(O)—Y |
| 4 | A-NHR$^3$ as a substituent | ClC(O)—CR$^3$R$^{3\prime}$-Y | A-NR$^3$-C(O)—CR$^3$R$^{3\prime}$-Y |
| 5 | a secondary NH as part of a ring or chain | ClC(O)—CR$^3$R$^{3\prime}$-Y | A-C(O)—CR$^3$R$^{3\prime}$-Y |
| 6 | A-OH as a substituent | ClC(O)—CR$^3$R$^{3\prime}$-Y | A-O—C(O)—CR$^3$R$^{3\prime}$-Y |
| 7 | A-NHR$^3$ as a substituent | ClC(O)NR$^3$-Y | A-NR$^3$-C(O)NR$^3$-Y |
| 8 | a secondary NH as part of a ring or chain | ClC(O)NR$^3$-Y | A-C(O)NR$^3$-Y |
| 9 | A-OH as a substituent | ClC(O)NR$^3$-Y | A-O—C(O)NR$^3$-Y |
| 10 | A-NHR$^3$ as a substituent | ClSO$_2$-Y | A-NR$^3$-SO$_2$-Y |
| 11 | a secondary NH as part of a ring or chain | ClSO$_2$-Y | A-SO$_2$-Y |
| 12 | A-NHR$^3$ as a substituent | ClSO$_2$-CR$^3$R$^{3\prime}$-Y | A-NR$^3$-SO$_2$-CR$^3$R$^{3\prime}$-Y |
| 13 | a secondary NH as part of a ring or chain | ClSO$_2$-CR$^3$R$^{3\prime}$-Y | A-SO$_2$-CR$^3$R$^{3\prime}$-Y |
| 14 | A-NHR$^3$ as a substituent | ClSO$_2$-NR$^3$-Y | A-NR$^3$-SO$_2$-NR$^3$-Y |
| 15 | a secondary NH as part of a ring or chain | ClSO$_2$-NR$^3$-Y | A-SO$_2$-NR$^3$-Y |
| 16 | A-C(O)Cl | HO-Y as a substituent | A-C(O)—O—Y |
| 17 | A-C(O)Cl | NHR$^3$-Y as a substituent | A-C(O)-NR$^3$-Y |
| 18 | A-C(O)Cl | a secondary NH as part of a ring or chain | A-C(O)—Y |
| 19 | A-CR$^3$R$^{3\prime}$C(O)Cl | HO-Y as a substituent | A-CR$^3$R$^{3\prime}$C(O)—O—Y |
| 20 | A-CR$^3$R$^{3\prime}$C(O)Cl | NHR$^3$-Y as a substituent | A-CR$^3$R$^{3\prime}$C(O)-NR$^3$Y |
| 21 | A-CR$^3$R$^{3\prime}$C(O)Cl | a secondary NH as part of a ring or chain | A-C(R$^3$)$_2$C(O)—Y |
| 22 | A-SO$_2$Cl | NHR$^3$-Y as a substituent | A-SO$_2$-NR$^3$-Y |
| 23 | A-SO$_2$Cl | a secondary NH as part of a ring or chain | A-SO$_2$-Y |
| 24 | A-CR$^3$R$^{3\prime}$SO$_2$Cl | NHR$^3$-Y as a substituent | A-CR$^3$R$^{3\prime}$SO$_2$-NR$^3$-Y |
| 25 | A-CR$^3$R$^{3\prime}$SO$_2$Cl | a secondary NH as part of a ring or chain | A-CR$^3$R$^{3\prime}$SO$_2$-Y |

The chemistry of Table 1 can be carried out in aprotic solvents such as a chlorocarbon, pyridine, benzene or toluene, at temperatures ranging from −20° C. to the reflux point of the solvent and with or without a trialkylamine base.

TABLE 2

Preparation of ketone linkages between A and B.

| Rxn. No. | if A contains: | then the reactive substituent of Y is: | to give the following product A-X-Y: |
|---|---|---|---|
| 1 | A-C(O)Cl | BrMg-Y | A-C(O)—Y |
| 2 | A-CR$^3$R$^{3\prime}$C(O)Cl | BrMg-Y | A-CR$^3$R$^{3\prime}$$_2$C(O)—Y |
| 3 | A-C(O)Cl | BrMgCR$^3$R$^{3\prime}$-Y | A-C(O)CR$^3$R$^{3\prime}$-Y |
| 4 | A-CR$^3$R$^{3\prime}$C(O)Cl | BrMgCR$^3$R$^{3\prime}$-Y | A-CR$^3$R$^{3\prime}$C(O)CR$^3$R$^{3\prime}$-Y |

The coupling chemistry of Table 2 can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromideedimethyl sulfide complex in dimethyl sulfide as a solvent or with a varient thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (Tetrahedron Lett., (1984) 4805), or a coupling mediated by manganese (II) catalysis (Cahiez and Laboue, Tetrahedron Lett., 33(31), (1992) 4437).

TABLE 3

Preparation of ether and thioether linkages between A and B

| Rxn. No. | if A contains: | then the reactive substituent of Y is: | to give the following product A-X-Y: |
|---|---|---|---|
| 1 | A-OH | Br-Y | A-O—Y |
| 2 | A-CR$^3$R$^{3\prime}$-OH | Br-Y | A-CR$^3$R$^{3\prime}$O—Y |
| 3 | A-OH | Br-CR$^3$R$^{3\prime}$-Y | A-OCR$^3$R$^{3\prime}$-Y |
| 4 | A-SH | Br-Y | A-S-Y |
| 5 | A-CR$^3$R$^{3\prime}$-SH | Br-Y | A-CR$^3$R$^{3\prime}$S—Y |
| 6 | A-SH | Br-CR$^3$R$^{3\prime}$-Y | A-SCR$^3$R$^{3\prime}$-Y |

The ether and thioether linkages of Table 3 can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE 4

Preparation of -SO- and -SO2- linkages from thioethers of Table 3.

| Rxn. No. | if the starting material is: | and it is oxidized with Alumina (wet)/ Oxone (Greenhalgh, Synlett, (1992) 235) the product is: | and it is oxidized with m-chloroperbenzoic acid (Satoh et al., Chem. Lett. (1992) 381, the product is: |
|---|---|---|---|
| 1 | A-S-Y | A-S(O)—Y | A-SO$_2$-Y |
| 2 | A-CR$^3$R$^{3\prime}$S—Y | A-CR$^3$R$^{3\prime}$S(O)—Y | A-CR$^3$R$^{3\prime}$SO$_2$-Y |
| 3 | A-SCR$^3$R$^{3\prime}$-Y | A-S(O)CR$^3$R$^{3\prime}$-Y | A-SO$_2$CR$^3$R$^{3\prime}$-Y |

The thioethers of Table 3 serve as a convenient starting material for the preparation of the sulfoxide and sulfone analogs of Table 4. A combination of wet alumina and oxone provides a reliable reagent for the oxidation of the thioether to the sulfoxide while m-chloroperbenzoic acid oxidation will give the sulfone.

Scheme VII:
Preparation of analogs where Z = —C(O)— or —SO₂.

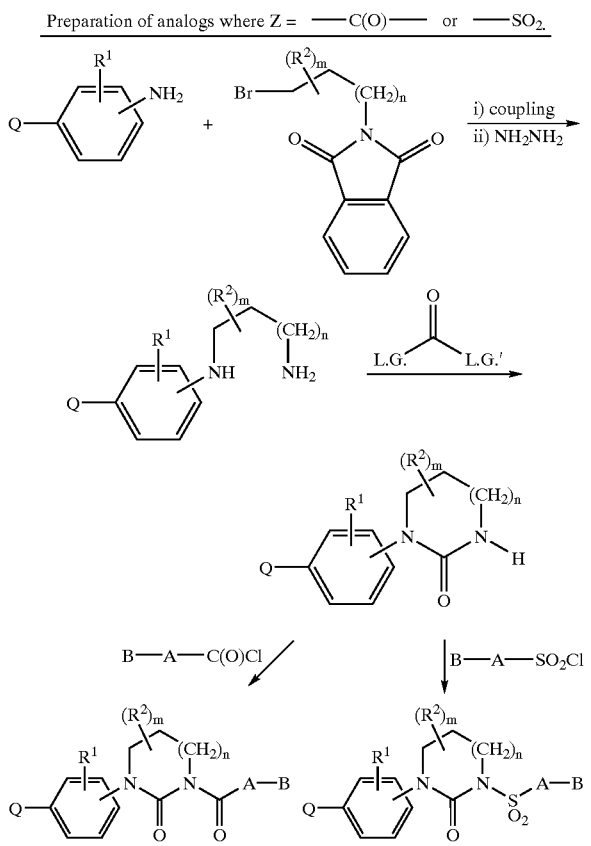

A cyclic urea precursor of Formula 1 which is suitable for the preparation of analogs where Z=—C(O)— or —SO₂— can be synthesized by an adaptation of the chemistry outlined in Scheme I. The approach in Scheme VII makes use of a N-hydrazino-alkylbromide as the alkylating agent for the aniline derivative. The alkylation product is then deprotected according to a method proscribed by Greene and Wutts and cyclized by treatment of the resulting diamine with phosgene or one of its equivilents. The resulting cyclic urea can be treated with a strong base such as sodium hydride or potassium t-butoxide in an aprotic solvent like dimethyl formamide, dimethylsulfoxide or toluene. This mixture is quenched with an acid chloride or sulfonyl chloride analog of A—B at a temperature ranging from −78° C. to the reflux point of the solvent.

Scheme VIII:
The Pinner method to transform the cyclic urea precursor where Z = —CN to Formula 1.

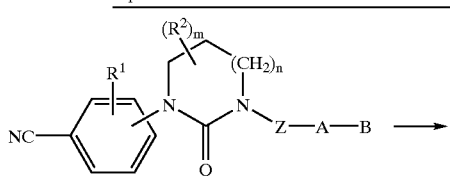

-continued

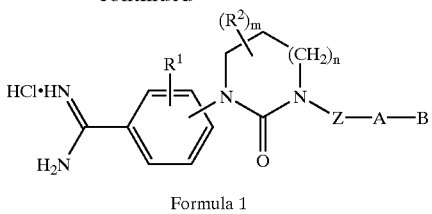

Formula 1

The final transformation of the cyclic urea precursor of Formula 1 prepared in Schemes I to VII to Formula 1 is outlined in Scheme VIII. The preferred method was first described by Pinner and Klein (Ber., 10, 1889 (1877); for a more recent review see: Decroix, *J. Chem. Res.*, 134 (1978)). By this method the nitrile is dissolved in an anhydrous alcohol or a mixture of 1 equivalent or greater of an alcohol and an anhydrous aprotic co-solvent such as a chlorohydrocarbon or an acetate ester of the selected alcohol (i.e., methyl acetate for methyl alcohol). Typically, this mixture is cooled below ambient temperature and dry hydrogen chloride gas is added slowly to the reaction mixture until the solvent is saturated. This saturated solution is sealed and stirred at ambient temperature or lower to form an imidate intermediate which is isolated and characterized. The imidate is then dissolved in a dry alcohol solvent and excess ammonia in the form of a gas, a standardized ammonia/alcohol solution, solid ammonium acetate or ammonium carbonate is added. The crude compound is conveniently purified by reverse phase HPLC or recrystallization to give the cyclic urea defined by Formula 1.

Scheme IX outlines the general route for the preparation of 5-membered aryl- or heteroaryl-fused examples of Formula II. The preparation of the biaryl amine intermediate can be accomplished by the palladium catalyzed coupling of the substituted aniline to the triflate ester according to the method of Louie et. al., (*J. Org. Chem.*1997, 62, 1268–1273).

Scheme IX:
Preparation of precursors to 5-membered heteroaryl-fused examples of Formula II

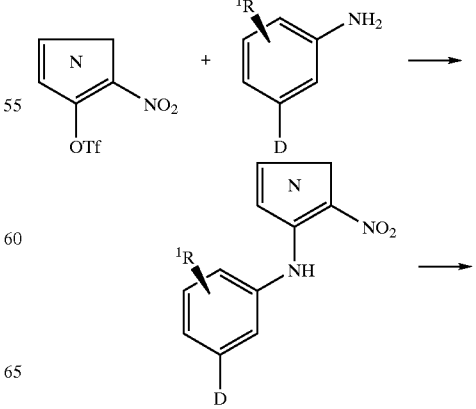

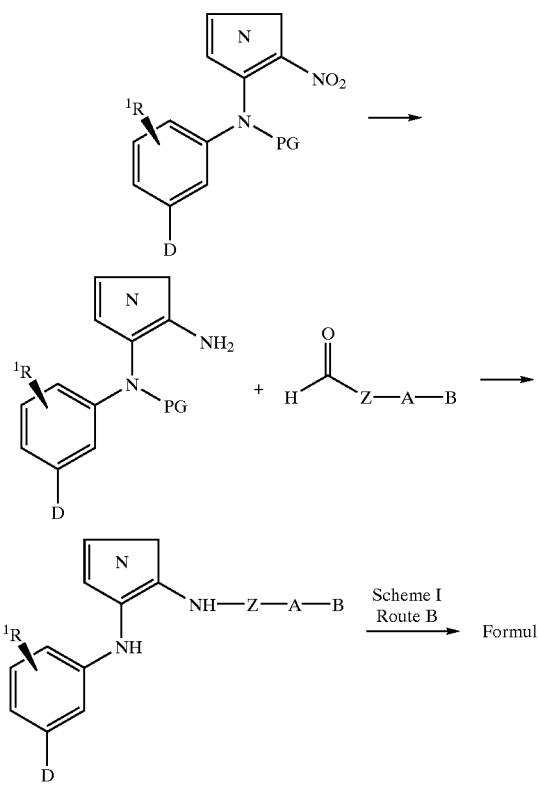

The aniline nitrogen can then be protected as a carbamate, the nitro group reduced to the amine. This amine can be coupled with a Z—A—B group in which Z incorporates a carbonyl group, such as an aldehyde, which can be used as a reactive partner in a reductive alkylation of the newly generated amine. The resulting intermediate can then be processed according to the art described for Route B of Scheme I.

Scheme X:
Preparation of precursors to 6-membered aryl- or heteroaryl-fused examples of Formula II Route A

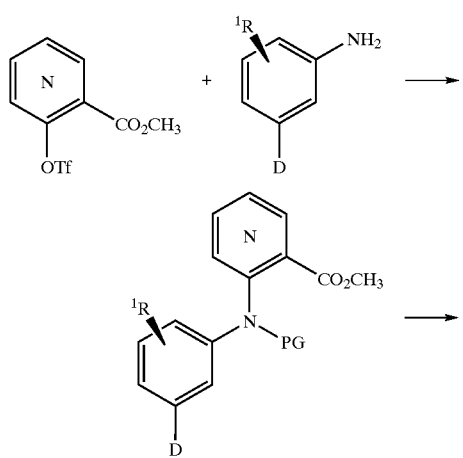

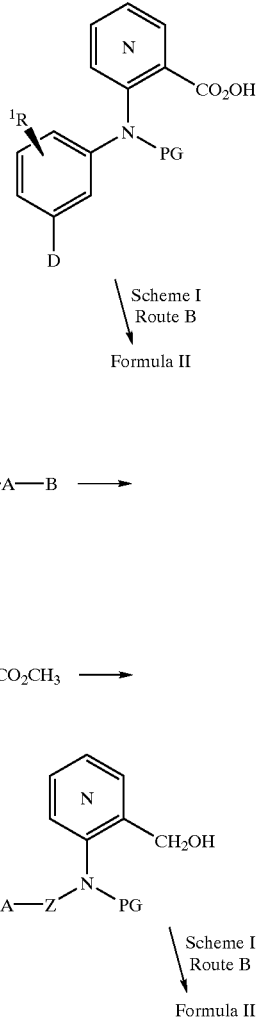

The steps which can be used for the regiocontrolled preparation of both isomers of the 6-membered aryl- or heteroaryl-fused examples of Formula II is outline in Routes A and B of Scheme X. One regioisomer is available by applying the chemistry developed by Louie et al. to the triflate of the salicylate ester in Route A. Following protection of the resulting biaryl amine, the ester can be reduced by lithium borohydride or some other compatible hydride reducing agent and then processed further as outline in Route B of Scheme I.

The alternative regioisomer of Formula II contemplated by this invention can be prepared according to Route B of Scheme X. To effect the palladium catalyzed coupling of the H2N—Z—A—B group with the triflate salicylate ester the conditions reported by Wolfe and Buchwald (Pd(OAc)$_2$, BiNAP, NaO-t-Bu, toluene; *J. Org. Chem.* 1997, 62, 1264–1267) are optimal. The amine coupling product is then suitably N-protected and the ester functionality is reduce to the benzylic alcohol. This intermediate is then treated further according to the methods outlined in Scheme I, Route B.

Scheme XI:
Preparation of precursors to 7-membered aryl- or heteroaryl-fused examples of Formula II

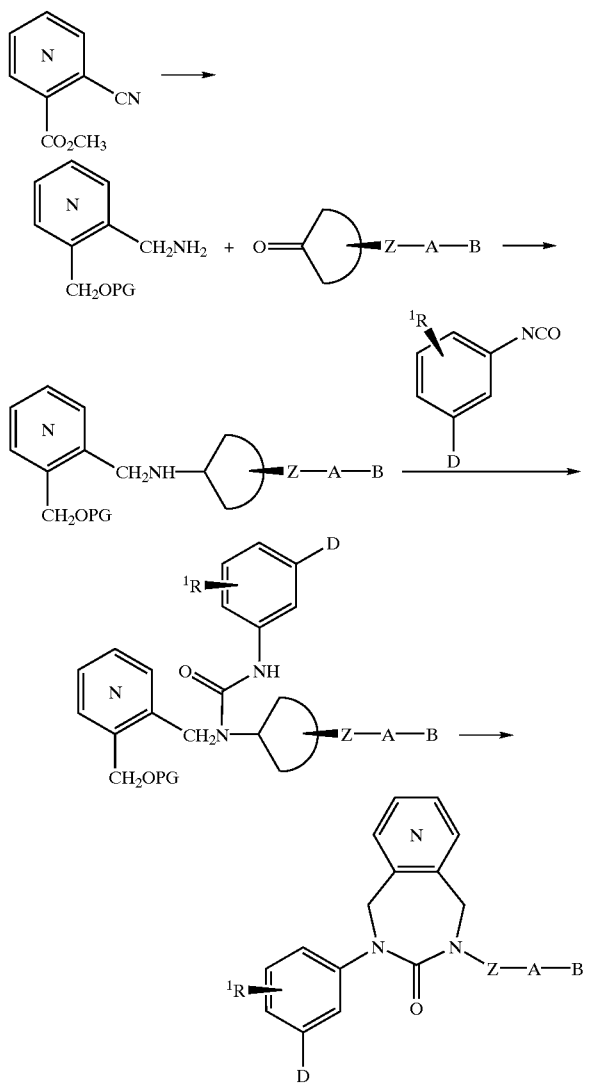

Scheme XII:
Preparation of precursors to alternative regioisomers of 7-membered aryl- or heteroaryl-fused examples of Formula II Route A

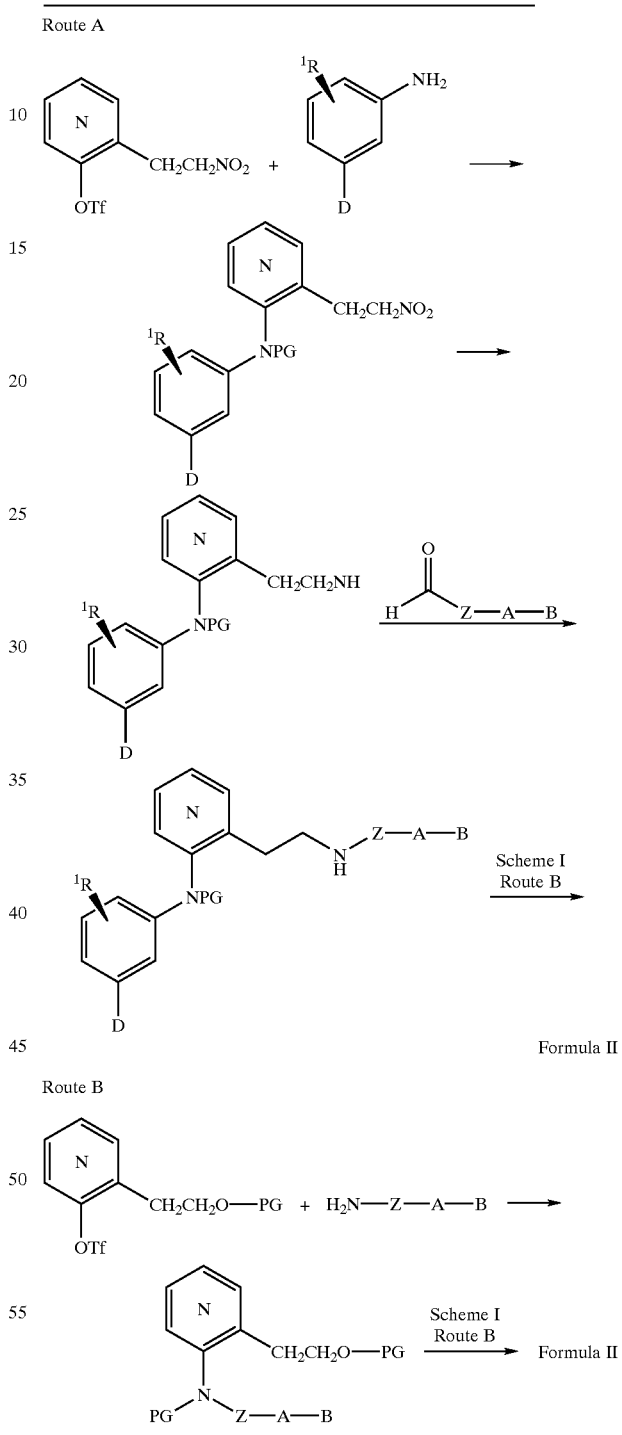

Route B

Formula II

Scheme XI describes the route used to prepare a precursor to one regioisomer of the 7-membered aryl- or heteroaryl-fused example of Formula II. The point of departure is usually the 2-cyano substituted aryl- or heteroaryl-ester. Lithium aluminum hydride reduction of these compounds leads to the corresponding amino alcohol which can then be selectively O-protected with a silyl protecting group, preferably the t-butyl dimethylsilyl group. This material is now ready for reductive alkylation by a Z—A—B group in which Z— contains a carbonyl compound such as an aldehyde, ketone or cyclic ketone. In our experience this transformation can best be performed using a mixture of sodium cyanoborohydride and zinc chloride in tetrahydrofuran solvent. Following reductive alkylation the resulting secondary amine is reacted with an aryl isocyanate in an inert solvent such as dimethylformamide. The isocyanate addition product can then be O-deprotected, and the benzylic alcohol be transformed to the benzylic chloride with a mixture of methanesulfonyl chloride and triethylamine in chloroform or dichloromethane. The benzylic chloride is then cyclized to the 7-membered ring precursor to Formula II with sodium hydride in dimethylformamide at 0° C.

Routes to alternative regioisomers for 7-membered aryl- or heteroaryl-fused examples of Formula II are demonstrated in Scheme XII. In Route A, the phenethylnitro triflate can undergo a palladium catalyzed coupling with the aniline analog according to the procedure of Louie et al. The coupled product is then N-protected, usually as a carbamate or amide, then the nitro group is reduced to the amine by catalytic hydrogenation or with tin(II) chloride in aqueous or alcohol solvent. A Z—A—B group in which Z— incorporates a carbonyl functionality can then be used as a partner in a reductive alkylation with the primary amine function under the conditions described previously. This intermediate can then be submitted to the chemistry described in Scheme I, Route B to obtain a compound of Formula II. Route B describes the coupling of a protected phenethyl alcohol triflate with an amine containing Z—A—B group under the conditions recommended by Wolfe and Buchwald. This product is then N-protected as a suitable carbamate or amide and then processed by the chemistry described in Route B of Scheme I.

Other features of the invention will become apparent in the course of the following descriptions of exemplary embodiments which are given for illustration fo the invention and are not intended to be limiting thereof.

EXAMPLES

The synthesis of representative compounds according to the invention is described in further detail below with reference to the following specific, but non-limiting examples.

Abbreviations used in the Examples are defined as follows: "°C" for degrees Celsius, "d" for doublet, "dd" for doublet of doublets, "DAST" for diethylaminosulfur trifluoride, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography.

Example 1

Preparation of N-(3-amidinophenyl)-N'-(1-benzylpiperidin-4-yl)cyclopentylurea 4-(2-Hydroxyethyl)amino-1-benzylpiperidine A mixture of 4-amino-1-benzylplperidine (1.0 g, 5.3 mmol, 1.1 mL) and bromoethanol (0.662 g, 5.3 mmol, 0.375 mL) was stirred under a $N_2$ atmosphere for 18 h at ambient temperature. This material was used in directly in the next step (1.82 g). LRMS (M+H)$^+$ m/z 235.

N-(3-Cyanophenyl)-N'-(2-hydroxyethyl)-N'-(1-benzylpiperidin-4-yl)urea

To a stirred solution of 4-(2-hydroxyethyl)-amino-1-benzylpiperidine (1.82 g), and triethylamine (0.789 g, 7.8 mmol) in DMF (50 mL) was added 3-cyanophenylisocyanate (1.12 g, 7.8 mmol). This mixture was heated at 60° C. for 18 under a $N_2$ atmosphere. The reaction was diluted with water and extracted with ethyl acetate, dried with $MgSO_4$, filtered and concentrated to give the desired product, N-(3-cyanophenyl)-N'-(2-hydroxyethyl)-N'-(1-benzylpiperidin-4-yl)urea (2.04 g, 5.3 mmol). LRMS (M+H)$^+$ m/z 379.

N-(3-Cyanophenyl)-N'-(1-benzylpiperidin-4-yl) cyclopentylurea

To a stirred solution of N-(3-cyanophenyl)-N'-(2-hydroxyethyl)-N'-(1-benzylpiperidin-4-yl)urea (2.04 g, 5.3 mmol) in chloroform at −10° C. was added a few drops of pyridine followed by thionyl chloride (0.702 g, 5.9 mmol). This mixture was stirred for 2 h then heated at reflux for 1 h. It was concentrated in vacuo, dissolved in ethanol (50 ml) and a solution of potassium hydroxide (10%) in ethanol (15 mL) was added and refluxed for 2 h. The mixture was cooled then evaporated; it was dissoved in ethyl acetate, washed with water and brine then dried ($MgSO_4$). After removal of the solvent, the residue was purified by silica gel chromatography using ethyl acetate as the eluant. There was obtained 0.59 g of N-(3-cyanophenyl)-N'-(1-benzylpiperidin-4-yl)cyclopentylurea. LRMS (M+H)$^+$ m/z 361.

N-(3-Amidinophenyl)-N'-(1-benzylpiperidin-4-yl) cyclopentylurea

A stirred solution of N-(3-cyanophenyl)-N'-(1-benzylpiperidin-4-yl)cyclopentylurea (56 mg) in anhydrous methanol (10 ml) was cooled to 0° C. and saturated with dry hydrogen chloride gas. This mixture was tightly stoppered and stirred at ambient temperature for 18 h. The solution was evaporated to dryness and the residual hydrogen chloride gas removed by pumping on the imidate salt for 18 h. The imidate was dissolved in anhydrous methanol (10 ml) and ammonium acetate (100 mg) was added. The mixture was stirred at ambient temperature for 24 h, then evaporated to give 55 mg of crude product. Purification of this material by reverse phase HPLC gave 26 mg of N-(3-amidinophenyl)-N'-(1-benzylpiperidin-4-yl)cyclopentylurea as the bis-trifluoroacetic acid salt; HRMS Calc. 378.229386, found 378.229774; $^1$H NMR ($CD_3OD$) d: 2.05–2.21 (m, 4H), 3.18 (dd, 2H, J=11 Hz, J=6.0 Hz), 3.58 (dd, 4H, J=11 Hz, J=6.0 Hz), 3.98 (t, 2H, J=7.5 Hz), 4.02 (m,1H), 4.32 (s, 1H), 7.45 (m, 7H), 7.81 (d,1, J=7.5 Hz), 8.01 (s,1H).

Example 2

Preparation of N-(3-amidinophenyl)-N'-(1-benzylpiperidin-4-yl)cyclohexylurea 4-(3-Hydroxypropyl)amino-1-benzylpiperidine This material was prepared in the same fashion as its lower homolog 4-(2-hydroxyethyl)amino-1-benzylpiperidine using 3-bromopropanol rather than 2-bromoethanol.

N-(3-Amidinophenyl)-N'-(1-benzylpiperidin-4-yl) cyclohexylurea

This material was prepared from 4-(3-hydroxypropyl)-amino-1-benzylpiperidine by the same route employed in the synthesis of N-(3-amidinophenyl)-N'-(1-benzylpiperidin-4-yl)cyclopentylurea. There was obtained 26 mg of the desired product as the bis-tifluoroacetic acid salt after purification by reverse phase HPLC. LRMS (M+2H)$^{2+}$ m/z 196.7, (M+H)$^+$ m/z 392;$^1$H NMR ($CD_3OD$): d 2.23 (m, 6H), 3.21 (bt, 2H), 3.58 (t, 2H, J=5.12 Hz), 3.62 (m, 2H), 4.39 (m, 3H), 4.53 (t, 2H, J=5.12 Hz), 7.51 (m, 5H), 7.62–7.78 (m, 3H), 7.81 (s, 1H).

Example 3

Preparation of N-(3-amidinophenyl)-N'-(4-amidinophenyl)cycloheptylurea

N-(3-cyanophenyl)-N'-(4-cyanophenyl)urea m-Cyanoaniline (0.5 g, 3.38 mmol) and p-cyanophenylisocyanate (0.49 g, 3.38 mmol) were dissolved in dimethylformaide (8 ml) and triethylamine (1 ml). The reaction was stirred at ambient temperature under a nitrogen atmosphere for 24 h. The reaction was poured into water and extracted with ethyl acetate. The organic layer was washed with water (3×), brine, dried (MgSO$_4$) and concentrated to give a amorphous solid. This was triturated to a crystalline white solid with ethyl ether. This solid was filtered and washed with ether to give N-(3-cyanophenyl)-N'-(4-cyanophenyl)urea as a white powder (0.92 g, mp 183–5° C.); LRMS (M+H)$^+$ m/z 280, (M+NH$_4$)$^+$ m/z 297; $^1$H NMR (DMSO-d$_6$): 9.32(s, 1H), 9.21(s, 1H), 7.97(s, 1H), 7.75–7.6(m, 5H), 7.55–7.4(m, 2H).

N-(3-cyanophenyl)-N'-(4-cyanopheryl) cycloheptylurea

N-(3-Cyanophenyl)-N'-(4-cyanophenyl)urea (0.25 g, 0.95 mmol) was dissolved in DMF (2 ml) and added to a cooled slurry of sodium hydride (0.80 g, 2.0 mmol, hexane washed to remove the mineral oil) in dimethylformamide (25 ml) under a nitrogen atmosphere. After stirring for 15 min, 1,4-dibromobutane (0.25 g, 0.95 mmol) was added slowly. The reaction was stirred at 0° C. for 1 h and then allowed to warm to 75° C. for 3 h. To the reaction additional sodium hydride was added and the reaction was heated to 75° C. for an additional 6 h. The reaction was allowed to cool to ambient temperature, was poured into 1N HCl and extracted with ethyl acetate. The organic layer was washed with water and brine, then dried (MgSO$_4$) and concentrated to give a viscous oil. The oil was purified by flash chromatography on silica gel eluting with methylene chloride: ethyl acetate 95:5 to give N-(3-cyanophenyl)-N'-(4-cyanophenyl) cycloheptylurea as an oil (0.075 gm 0.24 mmol); LRMS (M+H)$^+$ m/z 317; $^1$H NMR (CDCl$_3$): 7.7–7.45(m, 6H), 7.4(d, 2H), 3.82(m, 4H), 1.95(m, 4H).

N-(3-amidinophenyl)-N'-(4-anidinophenyl) cycloheptylurea

Dry hydrogen chloride gas was bubbled through an ice cooled solution of N-(3-cyanophenyl)-N'-(4-cyanophenyl) cycloheptylurea (0.065 g, 0.21 mmol) in anhydrous ethanol (5 ml) under a nitrogen atmosphere for 15 min. The reaction was stoppered and allowed to warm to ambient temperature and stir overnight. The reaction was concentrated in vacuo to give a white amorphous solid. This was dissolved in anhydrous ethanol (5 ml) and ammonium carbonate (0.118 g, 1.23 mmol) was added. The reaction was stirred under a nitrogen atmosphere at ambient temperature overnight. The reaction mixture was concentrated in vacuo to give a white solid. The product was purfied by HPLC on a Vydec® C-18 column eluting with solvent mixture A (acetonitrile:water:TFA 80:20:0.3) and solvent mixture B (water:TFA 99.7:0.3) using a gradient starting with A:B at 3:97 and changing to A:B at 70:30 over 20 minutes. The major fraction was concentrated to give N-(3-amidinophenyl)-N'-(4-amidinophenyl)cycloheptylurea as a white solid (mp204–206° C.); LRMS (M+H)$^+$ m/z 351, (M+2H)$^{+2}$ m/z 176.2; HRMS calc. 351.1933, found 351.1936; $^1$H NMR (DMSO-d$_6$): 9.4(bs, 2H), 9.2(broad s, 2H), 9.18 (broad s, 2H), 7.95 (broad s, 2H), 7.8–7.5(m, 6H), 7.47 (d, 2H), 3.9(bd, 4H), 1.83(m, 4H).

Example 4

Preparation of N-(3-amidinophenyl)-N'-((4-amidinophenyl)methyl)cycloheptylurea

N-(3-cyanophenyl)-N'-((4-cyanophenyl)methyl)urea m-Cyanophenyl isocyanate (2.0 g, 13.9 mmol) and triethylamine (3.09 g, 30.5 mmol) in dimethylformamide (30 ml) was cooled to 0° C. and p-cyanobenzylamine hydrogen chloride (2.3 g, 13.9 mmol) in dimethylformamide (10 ml) was added dropwise. The reaction was thawed to ambient temperature and was stirred for 18 h. The reaction was poured into water and extracted with ethyl acetate. The ethyl acetate extract was washed with 1N HCl and brine, then dried (Na$_2$SO$_4$) and evaporated. The crude product was purified by flash chromatography on silica gel with 1:1 hexane:ethyl acetate as an eluent; there was obtained 0.54 g of pure N-(3-cyanophenyl)-N'-((4-cyanophenyl)methyl) urea; LRMS (M+H)$^+$ m/z 294.

N-(3-cyanophenyl)-N'-((4-cyanophenyl)methyl) cycloheptylurea

To a suspension of sodium hydride (0.29 g of a 60% suspension in mineral oil, 7.28 mmol) in dimethylformamide (45 ml) at ambient temperature was added a dimethylformamide solution (5 ml) of N-(3-cyanophenyl)-N'-((4-cyanophenyl)methyl)urea (0.67 g, 2.43 mmol). This mixture was stirred for 30 min before 1,4-dibromobutane (1.05 g, 4.85 mmol) in dimethylformamide (10 ml) was added over 20 min. The reaction was then heated at 70° C. for 1 h, after which analysis by thin layer chromatography (1:2 hexane-:ethyl acetate) demonstrated that all of the starting urea had been consumed. The cooled reaction mixture was poured into ice water and extracted with ethyl acetate (3×). The extract was washed with 1N HCl and brine, then dried (Na$_2$SO$_4$) and evaporated. The crude product was purified by flash chromatography on a column of silica gel with 1:1 hexane:ethyl acetate as the eluent. There was obtained 0.47 g of pure N-(3-cyanophenyl)-N'-((4-cyanophenyl)methyl) cycloheptyl-urea; LRMS: (M+H)$^+$ m/z 331.

N-(3-amidinophenyl)-N'-((4-amidinophenyl)methyl) cycloheptylurea

N-(3-Cyanophenyl)-N'-((4-cyanophenyl)methyl) cycloheptylurea (0.47 g, 1.42 mmol) was dissolved in a mixture of anhydrous chlorform (25 ml) and anhydrous methanol (10 ml). This solution was cooled to 0° C. and slowly saturated with dry hydrogen chloride gas. The reaction vessel was securely stoppered and stored in a refrigerator for 18 h; the solvent was removed in vacuo and there was obtained 0.59 g of the imidate as the hydrogen chloride salt; LRMS: (M+H)$^+$ m/z 396.

The imidate prepared above (0.59 g) was stirred in anhydrous methanol (25 ml) with ammonium carbonate (0.72 g, 7.49 mmol). After 72 h the solvent was removed in vacuo and the residue dissolved in water. The aqueous solution was washed with ethyl ether (3×), then the water removed by lyophillization. The product was purified by HPLC on a Vydec® C-18 column eluting with solvent mixture A (water:TFA 99.5:0.5) and solvent mixture B (acetonitrile:TFA 99.5:0.5) using a gradient starting with A at 100% and changing to B at 100% over 50 min. The fractions containing pure N-(3-amidinophenyl)-N'-((4-amidinophenyl)methyl)cycloheptylurea were collected and lyophillized to give 0.027 g of material; HRMS (M+H)$^+$ calc. 365.208985, found 365.209496.

Example 5

Preparation of N-(3-amidinophenyl)-N'-(1-amidinopiperidin-4-yl)cycloheptylurea

N-(3-Cyanophenyl)-N'-(1-benzylpiperidin-4-yl)urea m-Cyanophenyl isocyanate (1.0 g, 6.94 mmol) was dissolved in dimethylformamide (15 ml) and triethylamine (2 ml) under a nitrogen atmosphere, then 4-amino-1-benzylpiperidine (1.32 g, 6.94 mmol) was added slowly. The reaction was stirred at ambient temperature for 1 h and then at 70° C. for 2 h. The reaction was allowed to cool to ambient temperature and partioned between water and ethyl acetate. The organic layer was washed with water (2×) and brine then dried (MgSO$_4$) and concentrated to give a white amorphous solid. The solid was triturated with ethyl ether to give a white powder. The solids was filtered, washed with ethyl ether and dried to give N-(3-cyanophenyl)-N'-(1-benzylpiperidin-4-yl)cyclopentylurea as a white powder, (1.7 g, 74%, mp 165–6° C.); LRMS (M+H)$^+$ m/z 335; $^1$H NMR (CDCl$_3$): 7.62(s, 1H), 7.57(d, 1H), 7.15–7.2(M, 7H), 7.15(s, 1H), 5.05(d, 1H), 3.65(m, 1H), 3.5(s, 2H), 2.85(m, 2H), 2.1(m,2H), 1.95(m, 2H), 1.45(m,2H).

N-(3-Cyanophenyl)-N'-(1-benzylpiperidin-4-yl) cycloheptylurea

N-(3-Cyanophenyl)-N'-(1-benzylpiperidin-4-yl)urea (0.5 g, 1.49 mmol) was dissolved in DMF (25 ml) and 1,4 dibromobutane (0.33 g, 1.49 mmol) was added under a nitrogen atmosphere. The reaction was heated to 70° C. and sodium hydride (0.131 gm 3.3 mmol) was added portionwise over 20 minutes. The reaction was heated for 4 h then allowed to cool to ambient temperature. When cool, it was poured into water and extracted with ethyl acetate. The organic layer was washed water (2×) and brine, then dried (MgSO$_4$) and concentrated to give a viscous oil. The crude oil was purified by flash chromatography on silica gel eluting with methylene chloride: ethyl acetate 40:60 to give N-(3-cyanophenyl)-N'-(1-benzylpiperidin-4-yl) cycloheptylurea as an oil (0.37 g, 64%); LRMS (M+H)$^+$ m/z 389.4; $^1$H NMR (CDCl$_3$): 7.4–7.25(m, 9H), 3.9(m, 1H), 3.57(m, 2H), 3.42(s, 2H), 3.25(m, 2H), 2.87(m, 2H), 2.03(m, 2H), 1.8–1.5(m, 8H).

N-(3-Cyanophenyl)-N'-(piperidin-4-yl) cycloheptylurea

N-(3-Cyanophenyl)-N'-(1-benzylpiperidin-4-yl) cycloheptylurea (0.1 g 0.26 mmol) was dissolved in ethanol (10 ml) and cyclohexene (2 ml). Palladium hydroxide catalyst (0.05 g) was added and the reaction was heated at reflux under a nitrogen atmosphere. After 30 min the reaction was allowed to cool to ambient temperature, filtered and concentrated to give a viscous oil. The crude product was purified by flash chromatography on silica gel by eluting with methylene chloride:methanol 85:15 with 3% triethylamine. The product, N-(3-cyanophenyl)-N'-(piperidin-4-yl) cycloheptylurea, was concentrated to give an oil which crystallized from ethyl ether (0.05 g, 48%, mp 157–8° C.); LRMS (M+H)$^+$ m/z 299; $^1$H NMR (CDCl$_3$): 7.5–7.3(m, 4H), 4.05(m, 1H), 3.60(m, 2H), 3.32(m, 2H), 3.17(m, 2H), 2.72(m, 2H), 2.0–1.6(m, 8H).

N-(3-Cyanophenyl)-N'-(1-amidinopiperidin-4-yl) cycloheptylurea

N-(3-Cyanophenyl)-N'-(piperidin-4-yl)cycloheptylurea (0.05 g, 0.126 mmol) was dissolved in pyridine (2 ml) and 3,5-dimethylpyrazole-1-carboxamidine (0.037 g, 0.188 mmol) was added under a nitrogen atmosphere. The reaction was heated to 110° C. for 6 h, then was allowed to cool and was concentrated to give a viscous amber oil. The product was purfied by HPLC on a Vydec® C-18 column eluting with solvent mixture A (acetonitrile:water:TFA 80:20:0.3) and solvent mixture B (water:TFA 99.7:0.3) using a gradient starting with A:B at 3:97 and changing to A:B at 70:30 over 15 min. The product eluted at 13.8 minutes was concentrated to give N-(3-cyanophenyl)-N'-(1-amidinopiperidin-4-yl) cycloeptylurea as an amorphous solid (0.036 g); LRMS (M+H)$^+$ m/z 341.

-(3-Amidinophenyl)-N'-(1-amidinopiperidin-4-yl) cycloheptylurea

Dry hydrogen chloride gas was bubbled through an ice cooled solution of N-(3-cyanophenyl)-N'-(1-amidinopiperidin-4-yl)cycloheptylurea (0.03 g, 0.075 mmol) in anhydrous ethanol (5 ml) for 15 min. The reaction was stoppered, allowed to warm to ambient temperature and stirred for 24 h. The reaction was concentrated to give a viscous residue which was dissolved in anhydrous ethanol and ammonium carbonate (0.06 g, 0.63 mmol) was added. The reaction was stirred over night at ambient temperature and then concentrated in vacuo. The crude product appeared to be about 1:2 ratio of the desired product to starting material. Pure N-(3-amidinophenyl)-N'-(1-amidinopiperidin-4-yl)cycloheptylurea was isolated by HPLC on a Vydec® C-18 column eluting with solvent mixture A (acetonitrile:water:TFA 80:20:0.3) and solvent mixture B (water:TFA 99.7:0.3) using a gradient starting with A:B at 3:97 and changing to A:B at 70:30 over 20 min, to give two major fractions: N-(3-amidinophenyl)-N'-(1-amidinopiperidin-4-yl)cycloheptylurea, the desired product eluted at 13.3 minutes, (8.2 mg); LRMS (M+2H)$^{+2}$ m/z 179.8; HRMS calc. 358.2355, found 358.2349; $^1$H NMR (DMSO-d$_6$): 9.25(s, 2H), 9.0(s, 2H), 7.55–7.4(m, 4H), 7.32 (s, 4H), 3.95(m, 3H), 3.65(m, 2H), 3.25(m, 2H), 3.07(m, 2H), 1.8–1.6(m, 8H).

The second fraction, eluting at 18.1 min., was the starting material N-(3-cyanophenyl)-N'-(1-amidinopiperidin-4-yl) cycloheptylurea (16.6 mg); LRMS (M+H)$^+$ m/z 341.1; HRMS calc. 341.20898, found 3341.2077; $^1$H NMR (DMSO-d$_6$): 7.6(s, 1H), 7.5–7.4(m, 3H), 7.3(s, 4H), 4.0–3.9 (m, 3H), 3.6(m, 2H), 3.25(m, 2H), 3.05(m, 2H), 1.8–1.55(m, 8H).

Example 6

Preparation of N-(3-amidinophenvl)-N'-(1-benzylpiperidin-4-yl)cyclohentylurea

N-(3-Amidinophenyl)-N'-(1-benzylpiperidin-4-yl) cycloheptylurea

Dry hydrogen chloride gas was bubbled through an ice cooled solution of N-(3-cyanophenyl)-N'-(1-benzylpiperidin-4-yl)cycloheptylurea (0.03 g, 0.077 mmol) in anhydrous ethanol (10 ml) under a nitrogen atmosphere for 15 min. The reaction was stoppered, allowed to warm to ambient temperature and stirred for 24 h. The reaction was concentrated to a solid and dissolved in anhydrous ethanol (5 ml) and ammonium carbonate (0.023 g, 0.23 mmol) was added. The reaction mixture was stirred at ambient temperature overnight then was concentrated in vacuo. N-(3-Amidinophenyl)-N'-(1-benzylpiperidin-4-yl) cycloheptylurea was purified by HPLC on a Vydec® C-18 column eluting with solvent mixture A (acetonitrile:water:TFA 80:20:0.3) and solvent mixture B (water:TFA 99.7:0.3) using a gradient starting with A:B at 3:97 and changing to A:B at 70:30 over 15 min. The major fraction eluting at 15 minutes was concentrated to give N-(3-amidinophenyl)-N'-(1-benzylpiperidin-4-yl) cycloheptylurea as an amorphous solid; LRMS (M+H)$^+$ m/z 406, (M+2H)$^{+2}$ m/z 203.8; $^1$H NMR (DMSO-d$_6$): 9.52

(broad s, 1H), 9.27(s, 2H), 9.02(s, 2H), 7.5(m, 9H), 4.3(m,m, 2H), 3.95(m, 1H), 3.67(m, 2H), 3.42(m, 2H), 3.2(m,2H), 3.1(m, 2H), 2.05–1.6(m, 8H).

Example 7

Preparation of N-(3-amidinophenyl)-N'-(1-(α-phenethyl)piperidin-4-yl)cycloheptylurea N-(3-amidinophenyl)-N'-(1-(a-phenethyl)piperidin-4-yl)cycloheptylurea N-(3-amidinophenyl)-N'-(1-(a-phenethyl)piperidin-4-yl)cycloheptylurea was prepared by a method analogous to the preparation of N-(3-amidinophenyl)-N'-(1-benzylpiperidin-4-yl)cycloheptylurea starting with 4-amino-1-(a-phenethyl)piperidine rather than 4-amino-1-benzylpiperidine; HRMS: calc 420.276336, found 420.276129; $^1$H NMR (CD$_3$OD) d: 1.78 (d, 3H, J=6.95 Hz), 1.79 (m, 4H), 2.05 (m, 4H), 2.89 (m,3H), 3.38 (m, 2H), 3.76 (m,2H), 3.82 (broad d,2H), 3.92 (m,1)4.42 (q, 1H, J=6.95 Hz), 7.42 (broad s,5H), 7.52 (broad s, 3H), 7.60 (s, 1H).

Example 8

Preparation of N-(3-amidinophenyl)-N'-(1-((phenyl)methane)sulfonyl)-piperidin-4-yl)cycloheptylurea N-(3-Cyanophenyl)-N'-(1-(t-butoxycarbonyl)piperidin-4-yl)urea A mixture of 4-amino-N-(t-butoxycarbonyl)piperidine (0.133 mol, 30.5 g, prepared by the method of Mach, R. H. et al., J. Med. Chem. (1993) 36(23), 3707–20) and triethylamine (1.5 equivilents, 0.2 mol, 20.2 g, 27.8 ml) in dimethylformamide (230 ml) was cooled to 0° C. and m-cyanophenylisocyanate (1.1 equivilents, 0.146 mmol, 21.1 g) in dimethylformamide (70 ml) was added dropwise. The reaction was stirred at ambient temperature for 18 h. It was poured into water and extracted with ethyl acetate (3x). The ethyl acetate extracts were washed with 1N HCl and brine, then dried (Na$_2$SO$_4$) and evaporated to give 43.56 g of crude material. Pure N-(3-cyanophenyl)-N'-(1-(t-butoxycarbonyl)piperidin-4-yl)urea was isolated by flash chromatography on silica gel (1.2 kg) eluted with 2:1 hexane:ethyl acetate (6 L) then 1:1 heaxane ethyl acetate collected in 800 ml fractions. Fractions 9 thru 14 contained pure product, yield 21.69 g.

N-(3-Cyanophenyl)-N'-(1-(t-butoxycarbonyl)piperidin-4-yl)cycloheptylurea

A mixture of sodium hydride (2.44 g of a 60% suspension in mineral oil, 60.9 mmol) and dimethylformamide (350 ml) was stirred at ambient temperature for 5 min, then N-(3-cyanophenyl)-N'-(1-(t-butoxycarbonyl)piperidin-4-yl)urea (7.0 g, 20.3 mmol) in dimethylformamide (30 ml) was added dropwise. This mixture was stirred at ambient temperature for 30 min after which gas evolution ceased. 1,4-Dibromobutane (8.79 g, 40.6 mmol) in dimethylformamide (20 ml) was added slowly over 25 min. Following the addition of the alkylating agent the reaction mixture was heated at 70°–80° C. for 3 h then was stirred at ambient temperature for 18 h. The reaction mixture was poured into water (1 L) and extracted with ethyl acetate (4x250 ml). The ethyl acetate extracts were washed with brine (6x), dried (Na$_2$SO$_4$) and evaporated to give 10.58 g of crude product. Pure N-(3-cyanophenyl)-N'-(1-(t-butoxycarbonyl)piperidin-4-yl)cycloheptylurea was isolated by medium pressure chromatography on a silica gel column (600 g) by eluting with 2:1 hexane:ethyl acetate to give 3.20 g of pure product.

N-(3-Cyanophenyl)-N'-(piperidin-4-yl)cycloheptylurea

N-(3-Cyanophenyl)-N'-(1-(t-butoxycarbonyl)piperidin-4-yl)cycloheptylurea (3.2 g, 7.76 mmol) was stirred in dichloromethane (40 ml) and trifluoroacetic acid (40 ml) at ambient temperature for 1.5 h. The reaction mixture was evaporated and the residue taken up in water. The aqueous suspension was made basic (pH 11) by the dropwise addition of aqueous sodium hydroxide solution (50%). The basic aqueous suspension was extracted with ethyl acetate (2x); the ethyl acetate extracts were washed with brine, dried (Na$_2$SO$_4$), and evaporated to give N-(3-cyanophenyl)-N'-(piperidin-4-yl)cycloheptylurea (2.17 g, 7.28 mmol, 94%). This sample was in all respects identical to the sample of N-(3-cyanophenyl)-N'-(piperidin-4-yl)cycloheptylurea prepared in Example 5.

N-(3-Cyanophenyl)-N'-(1-((phenyl)methane)sulfonyl)piperidin-4-yl)cycloheptylurea N-(3-Cyanophenyl)-N'-(piperidin-4-yl)cycloheptylurea (2.07 g, 6.95 mmol) in tetrahydrofuran (100 ml) with triethylamine (7.64 mmol, 0.77 g, 1.1 ml) was cooled to 0° C. and a-toluenesulfonyl chloride (1.46 g, 7.64 mmol) in tetrahydrofuran (60 ml) was added dropwise. The reaction was allowed to cool to ambient temperature and was stirred for 18 h. The solvent was removed in vacuo and the residue patitioned between water and 5:1 ethyl acetate:acetone. The organic layer was washed with 1N HCl and 1N NaOH, then brine. It was dried (Na$_2$SO$_4$) and evaporated to give 2.63 g of crude product. Purification by medium pressure liquid chromatography on a silica gel column (350 g) gave N-(3-cyanophenyl)-N'-(1-((phenyl)methane)sulfonyl)piperidin-4-yl)cycloheptylurea (1.81 g, 4.0 mmol, 58%, mp 203–204° C.); HRMS (M+H)$^+$ calc. 453.196038, found 453.198085.

N-(3-amidinophenyl)-N'-(1-((phenyl)methane)sulfonyl)piperidin-4-yl)cycloheptylurea A solution of N-(3-cyanophenyl)-N'-(1-((phenyl)methane)-sulfonyl)piperidin-4-yl)cycloheptylurea (1.15 g, 2.54 mmol) in anhydrous methyl acetate (300 ml) was cooled to 0° C. and anhydrous methanol (0.81 g, 25.4 mmol, 1.02 ml) was added. The cooled solution was saturated with dry hydrogen chloride gas then was stoppered tightly and was left to stir at ambient temperature for 18 h. Analytical thin layer chromatography (5% methanol in chloroform) showed complete consumption of the starting nitrile. The methyl acetate solution was diluted with ethyl ether (1.7 L) then left to form crystals in the refrigerator over 18 h. After this time, precipitation of the imidate was complete and the intermediate product was isolated as the hydrogen chloride salt by filtration. The solid imidate was pumped on for several hours to remove any residual HCl and protect the product from moisture. This procedure gave 1.27 g of imidate hydrochloride (2.43 mmol, 96%, mp 131–134° C.).

The imidate prepared above (1.27 g, 2.43 mmol) was dissolved in dry methanol (50 ml) and 2N ammonia in methanol solution (24.3 mmol, 12.15 ml) was added. This reaction was stoppered and stirred at ambient temperature for 24 h. After this time, the solvent was removed in vacuo and the 1.27 g of crude product was isolated. The major contaminant (aproximately 50%) was the corresponding amide. This mixture was separated by HPLC on a Vydec® C-18 column eluting with solvent mixture A (water:TFA 99.5:0.5) and solvent mixture B (acetonitrile:TFA 99.5:0.5) using a gradient starting with A at 100% and changing to B at 100% over 50 min. The desired product, N-(3-amidinophenyl)-N'-(1-((phenyl)methane)sulfonyl)-piperidin-4-yl)cycloheptylurea, was eluted at 30 min; after collection of the fractions and lyophilization, 0.30 g of pure product was obtained as the trifluoroacetic acid salt (0.5 mmol, 20%, mp 208–209° C.); HRMS (M+H)$^+$ calc. 470.222587, found 470.219813.

The following Example 9 to 12 were prepared by essentially the same preparative methods as described above for Example 8; the only changes involved the sulfonylation or acylation of the common intermediate N-(3-cyanophenyl)-N'-(piperidin-4-yl)cycloheptylurea. In each case, however, the same procedure using the appropriate sulfonylating or acylating agent in tetrahydrofuran with triethylamine was used.

Example 9

Preparation of N-(3-amidinophenyl)-N'-(1-benzoylpiperidin-4-yl)cycloheptylurea N-(3-anidinophenyl)-N'-(1-benzoylpiperidin-4-yl) cycloheptylurea In this case the title compound was prepared by acylation of N-(3-cyanophenyl)-N'-(piperidin-4-In this case the title compound was prepared by acylation of N-(3-cyanophenyl)-N'-(piperidin-4-yl)cycloheptylurea with benzoyl chloride folowed by amidine formation as described above; HRMS (M+H)$^+$ calc. 421.223966, found 421.222804.

Example 10

Preparation of N-(3-amidinophenyl)-N'-(1-((phenyl)methane)carbonylpiperidin-4-yl)cycloheptylurea N-(3-amidinophenyl)-N'-(1-((phenyl)methane) carbonylpiperidin-4-yl)cycloheptylurea In this case the title compound was prepared by acylation of N-(3-cyanophenyl)-N'-(piperidin-4-yl)cycloheptylurea with phenylacetyl chloride folowed by amidine formation as described above; HRMS (M+H)$^+$ calc. 434.255601, found 434.255065.

Example 11

Prepraration of N-(3-amidinophenyl)-N'-(1-(phenyl) sulfonylpiperidin-4-yl)cycloheptylurea N-(3-amidinophenyl)-N'-(1-(phenyl) sulfonylpiperidin-4-yl)cycloheptylurea In this case the title compound was prepared by acylation of N-(3-cyanophenyl)-N'-(piperidin-4-yl)cycloheptylurea with benzoyl chloride folowed by amidine formation as described above; HRMS (M+H)$^+$ calc. 456.206937, found 456.204189.

Example 12

Preparation of N-(3-amidinophenyl)-N'-(1-(4-acetamidophenyl)sulfonylpiperidin-4-yl) cycloheptylurea N-(3-amidinophenyl)-N'-(1-(4-acetamidophenyl) sulfonylpiperidin-4-yl)cycloheptylurea In this case the title compound was prepared by sulfonylation of N-(3-cyanophenyl)-N'-(piperidin-4-yl) cycloheptylurea with (4-acetamidophenyl)sulfonyl chloride folowed by amidine formation as described above; HRMS (M+H)$^+$ calc. 513.228401, found 513.226577.

Example 13

Preparation of N-(3-amidinophenyl)-N'-(1-(2-aminophenyl)sulfonylpiperidin-4-yl)cycloheptylurea N-(3-cyanophenyl)-N'-(1-(2-nitrophenyl) sulfonylpiperidin-4-yl)cycloheptylurea N-(3-cyanophenyl)-N'-(piperidin-4-yl)cycloheptylurea (1.5 g, 5.03 mmol) in tetrahydrofuran (30 ml) and triethylamine (1.02 g, 10.06 mmol) was cooled to 0° C.

A solution of (2-nitrophenyl)sulfonyl chloride (1.3 g, 5.86 mmol) in tetrahydrofuran (5 ml) was added dropwise and the reaction was stirred at ambient temperature for 18 h.The solvent was removed in vacuo and the residue dissolved in ehtylacetate. The ethyl acetate solution was washed with 1N HCl and brine, then dried ($Na_2SO_4$) and evaporated. Pure N-(3-cyanophenyl)-N'-(1-(2-nitrophenyl)sulfonylpiperidin-4-yl)cycloheptylurea was isolated by flash chromatography on silica gel by first eluting with 2:1 hexane ehtyl acetate, then 1:1 hexane ethyl acetate. There was obtained 0.71 g of the title compound; LRMS (M+H)$^+$ m/z 484.

N-(3-cyanophenyl)-N'-(1-(2-aminophenyl) sulfonylpiperidin-4-yl)cycloheptylurea

N-(3-cyanophenyl)-N'-(1-(2-nitrophenyl)sulfonyl-piperidin-4-yl)cycloheptylurea (0.71 g, 1.47 mmol) in ethanol (90 ml) and water (10 ml) was stirred with zinc dust (3.2 g, 48.6 mmol) and calcium chloride (0.11 g, 0.95 mmol). This mixture was heated at reflux for 3 h then filtered hot through a Celite® pad and evaporated; 0.59 g of N-(3-cyanophenyl)-N'-(1-(2-aminophenyl)sulfonyl- piperidin-4-yl)cycloheptylurea was obtained; LRMS (M+H)$^+$ m/z 454.

N-(3-amidinophenyl)-N'-(1-(2-aminophenyl) sulfonylpiperidin-4-yl)cycloheptylurea N-(3-cyanophenyl)-N'-(1-(2-aminophenyl)sulfonyl-piperidin-4-yl)cycloheptylurea (0.20 g, 0.44 mmol) in anhydrous chloroform (25 ml) and anhydrous methanol (10 ml) was cooled to 0° C. and saturated with dry hydrogen chloride gas. The reaction vessel was securely stoppered and was stirred at ambient temperature for 18 h. The intermediate imidate was obtained as the hydrogen chloride salt (0.23 g) by removal of the solvent and residual hydrogen chloride in vacuo; LRMS (M+H)$^+$ m/z 486.

The imidate prepared above (0.23 g) and a 2N solution of ammonia in methanol (1.5 ml) were stirred in a tightly stopper flask at ambient temperature for 18 h. A mixture of the desired amidine and the corresponding amide were obtained anfter removal of the solvent. This mixture was separated by HPLC on a Vydec® C-18 column eluting with solvent mixture A (water:TFA 99.5:0.5) and solvent mixture B (acetonitrile:TFA 99.5:0.5) using a gradient starting with A at 100% and changing to B at 100% over 50 min. There was obtained 38 mg of the desired product N-(3-amidinophenyl)-N'-(1-(2-aminophenyl)sulfonyl-piperidin-4-yl)cycloheptylurea; HRMS (M+H)$^+$ calc. 471.217836, found 471.218097.

The corresponding amide side product N-(3-amidophenyl)-N'-(1-(2-aminophenyl)sulfonyl-piperidin-4-yl)cycloheptylurea was also isolated (46 mg); HRMS (M+H)$^+$ calc. 472.201852, found 472.202530.

The following Example 14 to 16 were prepared by essentially the same preparative methods as described above for Example 13; the only changes involved the sulfonylation of the common intermediate N-(3-cyanophenyl)-N'-(piperidin-4-yl)cycloheptylurea. In each case, however, the same procedure using the appropriate sulfonylating agent in tetrahydrofuran with triethylamine was used.

Example 14

Preparation of N-(3-amidinophenyl)-N'-(1-(3-aminophenyl)sulfonylpiperidin-4-yl)cycloheptylurea N-(3-amidinophenyl)-N'-(1-(3-aminophenyl)sulfonylpiperidin-4-yl)cycloheptylurea In this case the title compound was prepared by sulfonylation of N-(3-cyanophenyl)-N'-(piperidin-4-yl)cycloheptylurea with 3-nitrophenylsulfonyl chloride. This product was reduced by a mixture of zinc dust and calcium chloride in aqueous ethanol followed by amidine formation as described above to give the title compound; HRMS (M+H)$^+$ calc. 471.217836, found 471.219532.

Example 15

Preparation of N-(3-amidinophenyl)-N'-(1-(4-aminophenyl)sulfonylpiperidin-4-yl)cycloheptylurea N-(3-amidinophenyl)-N'-(1-(4-aminophenyl)sulfonylpiperidin-4-yl)cycloheptylurea In this case the title compound was prepared by sulfonylation of N-(3-cyanophenyl)-N'-(piperidin-4-yl)cycloheptylurea with 4-nitrophenylsulfonyl chloride. This product was reduced by a mixture of zinc dust and calcium chloride in aqueous ethanol followed by amidine formation as described above to give the title compound; HRMS (M+H)$^+$ calc. 471.217836, found 471.217059.

Example 16

Preparation of N-(3-amidinophenyl)-N'-(1-((2-aminophenyl)methane)sulfonyl)-piperidin-4-yl)cycloheptylurea N-(3-amidinophenyl)-N'-(1-((2-aminophenyl)methane)sulfonyl)-piperidin-4-yl)cycloheptylurea In this case the title compound was prepared by sulfonylation of N-(3-cyanophenyl)-N'-(piperidin-4-yl)cycloheptylurea with ((2-nitrophenyl)methane)sulfonyl chloride. This product was reduced by a mixture of zinc dust and calcium chloride in aqueous ethanol followed by amidine formation as described above to give the title compound; HRMS (M+H)$^+$ calc. 485.233486, found 485.235037.

Example 17

Preparation of N-(3-amidinophenyl)-N'-(1-((2-acetamidophenyl)methane)sulfonylpiperidin-4-yl)cycloheptylurea N-(3-cyanophenyl)-N'-(1-((2-aminophenyl)methane)sulfonyl-piperidin-4-yl)cycloheptylurea This material was prepared by sulfonylation of N-(3-cyanophenyl)-N'-(piperidin-4-yl)cycloheptylurea with ((2-nitrophenyl)methane)sulfonyl chloride in tetrahydrofuran and triethyl amine, as described for EXAMPLE 16. Reduction of the nitro group using zinc dust and calcium chloride in aqueous ethanol gave N-(3-cyanophenyl)-N'-(1-((2-aminophenyl)methane)sulfonyl-piperidin-4-yl)cycloheptylurea; LRMS (M+H)$^+$ m/z 468.

N-(3-cyanophenyl)-N'-(1-((2-acetamidophenyl)methane)sulfonyl-piperidin-4-yl)cycloheptylurea N-(3-cyanophenyl)-N'-(1-((2-aminophenyl)methane) sulfonylpiperidin-4-yl)cycloheptylurea (0.296 g, 0.63 mmol) in chloroform (30 ml) and triethylamine (0.13 g, 1.27 mmol) was cooled to 0° C. and acetyl chloride (0.06 g, 0.76 mmol) was added. The reaction was allowed to warm to ambient temperature and was stirred for 6 h. The solvent was removed in vacuo and the residue was dissolved in ethyl acetate and washed with 1N HCl and brine, then dried ($Na_2SO_4$) and evaporated. Purification by silica gel flash chromatography with 5% methanol in chloroform gave 194 mg of N-(3-cyanophenyl)-N'-(1-((2-acetamidophenyl) methane)sulfonyl-piperidin-4-yl)cycloheptylurea; LRMS (M+H)$^+$ m/z 510.

N-(3-amidinophenyl)-N'-(1-((2-acetamidophenyl)methane)sulfonylpiperidin-4-yl)cycloheptylurea N-(3-cyanophenyl)-N'-(1-((2-acetamidophenyl)methane) sulfonyl-piperidin-4-yl)cycloheptylurea (0.194 g, 0.38 mmol) in anhydrous methyl acetate (25 ml) and anhydrous methanol (10 ml) was cooled to 0° C. and saturated with dry hydrogen chloride gas. The reaction vessel was securely stoppered and was stirred at ambient temperature for 18 h. The intermediate imidate was obtained as the hydrogen chloride salt (0.174 g) by removal of the solvent and residual hydrogen chloride in vacuo; LRMS (M+H)$^+$ m/z 542.

The imidate prepared above (0.174 g) and a solution of ammonium acetate (0.15 g) in methanol (10 ml) were stirred at ambient temperature for 18 h. A mixture of the desired amidine and the corresponding amide were obtained after removal of the solvent. This mixture was separated by HPLC on a Vydec® C-18 column eluting with solvent mixture A (water:TFA 99.5:0.5) and solvent mixture B (acetonitrile:TFA 99.5:0.5) using a gradient starting with A at 100% and changing to B at 100% over 50 min. There was obtained 9.6 mg of the desired product N-(3-amidinophenyl)-N'-(1-((2-acetamidophenyl)methane)-sulfonylpiperidin-4-yl)cycloheptylurea; HRMS (M+H)$^+$ calc. 527.244051, found 527.246420.

The corresponding amide side product N-(3-amidophenyl)-N'-(1-((2-acetamidophenyl)methane)-sulfonylpiperidin-4-yl)cycloheptylurea was also isolated (8.5 mg); HRMS (M+H)$^+$ calc. 528.228066, found 528.236184.

Example 18

Preparation of 1-(1-benzoylpiperidin-4-yl)-3-(3-amidinophenyl)-5-ethenyl-2-imidazolidinone 1-(1-t-butoxycarbonylpiperidin-4-yl)-3-(3-amidinophenyl)-5-ethenyl-2-imidazolidinone A mixture of N-(3-cyanophenyl)-N'-(1-(t-butoxycarbonyl)-piperidin-4-yl)urea (0.50 g, 1.45 mmol) and sodium hydride (0.20 g of a 60% suspension in mineral oil, 8.3 mmol) in dimethylformamide was stirred at ambient temperature for 30 min. then cis-1,4-dichloro-2-butene (0.18 g, 1.44 mmol) was added. This mixture was heated at 70° C. for 4 h, after which an addition 0.2 g of 60% sodium hydride and 0.04 g of cis-1,4-dichloro-2-butene was added. The mixture was heated at 70° C. for an addition 2 h during which the remaining starting material was consumed. The reaction was diluted with brine (50 ml) and extracted with ethyl acetate (3×). The ethyl acetate extracts were washed with brine, then dried ($Na_2SO_4$) and evaporated. The residue was purified by flash chromatography on silica gel, eluting with 2:1 hexane:ethyl acetate to give 0.20 g of 1-(1-t-butoxycarbonylpiperidin-4-yl)-3-(3-amidinophenyl)-5-ethenyl-2-imidazolidinone; LRMS $(M+H)^+$ m/z 397.

1-(piperidin-4-yl)-3-(3-amidinophenyl)-5-ethenyl-2-imidazolidinone 1-(1-t-Butoxycarbonylpiperidin-4-yl)-3-(3-amidinophenyl)-5-ethenyl-2-imidazolidinone (1.32 g, 3.3 mmol) was stirred in 1:1 dichloromethane:trifluoroacetic acid (30 ml) for 4 h. This solvent was removed in vacuo, and 1.35 g of 1-(piperidin-4-yl)-3-(3-amidinophenyl)-5-ethenyl-2-imidazolidinone was obtained as the trifluoroacetic acid salt LRMS $(M+H)^+$ m/z 297.

1-(1-benzoylpiperidin-4-yl)-3-(3-cyanophenyl)-5-ethenyl-2-imidazolidinone

The free base of 1-(piperidin-4-yl)-3-(3-amidinophenyl)-5-ethenyl-2-imidazolidinone (1.99 g, 6.72 mmol) in tetrahydrofuran (50 ml) and triethylamine (1.36 g, 13.44 mmol) was cooled to 0° C. and benzoyl chloride in tetrahydrofuran (10 ml) was added. After 4 h the reaction was complete; the solvent was removed in vacuo and the residue dissolved in ethyl acetate. The ethyl acetate solution was washed with 1N HCl and brine, then dried ($Na_2SO_4$) and evaporated. The desired product was isolated by flash chromatography using silica get and 2:1 ethyl acetate as eluent. There was obtained 0.63 g of pure 1-(1-benzoylpiperidin-4-yl)-3-(3-cyanophenyl)-5-ethenyl-2-imidazolidinone; LRMS $(M+H)^+$ m/z 401.

1-(1-benzoylpiperidin-4-yl)-3-(3-amidinophenyl)-5-ethenyl-2-imidazolidinone 1-(1-Benzoylpiperidin-4-yl)-3-(3-cyanophenyl)-5-ethenyl-2-imidazolidinone (0.30 g, 0.75 mmol) in anhydrous 4:1 chloroform:methanol (25 ml) was cooled to 0° C. and saturated with dry hydrogen chloride gas. The reaction vessel was stoppered securely then left to stand at 10° C. for 72 h. The solvent was removed in vacuo to give 0.33 g of the imidate as the hydrogen chloride salt (0.75 mmol); LRMS $(M+H)^+$ m/z 433.

The imidate prepared above (0.33 g, 0.75 mmol) was dissolved in anhydrous methanol (10 ml) and ammonium carbonate (0.36 g, 3.76 mmol) was added. This mixture was stirred at ambient temperature for 18 h, then the solvent was removed in vacuo. The residue was dissolved in water (10 ml) and washed with diethyl ether (3×). The aqueous layer was lyophillized and the crude product was purified by HPLC on a Vydec® C-18 column eluting with solvent mixture A (water:TFA 99.5:0.5) and solvent mixture B (acetonitrile:TFA 99.5:0.5) using a gradient starting with A at 100% and changing to B at 100% over 50 min. The fractions containing pure 1-(1-benzoylpiperidin-4-yl)-3-(3-amidinophenyl)-5-ethenyl-2-imidazolidinone were collected and lyophillized to give 0.090 g of material; HRMS $(M+H)^+$ calc. 418.224300, found 418.223792.

The following Example 19 and 20 were prepared by essentially the same preparative methods as described above for Example 18; the only changes involved the sulfonylation of the common intermediate 1-(piperidin-4-yl)-3-(3-amidinophenyl)-5-ethenyl-2-imidazolidinone. In each case, however, the same procedure using the appropriate acylating or sulfonylating agent in tetrahydrofuran with triethylamine was used.

Example 19

Preparation of 1-(1-((phenyl)methane)sulfonyl) piperidin-4-yl)-3-(3-amidinophenyl)-5-ethenyl-2-imidazolidinone In this case the title compound was prepared by sulfonylation of 1-(piperidin-4-yl)-3-(3-amidinophenyl)-5-ethenyl-2-imidazolidinone with α-toluene sulfonyl chloride in tetrahydrofuran with triethylamine folowed by amidine formation as described above; HRMS $(M+H)^+$ calc. 468.206937, found 468.204978.

Example 20

Preparation of 1-(1-phenylsulfonylpiperidin-4-yl)-3-(3-amidinophenyl)-5-ethenyl-2-imidazolidinone In this case the title compound was prepared by sulfonylation of 1-(piperidin-4-yl)-3-(3-amidinophenyl)-5-ethenyl-2-imidazolidinone with phenylsulfonyl chloride in tetrahydrofuran with triethylamine folowed by amidine formation as described above; HRMS $(M+H)^+$ calc. 454.191287, found 454.191418.

Example 21

Preparation of 1,2,4,5-tetrahydro-2-((phenyl) methane)sulfonyl)piperidin-4-yl)-4-(3-amidinophenyl)-3H-2,4-benzodiazepin-3-one N-[methyl(2-((t-butyldimethylsilyloxy)methyl) phenyl)]-N-[(N-carbo-t-butoxy)piperidin-4-yl]amine A solution of methyl-2-cyanobenzoate (10 g, 62.11 mmol) in ethyl ether (300 mL) was added dropwise to a slurry of lithium aluminum hydride in ethyl ether (200 mL). After the addition was complete, more ether was added (200 mL) and the mixture heated at reflux for 2 h. The cooled reaction mixture was quenched by careful addition of succesive amounts of water (7.1 mL), 1N sodium hydroxide solution (7.1 mL) and water (21.3 mL). The reaction was filtered and evaporated to give 6.96 g (50.8 mmol) of 2-(aminomethyl) benzyl alcohol. This material was carried on without further purification.

The material from above was dissolved in tetrahydrofuran (140 mL) and cooled to 0° C. To this mixture was added imidazole (1.3 equivilents, 4.5 g, 66.04 mmol) and t-butyldimethylsilyl chloride (1.05 equivilents, 8.04 g, 53.34 mmol). The reaction mixture was stirred at ambient temperature for 18 h then was diluted with water (500 mL) and extracted with ethyl ether (3×150 mL). The ether extract was dried ($MgSO_4$) and evaporated to give 10.78 g (41 mmol) of the t-butyldimethylsilyl ether of 2-(aminomethyl)benzyl alcohol.

To a mixture of the t-butyldimethylsilyl ether prepared above (7.77 g, 29.5 mmol) and N-(carbo-t-butoxy)piperidin-4-one (5.88 g, 29.5 mmol) in methanol at 0° C. was added zinc chloride (4.02 g, 29.5 mmol) followed by sodium cyanoborohydride (2.04 g, 32.45 mmol). The reaction was thawed to ambient temperature and stirred for 18 h. After this time, the reaction was judged to be complete by TLC (20% methanol in chloroform); the solvent was removed by distillation in vaccuo and the residue partitioned between ethyl acetate and 1N hydrochloric acid solution. The ethyl acetate layer was washed with brine and dried (MgSO$_4$) then evaporated to give 11.66 g (26.87 mmol) of N-[methyl(2-((t-butyldimethylsilyloxy)methyl)phenyl)]-N-[(N'-carbo-t-butoxy)piperidin-4-yl]amine.

N-[methyl(2-(chloramethyl)phenyl)]-N-[(N'-carbo-t-butoxy)piperidin-4-yl]-(3-cyano)benzamide A mixture of 11.66 g (26.87 mmol) of N-[methyl(2-((t-butyldimethylsilyloxy)-methyl)phenyl)]-N-[(N-carbo-t-butoxy)piperidin-4-yl]amine and 3-cyanophenyl isocyanate (3.87 g, 26.87 mmol) in dimethyl-formamide (100 mL) was stirred at ambient temperature for 24 h. The reaction was judged to be complete by TLC (5% methanol in chloroform) and diluted with brine (500 mL). The suspension was extracted with ethyl acetate (150 mL) and the ethyl acetate extracts were washed with brine (5×100 mL) then dried (MgSO$_4$) and evaporated to give 14.54 g of crude material. This material was purified further by elution from a 400 gram column of silica gel with a mixture of ethyl acetate and hexane; the material isolated from the eluent was 11.66 g (20.17 mmol) of the pure isocyanate addition product.

A tetrahydrofuran solution (200 mL) of the purified isocyanate addition product (11.5 g, 20 mmol) was treated with solid tetra-n-butylammonium fluoride (5.75 g, 22 mmol). The reaction was complete in 30 min (TLC, 1:1 hexane:ethyl acetate) whereupon the solvent was removed by distillation in vaccuo and the residue partioned between ethyl acetae and water. The ethyl acetate layer was dried (MgSO$_4$) and evaporated to give 13.23 g of the desilylsted benzyl alcohol tainted with a silyl fluoro- or silyloxy-side product from the cleaved protecting group. This material was assumed to contain a quantitative yield of the desired benzyl alcohol (20 mmol) and dissolved in chloroform (300 mL). The cooled solution (0° C.) was treated with triethylamine (2.23 g, 3.1 mL, 22 mmol) followed by the dropwise addition of methanesulfonyl chloride (2.29 g, 1.55 mL, 20 mmol) in chloroform (50 mL). The reaction was allowed to thaw to ambient temperature and stirred for 18 h. The reaction was washed with 5% sodium hydrogensulfate solution (2×150 mL) then dried and evaporated to give 10.25 g of crude product as the benzyl chloride. A portion of this material (ca. 5 g) was purified further by elution from a 400 g column of silica gel with 3:1 hexane:ethyl acetate. The pure N-[methyl(2-(chloromethyl)phenyl)]-N-[(N'-carbo-t-butoxy)piperidin-4-yl]-(3-cyano)benzamide (3.1 g, 6.43 mmol) was isolated from the eluent as a white solid mp: 165–170° C.

1,2,4,5-tetrahydro-2-(piperidin-4-yl)-4-(3-cyanophenyl)-3H-2,4-benzodiazepin-3-one The pure N-[methyl(2-(chloromethyl)phenyl)]-N-[(N'-carbo-t-butoxy)piperidin-4-yl]-(3-cyano)benzamide (3.1 g, 6.43 mmol) was dissolved in dimethylformamide (30 mL), cooled to 0° C. and a 60% suspension of sodium hydride in mineral oil (0.52 g of suspension, 12.46 mmol) was added. The reaction was complete after 2 h at 0° C.; it was diluted with water (150 mL) and extracted with ethyl acetate (3×50 mL). The ethyl acetate solution was washed with brine (5×50 mL), then was dried and evaporated. The yield of the cyclized product was 2.7 g (6.05 mmol); this material was contaminated with a small amount of mineral oil but was carried on to the next step without further purification.

The t-butoxycarbonyl protecting group on the product prepared above (2.7 g, 6.05 mmol) was removed by treatment with 4N hydrogen chloride in dioxane (15 mL) at 0° C. for 3 h. The reaction mixture was purged with nitrogen gas, then evaporated. The residue was dissolved in water (50 mL) and washed with ethyl ether (2×25 mL). The water solution was made basic (pH 12) with 10% sodium hydroxide solution and the product extracted with ethyl acetate (3×50 mL). The ethyl acetate solution was washed with 1N aqueous sodium hydroxide, then was dried (MgSO$_4$) and evaporated to give 1.62 g (4.68 mmol) of 1,2,4,5-tetrahydro-2-(piperidin-4-yl)-4-(3-cyanophenyl)-3H-2,4-benzodiazepin-3-one as a tan solid, mp 115.8° C.; HRMS for C$_{21}$H$_{23}$N$_4$O (M+H)$^+$: calc. 347.187187, found 347.184824.

1,2,4,5-tetrahydro-2-((phenyl)methane)-sulfonyl) piperidin-4-yl)-4-(3-cyanophenyl)-3H-2,4-benzodiazepin-3-one A solution of 1,2,4,5-tetrahydro-2-(piperidin-4-yl)-4-(3-cyanophenyl)-3H-2,4-benzodiazepin-3-one (0.805 g, 2.33 mmol) in tetrahydrofuran (50 mL) was cooled to 0° C. and triethylamine (0.26 g, 0.36 mL 2.6 mmol) was added. To this mixture a tetrahydrofuran solution (25 mL) of benzylsulfonyl chloride (0.5 g, 2.6 mmol) was added dropwise. The reaction mixture was allowed to thaw to ambient temperature and stirred for 24 h.TLC indicated that the reaction was complete (10% methanol in chloroform). The mixture was evaporated and the residue suspended in a 3:1 mixture of water:1N hydrogen chloride solution. The product solidified, the suspension was filtered and the resulting powder air-dried, to give 0.89 g of crude product. This material was purified further by flash chromatography with a column of silica gel (80 g) and eluting with 2:1 then 1:1 hexane:ethyl acetate. From the eluent there was isolated 0.41 g (0.82 mmol) of pure 1,2,4,5-tetrahydro-2-((phenyl)methane)-sulfonyl)piperidin-4-yl)-4-(3-cyanophenyl)-3H-2,4-benzodiazepin-3-one, mp: 205–207° C.

1,2,4,5-tetrahydro-2-((phenyl)methane)-sulfonyl) piperidin-4-yl)-4-(3-amidinophenyl)-3H-2,4-benzodiazepin-3-one A solution of 0.41 g (0.82 mmol) of pure 1,2,4,5-tetrahydro-2-((phenyl)methane)-sulfonyl)piperidin-4-yl)-4-(3-cyanophenyl)-3H-2,4-benzodiazepin-3-one in chloroform (10 mL) was added to a saturated solution of dry, gaseous hydrogen chloride in dry methanol (10 mL) and chloroform (50 mL) at −78° C. The reaction vessel was stoppered tightly and allowed to thaw to ambient temperature; this mixture was maintained in this fashion for 18 h. After this time, excess hydrogen chloride gas was removed from the reaction mixture by purging with a stream of dry nitrogen gas; the solution was then evaporated and pumped on for several hours to remove traces of free hydrogen chloride gas. The resulting imidate was detected by LRMS:m/z (M+H)$^+$=533. This material was dissolved in a solution of dry chloroform (20 mL) and 2.0 M ammonia in methanol (5 mL, 10 mmol), the reaction vessel was stoppered tightly and stirred at ambient temperature for 6 days. The reaction mixture was evaporated and there was obtained about 0.45 g of the amidine product contaiminated with the amide side product. This mixture was purified by HPLC, eluting with a an aqueous phase of 0.05% trifluoroacetic acid in water and an organic phase of 0.05% trifluoroacetic acid in acetonitrile. The product, 1,2,4,5-tetrahydro-2-((phenyl)methane)-sulfonyl)piperidin-4-yl)-4-(3-amidinophenyl)-3H-2,4-benzodiazepin-3-one (0.11 g, 0.17 mmol), was isolated as the trifluoroacetic acid salt by lyophylization of the appropriate fractions; mp: 210–211° C.; purity>99.5% (HPLC); HRMS: (M+H)$^+$ for C$_{28}$H$_{31}$N$_5$SO$_3$, calc. 518.222587, found 518.221085.

Example 22

Preparation of 1,2,4,5-tetrahydro-2-(thiopen-2-yl)-sulfonyl)piperidin-4-yl)-4-(3-amidinophenyl)-3H-2,4-benzodiazepin-3-one The intermediate 1,2,4,5-tetrahydro-2-(piperidin-4-yl)-4-(3-cyanophenyl)-3H-2,4-benzodiazepin-3-one was sulfonylated with (thiophen-2-yl)sulfonyl chloride according to the procedure outlined for the preparation of 1,2,4,5-tetrahydro-2-((phenyl)methane)-sulfonyl)piperidin-4-yl)-4-(3-cyanophenyl)-3H-2,4-benzodiazepin-3-one in EXAMPLE 21.

The title compound was obtained via the imidate according to the procedure for 1,2,4,5-tetrahydro-2-((phenyl) methane)sulfonyl)piperidin-4-yl)-4-(3-amidinophenyl)-3H-2,4-benzodiazepin-3-one of EXAMPLE 21 by starting with the intermediate prepared above. LRMS: m/z=509; mp=119–120° C.

Example 23

Preparation of 1,2,4,5-tetrahydro-2-((phenyl)methane)sulfonyl)piperidin-4-yl)-4-(3-amidinophenyl)-7,8-dimethoxy-3H-2,4-benzodiazepin-3-one The intermediate 1,2,4,5-tetrahydro-2-(piperidin-4-yl)-4-(3-cyanophenyl)-7,8-dimethoxy-3H-2,4-benzodiazepin-3-one was prepared from methyl 3,4-dimethoxy-6-cyanobenzoate according to the procedure for the preparation of 1,2,4,5-tetrahydro-2-(piperidin-4-yl)-4-(3-cyanophenyl)-3H-2,4-benzodiazepin-3-one in EXAMPLE 21.

The intermediate 1,2,4,5-tetrahydro-2-(piperidin-4-yl)-4-(3-cyanophenyl)-7,8-dimethoxy-3H-2,4-benzodiazepin-3-one was sulfonylated with benzylsulfonyl chloride according to the procedure outlined for the preparation of 1,2,4,5-tetrahydro-2-((phenyl)methane)sulfonyl)piperidin-4-yl)-4-(3-cyanophenyl)-3H-2,4-benzodiazepin-3-one in EXAMPLE 21.

The title compound was obtained via the imidate according to the procedure for 1,2,4,5-tetrahydro-2-((phenyl) methane)sulfonyl)piperidin-4-yl)-4-(3-amidinophenyl)-3H-2,4-benzodiazepin-3-one of EXAMPLE 21 by starting with the intermediate prepared above. HRMS: $(M+H)^+$ for $C_{30}H_{35}N_5O_5S$, calc. 578.243716, found 578.245119.

Example 24

Preparation of 1,2,4,5-tetrahydro-2-(thiophen-2-yl)-sulfonyl)piperidin-4-yl)-4-(3-amidinophenyl)-7,8-dimethoxy-3H-2,4-benzodiazepin-3-one The intermediate 1,2,4,5-tetrahydro-2-(piperidin-4-yl)-4-(3-cyanophenyl)-7,8-dimethoxy-3H-2,4-benzodiazepin-3-one was prepared from methyl 3,4-dimethoxy-6-cyanobenzoate according to the procedure for the preparation of 1,2,4,5-tetrahydro-2-(piperidin-4-yl)-4-(3-cyanophenyl)-3H-2,4-benzodiazepin-3-one in EXAMPLE 21.

The intermediate 1,2,4,5-tetrahydro-2-(piperidin-4-yl)-4-(3-cyanophenyl)-7,8-dimethoxy-3H-2,4-benzodiazepin-3-one was sulfonylated with (thiophen-2-yl)sulfonyl chloride according to the procedure outlined for the preparation of 1,2,4,5-tetrahydro-2-((phenyl)methane)sulfonyl)piperidin-4-yl)-4-(3-cyanophenyl)-3H-2,4-benzodiazepin-3-one in EXAMPLE 21.

The title compound was obtained via the imidate according to the procedure for 1,2,4,5-tetrahydro-2-((phenyl) methane)sulfonyl)piperidin-4-yl)-4-(3-amidinophenyl)-3H-2,4-benzodiazepin-3-one of EXAMPLE 21 by starting with the intermediate prepared above. HRMS: $(M+H)^+$ for $C_{27}H_{31}N_5O_5S_2$, calc. 570.184488, found 570.186900.

Examples 25 to 55
(Shown in Table 7)

Examples 25 to 55 were prepared by essentially the same preparative methods as described above for Example 8; the only changes involved the sulfonylation, alkylation or acylation of the common intermediate N-(3-cyanophenyl)-N'-(piperidin-4-yl)cycloheptylurea. In each case, the same procedure using the appropriate sulfonyl chloride, sulfamoyl chloride, alkyl chloride or acyl chloride in tetrahydrofuran with triethylamine was used. Following imidate formation, the reaction with methanolic ammonia to give the amidine product was executed as described in Example 13.

An exceptional case was the preparation of Example 28; this product was obtained as a by-product of the formation of the amidine Example 29. During the methanolic ammonia step competing deacylation of Example 29 led to the formation of Example 28. Both Examples 28 and 29 were obtained pure and homogeneous by HPLC purification of the mixture obtained during amidine formation under standard preparative HPLC purification conditions.

Example 56

Preparation of N-(3-amidinophenyl)-N'-((1-((phenyl)-1,1-dimethyl)methane)sulfonyl)-piperidin-4-yl)cyclohetylurea The title compound was prepared from N-(3-cyanophenyl)-N'-(1-((phenyl)methane)sulfonyl)piperidin-4-yl)cycloheptylurea found in Example 8

N-(3-cyanophenyl)-N'-(1-((phenyl)methane)sulfonyl) piperidin-4-yl)cycloheptylurea (1.94 g, 4.29 mmol) in dimethylformamide (25 mL) was cooled to −10° C. and 1M potassium t-butoxide solution in tetrahydrofuran (12.9 mL, 12.9 mmol) was added dropwise. The reaction was stirred for 15 min at −10° C. then methyl iodide (1.83 g, 12.9 mmol) was added. After 2 h reaction was complete by TLC; the reaction mixture was poured into water (200 mL), then was extracted with ethyl acetate (3×50 mL). The ethyl acetate extracts were washed with water (5×50 mL), dried ($MgSO_4$) and evaporated to give 0.55 g of N-(3-cyanophenyl)-N'-((1-((phenyl)-1,1-dimethyl)methane)sulfonyl)-piperidin-4-yl) cycloheptylurea; LRMS $(M+NH_4)^+$ m/z=498.

To 0.55 g of N-(3-cyanophenyl)-N'-((1-((phenyl)-1,1-dimethyl)methane)-sulfonyl)-piperidin-4-yl) cycloheptylurea (1.14 mmol) in pyridine (20 mL) with triethylamine (1 mL) was passed a stream of gaseous hydrogen sulfide for 30 min. The reaction mixture was stoppered tightly and allowed to stand for 18 h. The solution was then poured into 1N hydrochloric acid solution (250 mL) and extracted with ethyl acetate (3×50 mL). The ethyl acetate solution was dried and evaportated to give 0.53 g (1.03 mmol) of N-(3-thioamidophenyl)-N'-((1-((phenyl)-1,1-dimethyl)methane)-sulfonyl)-piperidin-4-yl) cycloheptylurea; LRMS $(M+H)^+$ m/z=515.

The product prepared above, 0.53 g (1.03 mmol) of N-(3-thioamidophenyl)-N'-((1-((phenyl)-1,1-dimethyl) methane)sulfonyl)-piperidin-4-yl)cycloheptylurea, was stirred in methyl iodide (10 mL) for 2 h. The reaction was then evaporated to give 0.62 g (1.03 mmol) of the thioimidate.

The thioimidate (0.62 g, 1.03 mmol) was stirred with ammonium acetate (0.45 g, 5.9 mmol) in methanol (20 mL) and heated at 60° C. for 2 h. The reaction was then evaporated, the residue stirred in dichloromethane, the insoluable material removed by filtration and the dichloromethane solution evaporated to give ca. 0.5 g of crude amidine. This material was purified by HPLC (gradient elution with a mixture of 0.05% aqueous trifluoroacetic acid and 0.05% trifluoroacetic acid in acetonitrile) to give 0.143 g of the title compound following lyophylization of the appropriate fractions; HRMS (M+H)$^+$ calc. 489.253887, found 498.252412.

Example 57

Preparation of N-(3-amidinophenyl)-N'-(methyl ((phenylmethane)carbamide)morpholin-3-yl)) cycloheptylurea N-benzyl 3-(aminomethyl)morpholine N-benzyl 3-(chloromethyl)morpholine (10 g, 44.3 mmol) in dimethylformamide (200 mL) with sodium azide (8.64 g, 133 mmol) and potassium iodide (0.73 g) was heated at 100° C. for 72 h. The reaction was poured into water (1 L) and extracted with ethyl acetate (3×150 mL). The ethyl acetate layer was washed with water (5×150 mL), then dried (MgSO$_4$) and evaporated to give 9.28 g of material. This was purified further by flash chromatography using 3:1 hexane-:ethyl acetate as the eluent. There was obtained 7.89 g of the pure azide.

The material prepared above was dissolved in methanol (300 mL) and palladium hydroxide catalyst (1.0 g) was added. This mixture was stirred under an atmosphere of hydrogen gas at ambient pressure for 2 h, whereupon selective reduction of the azide group was complete. The reaction mixture was purged with nitrogen gas and the catalyst removed by filtration through a Celite pad.After removal of the solvent there was obtained 5.80 g of N-benzyl 3-(aminomethyl)morpholine (28.1 mmol); LRMS (M+H)$^+$ m/z=207.

N-(3-cyanophenyl)-N'-(methyl(N-methyl(phenyl)) morpholin-3-yl))cycloheptylurea

A mixture of 5.80 g of N-benzyl 3-(aminomethyl) morpholine (28.1 mmol) and 3-cyanophenyl isocyanate (4.46 g, 31 mmol) in dimethylformamide (100 mL) was stirred at ambient temperature for 18 h. The reaction was diluted with water (500 mL) then extracted with ethyl acetate (3×100 mL). The ethyl acetate solution was washed with water (5×100 mL), dried (MgSO$_4$) and evaporated to give 9.49 g of the urea (27.1 mmol); LRMS (M+H)$^+$ m/z=351.

To a mixture of sodium hydride (3.25 g of a 60% suspension in mineral oil, 81.3 mmol) in dimethylformamide (450 mL) was added dropwise 9.49 g of the urea (27.1 mmol) prepared above as a solution in dimethylformamide (50 mL). This mixture was stirred for 30 min, then 1.71 g of 1,4-dibromobutane (54.2 mmol) in dimethylformamide (40 mL) was added slowly. The reaction was heated to 70° C. for 6 h then poured into water (2 L) and extracted with ethyl acetate (3×250 mL). The ethyl acetate extract was washed with water (5×250 mL), was dried (MgSO$_4$) and evaporated. The residue was purified by flash chromatography using 2:1 hexane:ethyl acetate as an eluent. There was obtained 7.59 g of N-(3-cyanophenyl)-N'-(methyl(N-methyl(phenyl)) morpholin-3-yl))cycloheptylurea; LRMS (M+H)$^+$ m/z=405.

N-(3-cyanophenyl)-N'-(methyl(morpholin-3-yl)) cycloheptylurea

To N-(3-cyanophenyl)-N'-(methyl(N-methyl(phenyl)) morpholin-3-yl))cycloheptylurea (4.66 g, 11.55 mmol) in dichloromethane (100 mL) was added 1-chloroethyl chloroformate (1.81 g, 12.7 mmol) in dichloromethane (10 mL). After 2 h the reaction was complete by TLC; the solvent was removed by evaporation in vaccuo and replaced by methanol (60 mL). The mixture was refluxed for 1 h then the solvent evaporated to give 3.53 g of N-(3-cyanophenyl)-N'-(methyl (morpholin-3-yl))cycloheptylurea; LRMS (M+H)$^+$ m/z= 315.

N-(3-cyanophenyl)-N'-(methyl((phenylmethane) carbamide)-morpholin-3-yl))cycloheptylurea To 1.0 g of N-(3-cyanophenyl)-N'-(methyl(morpholin-3-yl))cycloheptylurea (3.18 mmol) in tetrahydrofuran (30 mL) with triethylamine (0.68 g, 6.7 mmol) at 0° C. was added phenylacetyl chloride (0.54 g, 3.5 mmol) in tetrahydrofuran (10 mL). The mixture was allowed to thaw to ambient temperature and stirred for 18 h. After this time, the solvent was removed by evaporation in vaccuo and the residue purified by flash chromatography with 10% methanol in chloroform used as the eluent. There was obtained 1.17 g (2.7 mmol) of N-(3-cyanophenyl)-N'-(methyl((phenylmethane)carbamide)morpholin-3-yl))cycloheptylurea as product; LRMS (M+H)$^+$ m/z=433.

N-(3-amidinophenyl)-N'-(methyl((phenyl-methane) carbamide)-morpholin-3-yl))cycloheptylurea To a saturated solution of gaseous hydrogen chloride in dry chloroform (20 mL) and dry methanol (8 mL) at −78° C. was added dropwise a chloroform (5 mL) solution of 1.17 g (2.7 mmol) of N-(3-cyanophenyl)-N'-(methyl((phenylmethane)carbamide)morpholin-3-yl))cycloheptylurea. This mixture was stoppered tightly, was allowed to thaw to ambient temperature and was stirred for 18 h. The solvent was removed in vaccuo to give 1.04 g of the corresponding imidate; LRMS (M+H)$^+$ m/z=465.

The imidate prepared above was dissolved in 2M ammonia in methanol solution (6.72 mmol, 3.36 mL), the flask was stoppered securely and the mixture stirred at ambient temperature for 18 h. After this time the solvent was removed in vaccuo and the residue (ca. 1.2 g) was purified by HPLC (gradient elution with a mixture of 0.05% aqueous trifluoroacetic acid and 0.05% trifluoroacetic acid in acetonitrile) to give 0.12 g of N-(3-amidinophenyl)-N'-(methyl((phenylmethane)carbamide)-morpholin-3-yl))cycloheptylurea; mp 49–53° C.; HRMS (M+H)$^+$: calc. 450.250515, found 450.251817.

Example 58

Preparation of N-(3-amidinophenyl)-N'-(methyl ((thiophen-2-yl)sulfonyl)morpholin-3-yl)) cycloheptylurea This compound was prepared by the same methods used for Example 57. Starting with the common intermediate N-(3-cyanophenyl)-N'-(methyl(morpholin-3-yl)) cycloheptylurea, this material was sulfonylated with (thiophen-2-yl)sulfonyl chloride using the same conditions for the acylation described above. There was obtained 0.75 g of the sulfonylation product following purification by flash chromatography using a gradient of 2:1 hexane:ethyl acetate to 1:2 hexane:ethyl acetate as a gradient; LRMS (M+H)$^+$ m/z=461.

The imidate and subsequently, the amidine N-(3-amidinophenyl)-N'-(methyl((thiophen-2-yl)sulfonyl)morpholin-3-yl))cycloheptylurea were obtained as described. Following HPLC purification 0.32 g of the title compound was isolated; mp 78–83° C.; HRMS (M+H)+: calc. 478.158273, found 478.156983.

Example 59

Preparation of N-(3-amidinophenyl)-N'-(methyl((phenylmethane)sulfonyl)morpholin-3-yl))cycloheptylurea This compound was prepared by the same methods used for Example 57. Starting with the common intermediate N-(3-cyanophenyl)-N'-(methyl(morpholin-3-yl))cycloheptylurea, this material was sulfonylated with (phenyl)methylsulfonyl chloride using the same conditions for the acylation described above. There was obtained 0.68 g of the sulfonylation product following purification by flash chromatography using a gradient of 1:1 hexane:ethyl acetate to 1:3 hexane:ethyl acetate as a gradient; LRMS (M+H)+ m/z=469.

The imidate and subsequently, the amidine N-(3-amidinophenyl)-N'-(methyl((phenylmethane)sulfonyl)morpholin-3-yl))cycloheptylurea were obtained as described above. Following HPLC purification 0.102 g of the title compound was isolated; mp 45–53° C.; HRMS (M+H)+: calc. 486.217502, found 486.217928.

Example 60

Preparation of N-(3-amidinophenyl)-N'-((N-benzyl)piperidin-3-yl)cycloheptylurea

N-Benzyl 3-aminopiperidine

To 10.0 g of N-benzyl 3-hydroxypiperidine hydrogen chloride salt (44 mmol) in chloroform (200 mL) with triethylamine (9.34 g, 92.4 mmol) at 0° C. was added dropwise methanesulfonyl chloride (5.54 g, 48.4 mmol) in chloroform (10 mL). The reaction mixture was allowed to thaw to ambient temperature and stirred 72 h. After this time, the solvent was removed in vaccuo, the residue was dissolved in ethyl acetate (200 mL) and washed with water (200 mL). The organic solution was dried (MgSO$_4$) and evaporated to give 9.1 g (33.8 mmol) of the mesitylate.

The material prepared above was dissolved in dimethylformamide (200 mL) and stirred at 100° C. with sodium azide (11 g, 170 mmol). After 48 h the reaction was complete by TLC; it was diluted with brine (200 mL) and extracted with ethyl acetate (3×100 mL). The ethyl acetate extracts were washed with water (5×100 mL), then dried and evaporated to give 6.12 g of the azide; LRMS (M+H)+ m/z=217.

The azide (6.12 g, 28.4 mmol) in methanol (250 mL) with palladium hydroxide catalyst (1.0 g) was stirred under an atmosphere of hydrogen gas at ambient pressure for 1 h 15 min. After this time selective reduction of the azide was complete. The reaction mixture was purged with nitrogen gas and the catalyst removed by filtration through a Celite pad. The solvent was removed by distillation in vaccuo to give 4.3 g of N-benzyl 3-aminopiperidine; LRMS (M+H)+ m/z=191.

N-(3-cyanophenyl)-N'-((N-benzyl)piperidin-3-yl)cycloheptylurea

A mixture of 4.3 g of N-benzyl 3-aminopiperidine (22.6 mmol) and 3-cyanophenyl isocyanate (3.58 g, 24.9 mmol) in dimethylformamide (100 mL) was stirred at ambient temperature for 18 h. The reaction was diluted with water (500 mL) and extracted with ethyl acetate (3×150 mL). The organic solution was washed with water (5×100 mL), dried and evaporated. This material was purified further by flash chromatography on silica gel using a gradient of 1:1 to 3:1 ethyl acetate:hexane. There was obtained 3.18 g of the pure urea (9.52 mmol); LRMS (M+H)+ m/z=335.

To 1.14 g of sodium hydride (60% suspension, 28.6 mmol) in dimethylformamide (160 mL) was added a dimethylformamide (20 mL) solution of the urea (3.18 g, 9.52 mmol). After 30 min, 1,4-dibromobutane (4.32 g, 20 mmol) in dimethylformamide (10 mL) was added dropwise, then the mixture was heated to 70° C. for 3 h. The reaction was diluted with water (700 mL) and extracted with ethyl acetate (3×100 mL). The organic solution was washed with water (5×100 mL), dried (MgSO$_4$) and evaporated. The residue was purified by flash chromatography on silica gel using an elution gradient of 5 to 10% methanol in chloroform. There was obtaine 3.17 g of N-(3-cyanophenyl)-N'-((N-benzyl)piperidin-3-yl)cycloheptylurea; LRMS (M+H)+ m/z=389.

N-(3-amidinophenyl)-N'-((N-benzyl)piperidin-3-yl)cycloheptylurea

To a saturated solution of hydrogen chloride gas in dry methanol (8 mL) and dry chloroform (15 mL) at −78° C. was added a chloroform (5 mL) solution of N-(3-cyanophenyl)-N'-((N-benzyl)piperidin-3-yl)cycloheptyl-urea (0.5 g, 1.29 mmol). The reaction mixture was stoppered securely and allowed to stir at ambient temperature for 18 h. After this time the solvent was removed in vaccuo and 0.49 g of the imidate hydrochloride salt was obtained; LRMS (M+H)+ m/z=422.

The imidate obtained above was dissolved in 2M ammonia in methanol (1.75 mL, 3.5 mmol). The reaction vessel was stoppered securely and the mixture stirred at ambient temperature for 18 h. After this time the solvent was removed in vaccuo and the residue was purified by HPLC (gradient elution with a mixture of 0.05% aqueous trifluoroacetic acid and 0.05% trifluoroacetic acid in acetonitrile) to give 0.015 g of pure N-(3-amidinophenyl)-N'-((N-benzyl)piperidin-3-yl)cycloheptylurea; HRMS (M+H)+: calc.406.260686, found 406.259064.

Example 61

Preparation of N-(3-amidinophenyl)-N'-((N-(benzyl)sulfonyl)piperidin-3-yl)cycloheptylurea N-(3-cyanophenyl)-N'-(piperidin-3-yl)cycloheptylurea A mixture of N-(3-cyanophenyl)-N'-((N-benzyl)piperidin-3-yl)cycloheptyl-urea (prepared in Example 60, 2.7 g, 6.98 mmol) and α-chloroethyl chloroformate (1.09 g, 7.65 mmol) was stirred at ambient temperature for 2.5 h, whereupon the reaction was complete as judged by TLC. The solvent was removed by evaporation in vaccuo and was replaced with methanol (40 mL). The reaction was heated at reflux until all of the newly formed intermediate was consumed as indicated by TLC. Evaporation of the solvent gave 2.49 g of N-(3-cyanophenyl)-N'-(piperidin-3-yl)cycloheptylurea; LRMS (M+H)+ m/z 299.

N-(3-cyanophenyl)-N'-((N-(benzyl)sulfonyl)piperidin-3-yl)cycloheptylurea

To N-(3-cyanophenyl)-N'-(piperidin-3-yl)cycloheptylurea (1.2 g, 4.03 mmol) and triethylamine (0.85 g, 8.46 mmol) in tetrahydrofuran (30 mL) at 0° C. was added benzylsulfonyl chloride (0.92 g, 4.83 mmol) in tetrahydrofuran solution (10 mL). The reaction was allowed to thaw to ambient temperature then stirred for 18 h. The reaction mixture was evaporated and the residue was dissolved in ethyl acetate (100 mL). The organic solution was washed with 1N sodium hydroxide solution (100 mL), 1N hydrochloric acid (100 mL) and saturated sodium hydrogen carbonate (100 mL). The solution was dried (MgSO$_4$) and evaporated to give 0.99 g (2.19 mmol) of N-(3-cyanophenyl)-N'-((N-(benzyl)-sulfonyl)piperidin-3-yl)cycloheptylurea; LRMS (M+H)$^+$ m/z=453.

N-(3-amidinophenyl)-N'-((N-(benzyl)sulfonyl)piperidin-3-yl)cycloheptylurea

To a −78° C. saturated solution of hydrogen chloride gas in dry chloroform (20 mL) and methanol(10 mL) was added 0.99 g (2.19 mmol) of N-(3-cyanophenyl)-N'-((N-(benzyl)-sulfonyl)piperidin-3-yl)cycloheptylurea in chloroform (5 mL). The reaction vessel was stoppered securely, was allowed to thaw to ambient temperature and was stirred 18 h. After this time the solvent was removed by evaporation in vaccuo and there was obtained 1.04 g of the imidate as the hydrogen chloride salt; LRMS (M+H)$^+$ m/z=485.

The imidate prepared above was dissolved in 2M ammonia in methanol solution (3.22 mL, 6.44 mmol). The reaction was stoppered securely and was stirred for 18 h. Following removal of the solvent and purification by HPLC (gradient elution with a mixture of 0.05% aqueous trifluoroacetic acid and 0.05% trifluoroacetic acid in acetonitrile) there was obtained 0.316 g of N-(3-amidinophenyl)-N'-((N-(benzyl)-sulfonyl)piperidin-3-yl)cycloheptylurea; HRMS (M+H)$^+$: calc.470.225587, found 470.221857.

Additionally, there was isolated as a slower eluting peak 0.066 g of the amide side product, N-(3-amidophenyl)-N'-((N-(benzyl)sulfonyl)piperidin-3-yl)cycloheptylurea.

Example 62

Preparation of N-(3-amidinophenyl)-N'-((N-(thiophen-2-vl)sulfonyl)piperidin-3-yl)cycloheptylurea This compound was prepared by the same methods used for Example 61. Starting with the common intermediate N-(3-cyanophenyl)-N'-(piperidin-3-yl)cycloheptylurea, this material was sulfonylated with (thiophen-2-yl)sulfonyl chloride using the same conditions for the sulfonylation described above. There was obtained 0.87 g of the sulfonylation product following purification by flash chromatography using a gradient of 2:1 hexane:ethyl acetate to 1:1 hexane:ethyl acetate as a gradient; LRMS (M+H)$^+$ m/z=445.

The imidate and subsequently, the amidine N-(3-amidinophenyl)-N'-((N-(thiophen-2-yl)sulfonyl)piperidin-3-yl)cycloheptylurea were obtained as described above. Following HPLC purification 0.234 g of the title compound was isolated; HRMS (M+H)$^+$: calc. 462.163359, found 462.164841.

Additionally, there was isolated as a slower eluting peak 0.045 g of the amide side product, N-(3-amidophenyl)-N'-((N-(thiophen-2-yl)sulfonyl)piperidin-3-yl)cycloheptylurea; HRMS (M+H)$^+$: calc. 463.147374, found 463.146300.

Example 63

Preparation of N-(3-amidinophenyl)-N'-(4-(2-sulfonamidophenyl)phenyl)cycloheptylurea

N-(3-cyanophenyl)-N'-(4-bromophenyl)cycloheptylurea

A mixture of 3-cyanophenyl isocyanate (3.76 g, 26.1 mmol) and 4-bromoaniline (4.5 g, 26.1 mmol) in 1:1 tetrahydrofuran:chloroform (100 mL). After 72 h at ambient temperature, product was isolated by filtration, the filtrate was washed with cold chloroform and air dried to give 6.6 g of N-(3-cyanophenyl)-N'-(4-bromophenyl)urea (21 mmol).

To 1.41 g of sodium hydride (60% suspension, 33.6 mmol) in dimethylformamide (300 mL) was added a dimethylformamide (20 mL) solution of 6.6 g of N-(3-cyanophenyl)-N'-(4-bromophenyl)urea (21 mmol). After 30 min, 1,4-dibromobutane (6.2 g, 28.6 mmol) in dimethylformamide (10 mL) was added dropwise, then the mixture was heated to 60° C. for 2 h and then was stirred at ambient temperature for 18 h. The reaction was diluted with water (700 mL) and extracted with ethyl acetate (3×100 mL). The organic solution was washed with water (5×100 mL), dried (MgSO$_4$) and evaporated. The residue was purified by flash chromatography on silica gel using an elution gradient of 5 to 10% methanol in chloroform. There was obtained 3.68 g of N-(3-cyanophenyl)-N'-(4-bromophenyl)cycloheptylurea.

N-(3-cyanophenyl)-N'-(4-(2-((N-t-butyl)sulfonamido)phenyl)phenyl)cycloheptylurea A mixture of N-(3-cyanophenyl)-N'-(4-bromophenyl)cycloheptylurea (4.0 g, 10.81 mmol), 2-((N-t-butyl)sulfonamido)phenylboronic acid (3.9 g, 15.2 mmol), tetrabutylammonium bromide (0.203 g) and sodium carbonate (2.47 g) in benzene (170 mL) was thoroughly purged with dry nitrogen gas. Tetrakis(triphenylphosphine)palladium(0) catalyst (0.635 g) was added and the mixture was heated at reflux under a nitrogen atmosphere for 18 h. The benzene solution was washed with water (3×100 mL) and brine (100 mL), then dried (MgSO$_4$) and evaporated. The crude product was triturated with n-butylchloride, filtered and air dried to give 3.92 g of N-(3-cyanophenyl)-N'-(4-(2-((N-t-butyl)sulfon-amido)phenyl)-phenyl)cycloheptylurea.

N-(3-amidinophenyl)-N'-(4-(2-sulfonamidophenyl)phenyl)cycloheptylurea

A solution of 3.0 g of N-(3-cyanophenyl)-N'-(4-(2-((N-t-butyl)sulfon-amido)phenyl)phenyl)cycloheptylurea (5.98 mmol) in dry methanol (40 mL) and dry chloroform (300 mL) was saturated with hydrogen chloride gas with ice cooling. This solution was stoppered tightly and was stirred for 18 h at ambient temperature. The solvent was removed by evaporation and the residue dissolved in 2M ammonia in methanol (60 mmol, 30 mL). This solution was stirred in a securely stoppered reaction vessel for 48 h at ambient temperature. After this time the solvent was removed in vaccuo and 2.28 g of crude product was obtained. A portion (0.735 g) of this material was purified by HPLC (gradient elution with a mixture of 0.05% aqueous trifluoroacetic acid and 0.05% trifluoroacetic acid in acetonitrile) to give 0.396 g of pure N-(3-amidinophenyl)-N'-(4-(2-sulfonamidophenyl)phenyl)cycloheptylurea; mp 163–166° C. HRMS (M+H)$^+$: calc.464.175637, found 464.177525.

Example 64

Preparation of N-(3-amidinophenyl)-N'-(5-(2-sulfonamidophenyl)pyridin-2-yl)cycloheptylurea Example 64 was prepared by a procedure similar to that used for Example 63 with the exception that 2-amino-5-bromopyridine was substituted for 4-bromoaniline in the intial step. There was obtained 0.043 g of N-(3-amidinophenyl)-N'-(5-(2-sulfonamido-phenyl)pyridin-2-yl)cycloheptylurea as a bis trifluoroacetate salt; mp 75–79° C.; HRMS (M+H)$^+$: calc. 465.170886, found 465.170759.

Example 65

Preparation of N-(3-amidinophenyl)-N'-(methyl(4-(2-sulfonamidophenyl)phenyl))cycloheptylurea N-(3-cyanophenyl)-N'-(methyl(4-bromo)phenyl)urea A mixture of 4-bromobenzyl amine (3.81 g, 20 mmol) and 3-cyanophenyl isocyanate (2.65 g, 18.4 mmol) in dimethylformamide (60 mL) was stirred at ambient temperature for 48 h. The reaction was partioned between 1N hydrochloric acid solution (200 mL) and ethyl acetate (200 mL). The ethyl acetate solution was washed with water (5×100 mL), then dried (MgSO$_4$) and evaporated to give 5.33 g of N-(3-cyanophenyl)-N'-(methyl(4-bromo)phenyl)urea.

N-(3-cyanophenyl)-N'-(methyl(4-bromophenyl)) cycloheptylurea

To 1.82 g of sodium hydride (60% suspension, 45.3 mmol) in dimethylformamide (270 mL) was added a dimethylformamide (30 mL) solution of the N-(3-cyanophenyl)-N'-(methyl(4-bromo)phenyl)urea (4.98 g g, 15.1 mmol). After 30 min, 1,4-dibromobutane (6.52 g, 30.2 mmol) in dimethylformamide (10 mL) was added dropwise, This mixture was heated to 70° C. for 3 h then cooled to ambient temperature and stirred for 48 h. The reaction was diluted with water (1 L) and extracted with ethyl acetate (4×250 mL). The organic solution was washed with water (5×150 mL), dried (MgSO$_4$) and evaporated. The residue was purified by flash chromatography on silica gel eluting with 1% methanol in chloroform. There was obtained 2.3 g of N-(3-cyanophenyl)-N'-(methyl(4-bromophenyl))cycloheptylurea.

N-(3-cyanophenyl)-N'-(methyl(4-(2-(N-t-buty) sulfonamidophenyl)phenyl))cycloheptylurea A mixture of N-(3-cyanophenyl)-N'-(methyl(4-bromophenyl))cycloheptylurea (1.24 g, 3.2 mmol), 2-((N-t-butyl)sulfonamido)phenylboronic acid (1.17 g, 4.5 mmol), tetrabutylammonium bromide (0.06 g) and sodium carbonate (0.73 g) in benzene (50 mL) and water (5 mL) was thoroughly purged with dry nitrogen gas. Tetrakis(triphenylphosphine)palladium(0) catalyst (0.188 g) was added and the mixture was heated at reflux under a nitrogen atmosphere for 18 h. The benzene solution was washed with water (3×100 mL) and brine (100 mL), then dried (MgSO$_4$) and evaporated to give 2.0 g of crude product. Recrystallization from acetone gave 0.80 g of N-(3-cyanophenyl)-N'-(methyl(4-(2-(N-t-buty)sulfonamido-phenyl)phenyl))cycloheptylurea; mp 177–179° C.

An additional 0.365 g of product was recovered from the mother liquors by silica gel chromatography using 1% methanol in chloroform as an eluent.

N-(3-cyanophenyl)-N'-(methyl(4-(2-sulfonamidophenyl)phenyl))cycloheptylurea

A solution of 1.17 g of N-(3-cyano-phenyl)-N'-(methyl (4-(2-(N-t-buty)sulfonamidophenyl)phenyl)) cycloheptylurea (2.27 mmol) in trifluoroacetic acid (30 mL) was heated at reflux for 1 h. The reaction was evaporated and the residue suspended in 10% sodium hydroxide solution (30 mL). The suspension was extracted with ethyl acetate (50 mL), the extracts were washed with 10% sodium hydroxide solution (2×25 mL) and brine (25 mL). The solution was dried (MgSO$_4$) and evaporated to give 0.72 g of crude product. This material was purified by column chromatography using a gradient of 1.5 to 2.5% methanol in chloroform. There was obtained 0.55 g of N-(3-cyanophenyl)-N'-(methyl(4-(2-sulfonamidophenyl)phenyl)) cycloheptylurea.

N-(3-amidinophenyl)-N'-(methyl(4-(2-sulfonamidophenyl)phenyl))cycloheptylurea

A solution of 0.55 g of N-(3-cyanophenyl)-N'-(methyl(4-(2-sulfonamidophenyl)phenyl))cycloheptylurea (1.2 mmol) in dry methyl acetate (70 mL) and dry methanol (0.192 g, 0.24 mL, 6.0 mmol) was cooled to 0° C. and saturated with dry hydrogen chloride gas. The reaction was stoppered tightly and stirred at ambient temperature 18 h. Precipitation of the imidate product was initiated by the addition of ethyl ether (70 mL) to the cold solution. The solid was isolated by filtration and maintained in vaccuo for 18 h to remove the last traces of hydrogen chloride gas; there was obtained 0.50 g of the imidate as the hydrogen chloride salt.

The imidate from above was stirred for 18 h in a methanol (20 mL) solution of ammonium acetate (0.462 g, 6 mmol). The reaction was evaporated and partioned between ethyl acetate (50 mL) and IN hydrochloric acid (50 mL). The ethyl acetate solution was dried and evaporated to give 0.16 g of the amide side-product. Lyophylization of the hydrochloric acid solution gave 0.39 g of the crude amidine. Purification of this material by HPLC (gradient elution with a mixture of 0.05% aqueous trifluoroacetic acid and 0.05% trifluoroacetic acid in acetonitrile) gave 0.258 g of N-(3-amidinophenyl)-N'-(methyl(4-(2-sulfonamidophenyl)phenyl)) cycloheptylurea as the trifluoroacetic acid salt; mp 90–94° C.; HRMS (M+H)$^+$ calc. 478.191671, found 478.191287.

TABLE 5

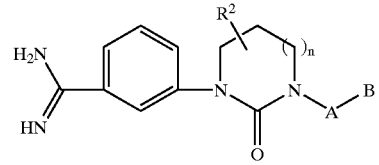

| Ex. | n | R$^2$ | A | B | HRMS (M + H)$^+$ m/z |
|---|---|---|---|---|---|
| 1 | 0 | H | 4-piperidinyl | N-benzyl | 378.229774 |
| 2 | 1 | H | 4-piperidinyl | N-benzyl | LRMS (M + H)$^+$ m/z 392 |
| 3 | 2 | H | phenyl | 4-amidino | 351.1936 |
| 4 | 2 | H | benzyl | 4-amidino | 365.209496 |
| 5 | 2 | H | 4-piperidinyl | N-(amidino) | 358.2349 |
| 6 | 2 | H | 4-piperidinyl | N-benzyl | LRMS (M + H)$^+$ m/z 406 |
| 7 | 2 | H | 4-piperidinyl | N-(1-phenethyl)) | 420.276129 |
| 8 | 2 | H | 4-piperidinyl | N-benzylsulfonyl | 470.219813 |
| 9 | 2 | H | 4-piperidinyl | N-benzoyl | 421.222804 |
| 10 | 2 | H | 4-piperidinyl | N-benzylcarbonyl | 434.255065 |
| 11 | 2 | H | 4-piperidinyl | N-phenylsulfonyl | 456.204189 |
| 12 | 2 | H | 4-piperidinyl | N-(4-acetamido-phenylsulfonyl) | 513.226577 |
| 13 | 2 | H | 4-piperidinyl | N-(2-amino-phenylsulfonyl) | 471.218097 |
| 14 | 2 | H | 4-piperidinyl | N-(3-amino-phenylsulfonyl) | 471.219532 |
| 15 | 2 | H | 4-piperidinyl | N-(4-amino-phenylsulfonyl) | 471.217059 |
| 16 | 2 | H | 4-piperidinyl | N-(2-aminophenyl-methane-sulfonyl) | 485.235037 |
| 17 | 2 | H | 4-piperidinyl | N-(2-acetamido-phenylmethane-sulfonyl) | 527.246420 |

TABLE 5-continued

| Ex. | n | R² | A | B | HRMS (M + H)⁺ m/z |
|---|---|---|---|---|---|
| 18 | 0 | —CH=CH₂ | 4-piperidinyl | N-phenylmethane-carbonyl | 418.223792 |
| 19 | 0 | —CH=CH₂ | 4-piperidinyl | N-benzylsulfonyl | 468.204978 |
| 20 | 0 | —CH=CH₂ | 4-piperidinyl | N-phenylsulfonyl | 454.191418 |

TABLE 6

| Ex. | R¹⁰ | B | HRMS (M + H)⁺ m/z |
|---|---|---|---|
| 21 | H | benzylsulfonyl | 518.221085 |
| 22 | H | 2-thiophenylsulfonyl | LRMS: m/z = 509 |
| 23 | 7,8-di-OCH₃ | benzylsulfonyl | 578.245119 |
| 24 | 7,8-di-OCH₃ | 2-thiophenylsulfonyl | 570.186900 |

TABLE 7

| Ex. | Z—A | B* | HRMS (M + H)⁺ m/z |
|---|---|---|---|
| 25 | 4-piperidinyl | 2-fluorophenylsulfonyl | 474.198031 |
| 26 | 4-piperidinyl | isopropylsulfonyl | 422.222957 |
| 27 | 4-piperidinyl | 8-quinolinylsulfonyl | 507.217649 |
| 28 | 4-piperidinyl | 1-(5-amino-4-methylthiazolyl)sulfonyl | 492.183742 |
| 29 | 4-piperidinyl | 1-(5-N-acetylamino-4-methylthiazolyl)sulfonyl | 534.193475 |

TABLE 7-continued

| Ex. | Z—A | B* | HRMS (M + H)⁺ m/z |
|---|---|---|---|
| 30 | 4-piperidinyl | (benzothiadiazolyl-SO₂-) | 514.168829 |
| 31 | 4-piperidinyl | 2-(5-chlorothiophenyl) | 497.124056 |
| 32 | 4-piperidinyl | 3-(2-carbomethoxy)thiophenylsulfonyl | 520.168929 |
| 33 | 4-piperidinyl | 2-thiophenylsulfonyl | 462.163248 |
| 34 | 4-piperidinyl | 2-carbomethoxyphenylsulfonyl | 514.212199 |
| 35 | 4-piperidinyl | 2-pyridylmethyl | 407.258632 |
| 36 | 4-piperidinyl | 3-pyridylmethyl | 407.255034 |
| 37 | 4-piperidinyl | cyclohexylaminosulfonyl | 477.2646 |
| 38 | 4-piperidinyl | isopropylaminosulfonyl | 437.2339 |
| 39 | 4-piperidinyl | phenylaminosulfonyl | 471.2182 |
| 40 | 4-piperidinyl | phenylaminocarbonyl | 435.2519 |
| 41 | 4-piperidinyl | cyclohexylaminocarbonyl | 441.2968 |
| 42 | 4-piperidinyl | phenyl-N-methylaminosulfonyl | 485.2340 |
| 43 | 4-piperidinyl | 4-pyridylmethyl | 407.255561 |
| 44 | 4-piperidinyl | 3-pyridylmethylsulfonyl | 471.218739 |
| 45 | 4-piperidinyl | 1-naphthylsulfonyl | 506.222676 |
| 46 | 4-piperidinyl | 2-naphthylsulfonyl | 506.221512 |
| 47 | 4-piperidinyl | 5-(2-phenylsulfonyl-thiophenyl)sulfonyl | 602.158636 |
| 48 | 4-piperidinyl | 3-pyridylsulfonyl | 457.204869 |
| 49 | 4-piperidinyl | 2-(4-phenylsulfonyl-thiophenyl)sulfonyl | 602.157432 |
| 50 | 4-piperidinyl | 5-(N-methylimidazolyl)sulfonyl | 460.213785 |
| 51 | 4-piperidinyl | 2-pyridylmethylsulfonyl | 471.219270 |
| 52 | 4-piperidinyl | 2-thiophenylmethyl | 412.216008 |
| 53 | 4-piperidinyl | 4-fluorophenylsulfonyl | 474.199222 |
| 54 | 4-piperidinyl | 4-fluorophenylmethylsulfonyl | 488.210708 |
| 53 | 4-piperidinyl | 3,5-bistrifluoromethyl-phenylsulfonyl | 592.181914 |
| 54 | 4-piperidinyl | 2-trifluoromethylphenylsulfonyl | 524.193512 |
| 55 | 4-piperidinyl | 2-pyridylsulfonyl | 457.202166 |
| 56 | 4-piperidinyl | (1,1-dimethyl-1-phenyl)methylsulfonyl | 498.252412 |
| 57 | 3-morpholinyl-methyl | N-(benzylcarbonyl) | 450.251817 |
| 58 | 3-morpholinyl-methyl | N-(thiophen-2-ylsulfonyl) | 478.156983 |
| 59 | 3-morpholinyl-methyl | N-(benzylsulfonyl) | 486.217928 |
| 60 | 3-piperidinyl | N-benzyl | 406.259064 |
| 61 | 3-piperidinyl | N-(benzylsulfonyl) | 470.221857 |
| 62 | 3-piperidinyl | N-(thiophenylsulfonyl) | 462.164841 |
| 63 | phenyl | 2-sulfonamidophenyl | 464.177525 |
| 64 | 2-pyridyl | 2-sulfonamidophenyl | 465.170759 |
| 65 | benzyl | 2-sulfonamidophenyl | 478.191287 |

*Unless otherwise indicated, group B is substituted on A para to Z, if present, and the cyclourea.

TABLE 8

Structure: H2N-C(=NH)-phenyl-N(ring with R² at position, (CH2)n)-N-Z-pyridyl(A1,A2)-B, with C=O in ring

| Ex. | n | R² | Z | A¹ | A² | B |
|---|---|---|---|---|---|---|
| 101 | 0 | H | bond | CH | CH | amino |
| 102 | 0 | H | bond | CH | CH | amidino |
| 103 | 0 | H | bond | CH | CH | guanidino |
| 104 | 0 | H | bond | CH | CH | 2-sulfamidophenyl |
| 105 | 0 | H | bond | CH | CH | 2-trifluoromethylphenyl |
| 106 | 0 | OH | bond | CH | CH | amino |
| 107 | 0 | OH | bond | CH | CH | amidino |
| 108 | 0 | OH | bond | CH | CH | guanidino |
| 109 | 0 | OH | bond | CH | CH | 2-sulfamidophenyl |
| 110 | 0 | OH | bond | CH | CH | 2-trifluoromethylphenyl |
| 111 | 0 | NHC(O)CH$_3$ | bond | CH | CH | amino |
| 112 | 0 | NHC(O)CH$_3$ | bond | CH | CH | amidino |
| 113 | 0 | NHC(O)CH$_3$ | bond | CH | CH | guanidino |
| 114 | 0 | NHC(O)CH$_3$ | bond | CH | CH | 2-sulfamidophenyl |
| 115 | 0 | NHC(O)CH$_3$ | bond | CH | CH | 2-trifluoromethylphenyl |
| 116 | 0 | NHSO$_2$CH$_3$ | bond | CH | CH | amino |
| 117 | 0 | NHSO$_2$CH$_3$ | bond | CH | CH | amidino |
| 118 | 0 | NHSO$_2$CH$_3$ | bond | CH | CH | guanidino |
| 119 | 0 | NHSO$_2$CH$_3$ | bond | CH | CH | 2-sulfamidophenyl |
| 120 | 0 | NHSO$_2$CH$_3$ | bond | CH | CH | 2-trifluoromethylphenyl |
| 121 | 0 | OCH$_3$ | bond | CH | CH | amino |
| 122 | 0 | OCH$_3$ | bond | CH | CH | amidino |
| 123 | 0 | OCH$_3$ | bond | CH | CH | guanidino |
| 123 | 0 | OCH$_3$ | bond | CH | CH | 2-sulfamidophenyl |
| 125 | 0 | OCH$_3$ | bond | CH | CH | 2-trifluoromethylphenyl |
| 126 | 0 | OCH$_2$C$_6$H$_5$ | bond | CH | CH | amino |
| 127 | 0 | OCH$_2$C$_6$H$_5$ | bond | CH | CH | amidino |
| 128 | 0 | OCH$_2$C$_6$H$_5$ | bond | CH | CH | guanidino |
| 129 | 0 | OCH$_2$C$_6$H$_5$ | bond | CH | CH | 2-sulfamidophenyl |
| 130 | 0 | OCH$_2$C$_6$H$_5$ | bond | CH | CH | 2-trifluoromethylphenyl |
| 131 | 0 | H | CH$_2$ | CH | CH | amino |
| 132 | 0 | H | CH$_2$ | CH | CH | amidino |
| 133 | 0 | H | CH$_2$ | CH | CH | guanidino |
| 134 | 0 | H | CH$_2$ | CH | CH | 2-sulfamidophenyl |
| 135 | 0 | H | CH$_2$ | CH | CH | 2-trifluoromethylphenyl |
| 136 | 0 | OH | CH$_2$ | CH | CH | amino |
| 137 | 0 | OH | CH$_2$ | CH | CH | amidino |
| 138 | 0 | OH | CH$_2$ | CH | CH | guanidino |
| 139 | 0 | OH | CH$_2$ | CH | CH | 2-sulfamidophenyl |
| 140 | 0 | OH | CH$_2$ | CH | CH | 2-trifluoromethylphenyl |
| 141 | 0 | NHC(O)CH$_3$ | CH$_2$ | CH | CH | amino |
| 142 | 0 | NHC(O)CH$_3$ | CH$_2$ | CH | CH | amidino |
| 143 | 0 | NHC(O)CH$_3$ | CH$_2$ | CH | CH | guanidino |
| 144 | 0 | NHC(O)CH$_3$ | CH$_2$ | CH | CH | 2-sulfamidophenyl |
| 145 | 0 | NHC(O)CH$_3$ | CH$_2$ | CH | CH | 2-trifluoromethylphenyl |
| 146 | 0 | NHSO$_2$CH$_3$ | CH$_2$ | CH | CH | amino |
| 147 | 0 | NHSO$_2$CH$_3$ | CH$_2$ | CH | CH | amidino |
| 148 | 0 | NHSO$_2$CH$_3$ | CH$_2$ | CH | CH | guanidino |
| 149 | 0 | NHSO$_2$CH$_3$ | CH$_2$ | CH | CH | 2-sulfamidophenyl |
| 150 | 0 | NHSO$_2$CH$_3$ | CH$_2$ | CH | CH | 2-trifluoromethylphenyl |
| 151 | 0 | OCH$_3$ | CH$_2$ | CH | CH | amino |
| 152 | 0 | OCH$_3$ | CH$_2$ | CH | CH | amidino |
| 153 | 0 | OCH$_3$ | CH$_2$ | CH | CH | guanidino |
| 154 | 0 | OCH$_3$ | CH$_2$ | CH | CH | 2-sulfamidophenyl |
| 155 | 0 | OCH$_3$ | CH$_2$ | CH | CH | 2-trifluoromethylphenyl |
| 156 | 0 | OCH$_2$C$_6$H$_5$ | CH$_2$ | CH | CH | amino |
| 157 | 0 | OCH$_2$C$_6$H$_5$ | CH$_2$ | CH | CH | amidino |
| 158 | 0 | OCH$_2$C$_6$H$_5$ | CH$_2$ | CH | CH | guanidino |
| 159 | 0 | OCH$_2$C$_6$H$_5$ | CH$_2$ | CH | CH | 2-sulfamidophenyl |
| 160 | 0 | OCH$_2$C$_6$H$_5$ | CH$_2$ | CH | CH | 2-trifluoromethylphenyl |
| 161 | 0 | H | bond | N | CH | amino |
| 162 | 0 | H | bond | N | CH | amidino |
| 163 | 0 | H | bond | N | CH | guanidino |
| 164 | 0 | H | bond | N | CH | 2-sulfamidophenyl |
| 165 | 0 | H | bond | N | CH | 2-trifluoromethylphenyl |
| 166 | 0 | OH | bond | N | CH | amino |
| 167 | 0 | OH | bond | N | CH | amidino |
| 168 | 0 | OH | bond | N | CH | guanidino |
| 169 | 0 | OH | bond | N | CH | 2-sulfamidophenyl |
| 170 | 0 | OH | bond | N | CH | 2-trifluoromethylphenyl |
| 171 | 0 | NHC(O)CH$_3$ | bond | N | CH | amino |
| 172 | 0 | NHC(O)CH$_3$ | bond | N | CH | amidino |
| 173 | 0 | NHC(O)CH$_3$ | bond | N | CH | guanidino |
| 174 | 0 | NHC(O)CH$_3$ | bond | N | CH | 2-sulfamidophenyl |
| 175 | 0 | NHC(O)CH$_3$ | bond | N | CH | 2-trifluoromethylphenyl |
| 176 | 0 | NHSO$_2$CH$_3$ | bond | N | CH | amino |
| 177 | 0 | NHSO$_2$CH$_3$ | bond | N | CH | amidino |
| 178 | 0 | NHSO$_2$CH$_3$ | bond | N | CH | guanidino |
| 179 | 0 | NHSO$_2$CH$_3$ | bond | N | CH | 2-sulfamidophenyl |
| 180 | 0 | NHSO$_2$CH$_3$ | bond | N | CH | 2-trifluoromethylphenyl |
| 181 | 0 | OCH$_3$ | bond | N | CH | amino |
| 182 | 0 | OCH$_3$ | bond | N | CH | amidino |
| 183 | 0 | OCH$_3$ | bond | N | CH | guanidino |
| 184 | 0 | OCH$_3$ | bond | N | CH | 2-sulfamidophenyl |
| 185 | 0 | OCH$_3$ | bond | N | CH | 2-trifluoromethylphenyl |
| 186 | 0 | OCH$_2$C$_6$H$_5$ | bond | N | CH | amino |
| 187 | 0 | OCH$_2$C$_6$H$_5$ | bond | N | CH | amidino |
| 188 | 0 | OCH$_2$C$_6$H$_5$ | bond | N | CH | guanidino |
| 189 | 0 | OCH$_2$C$_6$H$_5$ | bond | N | CH | 2-sulfamidophenyl |
| 190 | 0 | OCH$_2$C$_6$H$_5$ | bond | N | CH | 2-trifluoromethylphenyl |
| 191 | 0 | H | CH$_2$ | N | CH | amino |
| 192 | 0 | H | CH$_2$ | N | CH | amidino |
| 193 | 0 | H | CH$_2$ | N | CH | guanidino |
| 194 | 0 | H | CH$_2$ | N | CH | 2-sulfamidophenyl |
| 195 | 0 | H | CH$_2$ | N | CH | 2-trifluoromethylphenyl |
| 196 | 0 | OH | CH$_2$ | N | CH | amino |
| 197 | 0 | OH | CH$_2$ | N | CH | amidino |
| 198 | 0 | OH | CH$_2$ | N | CH | guanidino |
| 199 | 0 | OH | CH$_2$ | N | CH | 2-sulfamidophenyl |
| 200 | 0 | OH | CH$_2$ | N | CH | 2-trifluoromethylphenyl |
| 201 | 0 | NHC(O)CH$_3$ | CH$_2$ | N | CH | amino |
| 202 | 0 | NHC(O)CH$_3$ | CH$_2$ | N | CH | amidino |
| 203 | 0 | NHC(O)CH$_3$ | CH$_2$ | N | CH | guanidino |
| 204 | 0 | NHC(O)CH$_3$ | CH$_2$ | N | CH | 2-sulfamidophenyl |
| 205 | 0 | NHC(O)CH$_3$ | CH$_2$ | N | CH | 2-trifluoromethylphenyl |
| 206 | 0 | NHSO$_2$CH$_3$ | CH$_2$ | N | CH | amino |
| 207 | 0 | NHSO$_2$CH$_3$ | CH$_2$ | N | CH | amidino |
| 208 | 0 | NHSO$_2$CH$_3$ | CH$_2$ | N | CH | guanidino |
| 209 | 0 | NHSO$_2$CH$_3$ | CH$_2$ | N | CH | 2-sulfamidophenyl |
| 210 | 0 | NHSO$_2$CH$_3$ | CH$_2$ | N | CH | 2-trifluoromethylphenyl |
| 211 | 0 | OCH$_3$ | CH$_2$ | N | CH | amino |
| 212 | 0 | OCH$_3$ | CH$_2$ | N | CH | amidino |
| 213 | 0 | OCH$_3$ | CH$_2$ | N | CH | guanidino |
| 214 | 0 | OCH$_3$ | CH$_2$ | N | CH | 2-sulfamidophenyl |
| 215 | 0 | OCH$_3$ | CH$_2$ | N | CH | 2-trifluoromethylphenyl |
| 216 | 0 | OCH$_2$C$_6$H$_5$ | CH$_2$ | N | CH | amino |
| 217 | 0 | OCH$_2$C$_6$H$_5$ | CH$_2$ | N | CH | amidino |
| 218 | 0 | OCH$_2$C$_6$H$_5$ | CH$_2$ | N | CH | guanidino |
| 219 | 0 | OCH$_2$C$_6$H$_5$ | CH$_2$ | N | CH | 2-sulfamidophenyl |
| 220 | 0 | OCH$_2$C$_6$H$_5$ | CH$_2$ | N | CH | 2-trifluoromethylphenyl |
| 221 | 0 | H | bond | N | N | amino |
| 222 | 0 | H | bond | N | N | amidino |
| 223 | 0 | H | bond | N | N | guanidino |
| 224 | 0 | H | bond | N | N | 2-sulfamidophenyl |
| 225 | 0 | H | bond | N | N | 2-trifluoromethylphenyl |
| 226 | 0 | OH | bond | N | N | amino |
| 227 | 0 | OH | bond | N | N | amidino |
| 228 | 0 | OH | bond | N | N | guanidino |
| 229 | 0 | OH | bond | N | N | 2-sulfamidophenyl |
| 230 | 0 | OH | bond | N | N | 2-trifluoromethylphenyl |
| 231 | 0 | NHC(O)CH$_3$ | bond | N | N | amino |
| 232 | 0 | NHC(O)CH$_3$ | bond | N | N | amidino |
| 233 | 0 | NHC(O)CH$_3$ | bond | N | N | guanidino |
| 234 | 0 | NHC(O)CH$_3$ | bond | N | N | 2-sulfamidophenyl |
| 235 | 0 | NHC(O)CH$_3$ | bond | N | N | 2-trifluoromethylphenyl |
| 236 | 0 | NHSO$_2$CH$_3$ | bond | N | N | amino |

TABLE 8-continued

![Structure: H2N-C(=NH)-phenyl-N(ring with R2, n CH2 groups)-C(=O)-N-Z-pyridyl(A1,A2)-B]

| Ex. | n | R² | Z | A¹ | A² | B |
|---|---|---|---|---|---|---|
| 237 | 0 | NHSO$_2$CH$_3$ | bond | N | N | amidino |
| 238 | 0 | NHSO$_2$CH$_3$ | bond | N | N | guanidino |
| 239 | 0 | NHSO$_2$CH$_3$ | bond | N | N | 2-sulfamidophenyl |
| 240 | 0 | NHSO$_2$CH$_3$ | bond | N | N | 2-trifluoromethylphenyl |
| 241 | 0 | OCH$_3$ | bond | N | N | amino |
| 242 | 0 | OCH$_3$ | bond | N | N | amidino |
| 243 | 0 | OCH$_3$ | bond | N | N | guanidino |
| 244 | 0 | OCH$_3$ | bond | N | N | 2-sulfamidophenyl |
| 245 | 0 | OCH$_3$ | bond | N | N | 2-trifluoromethylphenyl |
| 246 | 0 | OCH$_2$C$_6$H$_5$ | bond | N | N | amino |
| 247 | 0 | OCH$_2$C$_6$H$_5$ | bond | N | N | amidino |
| 248 | 0 | OCH$_2$C$_6$H$_5$ | bond | N | N | guanidino |
| 249 | 0 | OCH$_2$C$_6$H$_5$ | bond | N | N | 2-sulfamidophenyl |
| 250 | 0 | OCH$_2$C$_6$H$_5$ | bond | N | N | 2-trifluoromethylphenyl |
| 251 | 0 | H | CH$_2$ | N | N | amino |
| 252 | 0 | H | CH$_2$ | N | N | amidino |
| 253 | 0 | H | CH$_2$ | N | N | guanidino |
| 254 | 0 | H | CH$_2$ | N | N | 2-sulfamidophenyl |
| 255 | 0 | H | CH$_2$ | N | N | 2-trifluoromethylphenyl |
| 256 | 0 | OH | CH$_2$ | N | N | amino |
| 257 | 0 | OH | CH$_2$ | N | N | amidino |
| 258 | 0 | OH | CH$_2$ | N | N | guanidino |
| 259 | 0 | OH | CH$_2$ | N | N | 2-sulfamidophenyl |
| 260 | 0 | OH | CH$_2$ | N | N | 2-trifluoromethylphenyl |
| 261 | 0 | NHC(O)CH$_3$ | CH$_2$ | N | N | amino |
| 262 | 0 | NHC(O)CH$_3$ | CH$_2$ | N | N | amidino |
| 263 | 0 | NHC(O)CH$_3$ | CH$_2$ | N | N | guanidino |
| 264 | 0 | NHC(O)CH$_3$ | CH$_2$ | N | N | 2-sulfamidophenyl |
| 265 | 0 | NHC(O)CH$_3$ | CH$_2$ | N | N | 2-trifluoromethylphenyl |
| 266 | 0 | NHSO$_2$CH$_3$ | CH$_2$ | N | N | amino |
| 267 | 0 | NHSO$_2$CH$_3$ | CH$_2$ | N | N | amidino |
| 268 | 0 | NHSO$_2$CH$_3$ | CH$_2$ | N | N | guanidino |
| 269 | 0 | NHSO$_2$CH$_3$ | CH$_2$ | N | N | 2-sulfamidophenyl |
| 270 | 0 | NHSO$_2$CH$_3$ | CH$_2$ | N | N | 2-trifluoromethylphenyl |
| 271 | 0 | OCH$_3$ | CH$_2$ | N | N | amino |
| 272 | 0 | OCH$_3$ | CH$_2$ | N | N | amidino |
| 273 | 0 | OCH$_3$ | CH$_2$ | N | N | guanidino |
| 274 | 0 | OCH$_3$ | CH$_2$ | N | N | 2-sulfamidophenyl |
| 275 | 0 | OCH$_3$ | CH$_2$ | N | N | 2-trifluoromethylphenyl |
| 276 | 0 | OCH$_2$C$_6$H$_5$ | CH$_2$ | N | N | amino |
| 277 | 0 | OCH$_2$C$_6$H$_5$ | CH$_2$ | N | N | amidino |
| 278 | 0 | OCH$_2$C$_6$H$_5$ | CH$_2$ | N | N | guanidino |
| 279 | 0 | OCH$_2$C$_6$H$_5$ | CH$_2$ | N | N | 2-sulfamidophenyl |
| 280 | 0 | OCH$_2$C$_6$H$_5$ | CH$_2$ | N | N | 2-trifluoromethylphenyl |

TABLE 9

![Structure: H2N-C(=NH)-phenyl-N(ring with R2, n CH2 groups)-C(=O)-N-Z-pyridyl(A1,A2)-B]

| Ex. | n | R² | Z | A¹ | A² | B |
|---|---|---|---|---|---|---|
| 301 | 1 | H | bond | CH | CH | amino |
| 302 | 1 | H | bond | CH | CH | amidino |
| 303 | 1 | H | bond | CH | CH | guanidino |
| 304 | 1 | H | bond | CH | CH | 2-sulfamidophenyl |
| 305 | 1 | H | bond | CH | CH | 2-trifluoromethylphenyl |
| 306 | 1 | OH | bond | CH | CH | amino |
| 307 | 1 | OH | bond | CH | CH | amidino |
| 308 | 1 | OH | bond | CH | CH | guanidino |
| 309 | 1 | OH | bond | CH | CH | 2-sulfamidophenyl |
| 310 | 1 | OH | bond | CH | CH | 2-trifluoromethylphenyl |
| 311 | 1 | NHC(O)CH$_3$ | bond | CH | CH | amino |
| 312 | 1 | NHC(O)CH$_3$ | bond | CH | CH | amidino |
| 313 | 1 | NHC(O)CH$_3$ | bond | CH | CH | guanidino |
| 314 | 1 | NHC(O)CH$_3$ | bond | CH | CH | 2-sulfamidophenyl |
| 315 | 1 | NHC(O)CH$_3$ | bond | CH | CH | 2-trifluoromethylphenyl |
| 316 | 1 | NHSO$_2$CH$_3$ | bond | CH | CH | amino |
| 317 | 1 | NHSO$_2$CH$_3$ | bond | CH | CH | amidino |
| 318 | 1 | NHSO$_2$CH$_3$ | bond | CH | CH | guanidino |
| 319 | 1 | NHSO$_2$CH$_3$ | bond | CH | CH | 2-sulfamidophenyl |
| 320 | 1 | NHSO$_2$CH$_3$ | bond | CH | CH | 2-trifluoromethylphenyl |
| 321 | 1 | OCH$_3$ | bond | CH | CH | amino |
| 322 | 1 | OCH$_3$ | bond | CH | CH | amidino |
| 323 | 1 | OCH$_3$ | bond | CH | CH | guanidino |
| 324 | 1 | OCH$_3$ | bond | CH | CH | 2-sulfamidophenyl |
| 325 | 1 | OCH$_3$ | bond | CH | CH | 2-trifluoromethylphenyl |
| 326 | 1 | OCH$_2$C$_6$H$_5$ | bond | CH | CH | amino |
| 327 | 1 | OCH$_2$C$_6$H$_5$ | bond | CH | CH | amidino |
| 328 | 1 | OCH$_2$C$_6$H$_5$ | bond | CH | CH | guanidino |
| 329 | 1 | OCH$_2$C$_6$H$_5$ | bond | CH | CH | 2-sulfamidophenyl |
| 330 | 1 | OCH$_2$C$_6$H$_5$ | bond | CH | CH | 2-trifluoromethylphenyl |
| 331 | 1 | H | CH$_2$ | CH | CH | amino |
| 332 | 1 | H | CH$_2$ | CH | CH | amidino |
| 333 | 1 | H | CH$_2$ | CH | CH | guanidino |
| 334 | 1 | H | CH$_2$ | CH | CH | 2-sulfamidophenyl |
| 335 | 1 | H | CH$_2$ | CH | CH | 2-trifluoromethylphenyl |
| 336 | 1 | OH | CH$_2$ | CH | CH | amino |
| 337 | 1 | OH | CH$_2$ | CH | CH | amidino |
| 338 | 1 | OH | CH$_2$ | CH | CH | guanidino |
| 339 | 1 | OH | CH$_2$ | CH | CH | 2-sulfamidophenyl |
| 340 | 1 | OH | CH$_2$ | CH | CH | 2-trifluoromethylphenyl |
| 341 | 1 | NHC(O)CH$_3$ | CH$_2$ | CH | CH | amino |
| 342 | 1 | NHC(O)CH$_3$ | CH$_2$ | CH | CH | amidino |
| 343 | 1 | NHC(O)CH$_3$ | CH$_2$ | CH | CH | guanidino |
| 344 | 1 | NHC(O)CH$_3$ | CH$_2$ | CH | CH | 2-sulfamidophenyl |
| 345 | 1 | NHC(O)CH$_3$ | CH$_2$ | CH | CH | 2-trifluoromethylphenyl |
| 346 | 1 | NHSO$_2$CH$_3$ | CH$_2$ | CH | CH | amino |
| 347 | 1 | NHSO$_2$CH$_3$ | CH$_2$ | CH | CH | amidino |
| 348 | 1 | NHSO$_2$CH$_3$ | CH$_2$ | CH | CH | guanidino |
| 349 | 1 | NHSO$_2$CH$_3$ | CH$_2$ | CH | CH | 2-sulfamidophenyl |
| 350 | 1 | NHSO$_2$CH$_3$ | CH$_2$ | CH | CH | 2-trifluoromethylphenyl |
| 351 | 1 | OCH$_3$ | CH$_2$ | CH | CH | amino |
| 352 | 1 | OCH$_3$ | CH$_2$ | CH | CH | amidino |
| 353 | 1 | OCH$_3$ | CH$_2$ | CH | CH | guanidino |
| 354 | 1 | OCH$_3$ | CH$_2$ | CH | CH | 2-sulfamidophenyl |
| 355 | 1 | OCH$_3$ | CH$_2$ | CH | CH | 2-trifluoromethylphenyl |
| 356 | 1 | OCH$_2$C$_6$H$_5$ | CH$_2$ | CH | CH | amino |
| 357 | 1 | OCH$_2$C$_6$H$_5$ | CH$_2$ | CH | CH | amidino |
| 358 | 1 | OCH$_2$C$_6$H$_5$ | CH$_2$ | CH | CH | guanidino |
| 359 | 1 | OCH$_2$C$_6$H$_5$ | CH$_2$ | CH | CH | 2-sulfamidophenyl |
| 360 | 1 | OCH$_2$C$_6$H$_5$ | CH$_2$ | CH | CH | 2-trifluoromethylphenyl |
| 361 | 1 | H | bond | N | CH | amino |
| 362 | 1 | H | bond | N | CH | amidino |
| 363 | 1 | H | bond | N | CH | guanidino |
| 364 | 1 | H | bond | N | CH | 2-sulfamidophenyl |
| 365 | 1 | H | bond | N | CH | 2-trifluoromethylphenyl |
| 366 | 1 | OH | bond | N | CH | amino |
| 367 | 1 | OH | bond | N | CH | amidino |
| 368 | 1 | OH | bond | N | CH | guanidino |
| 369 | 1 | OH | bond | N | CH | 2-sulfamidophenyl |
| 370 | 1 | OH | bond | N | CH | 2-trifluoromethylphenyl |
| 371 | 1 | NHC(O)CH$_3$ | bond | N | CH | amino |
| 372 | 1 | NHC(O)CH$_3$ | bond | N | CH | amidino |
| 373 | 1 | NHC(O)CH$_3$ | bond | N | CH | guanidino |
| 374 | 1 | NHC(O)CH$_3$ | bond | N | CH | 2-sulfamidophenyl |
| 375 | 1 | NHC(O)CH$_3$ | bond | N | CH | 2-trifluoromethylphenyl |

TABLE 9-continued

| Ex. | n | R² | Z | A¹ | A² | B |
|---|---|---|---|---|---|---|
| 376 | 1 | NHSO₂CH₃ | bond | N | CH | amino |
| 377 | 1 | NHSO₂CH₃ | bond | N | CH | amidino |
| 378 | 1 | NHSO₂CH₃ | bond | N | CH | guanidino |
| 379 | 1 | NHSO₂CH₃ | bond | N | CH | 2-sulfamidophenyl |
| 380 | 1 | NHSO₂CH₃ | bond | N | CH | 2-trifluoromethylphenyl |
| 381 | 1 | OCH₃ | bond | N | CH | amino |
| 382 | 1 | OCH₃ | bond | N | CH | amidino |
| 383 | 1 | OCH₃ | bond | N | CH | guanidino |
| 384 | 1 | OCH₃ | bond | N | CH | 2-sulfamidophenyl |
| 385 | 1 | OCH₃ | bond | N | CH | 2-trifluoromethylphenyl |
| 386 | 1 | OCH₂C₆H₅ | bond | N | CH | amino |
| 387 | 1 | OCH₂C₆H₅ | bond | N | CH | amidino |
| 388 | 1 | OCH₂C₆H₅ | bond | N | CH | guanidino |
| 389 | 1 | OCH₂C₆H₅ | bond | N | CH | 2-sulfamidophenyl |
| 390 | 1 | OCH₂C₆H₅ | bond | N | CH | 2-trifluoromethylphenyl |
| 391 | 1 | H | CH₂ | N | CH | amino |
| 392 | 1 | H | CH₂ | N | CH | amidino |
| 393 | 1 | H | CH₂ | N | CH | guanidino |
| 394 | 1 | H | CH₂ | N | CH | 2-sulfamidophenyl |
| 395 | 1 | H | CH₂ | N | CH | 2-trifluoromethylphenyl |
| 396 | 1 | OH | CH₂ | N | CH | amino |
| 397 | 1 | OH | CH₂ | N | CH | amidino |
| 398 | 1 | OH | CH₂ | N | CH | guanidino |
| 399 | 1 | OH | CH₂ | N | CH | 2-sulfamidophenyl |
| 400 | 1 | OH | CH₂ | N | CH | 2-trifluoromethylphenyl |
| 401 | 1 | NHC(O)CH₃ | CH₂ | N | CH | amino |
| 402 | 1 | NHC(O)CH₃ | CH₂ | N | CH | amidino |
| 403 | 1 | NHC(O)CH₃ | CH₂ | N | CH | guanidino |
| 404 | 1 | NHC(O)CH₃ | CH₂ | N | CH | 2-sulfamidophenyl |
| 405 | 1 | NHC(O)CH₃ | CH₂ | N | CH | 2-trifluoromethylphenyl |
| 406 | 1 | NHSO₂CH₃ | CH₂ | N | CH | amino |
| 407 | 1 | NHSO₂CH₃ | CH₂ | N | CH | amidino |
| 408 | 1 | NHSO₂CH₃ | CH₂ | N | CH | guanidino |
| 409 | 1 | NHSO₂CH₃ | CH₂ | N | CH | 2-sulfamidophenyl |
| 410 | 1 | NHSO₂CH₃ | CH₂ | N | CH | 2-trifluoromethylphenyl |
| 411 | 1 | OCH₃ | CH₂ | N | CH | amino |
| 412 | 1 | OCH₃ | CH₂ | N | CH | amidino |
| 413 | 1 | OCH₃ | CH₂ | N | CH | guanidino |
| 414 | 1 | OCH₃ | CH₂ | N | CH | 2-sulfamidophenyl |
| 415 | 1 | OCH₃ | CH₂ | N | CH | 2-trifluoromethylphenyl |
| 416 | 1 | OCH₂C₆H₅ | CH₂ | N | CH | amino |
| 417 | 1 | OCH₂C₆H₅ | CH₂ | N | CH | amidino |
| 418 | 1 | OCH₂C₆H₅ | CH₂ | N | CH | guanidino |
| 419 | 1 | OCH₂C₆H₅ | CH₂ | N | CH | 2-sulfamidophenyl |
| 420 | 1 | OCH₂C₆H₅ | CH₂ | N | CH | 2-trifluoromethylphenyl |
| 421 | 1 | H | bond | N | N | amino |
| 422 | 1 | H | bond | N | N | amidino |
| 423 | 1 | H | bond | N | N | guanidino |
| 424 | 1 | H | bond | N | N | 2-sulfamidophenyl |
| 425 | 1 | H | bond | N | N | 2-trifluoromethylphenyl |
| 426 | 1 | OH | bond | N | N | amino |
| 427 | 1 | OH | bond | N | N | amidino |
| 428 | 1 | OH | bond | N | N | guanidino |
| 429 | 1 | OH | bond | N | N | 2-sulfamidophenyl |
| 430 | 1 | OH | bond | N | N | 2-trifluoromethylphenyl |
| 431 | 1 | NHC(O)CH₃ | bond | N | N | amino |
| 432 | 1 | NHC(O)CH₃ | bond | N | N | amidino |
| 433 | 1 | NHC(O)CH₃ | bond | N | N | guanidino |
| 434 | 1 | NHC(O)CH₃ | bond | N | N | 2-sulfamidophenyl |
| 435 | 1 | NHC(O)CH₃ | bond | N | N | 2-trifluoromethylphenyl |
| 436 | 1 | NHSO₂CH₃ | bond | N | N | amino |
| 437 | 1 | NHSO₂CH₃ | bond | N | N | amidino |
| 438 | 1 | NHSO₂CH₃ | bond | N | N | guanidino |
| 439 | 1 | NHSO₂CH₃ | bond | N | N | 2-sulfamidophenyl |
| 440 | 1 | NHSO₂CH₃ | bond | N | N | 2-trifluoromethylphenyl |
| 441 | 1 | OCH₃ | bond | N | N | amino |
| 442 | 1 | OCH₃ | bond | N | N | amidino |
| 443 | 1 | OCH₃ | bond | N | N | guanidino |
| 444 | 1 | OCH₃ | bond | N | N | 2-sulfamidophenyl |
| 445 | 1 | OCH₃ | bond | N | N | 2-trifluoromethylphenyl |
| 446 | 1 | OCH₂C₆H₅ | bond | N | N | amino |
| 447 | 1 | OCH₂C₆H₅ | bond | N | N | amidino |
| 448 | 1 | OCH₂C₆H₅ | bond | N | N | guanidino |
| 449 | 1 | OCH₂C₆H₅ | bond | N | N | 2-sulfamidophenyl |
| 450 | 1 | OCH₂C₆H₅ | bond | N | N | 2-trifluoromethylphenyl |
| 451 | 1 | H | CH₂ | N | N | amino |
| 452 | 1 | H | CH₂ | N | N | amidino |
| 453 | 1 | H | CH₂ | N | N | guanidino |
| 454 | 1 | H | CH₂ | N | N | 2-sulfamidophenyl |
| 455 | 1 | H | CH₂ | N | N | 2-trifluoromethylphenyl |
| 456 | 1 | OH | CH₂ | N | N | amino |
| 457 | 1 | OH | CH₂ | N | N | amidino |
| 458 | 1 | OH | CH₂ | N | N | guanidino |
| 459 | 1 | OH | CH₂ | N | N | 2-sulfamidophenyl |
| 460 | 1 | CH | CH₂ | N | N | 2-trifluoromethylphenyl |
| 461 | 1 | NHC(O)CH₃ | CH₂ | N | N | amino |
| 462 | 1 | NHC(O)CH₃ | CH₂ | N | N | amidino |
| 463 | 1 | NHC(O)CH₃ | CH₂ | N | N | guanidino |
| 464 | 1 | NHC(O)CH₃ | CH₂ | N | N | 2-sulfamidophenyl |
| 465 | 1 | NHC(O)CH₃ | CH₂ | N | N | 2-trifluoromethylphenyl |
| 466 | 1 | NHSO₂CH₃ | CH₂ | N | N | amino |
| 467 | 1 | NHSO₂CH₃ | CH₂ | N | N | amidino |
| 468 | 1 | NHSO₂CH₃ | CH₂ | N | N | guanidino |
| 469 | 1 | NHSO₂CH₃ | CH₂ | N | N | 2-sulfamidophenyl |
| 470 | 1 | NHSO₂CH₃ | CH₂ | N | N | 2-trifluoromethylphenyl |
| 471 | 1 | OCH₃ | CH₂ | N | N | amino |
| 472 | 1 | OCH₃ | CH₂ | N | N | amidino |
| 473 | 1 | OCH₃ | CH₂ | N | N | guanidino |
| 474 | 1 | OCH₃ | CH₂ | N | N | 2-sulfamidophenyl |
| 475 | 1 | OCH₃ | CH₂ | N | N | 2-trifluoromethylphenyl |
| 476 | 1 | OCH₂C₆H₅ | CH₂ | N | N | amino |
| 477 | 1 | OCH₂C₆H₅ | CH₂ | N | N | amidino |
| 478 | 1 | OCH₂C₆H₅ | CH₂ | N | N | guanidino |
| 479 | 1 | OCH₂C₆H₅ | CH₂ | N | N | 2-sulfamidophenyl |
| 480 | 1 | OCH₂C₆H₅ | CH₂ | N | N | 2-trifluoromethylphenyl |

TABLE 10

| Ex. | n | R² | Z | A¹ | A² | B |
|---|---|---|---|---|---|---|
| 501 | 2 | H | bond | CH | CH | amino |
| 502 | 2 | H | bond | CH | CH | guanidino |
| 503 | 2 | H | bond | CH | CH | 2-sulfamidophenyl |
| 504 | 2 | H | bond | CH | CH | 2-trifluoromethylphenyl |
| 505 | 2 | OH | bond | CH | CH | amino |
| 506 | 2 | OH | bond | CH | CH | amidino |
| 507 | 2 | OH | bond | CH | CH | guanidino |
| 508 | 2 | OH | bond | CH | CH | 2-sulfamidophenyl |
| 509 | 2 | OH | bond | CH | CH | 2-trifluoromethylphenyl |
| 510 | 2 | NHC(O)CH₃ | bond | CH | CH | amino |
| 511 | 2 | NHC(O)CH₃ | bond | CH | CH | amidino |
| 512 | 2 | NHC(O)CH₃ | bond | CH | CH | guanidino |
| 513 | 2 | NHC(O)CH₃ | bond | CH | CH | 2-sulfamidophenyl |
| 514 | 2 | NHC(O)CH₃ | bond | CH | CH | 2-trifluoromethylphenyl |

TABLE 10-continued

| Ex. | n | R² | Z | A¹ | A² | B |
|---|---|---|---|---|---|---|
| 515 | 2 | NHSO₂CH₃ | bond | CH | CH | amino |
| 516 | 2 | NHSO₂CH₃ | bond | CH | CH | amidino |
| 517 | 2 | NHSO₂CH₃ | bond | CH | CH | guanidino |
| 518 | 2 | NHSO₂CH₃ | bond | CH | CH | 2-sulfamidophenyl |
| 519 | 2 | NHSO₂CH₃ | bond | CH | CH | 2-trifluoromethylphenyl |
| 520 | 2 | OCH₃ | bond | CH | CH | amino |
| 521 | 2 | OCH₃ | bond | CH | CH | amidino |
| 522 | 2 | OCH₃ | bond | CH | CH | guanidino |
| 523 | 2 | OCH₃ | bond | CH | CH | 2-sulfamidophenyl |
| 524 | 2 | OCH₃ | bond | CH | CH | 2-trifluoromethylphenyl |
| 525 | 2 | OCH₂C₆H₅ | bond | CH | CH | amino |
| 526 | 2 | OCH₂C₆H₅ | bond | CH | CH | amidino |
| 527 | 2 | OCH₂C₆H₅ | bond | CH | CH | guanidino |
| 528 | 2 | OCH₂C₆H₅ | bond | CH | CH | 2-sulfamidophenyl |
| 529 | 2 | OCH₂C₆H₅ | bond | CH | CH | 2-trifluoromethylphenyl |
| 530 | 2 | H | CH₂ | CH | CH | amino |
| 531 | 2 | H | CH₂ | CH | CH | guanidino |
| 532 | 2 | H | CH₂ | CH | CH | 2-sulfamidophenyl |
| 533 | 2 | H | CH₂ | CH | CH | 2-trifluoromethylphenyl |
| 534 | 2 | OH | CH₂ | CH | CH | amino |
| 535 | 2 | OH | CH₂ | CH | CH | amidino |
| 536 | 2 | OH | CH₂ | CH | CH | guanidino |
| 537 | 2 | OH | CH₂ | CH | CH | 2-sulfamidophenyl |
| 538 | 2 | OH | CH₂ | CH | CH | 2-trifluoromethylphenyl |
| 539 | 2 | NHC(O)CH₃ | CH₂ | CH | CH | amino |
| 540 | 2 | NHC(O)CH₃ | CH₂ | CH | CH | amidino |
| 541 | 2 | NHC(O)CH₃ | CH₂ | CH | CH | guanidino |
| 542 | 2 | NHC(O)CH₃ | CH₂ | CH | CH | 2-sulfamidophenyl |
| 543 | 2 | NHC(O)CH₃ | CH₂ | CH | CH | 2-trifluoromethylphenyl |
| 544 | 2 | NHSO₂CH₃ | CH₂ | CH | CH | amino |
| 545 | 2 | NHSO₂CH₃ | CH₂ | CH | CH | amidino |
| 546 | 2 | NHSO₂CH₃ | CH₂ | CH | CH | guanidino |
| 547 | 2 | NHSO₂CH₃ | CH₂ | CH | CH | 2-sulfamidophenyl |
| 548 | 2 | NHSO₂CH₃ | CH₂ | CH | CH | 2-trifluoromethylphenyl |
| 549 | 2 | OCH₃ | CH₂ | CH | CH | amino |
| 550 | 2 | OCH₃ | CH₂ | CH | CH | amidino |
| 551 | 2 | OCH₃ | CH₂ | CH | CH | guanidino |
| 552 | 2 | OCH₃ | CH₂ | CH | CH | 2-sulfamidophenyl |
| 553 | 2 | OCH₃ | CH₂ | CH | CH | 2-trifluoromethylphenyl |
| 554 | 2 | OCH₂C₆H₅ | CH₂ | CH | CH | amino |
| 555 | 2 | OCH₂C₆H₅ | CH₂ | CH | CH | amidino |
| 556 | 2 | OCH₂C₆H₅ | CH₂ | CH | CH | guanidino |
| 557 | 2 | OCH₂C₆H₅ | CH₂ | CH | CH | 2-sulfamidophenyl |
| 558 | 2 | OCH₂C₆H₅ | CH₂ | CH | CH | 2-trifluoromethylphenyl |
| 559 | 2 | H | bond | N | CH | amino |
| 560 | 2 | H | bond | N | CH | amidino |
| 561 | 2 | H | bond | N | CH | guanidino |
| 562 | 2 | H | bond | N | CH | 2-sulfamidophenyl |
| 563 | 2 | H | bond | N | CH | 2-trifluoromethylphenyl |
| 564 | 2 | OH | bond | N | CH | amino |
| 565 | 2 | OH | bond | N | CH | amidino |
| 566 | 2 | OH | bond | N | CH | guanidino |
| 567 | 2 | OH | bond | N | CH | 2-sulfamidophenyl |
| 568 | 2 | OH | bond | N | CH | 2-trifluoromethylphenyl |
| 569 | 2 | NHC(O)CH₃ | bond | N | CH | amino |
| 570 | 2 | NHC(O)CH₃ | bond | N | CH | amidino |
| 571 | 2 | NHC(O)CH₃ | bond | N | CH | guanidino |
| 572 | 2 | NHC(O)CH₃ | bond | N | CH | 2-sulfamidophenyl |
| 573 | 2 | NHC(O)CH₃ | bond | N | CH | 2-trifluoromethylphenyl |
| 574 | 2 | NHSO₂CH₃ | bond | N | CH | amino |
| 575 | 2 | NHSO₂CH₃ | bond | N | CH | amidino |
| 576 | 2 | NHSO₂CH₃ | bond | N | CH | guanidino |
| 577 | 2 | NHSO₂CH₃ | bond | N | CH | 2-sulfamidophenyl |
| 578 | 2 | NHSO₂CH₃ | bond | N | CH | 2-trifluoromethylphenyl |
| 579 | 2 | OCH₃ | bond | N | CH | amino |
| 580 | 2 | OCH₃ | bond | N | CH | amidino |
| 581 | 2 | OCH₃ | bond | N | CH | guanidino |
| 582 | 2 | OCH₃ | bond | N | CH | 2-sulfamidophenyl |
| 583 | 2 | OCH₃ | bond | N | CH | 2-trifluoromethylphenyl |
| 584 | 2 | OCH₂C₆H₅ | bond | N | CH | amino |
| 585 | 2 | OCH₂C₆H₅ | bond | N | CH | amidino |
| 586 | 2 | OCH₂C₆H₅ | bond | N | CH | guanidino |
| 587 | 2 | OCH₂C₆H₅ | bond | N | CH | 2-sulfamidophenyl |
| 588 | 2 | OCH₂C₆H₅ | bond | N | CH | 2-trifluoromethylphenyl |
| 589 | 2 | H | CH₂ | N | CH | amino |
| 590 | 2 | H | CH₂ | N | CH | amidino |
| 591 | 2 | H | CH₂ | N | CH | guanidino |
| 592 | 2 | H | CH₂ | N | CH | 2-sulfamidophenyl |
| 593 | 2 | H | CH₂ | N | CH | 2-trifluoromethylphenyl |
| 594 | 2 | OH | CH₂ | N | CH | amino |
| 595 | 2 | OH | CH₂ | N | CH | amidino |
| 596 | 2 | OH | CH₂ | N | CH | guanidino |
| 597 | 2 | OH | CH₂ | N | CH | 2-sulfamidophenyl |
| 598 | 2 | OH | CH₂ | N | CH | 2-trifluoromethylphenyl |
| 599 | 2 | NHC(O)CH₃ | CH₂ | N | CH | amino |
| 600 | 2 | NHC(O)CH₃ | CH₂ | N | CH | amidino |
| 601 | 2 | NHC(O)CH₃ | CH₂ | N | CH | guanidino |
| 602 | 2 | NHC(O)CH₃ | CH₂ | N | CH | 2-sulfamidophenyl |
| 603 | 2 | NHC(O)CH₃ | CH₂ | N | CH | 2-trifluoromethylphenyl |
| 604 | 2 | NHSO₂CH₃ | CH₂ | N | CH | amino |
| 605 | 2 | NHSO₂CH₃ | CH₂ | N | CH | amidino |
| 606 | 2 | NHSO₂CH₃ | CH₂ | N | CH | guanidino |
| 607 | 2 | NHSO₂CH₃ | CH₂ | N | CH | 2-sulfamidophenyl |
| 608 | 2 | NHSO₂CH₃ | CH₂ | N | CH | 2-trifluoromethylphenyl |
| 609 | 2 | OCH₃ | CH₂ | N | CH | amino |
| 610 | 2 | OCH₃ | CH₂ | N | CH | amidino |
| 611 | 2 | OCH₃ | CH₂ | N | CH | guanidino |
| 612 | 2 | OCH₃ | CH₂ | N | CH | 2-sulfamidophenyl |
| 613 | 2 | OCH₃ | CH₂ | N | CH | 2-trifluoromethylphenyl |
| 614 | 2 | OCH₂C₆H₅ | CH₂ | N | CH | amino |
| 615 | 2 | OCH₂C₆H₅ | CH₂ | N | CH | amidino |
| 616 | 2 | OCH₂C₆H₅ | CH₂ | N | CH | guanidino |
| 617 | 2 | OCH₂C₆H₅ | CH₂ | N | CH | 2-sulfamidophenyl |
| 618 | 2 | OCH₂C₆H₅ | CH₂ | N | CH | 2-trifluoromethylphenyl |
| 619 | 2 | H | bond | N | N | amino |
| 620 | 2 | H | bond | N | N | amidino |
| 621 | 2 | H | bond | N | N | guanidino |
| 622 | 2 | H | bond | N | N | 2-sulfamidophenyl |
| 623 | 2 | H | bond | N | N | 2-trifluoromethylphenyl |
| 624 | 2 | OH | bond | N | N | amino |
| 625 | 2 | OH | bond | N | N | amidino |
| 626 | 2 | OH | bond | N | N | guanidino |
| 627 | 2 | OH | bond | N | N | 2-sulfamidophenyl |
| 628 | 2 | OH | bond | N | N | 2-trifluoromethylphenyl |
| 629 | 2 | NHC(O)CH₃ | bond | N | N | amino |
| 630 | 2 | NHC(O)CH₃ | bond | N | N | amidino |
| 631 | 2 | NHC(O)CH₃ | bond | N | N | guanidino |
| 632 | 2 | NHC(O)CH₃ | bond | N | N | 2-sulfamidophenyl |
| 633 | 2 | NHC(O)CH₃ | bond | N | N | 2-trifluoromethylphenyl |
| 634 | 2 | NHSO₂CH₃ | bond | N | N | amino |
| 635 | 2 | NHSO₂CH₃ | bond | N | N | amidino |
| 636 | 2 | NHSO₂CH₃ | bond | N | N | guanidino |
| 637 | 2 | NHSO₂CH₃ | bond | N | N | 2-sulfamidophenyl |
| 638 | 2 | NHSO₂CH₃ | bond | N | N | 2-trifluoromethylphenyl |
| 639 | 2 | OCH₃ | bond | N | N | amino |
| 640 | 2 | OCH₃ | bond | N | N | amidino |
| 641 | 2 | OCH₃ | bond | N | N | guanidino |
| 642 | 2 | OCH₃ | bond | N | N | 2-sulfamidophenyl |
| 643 | 2 | OCH₃ | bond | N | N | 2-trifluoromethylphenyl |
| 644 | 2 | OCH₂C₆H₅ | bond | N | N | amino |
| 645 | 2 | OCH₂C₆H₅ | bond | N | N | amidino |
| 646 | 2 | OCH₂C₆H₅ | bond | N | N | guanidino |
| 647 | 2 | OCH₂C₆H₅ | bond | N | N | 2-sulfamidophenyl |
| 648 | 2 | OCH₂C₆H₅ | bond | N | N | 2-trifluoromethylphenyl |
| 649 | 2 | H | CH₂ | N | N | amino |
| 650 | 2 | H | CH₂ | N | N | amidino |

TABLE 10-continued

| Ex. | n | R² | Z | A¹ | A² | B |
|---|---|---|---|---|---|---|
| 651 | 2 | H | CH₂ | N | N | guanidino |
| 652 | 2 | H | CH₂ | N | N | 2-sulfamidophenyl |
| 653 | 2 | H | CH₂ | N | N | 2-trifluoromethylphenyl |
| 654 | 2 | OH | CH₂ | N | N | amino |
| 655 | 2 | OH | CH₂ | N | N | amidino |
| 656 | 2 | OH | CH₂ | N | N | guanidino |
| 657 | 2 | OH | CH₂ | N | N | 2-sulfamidophenyl |
| 658 | 2 | OH | CH₂ | N | N | 2-trifluoromethylphenyl |
| 659 | 2 | NHC(O)CH₃ | CH₂ | N | N | amino |
| 660 | 2 | NHC(O)CH₃ | CH₂ | N | N | amidino |
| 661 | 2 | NHC(O)CH₃ | CH₂ | N | N | guanidino |
| 662 | 2 | NHC(O)CH₃ | CH₂ | N | N | 2-sulfamidophenyl |
| 663 | 2 | NHC(O)CH₃ | CH₂ | N | N | 2-trifluoromethylphenyl |
| 664 | 2 | NHSO₂CH₃ | CH₂ | N | N | amino |
| 665 | 2 | NHSO₂CH₃ | CH₂ | N | N | amidino |
| 666 | 2 | NHSO₂CH₃ | CH₂ | N | N | guanidino |
| 667 | 2 | NHSO₂CH₃ | CH₂ | N | N | 2-sulfamidophenyl |
| 668 | 2 | NHSO₂CH₃ | CH₂ | N | N | 2-trifluoromethylphenyl |
| 669 | 2 | OCH₃ | CH₂ | N | N | amino |
| 670 | 2 | OCH₃ | CH₂ | N | N | amidino |
| 671 | 2 | OCH₃ | CH₂ | N | N | guanidino |
| 672 | 2 | OCH₃ | CH₂ | N | N | 2-sulfamidophenyl |
| 673 | 2 | OCH₃ | CH₂ | N | N | 2-trifluoromethylphenyl |
| 674 | 2 | OCH₂C₆H₅ | CH₂ | N | N | amino |
| 675 | 2 | OCH₂C₆H₅ | CH₂ | N | N | amidino |
| 676 | 2 | OCH₂C₆H₅ | CH₂ | N | N | guanidino |
| 677 | 2 | OCH₂C₆H₅ | CH₂ | N | N | 2-sulfamidophenyl |
| 678 | 2 | OCH₂C₆H₅ | CH₂ | N | N | 2-trifluoromethylphenyl |

TABLE 11

| Ex. | n | R² | Z | A¹ | A² | B |
|---|---|---|---|---|---|---|
| 701 | 0 | H | bond | CH | CH | imidazol-1-yl |
| 702 | 0 | H | bond | CH | CH | morpholin-1-yl |
| 703 | 0 | H | bond | CH | CH | 2-methylimidazol-1-yl |
| 704 | 0 | H | bond | CH | CH | pyridin-3-yl |
| 705 | 0 | H | bond | CH | CH | 2-(5'-trifluoromethyl)tetrazol-1'-yl |
| 706 | 0 | H | bond | CH | CH | pyrazol-1-yl |
| 707 | 0 | H | bond | CH | CH | phenyl |
| 708 | 0 | H | bond | CH | CH | cyclohexyl |
| 709 | 0 | H | bond | CH | CH | N,N-dimethylsulfamido |
| 710 | 0 | H | bond | CH | CH | N,N-dimethylamido |
| 711 | 0 | H | bond | N | CH | imidazol-1-yl |
| 712 | 0 | H | bond | N | CH | morpholin-1-yl |
| 713 | 0 | H | bond | N | CH | 2-methylimidazol-1-yl |
| 714 | 0 | H | bond | N | CH | pyridin-3-yl |
| 715 | 0 | H | bond | N | CH | 2-(5'-trifluoromethyl)tetrazol-1'-yl |
| 716 | 0 | H | bond | N | CH | pyrazol-1-yl |
| 717 | 0 | H | bond | N | CH | phenyl |
| 718 | 0 | H | bond | N | CH | cyclohexyl |
| 719 | 0 | H | bond | N | CH | N,N-dimethylsulfamido |
| 720 | 0 | H | bond | N | CH | N,N-dimethylamido |
| 721 | 0 | H | bond | N | N | imidazol-1-yl |
| 722 | 0 | H | bond | N | N | morpholin-1-yl |
| 723 | 0 | H | bond | N | N | 2-methylimidazol-1-yl |
| 724 | 0 | H | bond | N | N | pyridin-3-yl |
| 725 | 0 | H | bond | N | N | 2-(5'-trifluoromethyl)tetrazol-1'-yl |
| 726 | 0 | H | bond | N | N | pyrazol-1-yl |
| 727 | 0 | H | bond | N | N | phenyl |
| 728 | 0 | H | bond | N | N | cyclohexyl |
| 729 | 0 | H | bond | N | N | N,N-dimethylsulfamido |
| 730 | 0 | H | bond | N | N | N,N-dimethylamido |
| 731 | 0 | H | bond | F | CH | imidazol-1-yl |
| 732 | 0 | H | bond | F | CH | morpholin-1-yl |
| 733 | 0 | H | bond | F | CH | 2-methylimidazol-1-yl |
| 734 | 0 | H | bond | F | CH | pyridin-3-yl |
| 735 | 0 | H | bond | F | CH | 2-(5'-trifluoromethyl)tetrazol-1'-yl |
| 736 | 0 | H | bond | F | CH | pyrazol-1-yl |
| 737 | 0 | H | bond | F | CH | phenyl |
| 738 | 0 | H | bond | F | CH | cyclohexyl |
| 739 | 0 | H | bond | F | CH | N,N-dimethylsulfamido |
| 740 | 0 | H | bond | F | CH | N,N-dimethylamido |
| 741 | 0 | H | bond | Cl | CH | imidazol-1-yl |
| 742 | 0 | H | bond | Cl | CH | morpholin-1-yl |
| 743 | 0 | H | bond | Cl | CH | 2-methylimidazol-1-yl |
| 744 | 0 | H | bond | Cl | CH | pyridin-3-yl |
| 745 | 0 | H | bond | Cl | CH | 2-(5'-trifluoromethyl)tetrazol-1'-yl |
| 746 | 0 | H | bond | Cl | CH | pyrazol-1-yl |
| 747 | 0 | H | bond | Cl | CH | phenyl |
| 748 | 0 | H | bond | Cl | CH | cyclohexyl |
| 749 | 0 | H | bond | Cl | CH | N,N-dimethylsulfamido |
| 750 | 0 | H | bond | Cl | CH | N,N-dimethylamido |
| 751 | 0 | H | bond | Br | CH | imidazol-1-yl |
| 752 | 0 | H | bond | Br | CH | morpholin-1-yl |
| 753 | 0 | H | bond | Br | CH | 2-methylimidazol-1-yl |
| 754 | 0 | H | bond | Br | CH | pyridin-3-yl |
| 755 | 0 | H | bond | Br | CH | 2-(5'-trifluoromethyl)tetrazol-1'-yl |
| 756 | 0 | H | bond | Br | CH | pyrazol-1-yl |
| 757 | 0 | H | bond | Br | CH | phenyl |
| 758 | 0 | H | bond | Br | CH | cyclohexyl |
| 759 | 0 | H | bond | Br | CH | N,N-dimethylsulfamido |
| 760 | 0 | H | bond | Br | CH | N,N-dimethylamido |
| 761 | 0 | H | CH₂ | CH | CH | imidazol-1-yl |
| 762 | 0 | H | CH₂ | CH | CH | morpholin-1-yl |
| 763 | 0 | H | CH₂ | CH | CH | 2-methylimidazol-1-yl |
| 764 | 0 | H | CH₂ | CH | CH | pyridin-3-yl |
| 765 | 0 | H | CH₂ | CH | CH | 2-(5'-trifluoromethyl)tetrazol-1'-yl |
| 766 | 0 | H | CH₂ | CH | CH | pyrazol-1-yl |
| 767 | 0 | H | CH₂ | CH | CH | phenyl |
| 768 | 0 | H | CH₂ | CH | CH | cyclohexyl |
| 769 | 0 | H | CH₂ | CH | CH | N,N-dimethylsulfamido |
| 770 | 0 | H | CH₂ | CH | CH | N,N-dimethylamido |
| 771 | 0 | H | CH₂ | N | CH | imidazol-1-yl |
| 772 | 0 | H | CH₂ | N | CH | morpholin-1-yl |
| 773 | 0 | H | CH₂ | N | CH | 2-methylimidazol-1-yl |
| 774 | 0 | H | CH₂ | N | CH | pyridin-3-yl |
| 775 | 0 | H | CH₂ | N | CH | 2-(5'-trifluoromethyl)tetrazol-1'-yl |
| 776 | 0 | H | CH₂ | N | CH | pyrazol-1-yl |
| 777 | 0 | H | CH₂ | N | CH | phenyl |
| 778 | 0 | H | CH₂ | N | CH | cyclohexyl |
| 779 | 0 | H | CH₂ | N | CH | N,N-dimethylsulfamido |
| 780 | 0 | H | CH₂ | N | CH | N,N-dimethylamido |
| 781 | 0 | H | CH₂ | N | N | imidazol-1-yl |
| 782 | 0 | H | CH₂ | N | N | morpholin-1-yl |
| 783 | 0 | H | CH₂ | N | N | 2-methylimidazol-1-yl |

TABLE 11-continued

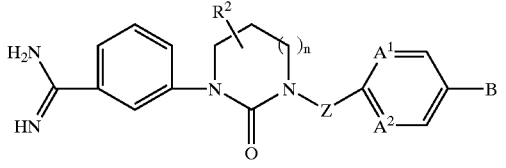

| Ex. | n | R² | Z | A¹ | A² | B |
|---|---|---|---|---|---|---|
| 784 | 0 | H | CH₂ | N | N | pyridin-3-yl |
| 785 | 0 | H | CH₂ | N | N | 2-(5'-trifluoromethyl)tetrazol-1'-yl |
| 786 | 0 | H | CH₂ | N | N | pyrazol-1-yl |
| 787 | 0 | H | CH₂ | N | N | phenyl |
| 788 | 0 | H | CH₂ | N | N | cyclohexyl |
| 789 | 0 | H | CH₂ | N | N | N,N-dimethylsulfamido |
| 790 | 0 | H | CH₂ | N | N | N,N-dimethylamido |
| 791 | 0 | H | CH₂ | F | CH | imidazol-1-yl |
| 792 | 0 | H | CH₂ | F | CH | morpholin-1-yl |
| 793 | 0 | H | CH₂ | F | CH | 2-methylimidazol-1-yl |
| 794 | 0 | H | CH₂ | F | CH | pyridin-3-yl |
| 795 | 0 | H | CH₂ | F | CH | 2-(5'-trifluoromethyl)tetrazol-1'-yl |
| 796 | 0 | H | CH₂ | F | CH | pyrazol-1-yl |
| 797 | 0 | H | CH₂ | F | CH | phenyl |
| 798 | 0 | H | CH₂ | F | CH | cyclohexyl |
| 799 | 0 | H | CH₂ | F | CH | N,N-dimethylsulfamido |
| 800 | 0 | H | CH₂ | F | CH | N,N-dimethylamido |
| 801 | 0 | H | CH₂ | Cl | CH | imidazol-1-yl |
| 802 | 0 | H | CH₂ | Cl | CH | morpholin-1-yl |
| 803 | 0 | H | CH₂ | Cl | CH | 2-methylimidazol-1-yl |
| 804 | 0 | H | CH₂ | Cl | CH | pyridin-3-yl |
| 805 | 0 | H | CH₂ | Cl | CH | 2-(5'-trifluoromethyl)tetrazol-1'-yl |
| 806 | 0 | H | CH₂ | Cl | CH | pyrazol-1-yl |
| 807 | 0 | H | CH₂ | Cl | CH | phenyl |
| 808 | 0 | H | CH₂ | Cl | CH | cyclohexyl |
| 809 | 0 | H | CH₂ | Cl | CH | N,N-dimethylsulfamido |
| 810 | 0 | H | CH₂ | Cl | CH | N,N-dimethylamido |
| 811 | 0 | H | CH₂ | Br | CH | imidazol-1-yl |
| 812 | 0 | H | CH₂ | Br | CH | morpholin-1-yl |
| 813 | 0 | H | CH₂ | Br | CH | 2-methylimidazol-1-yl |
| 814 | 0 | H | CH₂ | Br | CH | pyridin-3-yl |
| 815 | 0 | H | CH₂ | Br | CH | 2-(5'-trifluoromethyl)tetrazol-1'-yl |
| 816 | 0 | H | CH₂ | Br | CH | pyrazol-1-yl |
| 817 | 0 | H | CH₂ | Br | CH | phenyl |
| 818 | 0 | H | CH₂ | Br | CH | cyclohexyl |
| 819 | 0 | H | CH₂ | Br | CH | N,N-dimethylsulfamido |
| 820 | 0 | H | CH₂ | Br | CH | N,N-dimethylamido |
| 821 | 0 | OH | bond | F | CH | pyrazol-1-yl |
| 822 | 0 | OH | bond | F | CH | phenyl |
| 823 | 0 | OH | bond | F | CH | cyclohexyl |
| 824 | 0 | OH | bond | F | CH | N,N-dimethylsulfamido |
| 825 | 0 | OH | bond | F | CH | N,N-dimethylamido |
| 826 | 0 | NHC(O)CH₃ | bond | Cl | CH | imidazol-1-yl |
| 827 | 0 | NHC(O)CH₃ | bond | Cl | CH | morpholin-1-yl |
| 828 | 0 | NHC(O)CH₃ | bond | Cl | CH | 2-methylimidazol-1-yl |
| 829 | 0 | NHC(O)CH₃ | bond | Cl | CH | pyridin-3-yl |
| 830 | 0 | NHC(O)CH₃ | bond | Cl | CH | 2-(5'-trifluoromethyl)tetrazol-1'-yl |
| 831 | 0 | NHSO₂CH₃ | bond | Cl | CH | pyrazol-1-yl |
| 832 | 0 | NHSO₂CH₃ | bond | Cl | CH | phenyl |
| 833 | 0 | NHSO₂CH₃ | bond | Cl | CH | cyclohexyl |
| 834 | 0 | NHSO₂CH₃ | bond | Cl | CH | N,N-dimethylsulfamido |
| 835 | 0 | NHSO₂CH₃ | bond | Cl | CH | N,N-dimethylamido |
| 836 | 0 | OCH₃ | bond | Br | CH | imidazol-1-yl |
| 837 | 0 | OCH₃ | bond | Br | CH | morpholin-1-yl |
| 838 | 0 | OCH₃ | bond | Br | CH | 2-methylimidazol-1-yl |
| 839 | 0 | OCH₃ | bond | Br | CH | pyridin-3-yl |
| 840 | 0 | OCH₃ | bond | Br | CH | 2-(5'-trifluoromethyl)tetrazol-1'-yl |
| 841 | 0 | OCH₂C₆H₅ | bond | Br | CH | pyrazol-1-yl |
| 842 | 0 | OCH₂C₆H₅ | bond | Br | CH | phenyl |
| 843 | 0 | OCH₂C₆H₅ | bond | Br | CH | cyclohexyl |
| 844 | 0 | OCH₂C₆H₅ | bond | Br | CH | N,N-dimethylsulfamido |
| 845 | 0 | OCH₂C₆H₅ | bond | Br | CH | N,N-dimethylamido |
| 846 | 0 | OH | CH₂ | CH | CH | pyrazol-1-yl |
| 847 | 0 | OH | CH₂ | CH | CH | phenyl |
| 848 | 0 | OH | CH₂ | CH | CH | cyclohexyl |
| 849 | 0 | OH | CH₂ | CH | CH | N,N-dimethylsulfamido |
| 850 | 0 | OH | CH₂ | CH | CH | N,N-dimethylamido |
| 851 | 0 | NHC(O)CH₃ | CH₂ | N | CH | imidazol-1-yl |
| 852 | 0 | NHC(O)CH₃ | CH₂ | N | CH | morpholin-1-yl |
| 853 | 0 | NHC(O)CH₃ | CH₂ | N | CH | 2-methylimidazol-1-yl |
| 854 | 0 | NHC(O)CH₃ | CH₂ | N | CH | pyridin-3-yl |
| 855 | 0 | NHC(O)CH₃ | CH₂ | N | CH | 2-(5'-trifluoromethyl)tetrazol-1'-yl |
| 856 | 0 | NHSO₂CH₃ | CH₂ | N | CH | pyrazol-1-yl |
| 857 | 0 | NHSO₂CH₃ | CH₂ | N | CH | phenyl |
| 858 | 0 | NHSO₂CH₃ | CH₂ | N | CH | cyclohexyl |
| 859 | 0 | NHSO₂CH₃ | CH₂ | N | CH | N,N-dimethylsulfamido |
| 860 | 0 | NHSO₂CH₃ | CH₂ | N | CH | N,N-dimethylamido |
| 861 | 0 | OCH₃ | CH₂ | N | N | imidazol-1-yl |
| 862 | 0 | OCH₃ | CH₂ | N | N | morpholin-1-yl |
| 863 | 0 | OCH₃ | CH₂ | N | N | 2-methylimidazol-1-yl |
| 864 | 0 | OCH₃ | CH₂ | N | N | pyridin-3-yl |
| 865 | 0 | OCH₃ | CH₂ | N | N | 2-(5'-trifluoromethyl)tetrazol-1'-yl |
| 866 | 0 | OCH₂C₆H₅ | CH₂ | N | N | pyrazol-1-yl |
| 867 | 0 | OCH₂C₆H₅ | CH₂ | N | N | phenyl |
| 868 | 0 | OCH₂C₆H₅ | CH₂ | N | N | cyclohexyl |
| 869 | 0 | OCH₂C₆H₅ | CH₂ | N | N | N,N-dimethylsulfamido |
| 870 | 0 | OCH₂C₆H₅ | CH₂ | N | N | N,N-dimethylamido |

TABLE 12

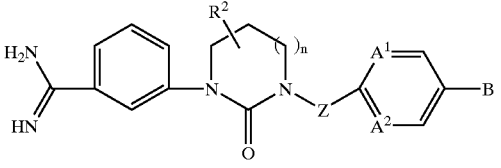

| Ex. | n | R² | Z | A¹ | A² | B |
|---|---|---|---|---|---|---|
| 901 | 1 | H | bond | CH | CH | imidazol-1-yl |
| 902 | 1 | H | bond | CH | CH | morpholin-1-yl |
| 903 | 1 | H | bond | CH | CH | 2-methylimidazol-1-yl |
| 904 | 1 | H | bond | CH | CH | pyridin-3-yl |
| 905 | 1 | H | bond | CH | CH | 2-(5'-trifluoromethyl)tetrazol-1'-yl |
| 906 | 1 | H | bond | CH | CH | pyrazol-1-yl |
| 907 | 1 | H | bond | CH | CH | phenyl |
| 908 | 1 | H | bond | CH | CH | cyclohexyl |
| 909 | 1 | H | bond | CH | CH | N,N-dimethylsulfamido |
| 910 | 1 | H | bond | CH | CH | N,N-dimethylamido |
| 911 | 1 | H | bond | N | CH | imidazol-1-yl |
| 912 | 1 | H | bond | N | CH | morpholin-1-yl |
| 913 | 1 | H | bond | N | CH | 2-methylimidazol-1-yl |
| 914 | 1 | H | bond | N | CH | pyridin-3-yl |
| 915 | 1 | H | bond | N | CH | 2-(5'-trifluoromethyl)tetrazol-1'-yl |
| 916 | 1 | H | bond | N | CH | pyrazol-1-yl |
| 917 | 1 | H | bond | N | CH | phenyl |
| 918 | 1 | H | bond | N | CH | cyclohexyl |
| 919 | 1 | H | bond | N | CH | N,N-dimethylsulfamido |
| 920 | 1 | H | bond | N | CH | N,N-dimethylamido |
| 921 | 1 | H | bond | N | N | imidazol-1-yl |
| 922 | 1 | H | bond | N | N | morpholin-1-yl |

TABLE 12-continued

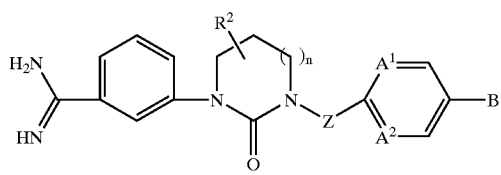

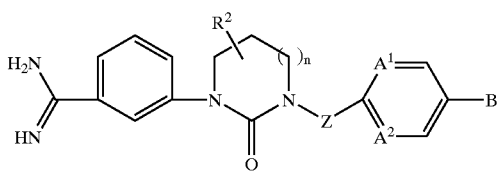

| Ex. | n | R² | Z | A¹ | A² | B |
|---|---|---|---|---|---|---|
| 923 | 1 | H | bond | N | N | 2-methylimidazol-1-yl |
| 924 | 1 | H | bond | N | N | pyridin-3-yl |
| 925 | 1 | H | bond | N | N | 2-(5'-trifluoromethyl)tetrazol-1'-yl |
| 926 | 1 | H | bond | N | N | pyrazol-1-yl |
| 927 | 1 | H | bond | N | N | phenyl |
| 928 | 1 | H | bond | N | N | cyclohexyl |
| 929 | 1 | H | bond | N | N | N,N-dimethylsulfamido |
| 930 | 1 | H | bond | N | N | N,N-dimethylamido |
| 931 | 1 | H | bond | F | CH | imidazol-1-yl |
| 932 | 1 | H | bond | F | CH | morpholin-1-yl |
| 933 | 1 | H | bond | F | CH | 2-methylimidazol-1-yl |
| 934 | 1 | H | bond | F | CH | pyridin-3-yl |
| 935 | 1 | H | bond | F | CH | 2-(5'-trifluoromethyl)tetrazol-1'-yl |
| 936 | 1 | H | bond | F | CH | pyrazol-1-yl |
| 937 | 1 | H | bond | F | CH | phenyl |
| 938 | 1 | H | bond | F | CH | cyclohexyl |
| 939 | 1 | H | bond | F | CH | N,N-dimethylsulfamido |
| 940 | 1 | H | bond | F | CH | N,N-dimethylamido |
| 941 | 1 | H | bond | Cl | CH | imidazol-1-yl |
| 942 | 1 | H | bond | Cl | CH | morpholin-1-yl |
| 943 | 1 | H | bond | Cl | CH | 2-methylimidazol-1-yl |
| 944 | 1 | H | bond | Cl | CH | pyridin-3-yl |
| 945 | 1 | H | bond | Cl | CH | 2-(5'-trifluoromethyl)tetrazol-1'-yl |
| 946 | 1 | H | bond | Cl | CH | pyrazol-1-yl |
| 947 | 1 | H | bond | Cl | CH | phenyl |
| 948 | 1 | H | bond | Cl | CH | cyclohexyl |
| 949 | 1 | H | bond | Cl | CH | N,N-dimethylsulfamido |
| 950 | 1 | H | bond | Cl | CH | N,N-dimethylamido |
| 951 | 1 | H | bond | Br | CH | imidazol-1-yl |
| 952 | 1 | H | bond | Br | CH | morpholin-1-yl |
| 953 | 1 | H | bond | Br | CH | 2-methylimidazol-1-yl |
| 954 | 1 | H | bond | Br | CH | pyridin-3-yl |
| 955 | 1 | H | bond | Br | CH | 2-(5'-trifluoromethyl)tetrazol-1'-yl |
| 956 | 1 | H | bond | Br | CH | pyrazol-1-yl |
| 957 | 1 | H | bond | Br | CH | phenyl |
| 958 | 1 | H | bond | Br | CH | cyclohexyl |
| 959 | 1 | H | bond | Br | CH | N,N-dimethylsulfamido |
| 960 | 1 | H | bond | Br | CH | N,N-dimethylamido |
| 961 | 1 | H | $CH_2$ | CH | CH | imidazol-1-yl |
| 962 | 1 | H | $CH_2$ | CH | CH | morpholin-1-yl |
| 963 | 1 | H | $CH_2$ | CH | CH | 2-methylimidazol-1-yl |
| 964 | 1 | H | $CH_2$ | CH | CH | pyridin-3-yl |
| 965 | 1 | H | $CH_2$ | CH | CH | 2-(5'-trifluoromethyl)tetrazol-1'-yl |
| 966 | 1 | H | $CH_2$ | CH | CH | pyrazol-1-yl |
| 967 | 1 | H | $CH_2$ | CH | CH | phenyl |
| 968 | 1 | H | $CH_2$ | CH | CH | cyclohexyl |
| 969 | 1 | H | $CH_2$ | CH | CH | N,N-dimethylsulfamido |
| 970 | 1 | H | $CH_2$ | CH | CH | N,N-dimethylamido |
| 971 | 1 | H | $CH_2$ | N | CH | imidazol-1-yl |
| 972 | 1 | H | $CH_2$ | N | CH | morpholin-1-yl |
| 973 | 1 | H | $CH_2$ | N | CH | 2-methylimidazol-1-yl |
| 974 | 1 | H | $CH_2$ | N | CH | pyridin-3-yl |
| 975 | 1 | H | $CH_2$ | N | CH | 2-(5'-trifluoromethyl)tetrazol-1'-yl |
| 976 | 1 | H | $CH_2$ | N | CH | pyrazol-1-yl |
| 977 | 1 | H | $CH_2$ | N | CH | phenyl |
| 978 | 1 | H | $CH_2$ | N | CH | cyclohexyl |
| 979 | 1 | H | $CH_2$ | N | CH | N,N-dimethylsulfamido |
| 980 | 1 | H | $CH_2$ | N | CH | N,N-dimethylamido |
| 981 | 1 | H | $CH_2$ | N | N | imidazol-1-yl |
| 982 | 1 | H | $CH_2$ | N | N | morpholin-1-yl |
| 983 | 1 | H | $CH_2$ | N | N | 2-methylimidazol-1-yl |
| 984 | 1 | H | $CH_2$ | N | N | pyridin-3-yl |
| 985 | 1 | H | $CH_2$ | N | N | 2-(5'-trifluoromethyl)tetrazol-1'-yl |
| 986 | 1 | H | $CH_2$ | N | N | pyrazol-1-yl |
| 987 | 1 | H | $CH_2$ | N | N | phenyl |
| 988 | 1 | H | $CH_2$ | N | N | cyclohexyl |
| 989 | 1 | H | $CH_2$ | N | N | N,N-dimethylsulfamido |
| 990 | 1 | H | $CH_2$ | N | N | N,N-dimethylamido |
| 991 | 1 | H | $CH_2$ | F | CH | imidazol-1-yl |
| 992 | 1 | H | $CH_2$ | F | CH | morpholin-1-yl |
| 993 | 1 | H | $CH_2$ | F | CH | 2-methylimidazol-1-yl |
| 994 | 1 | H | $CH_2$ | F | CH | pyridin-3-yl |
| 995 | 1 | H | $CH_2$ | F | CH | 2-(5'-trifluoromethyl)tetrazol-1'-yl |
| 996 | 1 | H | $CH_2$ | F | CH | pyrazol-1-yl |
| 997 | 1 | H | $CH_2$ | F | CH | phenyl |
| 998 | 1 | H | $CH_2$ | F | CH | cyclohexyl |
| 999 | 1 | H | $CH_2$ | F | CH | N,N-dimethylsulfamido |
| 1000 | 1 | H | $CH_2$ | F | CH | N,N-dimethylamido |
| 1001 | 1 | H | $CH_2$ | Cl | CH | imidazol-1-yl |
| 1002 | 1 | H | $CH_2$ | Cl | CH | morpholin-1-yl |
| 1003 | 1 | H | $CH_2$ | Cl | CH | 2-methylimidazol-1-yl |
| 1004 | 1 | H | $CH_2$ | Cl | CH | pyridin-3-yl |
| 1005 | 1 | H | $CH_2$ | Cl | CH | 2-(5'-trifluoromethyl)tetrazol-1'-yl |
| 1006 | 1 | H | $CH_2$ | Cl | CH | pyrazol-1-yl |
| 1007 | 1 | H | $CH_2$ | Cl | CH | phenyl |
| 1008 | 1 | H | $CH_2$ | Cl | CH | cyclohexyl |
| 1009 | 1 | H | $CH_2$ | Cl | CH | N,N-dimethylsulfamido |
| 1010 | 1 | H | $CH_2$ | Cl | CH | N,N-dimethylamido |
| 1011 | 1 | H | $CH_2$ | Br | CH | imidazol-1-yl |
| 1012 | 1 | H | $CH_2$ | Br | CH | morpholin-1-yl |
| 1013 | 1 | H | $CH_2$ | Br | CH | 2-methylimidazol-1-yl |
| 1014 | 1 | H | $CH_2$ | Br | CH | pyridin-3-yl |
| 1015 | 1 | H | $CH_2$ | Br | CH | 2-(5'-trifluoromethyl)tetrazol-1'-yl |
| 1016 | 1 | H | $CH_2$ | Br | CH | pyrazol-1-yl |
| 1017 | 1 | H | $CH_2$ | Br | CH | phenyl |
| 1018 | 1 | H | $CH_2$ | Br | CH | cyclohexyl |
| 1019 | 1 | H | $CH_2$ | Br | CH | N,N-dimethylsulfamido |
| 1020 | 1 | H | $CH_2$ | Br | CH | N,N-dimethylamido |
| 1021 | 1 | OH | bond | F | CH | pyrazol-1-yl |
| 1022 | 1 | OH | bond | F | CH | phenyl |
| 1023 | 1 | OH | bond | F | CH | cyclohexyl |
| 1024 | 1 | OH | bond | F | CH | N,N-dimethylsulfamido |
| 1025 | 1 | OH | bond | F | CH | N,N-dimethylamido |
| 1026 | 1 | NHC(O)CH₃ | bond | Cl | CH | imidazol-1-yl |
| 1027 | 1 | NHC(O)CH₃ | bond | Cl | CH | morpholin-1-yl |
| 1028 | 1 | NHC(O)CH₃ | bond | Cl | CH | 2-methylimidazol-1-yl |
| 1029 | 1 | NHC(O)CH₃ | bond | Cl | CH | pyridin-3-yl |
| 1030 | 1 | NHC(O)CH₃ | bond | Cl | CH | 2-(5'-trifluoromethyl)tetrazol-1'-yl |
| 1031 | 1 | NHSO₂CH₃ | bond | Cl | CH | pyrazol-1-yl |
| 1032 | 1 | NHSO₂CH₃ | bond | Cl | CH | phenyl |
| 1033 | 1 | NHSO₂CH₃ | bond | Cl | CH | cyclohexyl |
| 1034 | 1 | NHSO₂CH₃ | bond | Cl | CH | N,N-dimethylsulfamido |
| 1035 | 1 | NHSO₂CH₃ | bond | Cl | CH | N,N-dimethylamido |
| 1036 | 1 | OCH₃ | bond | Br | CH | imidazol-1-yl |
| 1037 | 1 | OCH₃ | bond | Br | CH | morpholin-1-yl |
| 1038 | 1 | OCH₃ | bond | Br | CH | 2-methylimidazol-1-yl |
| 1039 | 1 | OCH₃ | bond | Br | CH | pyridin-3-yl |
| 1040 | 1 | OCH₃ | bond | Br | CH | 2-(5'-trifluoromethyl)tetrazol-1'-yl |
| 1041 | 1 | OCH₂C₆H₅ | bond | Br | CH | pyrazol-1-yl |
| 1042 | 1 | OCH₂C₆H₅ | bond | Br | CH | phenyl |
| 1043 | 1 | OCH₂C₆H₅ | bond | Br | CH | cyclohexyl |
| 1044 | 1 | OCH₂C₆H₅ | bond | Br | CH | N,N-dimethylsulfamido |
| 1045 | 1 | OCH₂C₆H₅ | bond | Br | CH | N,N-dimethylamido |
| 1046 | 1 | OH | $CH_2$ | CH | CH | pyrazol-1-yl |

TABLE 12-continued

| Ex. | n | R² | Z | A¹ | A² | B |
|---|---|---|---|---|---|---|
| 1047 | 1 | OH | CH₂ | CH | CH | phenyl |
| 1048 | 1 | OH | CH₂ | CH | CH | cyclohexyl |
| 1049 | 1 | OH | CH₂ | CH | CH | N,N-dimethylsulfamido |
| 1050 | 1 | OH | CH₂ | CH | CH | N,N-dimethylamido |
| 1051 | 1 | NHC(O)CH₃ | CH₂ | N | CH | imidazol-1-yl |
| 1052 | 1 | NHC(O)CH₃ | CH₂ | N | CH | morpholin-1-yl |
| 1053 | 1 | NHC(O)CH₃ | CH₂ | N | CH | 2-methylimidazol-1-yl |
| 1054 | 1 | NHC(O)CH₃ | CH₂ | N | CH | pyridin-3-yl |
| 1055 | 1 | NHC(O)CH₃ | CH₂ | N | CH | 2-(5'-trifluoromethyl)tetrazol-1'-yl |
| 1056 | 1 | NHSO₂CH₃ | CH₂ | N | CH | pyrazol-1-yl |
| 1057 | 1 | NHSO₂CH₃ | CH₂ | N | CH | phenyl |
| 1058 | 1 | NHSO₂CH₃ | CH₂ | N | CH | cyclohexyl |
| 1059 | 1 | NHSO₂CH₃ | CH₂ | N | CH | N,N-dimethylsulfamido |
| 1060 | 1 | NHSO₂CH₃ | CH₂ | N | CH | N,N-dimethylamido |
| 1061 | 1 | OCH₃ | CH₂ | N | N | imidazol-1-yl |
| 1062 | 1 | OCH₃ | CH₂ | N | N | morpholin-1-yl |
| 1063 | 1 | OCH₃ | CH₂ | N | N | 2-methylimidazol-1-yl |
| 1064 | 1 | OCH₃ | CH₂ | N | N | pyridin-3-yl |
| 1065 | 1 | OCH₃ | CH₂ | N | N | 2-(5'-trifluoromethyl)tetrazol-1'-yl |
| 1066 | 1 | OCH₂C₆H₅ | CH₂ | N | N | pyrazol-1-yl |
| 1067 | 1 | OCH₂C₆H₅ | CH₂ | N | N | phenyl |
| 1068 | 1 | OCH₂C₆H₅ | CH₂ | N | N | cyclohexyl |
| 1069 | 1 | OCH₂C₆H₅ | CH₂ | N | N | N,N-dimethylsulfamido |
| 1070 | 1 | OCH₂C₆H₅ | CH₂ | N | N | N,N-dimethylamido |

TABLE 13

| Ex. | n | R² | Z | A¹ | A² | B |
|---|---|---|---|---|---|---|
| 1101 | 2 | H | bond | CH | CH | imidazol-1-yl |
| 1102 | 2 | H | bond | CH | CH | morpholin-1-yl |
| 1103 | 2 | H | bond | CH | CH | 2-methylimidazol-1-yl |
| 1104 | 2 | H | bond | CH | CH | pyridin-3-yl |
| 1105 | 2 | H | bond | CH | CH | 2-(5'-trifluoromethyl)tetrazol-1'-yl |
| 1106 | 2 | H | bond | CH | CH | pyrazol-1-yl |
| 1107 | 2 | H | bond | CH | CH | phenyl |
| 1108 | 2 | H | bond | CH | CH | cyclohexyl |
| 1109 | 2 | H | bond | CH | CH | N,N-dimethylsulfamido |
| 1110 | 2 | H | bond | CH | CH | N,N-dimethylamido |
| 1111 | 2 | H | bond | N | CH | imidazol-1-yl |
| 1112 | 2 | H | bond | N | CH | morpholin-1-yl |
| 1113 | 2 | H | bond | N | CH | 2-methylimidazol-1-yl |
| 1114 | 2 | H | bond | N | CH | pyridin-3-yl |
| 1115 | 2 | H | bond | N | CH | 2-(5'-trifluoromethyl)tetrazol-1'-yl |
| 1116 | 2 | H | bond | N | CH | pyrazol-1-yl |
| 1117 | 2 | H | bond | N | CH | phenyl |
| 1118 | 2 | H | bond | N | CH | cyclohexyl |
| 1119 | 2 | H | bond | N | CH | N,N-dimethylsulfamido |
| 1120 | 2 | H | bond | N | CH | N,N-dimethylamido |
| 1121 | 2 | H | bond | N | N | imidazol-1-yl |
| 1122 | 2 | H | bond | N | N | morpholin-1-yl |
| 1123 | 2 | H | bond | N | N | 2-methylimidazol-1-yl |
| 1124 | 2 | H | bond | N | N | pyridin-3-yl |
| 1125 | 2 | H | bond | N | N | 2-(5'-trifluoromethyl)tetrazol-1'-yl |
| 1126 | 2 | H | bond | N | N | pyrazol-1-yl |
| 1127 | 2 | H | bond | N | N | phenyl |
| 1128 | 2 | H | bond | N | N | cyclohexyl |
| 1129 | 2 | H | bond | N | N | N,N-dimethylsulfamido |
| 1130 | 2 | H | bond | N | N | N,N-dimethylamido |
| 1131 | 2 | H | bond | F | CH | imidazol-1-yl |
| 1132 | 2 | H | bond | F | CH | morpholin-1-yl |
| 1133 | 2 | H | bond | F | CH | 2-methylimidazol-1-yl |
| 1134 | 2 | H | bond | F | CH | pyridin-3-yl |
| 1135 | 2 | H | bond | F | CH | 2-(5'-trifluoromethyl)tetrazol-1'-yl |
| 1136 | 2 | H | bond | F | CH | pyrazol-1-yl |
| 1137 | 2 | H | bond | F | CH | phenyl |
| 1138 | 2 | H | bond | F | CH | cyclohexyl |
| 1139 | 2 | H | bond | F | CH | N,N-dimethylsulfamido |
| 1140 | 2 | H | bond | F | CH | N,N-dimethylamido |
| 1141 | 2 | H | bond | Cl | CH | imidazol-1-yl |
| 1142 | 2 | H | bond | Cl | CH | morpholin-1-yl |
| 1143 | 2 | H | bond | Cl | CH | 2-methylimidazol-1-yl |
| 1144 | 2 | H | bond | Cl | CH | pyridin-3-yl |
| 1145 | 2 | H | bond | Cl | CH | 2-(5'-trifluoromethyl)tetrazol-1'-yl |
| 1146 | 2 | H | bond | Cl | CH | pyrazol-1-yl |
| 1147 | 2 | H | bond | Cl | CH | phenyl |
| 1148 | 2 | H | bond | Cl | CH | cyclohexyl |
| 1149 | 2 | H | bond | Cl | CH | N,N-dimethylsulfamido |
| 1150 | 2 | H | bond | Cl | CH | N,N-dimethylamido |
| 1151 | 2 | H | bond | Br | CH | imidazol-1-yl |
| 1152 | 2 | H | bond | Br | CH | morpholin-1-yl |
| 1153 | 2 | H | bond | Br | CH | 2-methylimidazol-1-yl |
| 1154 | 2 | H | bond | Br | CH | pyridin-3-yl |
| 1155 | 2 | H | bond | Br | CH | 2-(5'-trifluoromethyl)tetrazol-1'-yl |
| 1156 | 2 | H | bond | Br | CH | pyrazol-1-yl |
| 1157 | 2 | H | bond | Br | CH | phenyl |
| 1158 | 2 | H | bond | Br | CH | cyclohexyl |
| 1159 | 2 | H | bond | Br | CH | N,N-dimethylsulfamido |
| 1160 | 2 | H | bond | Br | CH | N,N-dimethylamido |
| 1161 | 2 | H | CH₂ | CH | CH | imidazol-1-yl |
| 1162 | 2 | H | CH₂ | CH | CH | morpholin-1-yl |
| 1163 | 2 | H | CH₂ | CH | CH | 2-methylimidazol-1-yl |
| 1164 | 2 | H | CH₂ | CH | CH | pyridin-3-yl |
| 1165 | 2 | H | CH₂ | CH | CH | 2-(5'-trifluoromethyl)tetrazol-1'-yl |
| 1166 | 2 | H | CH₂ | CH | CH | pyrazol-1-yl |
| 1167 | 2 | H | CH₂ | CH | CH | phenyl |
| 1168 | 2 | H | CH₂ | CH | CH | cyclohexyl |
| 1169 | 2 | H | CH₂ | CH | CH | N,N-dimethylsulfamido |
| 1170 | 2 | H | CH₂ | CH | CH | N,N-dimethylamido |
| 1171 | 2 | H | CH₂ | N | CH | imidazol-1-yl |
| 1172 | 2 | H | CH₂ | N | CH | morpholin-1-yl |
| 1173 | 2 | H | CH₂ | N | CH | 2-methylimidazol-1-yl |
| 1174 | 2 | H | CH₂ | N | CH | pyridin-3-yl |
| 1175 | 2 | H | CH₂ | N | CH | 2-(5'-trifluoromethyl)tetrazol-1'-yl |
| 1176 | 2 | H | CH₂ | N | CH | pyrazol-1-yl |
| 1177 | 2 | H | CH₂ | N | CH | phenyl |
| 1178 | 2 | H | CH₂ | N | CH | cyclohexyl |
| 1179 | 2 | H | CH₂ | N | CH | N,N-dimethylsulfamido |
| 1180 | 2 | H | CH₂ | N | CH | N,N-dimethylamido |
| 1181 | 2 | H | CH₂ | N | N | imidazol-1-yl |
| 1182 | 2 | H | CH₂ | N | N | morpholin-1-yl |
| 1183 | 2 | H | CH₂ | N | N | 2-methylimidazol-1-yl |
| 1184 | 2 | H | CH₂ | N | N | pyridin-3-yl |

TABLE 13-continued

| Ex. | n | R² | Z | A¹ | A² | B |
|---|---|---|---|---|---|---|
| 1185 | 2 | H | CH₂ | N | N | 2-(5'-trifluoromethyl)tetrazol-1'-yl |
| 1186 | 2 | H | CH₂ | N | N | pyrazol-1-yl |
| 1187 | 2 | H | CH₂ | N | N | phenyl |
| 1188 | 2 | H | CH₂ | N | N | cyclohexyl |
| 1189 | 2 | H | CH₂ | N | N | N,N-dimethylsulfamido |
| 1190 | 2 | H | CH₂ | N | N | N,N-dimethylamido |
| 1191 | 2 | H | CH₂ | F | CH | imidazol-1-yl |
| 1192 | 2 | H | CH₂ | F | CH | morpholin-1-yl |
| 1193 | 2 | H | CH₂ | F | CH | 2-methylimidazol-1-yl |
| 1194 | 2 | H | CH₂ | F | CH | pyridin-3-yl |
| 1195 | 2 | H | CH₂ | F | CH | 2-(5'-trifluoromethyl)tetrazol-1'-yl |
| 1196 | 2 | H | CH₂ | F | CH | pyrazol-1-yl |
| 1197 | 2 | H | CH₂ | F | CH | phenyl |
| 1198 | 2 | H | CH₂ | F | CH | cyclohexyl |
| 1199 | 2 | H | CH₂ | F | CH | N,N-dimethylsulfamido |
| 1200 | 2 | H | CH₂ | F | CH | N,N-dimethylamido |
| 1201 | 2 | H | CH₂ | Cl | CH | imidazol-1-yl |
| 1202 | 2 | H | CH₂ | Cl | CH | morpholin-1-yl |
| 1203 | 2 | H | CH₂ | Cl | CH | 2-methylimidazol-1-yl |
| 1204 | 2 | H | CH₂ | Cl | CH | pyridin-3-yl |
| 1205 | 2 | H | CH₂ | Cl | CH | 2-(5'-trifluoromethyl)tetrazol-1'-yl |
| 1206 | 2 | H | CH₂ | Cl | CH | pyrazol-1-yl |
| 1207 | 2 | H | CH₂ | Cl | CH | phenyl |
| 1208 | 2 | H | CH₂ | Cl | CH | cyclohexyl |
| 1209 | 2 | H | CH₂ | Cl | CH | N,N-dimethylsulfamido |
| 1210 | 2 | H | CH₂ | Cl | CH | N,N-dimethylamido |
| 1211 | 2 | H | CH₂ | Br | CH | imidazol-1-yl |
| 1212 | 2 | H | CH₂ | Br | CH | morpholin-1-yl |
| 1213 | 2 | H | CH₂ | Br | CH | 2-methylimidazol-1-yl |
| 1214 | 2 | H | CH₂ | Br | CH | pyridin-3-yl |
| 1215 | 2 | H | CH₂ | Br | CH | 2-(5'-trifluoromethyl)tetrazol-1'-yl |
| 1216 | 2 | H | CH₂ | Br | CH | pyrazol-1-yl |
| 1217 | 2 | H | CH₂ | Br | CH | phenyl |
| 1218 | 2 | H | CH₂ | Br | CH | cyclohexyl |
| 1219 | 2 | H | CH₂ | Br | CH | N,N-dimethylsulfamido |
| 1220 | 2 | H | CH₂ | Br | CH | N,N-dimethylamido |
| 1221 | 2 | OH | bond | F | CH | pyrazol-1-yl |
| 1222 | 2 | OH | bond | F | CH | phenyl |
| 1223 | 2 | OH | bond | F | CH | cyclohexyl |
| 1224 | 2 | OH | bond | F | CH | N,N-dimethylsulfamido |
| 1225 | 2 | OH | bond | F | CH | N,N-dimethylamido |
| 1226 | 2 | NHC(O)CH₃ | bond | Cl | CH | imidazol-1-yl |
| 1227 | 2 | NHC(O)CH₃ | bond | Cl | CH | morpholin-1-yl |
| 1228 | 2 | NHC(O)CH₃ | bond | Cl | CH | 2-methylimidazol-1-yl |
| 1229 | 2 | NHC(O)CH₃ | bond | Cl | CH | pyridin-3-yl |
| 1230 | 2 | NHC(O)CH₃ | bond | Cl | CH | 2-(5'-trifluoromethyl)tetrazol-1'-yl |
| 1231 | 2 | NHSO₂CH₃ | bond | Cl | CH | pyrazol-1-yl |
| 1232 | 2 | NHSO₂CH₃ | bond | Cl | CH | phenyl |
| 1233 | 2 | NHSO₂CH₃ | bond | Cl | CH | cyclohexyl |
| 1234 | 2 | NHSO₂CH₃ | bond | Cl | CH | N,N-dimethylsulfamido |
| 1235 | 2 | NHSO₂CH₃ | bond | Cl | CH | N,N-dimethylamido |
| 1236 | 2 | OCH₃ | bond | Br | CH | imidazol-1-yl |
| 1237 | 2 | OCH₃ | bond | Br | CH | morpholin-1-yl |
| 1238 | 2 | OCH₃ | bond | Br | CH | 2-methylimidazol-1-yl |
| 1239 | 2 | OCH₃ | bond | Br | CH | pyridin-3-yl |
| 1240 | 2 | OCH₃ | bond | Br | CH | 2-(5'-trifluoromethyl)tetrazol-1'-yl |
| 1241 | 2 | OCH₂C₆H₅ | bond | Br | CH | pyrazol-1-yl |
| 1242 | 2 | OCH₂C₆H₅ | bond | Br | CH | phenyl |
| 1243 | 2 | OCH₂C₆H₅ | bond | Br | CH | cyclohexyl |
| 1244 | 2 | OCH₂C₆H₅ | bond | Br | CH | N,N-dimethylsulfamido |
| 1245 | 2 | OCH₂C₆H₅ | bond | Br | CH | N,N-dimethylamido |
| 1246 | 2 | OH | CH₂ | CH | CH | pyrazol-1-yl |
| 1247 | 2 | OH | CH₂ | CH | CH | phenyl |
| 1248 | 2 | OH | CH₂ | CH | CH | cyclohexyl |
| 1249 | 2 | OH | CH₂ | CH | CH | N,N-dimethylsulfamido |
| 1250 | 2 | OH | CH₂ | CH | CH | N,N-dimethylamido |
| 1251 | 2 | NHC(O)CH₃ | CH₂ | N | CH | imidazol-1-yl |
| 1252 | 2 | NHC(O)CH₃ | CH₂ | N | CH | morpholin-1-yl |
| 1253 | 2 | NHC(O)CH₃ | CH₂ | N | CH | 2-methylimidazol-1-yl |
| 1254 | 2 | NHC(O)CH₃ | CH₂ | N | CH | pyridin-3-yl |
| 1255 | 2 | NHC(O)CH₃ | CH₂ | N | CH | 2-(5'-trifluoromethyl)tetrazol-1'-yl |
| 1256 | 2 | NHSO₂CH₃ | CH₂ | N | CH | pyrazol-1-yl |
| 1257 | 2 | NHSO₂CH₃ | CH₂ | N | CH | phenyl |
| 1258 | 2 | NHSO₂CH₃ | CH₂ | N | CH | cyclohexyl |
| 1259 | 2 | NHSO₂CH₃ | CH₂ | N | CH | N,N-dimethylsulfamido |
| 1260 | 2 | NHSO₂CH₃ | CH₂ | N | CH | N,N-dimethylamido |
| 1261 | 2 | OCH₃ | CH₂ | N | N | imidazol-1-yl |
| 1262 | 2 | OCH₃ | CH₂ | N | N | morpholin-1-yl |
| 1263 | 2 | OCH₃ | CH₂ | N | N | 2-methylimidazol-1-yl |
| 1264 | 2 | OCH₃ | CH₂ | N | N | pyridin-3-yl |
| 1265 | 2 | OCH₃ | CH₂ | N | N | 2-(5'-trifluoromethyl)tetrazol-1'-yl |
| 1266 | 2 | OCH₂C₆H₅ | CH₂ | N | N | pyrazol-1-yl |
| 1267 | 2 | OCH₂C₆H₅ | CH₂ | N | N | phenyl |
| 1268 | 2 | OCH₂C₆H₅ | CH₂ | N | N | cyclohexyl |
| 1269 | 2 | OCH₂C₆H₅ | CH₂ | N | N | N,N-dimethylsulfamido |
| 1270 | 2 | OCH₂C₆H₅ | CH₂ | N | N | N,N-dimethylamido |

TABLE 14

| Ex. | n | R² | B |
|---|---|---|---|
| 1301 | 2 | H | benzoyl |
| 1302 | 2 | H | phenylacetyl |
| 1303 | 2 | H | phenylsulfoflyl |
| 1304 | 2 | H | benzylsulfonyl |
| 1305 | 2 | H | picolin-2-ylsulfonyl |
| 1306 | 2 | H | pyridin-2-ylsulfonyl |
| 1307 | 2 | H | picolin-2-yl |
| 1308 | 2 | H | (phenyl-N-methylamino)sulfonyl |
| 1309 | 2 | H | (1,1-dimethyl-1-phenyl)methylsulfonyl |
| 1310 | 2 | H | thiophen-2-ylmethyl |
| 1311 | 2 | OH | benzoyl |
| 1312 | 2 | OH | phenylacetyl |
| 1313 | 2 | OH | (phenyl-N-methylamino)sulfonyl |
| 1314 | 2 | OH | (1,1-dimethyl-1-phenyl)methylsulfonyl |
| 1315 | 2 | OH | picolin-2-ylsulfonyl |
| 1316 | 2 | OH | pyridin-2-ylsulfonyl |
| 1317 | 2 | OH | picolin-2-yl |
| 1318 | 2 | OH | thiophen-2-ylsulfonyl |
| 1319 | 2 | OH | thiophen-2-ylmethylsulfonyl |
| 1320 | 2 | OH | thiophen-2-ylmethyl |

TABLE 14-continued

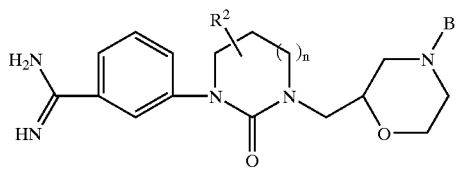

| Ex. | n | R² | B |
|---|---|---|---|
| 1321 | 2 | NHC(O)CH₃ | (phenyl-N-methylamino) sulfonyl |
| 1322 | 2 | NHC(O)CH₃ | (1,1-dimethyl-1-phenyl)methylsulfonyl |
| 1323 | 2 | NHC(O)CH₃ | phenylsulfonyl |
| 1324 | 2 | NHC(O)CH₃ | benzylsulfonyl |
| 1325 | 2 | NHC(O)CH₃ | picolin-2-ylsulfonyl |
| 1326 | 2 | NHC(O)CH₃ | pyridin-2-ylsulfonyl |
| 1327 | 2 | NHC(O)CH₃ | picolin-2-yl |
| 1328 | 2 | NHC(O)CH₃ | thiophen-2-ylsulfonyl |
| 1329 | 2 | NHC(O)CH₃ | thiophen-2-ylmethylsulfonyl |
| 1330 | 2 | NHC(O)CH₃ | thiophen-2-ylmethyl |
| 1331 | 2 | NHSO₂CH₃ | benzoyl |
| 1332 | 2 | NHSO₂CH₃ | phenylacetyl |
| 1333 | 2 | NHSO₂CH₃ | phenylsulfonyl |
| 1334 | 2 | NHSO₂CH₃ | benzylsulfonyl |
| 1335 | 2 | NHSO₂CH₃ | (phenyl-N-methylamino) sulfonyl |
| 1336 | 2 | NHSO₂CH₃ | (1,1-dimethyl-1-phenyl)methylsulfonyl |
| 1337 | 2 | NHSO₂CH₃ | picolin-2-yl |
| 1338 | 2 | NHSO₂CH₃ | thjophen-2-ylsulfonyl |
| 1339 | 2 | NHSO₂CH₃ | thiophen-2-ylmethylsulfonyl |
| 1340 | 2 | NHSO₂CH₃ | thiophen-2-ylmethyl |

TABLE 15

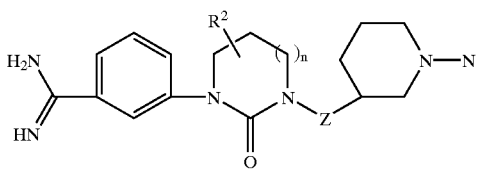

| Ex. | n | R² | Z | B |
|---|---|---|---|---|
| 1401 | 2 | H | bond | benzoyl |
| 1402 | 2 | H | bond | phenylacetyl |
| 1403 | 2 | H | bond | phenylsulfonyl |
| 1404 | 2 | H | bond | benzylsulfonyl |
| 1405 | 2 | H | bond | picolin-2-ylsulfonyl |
| 1406 | 2 | H | bond | pyridin-2-ylsulfonyl |
| 1407 | 2 | H | bond | picolin-2-yl |
| 1408 | 2 | H | bond | (phenyl-N-methylamino)sulfonyl |
| 1409 | 2 | H | bond | (1,1-dimethyl-1-phenyl)methylsulfonyl |
| 1410 | 2 | H | bond | thiophen-2-ylmethyl |
| 1411 | 2 | OH | bond | benzoyl |
| 1412 | 2 | OH | bond | phenylacetyl |
| 1413 | 2 | OH | bond | (phenyl-N-methylamino)sulfonyl |
| 1414 | 2 | OH | bond | (1,1-dimethyl-1-phenyl)methylsulfonyl |
| 1415 | 2 | OH | bond | picolin-2-ylsulfonyl |
| 1416 | 2 | OH | bond | pyridin-2-ylsulfonyl |
| 1417 | 2 | OH | bond | picolin-2-yl |
| 1418 | 2 | OH | bond | thiophen-2-ylsulfonyl |
| 1419 | 2 | OH | bond | thiophen-2-ylmethylsulfonyl |
| 1420 | 2 | OH | bond | thiophen-2-ylmethyl |
| 1421 | 2 | NHC(O)CH₃ | bond | (phenyl-N-methylamino)sulfonyl |

TABLE 15-continued

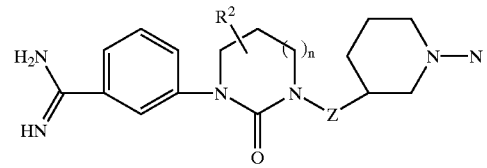

| Ex. | n | R² | Z | B |
|---|---|---|---|---|
| 1422 | 2 | NHC(O)CH₃ | bond | (1,1-dimethyl-1-phenyl)methylsulfonyl |
| 1423 | 2 | NHC(O)CH₃ | bond | phenylsulfonyl |
| 1424 | 2 | NHC(O)CH₃ | bond | benzylsulfonyl |
| 1425 | 2 | NHC(O)CH₃ | bond | picolin-2-ylsulfonyl |
| 1426 | 2 | NHC(O)CH₃ | bond | pyridin-2-ylsulfonyl |
| 1427 | 2 | NHC(O)CH₃ | bond | picolin-2-yl |
| 1428 | 2 | NHC(O)CH₃ | bond | thiophen-2-ylsulfonyl |
| 1429 | 2 | NHC(O)CH₃ | bond | thiophen-2-ylmethylsulfonyl |
| 1430 | 2 | NHC(O)CH₃ | bond | thiophen-2-ylmethyl |
| 1431 | 2 | NHSO₂CH₃ | bond | benzoyl |
| 1432 | 2 | NHSO₂CH₃ | bond | phenylacetyl |
| 1433 | 2 | NHSO₂CH₃ | bond | phenylsulfonyl |
| 1434 | 2 | NHSO₂CH₃ | bond | benzylsulfonyl |
| 1435 | 2 | NHSO₂CH₃ | bond | (phenyl-N-methylamino)sulfonyl |
| 1436 | 2 | NHSO₂CH₃ | bond | (1,1-dimethyl-1-phenyl)methylsulfonyl |
| 1437 | 2 | NHSO₂CH₃ | bond | picolin-2-yl |
| 1438 | 2 | NHSO₂CH₃ | bond | thiophen-2-ylsulfonyl |
| 1439 | 2 | NHSO₂CH₃ | bond | thiophen-2-ylmethylsulfonyl |
| 1440 | 2 | NHSO₂CH₃ | bond | thiophen-2-ylmethyl |

TABLE 16

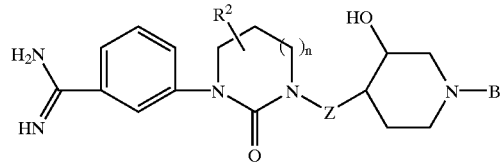

| Ex. | n | R² | Z | B |
|---|---|---|---|---|
| 1501 | 2 | H | bond | benzoyl |
| 1502 | 2 | H | bond | phenylacetyl |
| 1503 | 2 | H | bond | phenylsulfonyl |
| 1504 | 2 | H | bond | benzylsulfonyl |
| 1505 | 2 | H | bond | picolin-2-ylsulfonyl |
| 1506 | 2 | H | bond | pyridin-2-ylsulfonyl |
| 1507 | 2 | H | bond | picolin-2-yl |
| 1508 | 2 | H | bond | (phenyl-N-methylainino)sulfonyl |
| 1509 | 2 | H | bond | (1,1-dimethyl-1-phenyl)methylsulfonyl |
| 1510 | 2 | H | bond | thiophen-2-ylmethyl |
| 1511 | 2 | OH | bond | benzoyl |
| 1512 | 2 | OH | bond | phenylacetyl |
| 1513 | 2 | OH | bond | (phenyl-N-methylamino)sulfonyl |
| 1514 | 2 | OH | bond | (1,1-dimethyl-1-phenyl)methylsulfonyl |
| 1515 | 2 | OH | bond | picolin-2-ylsulfonyl |
| 1516 | 2 | OH | bond | pyridin-2-ylsulfonyl |
| 1517 | 2 | OH | bond | picolin-2-yl |
| 1518 | 2 | OH | bond | thiophen-2-ylsulfonyl |
| 1519 | 2 | OH | bond | thiophen-2-ylmethylsulfonyl |
| 1520 | 2 | OH | bond | thiophen-2-ylmethyl |
| 1521 | 2 | NHC(O)CH₃ | bond | (phenyl-N-methylamino)sulfonyl |
| 1522 | 2 | NHC(O)CH₃ | bond | (1,1-dimethyl-1-phenyl)methylsulfonyl |
| 1523 | 2 | NHC(O)CH₃ | bond | phenylsulfonyl |

TABLE 16-continued

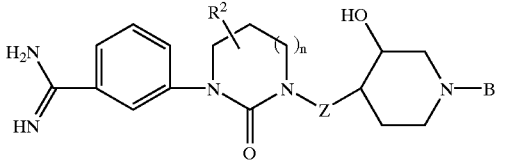

| Ex. | n | R² | Z | B |
|---|---|---|---|---|
| 1524 | 2 | NHC(O)CH₃ | bond | benzylsulfonyl |
| 1525 | 2 | NHC(O)CH₃ | bond | picolin-2-ylsulfonyl |
| 1526 | 2 | NHC(O)CH₃ | bond | pyridin-2-ylsulfonyl |
| 1527 | 2 | NHC(O)CH₃ | bond | picolin-2-yl |
| 1528 | 2 | NHC(O)CH₃ | bond | thiophen-2-ylsulfonyl |
| 1529 | 2 | NHC(O)CH₃ | bond | thiophen-2-ylmethylsulfonyl |
| 1530 | 2 | NHC(O)CH₃ | bond | thiophen-2-ylmethyl |
| 1531 | 2 | NHSO₂CH₃ | bond | benzoyl |
| 1532 | 2 | NHSO₂CH₃ | bond | phenylacetyl |
| 1533 | 2 | NHSO₂CH₃ | bond | phenylsulfonyl |
| 1534 | 2 | NHSO₂CH₃ | bond | benzylsulfonyl |
| 1535 | 2 | NHSO₂CH₃ | bond | (phenyl-N-methylamino)sulfonyl |
| 1536 | 2 | NHSO₂CH₃ | bond | (1-1-dimethyl-1-phenyl)methylsulfonyl |
| 1537 | 2 | NHSO₂CH₃ | bond | picolin-2-yl |
| 1538 | 2 | NHSO₂CH₃ | bond | thiophen-2-ylsulfonyl |
| 1539 | 2 | NHSO₂CH₃ | bond | thiophen-2-ylmethylsulfonyl |
| 1540 | 2 | NHSO₂CH₃ | bond | thiophen-2-ylmethyl |

TABLE 17

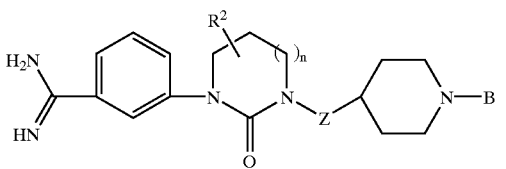

| Ex. | n | R² | z | B |
|---|---|---|---|---|
| 1601 | 2 | H | bond | picolin-2-ylsulfonyl |
| 1602 | 2 | H | bond | pyridin-2-ylsulfonyl |
| 1603 | 2 | H | bond | picolin-2-yl |
| 1604 | 2 | H | bond | thiophen-2-ylsulfonyl |
| 1605 | 2 | H | bond | thiophen-2-ylmethylsulfonyl |
| 1606 | 2 | H | bond | thiophen-2-ylmethyl |
| 1607 | 2 | H | bond | 4-fluorophenylsulfonyl |
| 1608 | 2 | H | bond | 4-fluorobenzylsulfonyl |
| 1609 | 2 | H | bond | phenylsulfonyl |
| 1610 | 2 | H | bond | benzylsulfonyl |
| 1611 | 2 | H | bond | (phenyl-N-methylamino)sulfonyl |
| 1612 | 2 | H | bond | (1,1-dimethyl-1-phenyl)methylsulfonyl |
| 1613 | 2 | OH | bond | picolin-2-ylsulfonyl |
| 1614 | 2 | OH | bond | pyridin-2-ylsulfonyl |
| 1615 | 2 | OH | bond | picolin-2-yl |
| 1616 | 2 | OH | bond | thiophen-2-ylsulfonyl |
| 1617 | 2 | OH | bond | thiophen-2-ylmethylsulfonyl |
| 1618 | 2 | OH | bond | thiophen-2-ylmethyl |
| 1619 | 2 | OH | bond | 4-fluorophenylsulfonyl |
| 1620 | 2 | OH | bond | 4-fluorobenzylsulfonyl |
| 1621 | 2 | OH | bond | (phenyl-N-methylamino)sulfonyl |
| 1622 | 2 | OH | bond | (1,1-dimethyl-1-phenyl)methylsulfonyl |
| 1623 | 2 | OCH₃ | bond | picolin-2-ylsulfonyl |
| 1624 | 2 | OCH₃ | bond | pyridin-2-ylsulfonyl |
| 1625 | 2 | OCH₃ | bond | picolin-2-yl |
| 1626 | 2 | OCH₃ | bond | thiophen-2-ylsulfonyl |
| 1627 | 2 | OCH₃ | bond | thiophen-2-ylmethylsulfonyl |
| 1628 | 2 | OCH₃ | bond | thiophen-2-ylmethyl |

TABLE 17-continued

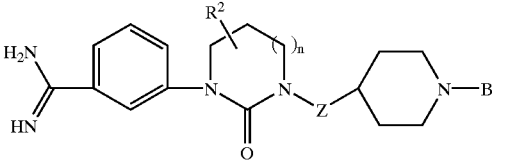

| Ex. | n | R² | z | B |
|---|---|---|---|---|
| 1629 | 2 | OCH₃ | bond | (phenyl-N-methylamino)sulfonyl |
| 1630 | 2 | OCH₃ | bond | (1,1-dimethyl-1-phenyl)methylsulfonyl |
| 1631 | 2 | OCH₃ | bond | phenylsulfonyl |
| 1632 | 2 | OCH₃ | bond | benzylsulfonyl |
| 1633 | 2 | OCH₂C₆H₅ | bond | picolin-2-ylsulfonyl |
| 1634 | 2 | OCH₂C₆H₅ | bond | pyridin-2-ylsulfonyl |
| 1635 | 2 | OCH₂C₆H₅ | bond | picolin-2-yl |
| 1636 | 2 | OCH₂C₆H₅ | bond | thiophen-2-ylsulfonyl |
| 1637 | 2 | OCH₂C₆H₅ | bond | (phenyl-N-methylamino)sulfonyl |
| 1638 | 2 | OCH₂C₆H₅ | bond | (1,1-dimethyl-1-phenyl)methylsulfonyl |
| 1639 | 2 | OCH₂C₆H₅ | bond | 4-fluorophenylsulfonyl |
| 1640 | 2 | OCH₂C₆H₅ | bond | 4-fluorobenzylsulfonyl |
| 1641 | 2 | OCH₂C₆H₅ | bond | phenylsulfonyl |
| 1642 | 2 | OCH₂C₆H₅ | bond | benzylsulfonyl |
| 1643 | 2 | NHC(O)CH₃ | bond | picolin-2-ylsulfonyl |
| 1644 | 2 | NHC(O)CH₃ | bond | pyridin-2-ylsulfonyl |
| 1645 | 2 | NHC(O)CH₃ | bond | (phenyl-N-methylamino)sulfonyl |
| 1646 | 2 | NHC(O)CH₃ | bond | (1,1-dimethyl-1-phenyl)methylsulfonyl |
| 1647 | 2 | NHC(O)CH₃ | bond | thiophen-2-ylmethylsulfonyl |
| 1648 | 2 | NHC(O)CH₃ | bond | thiophen-2-ylmethyl |
| 1649 | 2 | NHC(O)CH₃ | bond | 4-fluorophenylsulfonyl |
| 1650 | 2 | NHC(O)CH₃ | bond | 4-fluorobenzylsulfonyl |
| 1651 | 2 | NHC(O)CH₃ | bond | phenylsulfonyl |
| 1652 | 2 | NHC(O)CH₃ | bond | benzylsulfonyl |
| 1653 | 2 | NHC(O)OCH₃ | bond | (phenyl-N-methylamino)sulfonyl |
| 1654 | 2 | NHC(O)OCH₃ | bond | (1,1-dimethyl-1-phenyl)methylsulfonyl |
| 1655 | 2 | NHC(O)OCH₃ | bond | picolin-2-yl |
| 1656 | 2 | NHC(O)OCH₃ | bond | thiophen-2-ylsulfonyl |
| 1657 | 2 | NHC(O)OCH₃ | bond | thiophen-2-ylmethylsulfonyl |
| 1658 | 2 | NHC(O)OCH₃ | bond | thiophen-2-ylmethyl |
| 1659 | 2 | NHC(O)OCH₃ | bond | 4-fluorophenylsulfonyl |
| 1660 | 2 | NHC(O)OCH₃ | bond | 4-fluorobenzylsulfonyl |
| 1661 | 2 | NHC(O)OCH₃ | bond | phenyl-sulfonyl |
| 1662 | 2 | NHC(O)OCH₃ | bond | benzylsulfonyl |
| 1663 | 2 | NHC(O)NHCH₃ | bond | picolin-2-ylsulfonyl |
| 1664 | 2 | NHC(O)NHCH₃ | bond | pyridin-2-ylsulfonyl |
| 1665 | 2 | NHC(O)NHCH₃ | bond | picolin-2-yl |
| 1666 | 2 | NHC(O)NHCH₃ | bond | thiophen-2-ylsulfonyl |
| 1667 | 2 | NHC(O)NHCH₃ | bond | thiophen-2-ylmethylsulfonyl |
| 1668 | 2 | NHC(O)NHCH₃ | bond | thiophen-2-ylmethyl |
| 1669 | 2 | NHC(O)NHCH₃ | bond | 4-fluorophenylsulfonyl |
| 1670 | 2 | NHC(O)NHCH₃ | bond | 4-fluorobenzylsulfonyl |
| 1671 | 2 | NHC(O)NHCH₃ | bond | (phenyl-N-methylamino)sulfonyl |
| 1672 | 2 | NHC(O)NHCH₃ | bond | (1,1-dimethyl-1-phenyl)methylsulfonyl |
| 1673 | 2 | NHC(O)C₆H₅ | bond | picolin-2-ylsulfonyl |
| 1674 | 2 | NHC(O)C₆H₅ | bond | pyridin-2-ylsulfonyl |
| 1675 | 2 | NHC(O)C₆H₅ | bond | picolin-2-yl |
| 1676 | 2 | NHC(O)C₆H₅ | bond | thiophen-2-ylsulfonyl |
| 1677 | 2 | NHC(O)C₆H₅ | bond | thiophen-2-ylmethylsulfonyl |
| 1678 | 2 | NHC(O)C₆H₅ | bond | thiophen-2-ylmethyl |
| 1679 | 2 | NHC(O)C₆H₅ | bond | (phenyl-N-methylamino)sulfonyl |
| 1680 | 2 | NHC(O)C₆H₅ | bond | (1,1-dimethyl-1-phenyl)methylsulfonyl |
| 1681 | 2 | NHC(O)C₆H₅ | bond | phenylsulfonyl |
| 1682 | 2 | NHC(O)C₆H₅ | bond | benzylsulfonyl |
| 1683 | 2 | NHSO₂CH₃ | bond | picolin-2-ylsulfonyl |
| 1684 | 2 | NHSO₂CH₃ | bond | pyridin-2-ylsulfonyl |

TABLE 17-continued

| Ex. | n | R² | z | B |
|---|---|---|---|---|
| 1685 | 2 | NHSO₂CH₃ | bond | picolin-2-yl |
| 1686 | 2 | NHSO₂CH₃ | bond | thiophen-2-ylsulfonyl |
| 1687 | 2 | NHSO₂CH₃ | bond | (phenyl-N-methylamino)sulfonyl |
| 1688 | 2 | NHSO₂CH₃ | bond | (1,1-dimethyl-1-phenyl)methylsulfonyl |
| 1689 | 2 | NHSO₂CH₃ | bond | 4-fluorophenylsulfonyl |
| 1690 | 2 | NHSO₂CH₃ | bond | 4-fluorobenzylsulfonyl |
| 1691 | 2 | NHSO₂CH₃ | bond | phenylsulfonyl |
| 1692 | 2 | NHSO₂CH₃ | bond | benzylsulfonyl |
| 1693 | 2 | NHSO₂NHCH₃ | bond | picolin-2-ylsulfonyl |
| 1694 | 2 | NHSO₂NHCH₃ | bond | pyridin-2-ylsulfonyl |
| 1695 | 2 | NHSO₂NHCH₃ | bond | (phenyl-N-methylamino)sulfonyl |
| 1696 | 2 | NHSO₂NHCH₃ | bond | (1,1-dimethyl-1-phenyl)methylsulfonyl |
| 1697 | 2 | NHSO₂NHCH₃ | bond | thiophen-2-ylmethylsulfonyl |
| 1698 | 2 | NHSO₂NHCH₃ | bond | thiophen-2-ylmethyl |
| 1699 | 2 | NHSO₂NHCH₃ | bond | 4-fluorophenylsulfonyl |
| 1700 | 2 | NHSO₂NHCH₃ | bond | 4-fluorobenzylsulfonyl |
| 1701 | 2 | NHSO₂NHCH₃ | bond | phenylsulfonyl |
| 1702 | 2 | NHSO₂NHCH₃ | bond | benzylsulfonyl |
| 1703 | 2 | NHSO₂C₆H₅ | bond | (phenyl-N-methylamino)sulfonyl |
| 1704 | 2 | NHSO₂C₆H₅ | bond | (1,1-dimethyl-1-phenyl)methylsulfonyl |
| 1705 | 2 | NHSO₂C₆H₅ | bond | picolin-2-yl |
| 1706 | 2 | NHSO₂C₆H₅ | bond | thiophen-2-ylsulfonyl |
| 1707 | 2 | NHSO₂C₆H₅ | bond | thiophen-2-ylmethylsulfonyl |
| 1708 | 2 | NHSO₂C₆H₅ | bond | thiophen-2-ylmethyl |
| 1709 | 2 | NHSO₂C₆H₅ | bond | 4-fluorophenylsulfonyl |
| 1710 | 2 | NHSO₂C₆H₅ | bond | 4-fluorobenzylsulfonyl |
| 1711 | 2 | NHSO₂C₆H₅ | bond | phenylsulfonyl |
| 1712 | 2 | NHSO₂C₆H₅ | bond | benzylsulfonyl |

TABLE 18

| Ex. | n | R² | Z | B |
|---|---|---|---|---|
| 1801 | 2 | H | CH₂ | picolin-2-ylsulfonyl |
| 1802 | 2 | H | CH₂ | pyridin-2-ylsulfonyl |
| 1803 | 2 | H | CH₂ | picolin-2-yl |
| 1804 | 2 | H | CH₂ | thiophen-2-ylsulfonyl |
| 1805 | 2 | H | CH₂ | thiophen-2-ylmethylsulfonyl |
| 1806 | 2 | H | CH₂ | thiophen-2-ylmethyl |
| 1807 | 2 | H | CH₂ | 4-fluorophenylsulfonyl |
| 1808 | 2 | H | CH₂ | 4-fluorobenzylsulfonyl |
| 1809 | 2 | H | CH₂ | (phenyl-N-methylamino)sulfonyl |
| 1810 | 2 | H | CH₂ | (1,1-dimethyl-1-phenyl)methylsulfonyl |
| 1811 | 2 | OH | CH₂ | picolin-2-ylsulfonyl |
| 1812 | 2 | OH | CH₂ | pyridin-2-ylsulfonyl |
| 1813 | 2 | OH | CH₂ | picolin-2-yl |
| 1814 | 2 | OH | CH₂ | thiophen-2-ylsulfonyl |
| 1815 | 2 | OH | CH₂ | thiophen-2-ylmethylsulfonyl |
| 1816 | 2 | OH | CH₂ | thiophen-2-ylmethyl |
| 1817 | 2 | OH | CH₂ | 4-fluorophenylsulfonyl |
| 1818 | 2 | OH | CH₂ | 4-fluorobenzylsulfonyl |
| 1819 | 2 | OH | CH₂ | (phenyl-N-methylamino)sulfonyl |
| 1820 | 2 | OH | CH₂ | (1,1-dimethyl-1-phenyl)methylsulfonyl |
| 1821 | 2 | OCH₃ | CH₂ | picolin-2-ylsulfonyl |
| 1822 | 2 | OCH₃ | CH₂ | pyridin-2-ylsulfonyl |
| 1823 | 2 | OCH₃ | CH₂ | picolin-2-yl |
| 1824 | 2 | OCH₃ | CH₂ | thiophen-2-ylsulfonyl |
| 1825 | 2 | OCH₃ | CH₂ | thiophen-2-ylmethylsulfonyl |
| 1826 | 2 | OCH₃ | CH₂ | thiophen-2-ylmethyl |
| 1827 | 2 | OCH₃ | CH₂ | (phenyl-N-methylamino)sulfonyl |
| 1828 | 2 | OCH₃ | CH₂ | (1,1-dimethyl-1-phenyl)methylsulfonyl |
| 1829 | 2 | OCH₃ | CH₂ | phenylsulfonyl |
| 1830 | 2 | OCH₃ | CH₂ | benzylsulfonyl |
| 1831 | 2 | OCH₂C₆H₅ | CH₂ | picolin-2-ylsulfonyl |
| 1832 | 2 | OCH₂C₆H₅ | CH₂ | pyridin-2-ylsulfonyl |
| 1833 | 2 | OCH₂C₆H₅ | CH₂ | picolin-2-yl |
| 1834 | 2 | OCH₂C₆H₅ | CH₂ | thiophen-2-ylsulfonyl |
| 1835 | 2 | OCH₂C₆H₅ | CH₂ | (phenyl-N-methylamino)sulfonyl |
| 1836 | 2 | OCH₂C₆H₅ | CH₂ | (1,1-dimethyl-1-phenyl)methylsulfonyl |
| 1837 | 2 | OCH₂C₆H₅ | CH₂ | 4-fluorophenylsulfonyl |
| 1838 | 2 | OCH₂C₆H₅ | CH₂ | 4-fluorobenzylsulfonyl |
| 1839 | 2 | OCH₂C₆H₅ | CH₂ | phenylsulfonyl |
| 1840 | 2 | OCH₂C₆H₅ | CH₂ | benzyl sulfonyl |
| 1841 | 2 | NHC(O)CH₃ | CH₂ | picolin-2-ylsulfonyl |
| 1842 | 2 | NHC(O)CH₃ | CH₂ | pyridin-2-ylsulfonyl |
| 1843 | 2 | NHC(O)CH₃ | CH₂ | (phenyl-N-methylamino)sulfonyl |
| 1844 | 2 | NHC(O)CH₃ | CH₂ | (1,1-dimethyl-1-phenyl)methylsulfonyl |
| 1845 | 2 | NHC(O)CH₃ | CH₂ | thiophen-2-ylmethylsulfonyl |
| 1846 | 2 | NHC(O)CH₃ | CH₂ | thiophen-2-ylmethyl |
| 1847 | 2 | NHC(O)CH₃ | CH₂ | 4-fluorophenylsulfonyl |
| 1848 | 2 | NHC(O)CH₃ | CH₂ | 4-fluorobenzylsulfonyl |
| 1849 | 2 | NHC(O)CH₃ | CH₂ | phenylsulfonyl |
| 1850 | 2 | NHC(O)CH₃ | CH₂ | benzylsulfonyl |
| 1851 | 2 | NHC(O)OCH₃ | CH₂ | (phenyl-N-methylamino)sulfonyl |
| 1852 | 2 | NHC(O)OCH₃ | CH₂ | (1,1-dimethyl-1-phenyl)methylsulfonyl |
| 1853 | 2 | NHC(O)OCH₃ | CH₂ | picolin-2-yl |
| 1854 | 2 | NHC(O)OCH₃ | CH₂ | thiophen-2-ylsulfonyl |
| 1855 | 2 | NHC(O)OCH₃ | CH₂ | thiophen-2-ylmethylsulfonyl |
| 1856 | 2 | NHC(O)OCH₃ | CH₂ | thiophen-2-ylmethyl |
| 1857 | 2 | NHC(O)OCH₃ | CH₂ | 4-fluorophenylsulfonyl |
| 1858 | 2 | NHC(O)OCH₃ | CH₂ | 4-fluorobenzylsulfonyl |
| 1859 | 2 | NHC(O)OCH₃ | CH₂ | phenylsulfonyl |
| 1860 | 2 | NHC(O)OCH₃ | CH₂ | benzylsulfonyl |
| 1861 | 2 | NHC(O)NHCH₃ | CH₂ | picolin-2-ylsulfonyl |
| 1862 | 2 | NHC(O)NHCH₃ | CH₂ | pyridin-2-ylsulfonyl |
| 1863 | 2 | NHC(O)NHCH₃ | CH₂ | picolin-2-yl |
| 1864 | 2 | NHC(O)NHCH₃ | CH₂ | thiophen-2-ylsulfonyl |
| 1865 | 2 | NHC(O)NHCH₃ | CH₂ | thiophen-2-ylmethylsulfonyl |
| 1866 | 2 | NHC(O)NHCH₃ | CH₂ | thiophen-2-ylmethyl |
| 1867 | 2 | NHC(O)NHCH₃ | CH₂ | 4-fluorophenylsulfonyl |
| 1868 | 2 | NHC(O)NHCH₃ | CH₂ | 4-fluorobenzylsulfonyl |
| 1869 | 2 | NHC(O)NHCH₃ | CH₂ | (phenyl-N-methylamino)sulfonyl |
| 1870 | 2 | NHC(O)NHCH₃ | CH₂ | (1,1-dimethyl-1-phenyl)methylsulfonyl |
| 1871 | 2 | NHC(O)C₆H₅ | CH₂ | picolin-2-ylsulfonyl |

TABLE 18-continued

| Ex. | n | R² | Z | B |
|---|---|---|---|---|
| 1872 | 2 | NHC(O)C₆H₅ | CH₂ | pyridin-2-ylsulfonyl |
| 1873 | 2 | NHC(O)C₆H₅ | CH₂ | picolin-2-yl |
| 1874 | 2 | NHC(O)C₆H₅ | CH₂ | thiophen-2-ylsulfonyl |
| 1875 | 2 | NHC(O)C₆H₅ | CH₂ | thiophen-2-ylmethylsulfonyl |
| 1876 | 2 | NHC(O)C₆H₅ | CH₂ | thiophen-2-ylmethyl |
| 1877 | 2 | NHC(O)C₆H₅ | CH₂ | (phenyl-N-methylamino)sulfonyl |
| 1878 | 2 | NHC(O)C₆H₅ | CH₂ | (1,1-dimethyl-1-phenyl)methylsulfonyl |
| 1879 | 2 | NHC(O)C₆H₅ | CH₂ | phenylsulfonyl |
| 1880 | 2 | NHC(O)C₆H₅ | CH₂ | benzylsulfonyl |
| 1881 | 2 | NHSO₂CH₃ | CH₂ | picolin-2-ylsulfonyl |
| 1882 | 2 | NHSO₂CH₃ | CH₂ | pyridin-2-ylsulfonyl |
| 1883 | 2 | NHSO₂CH₃ | CH₂ | picolin-2-yl |
| 1884 | 2 | NHSO₂CH₃ | CH₂ | thiophen-2-ylsulfonyl |
| 1885 | 2 | NHSO₂CH₃ | CH₂ | (phenyl-N-methylamino)sulfonyl |
| 1886 | 2 | NHSO₂CH₃ | CH₂ | (1,1-dimethyl-1-phenyl)methylsulfonyl |
| 1887 | 2 | NHSO₂CH₃ | CH₂ | 4-fluorophenylsulfonyl |
| 1888 | 2 | NHSO₂CH₃ | CH₂ | 4-fluorobenzylsulfonyl |
| 1889 | 2 | NHSO₂CH₃ | CH₂ | phenylsulfonyl |
| 1890 | 2 | NHSO₂CH₃ | CH₂ | benzylsulfonyl |
| 1891 | 2 | NHSO₂NHCH₃ | CH₂ | picolin-2-ylsulfonyl |
| 1892 | 2 | NHSO₂NHCH₃ | CH₂ | pyridin-2-ylsulfonyl |
| 1893 | 2 | NHSO₂NHCH₃ | CH₂ | (phenyl-N-methylamino)sulfonyl |
| 1894 | 2 | NHSO₂NHCH₃ | CH₂ | (1,1-dimethyl-1-phenyl)methylsulfonyl |
| 1895 | 2 | NHSO₂NHCH₃ | CH₂ | thiophen-2-ylmethylsulfonyl |
| 1896 | 2 | NHSO₂NHCH₃ | CH₂ | thiophen-2-ylmethyl |
| 1897 | 2 | NHSO₂NHCH₃ | CH₂ | 4-fluorophenylsulfonyl |
| 1898 | 2 | NHSO₂NHCH₃ | CH₂ | 4-fluorobenzylsulfonyl |
| 1899 | 2 | NHSO₂NHCH₃ | CH₂ | phenylsulfonyl |
| 1900 | 2 | NHSO₂NHCH₃ | CH₂ | benzylsulfonyl |
| 1901 | 2 | NHSO₂C₆H₅ | CH₂ | (phenyl-N-methylamino)sulfonyl |
| 1902 | 2 | NHSO₂C₆H₅ | CH₂ | (1,1-dimethyl-1-phenyl)methylsulfonyl |
| 1903 | 2 | NHSO₂C₆H₅ | CH₂ | picolin-2-yl |
| 1904 | 2 | NHSO₂C₆H₅ | CH₂ | thiophen-2-ylsulfonyl |
| 1905 | 2 | NHSO₂C₆H₅ | CH₂ | thiophen-2-ylmethylsulfonyl |
| 1906 | 2 | NHSO₂C₆H₅ | CH₂ | thiophen-2-ylmethyl |
| 1907 | 2 | NHSO₂C₆H₅ | CH₂ | 4-fluorophenylsulfonyl |
| 1908 | 2 | NHSO₂C₆H₅ | CH₂ | 4-fluorobenzylsulfonyl |
| 1909 | 2 | NHSO₂C₆H₅ | CH₂ | phenylsulfonyl |
| 1910 | 2 | NHSO₂C₆H₅ | CH₂ | benzylsulfonyl |

TABLE 19

| Ex. | n | R² | Z | A* | B* |
|---|---|---|---|---|---|
| 2001 | 0 | H | (CH₂)₂O | phenyl | amino |
| 2002 | 0 | H | (CH₂)₂O | phenyl | amidino |
| 2003 | 0 | H | (CH₂)₂O | phenyl | guanidino |
| 2004 | 0 | H | (CH₂)₂O | phenyl | benzyl |
| 2005 | 0 | H | (CH₂)₂C(O) | phenyl | phenyl |
| 2006 | 0 | H | (CH₂)₂C(O) | phenyl | cyclohexyl |
| 2007 | 0 | H | (CH₂)₂C(O) | phenyl | 4-pyridyl |
| 2008 | 0 | H | (CH₂)₂C(O) | phenyl | 2-furanyl |
| 2009 | 0 | H | (CH₂)₂C(O)O | phenyl | piperidinyl |
| 2010 | 0 | H | (CH₂)₂C(O)O | phenyl | phenethyl |
| 2011 | 0 | H | (CH₂)₂C(O)O | phenyl | phenylcarbonyl |
| 2012 | 0 | H | (CH₂)₂C(O)O | phenyl | 2-aminophenylcarbonyl |
| 2013 | 0 | H | (CH₂)₂C(O)NH | phenyl | benzylcarbonyl |
| 2014 | 0 | H | (CH₂)₂C(O)NH | phenyl | 4-acetamidophenyl-methanecarbonyl |
| 2015 | 0 | H | (CH₂)₂C(O)NH | phenyl | phenylsulfonyl |
| 2016 | 0 | H | (CH₂)₂C(O)NH | phenyl | 4-amidinophenyl-sulfonyl |
| 2017 | 0 | H | (CH₂)₂NHC(O)NH | phenyl | benzylsulfonyl |
| 2018 | 0 | H | (CH₂)₂NHC(O)NH | phenyl | 4-methoxycarbonyl-phenylmethane-sulfonyl |
| 2019 | 0 | H | (CH₂)₂NHC(O)NH | phenyl | phenylsulfonamide |
| 2020 | 0 | H | (CH₂)₂NHC(O)NH | phenyl | 4-acetamidophenyl-sulfonamide |
| 2021 | 0 | H | (CH₂)₂S(O)₂NH | phenyl | phenylcarbamide |
| 2022 | 0 | H | (CH₂)₂S(O)₂NH | phenyl | 2-aminophenyl-carbamide |
| 2023 | 0 | H | (CH₂)₂S(O)₂NH | phenyl | benzylamine |
| 2024 | 0 | H | (CH₂)₂S(O)₂NH | phenyl | 4-amidinophenyl-methaneamine |
| 2025 | 0 | H | (CH₂)₂OCH₂ | phenyl | amino |
| 2026 | 0 | H | (CH₂)₂OCH₂ | phenyl | amidino |
| 2027 | 0 | H | (CH₂)₂OCH₂ | phenyl | guanidino |
| 2028 | 0 | H | (CH₂)₂OCH₂ | phenyl | benzyl |
| 2029 | 0 | H | (CH₂)₂C(O)CH₂ | phenyl | phenyl |
| 2030 | 0 | H | (CH₂)₂C(O)CH₂ | phenyl | cyclohexyl |
| 2031 | 0 | H | (CH₂)₂C(O)CH₂ | phenyl | 4-pyridyl |
| 2032 | 0 | H | (CH₂)₂C(O)CH₂ | phenyl | 2-furanyl |
| 2033 | 0 | H | (CH₂)₂C(O)OCH₂ | phenyl | piperidinyl |
| 2034 | 0 | H | (CH₂)₂C(O)OCH₂ | phenyl | phenethyl |
| 2035 | 0 | H | (CH₂)₂C(O)OCH₂ | phenyl | phenylcarbonyl |
| 2036 | 0 | H | (CH₂)₂C(O)OCH₂ | phenyl | 2-aminophenyl-carbonyl |
| 2037 | 0 | H | (CH₂)₂C(O)NHCH₂ | phenyl | benzylcarbonyl |
| 2038 | 0 | H | (CH₂)₂C(O)NHCH₂ | phenyl | 4-acetamidophenyl-methanecarbonyl |
| 2039 | 0 | H | (CH₂)₂C(O)NHCH₂ | phenyl | phenylsulfonyl |
| 2040 | 0 | H | (CH₂)₂C(O)NHCH₂ | phenyl | 4-amidinophenyl-sulfonyl |
| 2041 | 0 | H | (CH₂)₂NHC(O)NHCH₂ | phenyl | benzylsulfonyl |
| 2042 | 0 | H | (CH₂)₂NHC(O)NHCH₂ | phenyl | 4-methoxycarbonyl-phenylmethane-sulfonyl |
| 2043 | 0 | H | (CH₂)₂NHC(O)NHCH₂ | phenyl | phenylsulfonamide |
| 2044 | 0 | H | (CH₂)₂NHC(O)NHCH₂ | phenyl | 4-acetamidophenyl-sulfonamide |
| 2045 | 0 | H | (CH₂)₂S(O)₂NHCH₂ | phenyl | phenylcarbamide |
| 2046 | 0 | H | (CH₂)₂S(O)₂NHCH₂ | phenyl | 2-aminophenyl-carbamide |
| 2047 | 0 | H | (CH₂)₂S(O)₂NHCH₂ | phenyl | benzylamine |
| 2048 | 0 | H | (CH₂)₂S(O)₂NHCH₂ | phenyl | 4-amidinophenyl-methaneamine |

*B is substituted para to Z on A.

TABLE 20

[Structure: H₂N(HN=)C-phenyl-N(ring with R² and (CH₂)ₙ)-N-Z-A-B, where the ring is a cyclic urea with C=O]

| Ex. | n | R² | Z | A* | B* |
|---|---|---|---|---|---|
| 2101 | 1 | H | (CH₂)₂O | phenyl | amino |
| 2102 | 1 | H | (CH₂)₂O | phenyl | amidino |
| 2103 | 1 | H | (CH₂)₂O | phenyl | guanidino |
| 2104 | 1 | H | (CH₂)₂O | phenyl | benzyl |
| 2105 | 1 | H | (CH₂)₂C(O) | phenyl | phenyl |
| 2106 | 1 | H | (CH₂)₂C(O) | phenyl | cyclohexyl |
| 2107 | 1 | H | (CH₂)₂C(O) | phenyl | 4-pyridyl |
| 2108 | 1 | H | (CH₂)₂C(O) | phenyl | 2-furanyl |
| 2109 | 1 | H | (CH₂)₂C(O)O | phenyl | piperidinyl |
| 2110 | 1 | H | (CH₂)₂C(O)O | phenyl | phenethyl |
| 2111 | 1 | H | (CH₂)₂C(O)O | phenyl | phenylcarbonyl |
| 2112 | 1 | H | (CH₂)₂C(O)O | phenyl | 2-aminophenyl-carbonyl |
| 2113 | 1 | H | (CH₂)₂C(O)NH | phenyl | benzylcarbonyl |
| 2114 | 1 | H | (CH₂)₂C(O)NH | phenyl | 4-acetamidophenyl-methanecarbonyl |
| 2115 | 1 | H | (CH₂)₂C(O)NH | phenyl | phenylsulfonyl |
| 2116 | 1 | H | (CH₂)₂C(O)NH | phenyl | 4-amidinophenyl-sulfonyl |
| 2117 | 1 | H | (CH₂)₂NHC(O)NH | phenyl | benzylsulfonyl |
| 2118 | 1 | H | (CH₂)₂NHC(O)NH | phenyl | 4-methoxycarbonyl-phenylmethane-sulfonyl |
| 2119 | 1 | H | (CH₂)₂NHC(O)NH | phenyl | phenylsulfonamide |
| 2120 | 1 | H | (CH₂)₂NHC(O)NH | phenyl | 4-acetamidophenyl-sulfonamide |
| 2121 | 1 | H | (CH₂)₂S(O)₂NH | phenyl | phenylcarbamide |
| 2122 | 1 | H | (CH₂)₂S(O)₂NH | phenyl | 2-aminophenyl-carbamide |
| 2123 | 1 | H | (CH₂)₂S(O)₂NH | phenyl | benzylamine |
| 2124 | 1 | H | (CH₂)₂S(O)₂NH | phenyl | 4-amidinophenyl-methaneamine |
| 2125 | 1 | H | (CH₂)₂OCH₂ | phenyl | amino |
| 2126 | 1 | H | (CH₂)₂OCH₂ | phenyl | amidino |
| 2127 | 1 | H | (CH₂)₂OCH₂ | phenyl | guanidino |
| 2128 | 1 | H | (CH₂)₂OCH₂ | phenyl | benzyl |
| 2129 | 1 | H | (CH₂)₂C(O)CH₂ | phenyl | phenyl |
| 2130 | 1 | H | (CH₂)₂C(O)CH₂ | phenyl | cyclohexyl |
| 2131 | 1 | H | (CH₂)₂C(O)CH₂ | phenyl | 4-pyridyl |
| 2132 | 1 | H | (CH₂)₂C(O)CH₂ | phenyl | 2-furanyl |
| 2133 | 1 | H | (CH₂)₂C(O)OCH₂ | phenyl | piperidinyl |
| 2134 | 1 | H | (CH₂)₂C(O)OCH₂ | phenyl | phenethyl |
| 2135 | 1 | H | (CH₂)₂C(O)OCH₂ | phenyl | phenylcarbonyl |
| 2136 | 1 | H | (CH₂)₂C(O)OCH₂ | phenyl | 2-aminophenyl-carbonyl |
| 2137 | 1 | H | (CH₂)₂C(O)NHCH₂ | phenyl | benzylcarbonyl |
| 2138 | 1 | H | (CH₂)₂C(O)NHCH₂ | phenyl | 4-acetamidophenyl-methanecarbonyl |
| 2139 | 1 | H | (CH₂)₂C(O)NHCH₂ | phenyl | phenylsulfonyl |
| 2140 | 1 | H | (CH₂)₂C(O)NHCH₂ | phenyl | 4-amidinophenyl-sulfonyl |
| 2141 | 1 | H | (CH₂)₂NHC(O)NHCH₂ | phenyl | benzylsulfonyl |
| 2142 | 1 | H | (CH₂)₂NHC(O)NHCH₂ | phenyl | 4-methoxycarbonyl-phenylmethane-sulfonyl |
| 2143 | 1 | H | (CH₂)₂NHC(O)NHCH₂ | phenyl | phenylsulfonamide |
| 2144 | 1 | H | (CH₂)₂NHC(O)NHCH₂ | phenyl | 4-acetamidophenyl-sulfonamide |
| 2145 | 1 | H | (CH₂)₂S(O)₂NHCH₂ | phenyl | phenylcarbamide |
| 2146 | 1 | H | (CH₂)₂S(O)₂NHCH₂ | phenyl | 2-aminophenyl-carbamide |
| 2147 | 1 | H | (CH₂)₂S(O)₂NHCH₂ | phenyl | benzylamine |
| 2148 | 1 | H | (CH₂)₂S(O)₂NHCH₂ | phenyl | 4-amidinophenyl-methaneamine |

*B is substituted para to Z on A.

TABLE 21

[Same structure as Table 20]

| Ex. | n | R² | Z | A* | B* |
|---|---|---|---|---|---|
| 2201 | 2 | H | (CH₂)₂O | phenyl | amino |
| 2202 | 2 | H | (CH₂)₂O | phenyl | amidino |
| 2203 | 2 | H | (CH₂)₂O | phenyl | guanidino |
| 2204 | 2 | H | (CH₂)₂O | phenyl | benzyl |
| 2205 | 2 | H | (CH₂)₂C(O) | phenyl | phenyl |
| 2206 | 2 | H | (CH₂)₂C(O) | phenyl | cyclohexyl |
| 2207 | 2 | H | (CH₂)₂C(O) | phenyl | 4-pyridyl |
| 2208 | 2 | H | (CH₂)₂C(O) | phenyl | 2-furanyl |
| 2209 | 2 | H | (CH₂)₂C(O)O | phenyl | piperidinyl |
| 2210 | 2 | H | (CH₂)₂C(O)O | phenyl | phenethyl |
| 2211 | 2 | H | (CH₂)₂C(O)O | phenyl | phenylcarbonyl |
| 2212 | 2 | H | (CH₂)₂C(O)O | phenyl | 2-aminophenyl-carbonyl |
| 2213 | 2 | H | (CH₂)₂C(O)NH | phenyl | benzylcarbonyl |
| 2214 | 2 | H | (CH₂)₂C(O)NH | phenyl | 4-acetamidophenyl-methanecarbonyl |
| 2215 | 2 | H | (CH₂)₂C(O)NH | phenyl | phenylsulfonyl |
| 2216 | 2 | H | (CH₂)₂C(O)NH | phenyl | 4-amidinophenyl-sulfonyl |
| 2217 | 2 | H | (CH₂)₂NHC(O)NH | phenyl | benzylsulfonyl |
| 2218 | 2 | H | (CH₂)₂NHC(O)NH | phenyl | 4-methoxycarbonyl-phenylmethane-sulfonyl |
| 2219 | 2 | H | (CH₂)₂NHC(O)NH | phenyl | phenylsulfonamide |
| 2220 | 2 | H | (CH₂)₂NHC(O)NH | phenyl | 4-acetamidophenyl-sulfonamide |
| 2221 | 2 | H | (CH₂)₂S(O)₂NH | phenyl | phenylcarbamide |
| 2222 | 2 | H | (CH₂)₂S(O)₂NH | phenyl | 2-aminophenyl-carbamide |
| 2223 | 2 | H | (CH₂)₂S(O)₂NH | phenyl | benzylamine |
| 2224 | 2 | H | (CH₂)₂S(O)₂NH | phenyl | 4-amidinophenyl-methaneamine |
| 2225 | 2 | H | (CH₂)₂OCH₂ | phenyl | amino |
| 2226 | 2 | H | (CH₂)₂OCH₂ | phenyl | amidino |
| 2227 | 2 | H | (CH₂)₂OCH₂ | phenyl | guanidino |
| 2228 | 2 | H | (CH₂)₂OCH₂ | phenyl | benzyl |
| 2229 | 2 | H | (CH₂)₂C(O)CH₂ | phenyl | phenyl |
| 2230 | 2 | H | (CH₂)₂C(O)CH₂ | phenyl | cyclohexyl |
| 2231 | 2 | H | (CH₂)₂C(O)CH₂ | phenyl | 4-pyridyl |
| 2232 | 2 | H | (CH₂)₂C(O)CH₂ | phenyl | 2-furanyl |
| 2233 | 2 | H | (CH₂)₂C(O)OCH₂ | phenyl | piperidinyl |
| 2234 | 2 | H | (CH₂)₂C(O)OCH₂ | phenyl | phenethyl |
| 2235 | 2 | H | (CH₂)₂C(O)OCH₂ | phenyl | phenylcarbonyl |
| 2236 | 2 | H | (CH₂)₂C(O)OCH₂ | phenyl | 2-aminophenyl-carbonyl |
| 2237 | 2 | H | (CH₂)₂C(O)NHCH₂ | phenyl | benzylcarbonyl |
| 2238 | 2 | H | (CH₂)₂C(O)NHCH₂ | phenyl | 4-acetamidophenyl-methanecarbonyl |
| 2239 | 2 | H | (CH₂)₂C(O)NHCH₂ | phenyl | phenylsulfonyl |
| 2240 | 2 | H | (CH₂)₂C(O)NHCH₂ | phenyl | 4-amidinophenyl-sulfonyl |
| 2241 | 2 | H | (CH₂)₂NHC(O)NHCH₂ | phenyl | benzylsulfonyl |
| 2242 | 2 | H | (CH₂)₂NHC(O)NHCH₂ | phenyl | 4-methoxycarbonyl-phenylmethane-sulfonyl |
| 2243 | 2 | H | (CH₂)₂NHC(O)NHCH₂ | phenyl | phenylsulfonamide |
| 2244 | 2 | H | (CH₂)₂NHC(O)NHCH₂ | phenyl | 4-acetamidophenyl-sulfonamide |
| 2245 | 2 | H | (CH₂)₂S(O)₂NHCH₂ | phenyl | phenylcarbamide |
| 2246 | 2 | H | (CH₂)₂S(O)₂NHCH₂ | phenyl | 2-aminophenyl-carbamide |
| 2247 | 2 | H | (CH₂)₂S(O)₂NHCH₂ | phenyl | benzylamine |
| 2248 | 2 | H | (CH₂)₂S(O)₂NHCH₂ | phenyl | 4-amidinophenyl-methaneamine |

*B is substituted para to Z on A.

TABLE 22

| Ex. | n | Z | A* | B* |
|---|---|---|---|---|
| 2301 | 0 | (CH$_2$)$_2$O | 2-fluorophenyl | imidazol-1-yl |
| 2302 | 0 | (CH$_2$)$_2$O | 2-chlorophenyl | N,N-dimethylamido |
| 2303 | 0 | (CH$_2$)$_2$O | 2-bromophenyl | morpholin-1-yl |
| 2304 | 0 | (CH$_2$)$_2$O | 2-pyridyl | 2-methylindazol-1-yl |
| 2305 | 0 | (CH$_2$)$_2$O | 2-pyrimidinyl | N,N-dimethylsulfamido |
| 2306 | 0 | (CH$_2$)$_2$C(O) | 2-fluorophenyl | pyridin-3-yl |
| 2307 | 0 | (CH$_2$)$_2$C(O) | 2-chlorophenyl | 2-((5'-trifluormethyl)tetrazol-1'-yl)phenyl |
| 2308 | 0 | (CH$_2$)$_2$C(O) | 2-bromophenyl | pyrazol-1-yl |
| 2309 | 0 | (CH$_2$)$_2$C(O) | 2-pyridyl | cyclohexyl |
| 2310 | 0 | (CH$_2$)$_2$C(O)O | 2-pyrimidinyl | imidazol-1-yl |
| 2311 | 0 | (CH$_2$)$_2$C(O)O | 2-fluorophenyl | N,N-dimethylamido |
| 2312 | 0 | (CH$_2$)$_2$C(O)O | 2-chlorophenyl | morpholin-1-yl |
| 2313 | 0 | (CH$_2$)$_2$C(O)O | 2-bromophenyl | 2-methylindazol-1-yl |
| 2314 | 0 | (CH$_2$)$_2$C(O)NH | 2-pyridyl | N,N-dimethylsulfamido |
| 2315 | 0 | (CH$_2$)$_2$C(O)NH | 2-pyrimidinyl | pyridin-3-yl |
| 2316 | 0 | (CH$_2$)$_2$C(O)NH | 2-fluorophenyl | 2-((5'-trifluormethyl)tetrazol-1'-yl)phenyl |
| 2317 | 0 | (CH$_2$)$_2$C(O)NH | 2-chlorophenyl | pyrazol-1-yl |
| 2318 | 0 | (CH$_2$)$_2$C(O)NH | 2-bromophenyl | cyclohexyl |
| 2319 | 0 | (CH$_2$)$_2$NHC(O)NH | 2-pyridyl | imidazol-1-yl |
| 2320 | 0 | (CH$_2$)$_2$NHC(O)NH | 2-pyrimidinyl | N,N-dimethylamido |
| 2321 | 0 | (CH$_2$)$_2$NHC(O)NH | 2-fluorophenyl | morpholin-1-yl |
| 2322 | 0 | (CH$_2$)$_2$NHC(O)NH | 2-chlorophenyl | 2-methylindazol-1-yl |
| 2323 | 0 | (CH$_2$)$_2$S(O)$_2$NH | 2-bromophenyl | N,N-dimethylsulfamido |
| 2324 | 0 | (CH$_2$)$_2$S(O)$_2$NH | 2-pyridyl | pyridin-3-yl |
| 2325 | 0 | (CH$_2$)$_2$S(O)$_2$NH | 2-pyrimidinyl | 2-((5'-trifluormethyl)tetrazol-1'-yl)phenyl |
| 2326 | 0 | (CH$_2$)$_2$S(O)$_2$NH | 2-fluorophenyl | pyrazol-1-yl |
| 2327 | 0 | (CH$_2$)$_2$S(O)$_2$NH | 2-chlorophenyl | cyclohexyl |
| 2328 | 0 | (CH$_2$)$_2$OCH$_2$ | 2-bromophenyl | imidazol-1-yl |
| 2329 | 0 | (CH$_2$)$_2$OCH$_2$ | 2-pyridyl | N,N-dimethylamido |
| 2330 | 0 | (CH$_2$)$_2$OCH$_2$ | 2-pyrimidinyl | morpholin-1-yl |
| 2331 | 0 | (CH$_2$)$_2$OCH$_2$ | 2-fluorophenyl | 2-methylindazol-1-yl |
| 2332 | 0 | (CH$_2$)$_2$OCH$_2$ | 2-chlorophenyl | N,N-dimethylsulfamido |
| 2333 | 0 | (CH$_2$)$_2$C(O)CH$_2$ | 2-bromophenyl | pyridin-3-yl |
| 2334 | 0 | (CH$_2$)$_2$C(O)CH$_2$ | 2-pyridyl | 2-((5'-trifluormethyl)tetrazol-1'-yl)phenyl |
| 2335 | 0 | (CH$_2$)$_2$C(O)CH$_2$ | 2-pyrimidinyl | pyrazol-1-yl |
| 2336 | 0 | (CH$_2$)$_2$C(O)CH$_2$ | 2-fluorophenyl | cyclohexyl |
| 2337 | 0 | (CH$_2$)$_2$C(O)OCH$_2$ | 2-chlorophenyl | imidazol-1-yl |
| 2338 | 0 | (CH$_2$)$_2$C(O)OCH$_2$ | 2-bromophenyl | N,N-dimethylamido |
| 2339 | 0 | (CH$_2$)$_2$C(O)OCH$_2$ | 2-pyridyl | morpholin-1-yl |
| 2340 | 0 | (CH$_2$)$_2$C(O)OCH$_2$ | 2-pyrimidinyl | 2-methylindazol-1-yl |
| 2341 | 0 | (CH$_2$)$_2$C(O)OCH$_2$ | 2-fluorophenyl | N,N-dimethylsulfamido |
| 2342 | 0 | (CH$_2$)$_2$C(O)NHCH$_2$ | 2-chlorophenyl | pyridin-3-yl |
| 2343 | 0 | (CH$_2$)$_2$C(O)NHCH$_2$ | 2-bromophenyl | 2-((5'-trifluormethyl)tetrazol-1'-yl)phenyl |
| 2344 | 0 | (CH$_2$)$_2$C(O)NHCH$_2$ | 2-pyridyl | pyrazol-1-yl |
| 2345 | 0 | (CH$_2$)$_2$C(O)NHCH$_2$ | 2-pyrimidinyl | cyclohexyl |
| 2346 | 0 | (CH$_2$)$_2$NHC(O)NHCH$_2$ | 2-fluorophenyl | imidazol-1-yl |
| 2347 | 0 | (CH$_2$)$_2$NHC(O)NHCH$_2$ | 2-chlorophenyl | N,N-dimethylamido |
| 2348 | 0 | (CH$_2$)$_2$NHC(O)NHCH$_2$ | 2-bromophenyl | morpholin-1-yl |
| 2349 | 0 | (CH$_2$)$_2$NHC(O)NHCH$_2$ | 2-pyridyl | 2-methylindazol-1-yl |
| 2350 | 0 | (CH$_2$)$_2$NHC(O)NHCH$_2$ | 2-fluorophenyl | N,N-dimethylsulfamido |
| 2351 | 0 | (CH$_2$)$_2$S(O)$_2$NHCH$_2$ | 2-chlorophenyl | pyridin-3-yl |
| 2352 | 0 | (CH$_2$)$_2$S(O)$_2$NHCH$_2$ | 2-bromophenyl | 2-((5'-trifluormethyl)tetrazol-1'-yl)phenyl |
| 2353 | 0 | (CH$_2$)$_2$S(O)$_2$NHCH$_2$ | 2-pyridyl | pyrazol-1-yl |
| 2354 | 0 | (CH$_2$)$_2$S(O)$_2$NHCH$_2$ | 2-pyrimidinyl | cyclohexyl |

*B is substituted para to Z on A.

TABLE 23

[Structure: H2N-C(=NH)-phenyl-N(ring)-C(=O)-N-Z-A-B where ring is a 6-membered ring with (CH2)n]

| Ex. | n | Z | A* | B* |
|---|---|---|---|---|
| 2401 | 1 | (CH₂)₂O | 2-fluorophenyl | imidazol-1-yl |
| 2402 | 1 | (CH₂)₂O | 2-chlorophenyl | N,N-dimethylamido |
| 2403 | 1 | (CH₂)₂O | 2-bromophenyl | morpholin-1-yl |
| 2404 | 1 | (CH₂)₂O | 2-pyridyl | 2-methylindazol-1-yl |
| 2405 | 1 | (CH₂)₂O | 2-pyrimidinyl | N,N-dimethylsulfamido |
| 2406 | 1 | (CH₂)₂C(O) | 2-fluorophenyl | pyridin-3-yl |
| 2407 | 1 | (CH₂)₂C(O) | 2-chlorophenyl | 2-((5'-trifluormethyl)tetrazol-1'-yl)phenyl |
| 2408 | 1 | (CH₂)₂C(O) | 2-bromophenyl | pyrazol-1-yl |
| 2409 | 1 | (CH₂)₂C(O) | 2-pyridyl | cyclohexyl |
| 2410 | 1 | (CH₂)₂C(O)O | 2-pyrimidinyl | imidazol-1-yl |
| 2411 | 1 | (CH₂)₂C(O)O | 2-fluorophenyl | N,N-dimethylamido |
| 2412 | 1 | (CH₂)₂C(O)O | 2-chlorophenyl | morpholin-1-yl |
| 2413 | 1 | (CH₂)₂C(O)O | 2-bromophenyl | 2-methylindazol-1-yl |
| 2414 | 1 | (CH₂)₂C(O)NH | 2-pyridyl | N,N-dimethylsulfamido |
| 2415 | 1 | (CH₂)₂C(O)NH | 2-pyrimidinyl | pyridin-3-yl |
| 2416 | 1 | (CH₂)₂C(O)NH | 2-fluorophenyl | 2-((5'-trifluormethyl)tetrazol-1'-yl) phenyl |
| 2417 | 1 | (CH₂)₂C(O)NH | 2-chlorophenyl | pyrazol-1-yl |
| 2418 | 1 | (CH₂)₂C(O)NH | 2-bromophenyl | cyclohexyl |
| 2419 | 1 | (CH₂)₂NHC(O)NH | 2-pyridyl | imidazol-1-yl |
| 2420 | 1 | (CH₂)₂NHC(O)NH | 2-pyrimidinyl | N,N-dimethylamido |
| 2421 | 1 | (CH₂)₂NHC(O)NH | 2-fluorophenyl | morpholin-1-yl |
| 2422 | 1 | (CH₂)₂NHC(O)NH | 2-chlorophenyl | 2-methylindazol-1-yl |
| 2423 | 1 | (CH₂)₂S(O)₂NH | 2-bromophenyl | N,N-dimethylsulfamido |
| 2424 | 1 | (CH₂)₂S(O)₂NH | 2-pyridyl | pyridin-3-yl |
| 2425 | 1 | (CH₂)₂S(O)₂NH | 2-pyrimidinyl | 2-((5'-trifluormethyl)tetrazol-1'-yl)phenyl |
| 2426 | 1 | (CH₂)₂S(O)₂NH | 2-fluorophenyl | pyrazol-1-yl |
| 2427 | 1 | (CH₂)₂S(O)₂NH | 2-chlorophenyl | cyclohexyl |
| 2428 | 1 | (CH₂)₂OCH₂ | 2-bromophenyl | imidazol-1-yl |
| 2429 | 1 | (CH₂)₂OCH₂ | 2-pyridyl | N,N-dimethylamido |
| 2430 | 1 | (CH₂)₂OCH₂ | 2-pyrimidinyl | morpholin-1-yl |
| 2431 | 1 | (CH₂)₂OCH₂ | 2-fluorophenyl | 2-methylindazol-1-yl |
| 2432 | 1 | (CH₂)₂OCH₂ | 2-chlorophenyl | N,N-dimethylsulfamido |
| 2433 | 1 | (CH₂)₂C(O)CH₂ | 2-bromophenyl | pyridin-3-yl |
| 2434 | 1 | (CH₂)₂C(O)CH₂ | 2-pyridyl | 2-((5'-trifluormethyl)tetrazol-1'-yl)phenyl |
| 2435 | 1 | (CH₂)₂C(O)CH₂ | 2-pyrimidinyl | pyrazol-1-yl |
| 2436 | 1 | (CH₂)₂C(O)CH₂ | 2-fluorophenyl | cyclohexyl |
| 2437 | 1 | (CH₂)₂C(O)OCH₂ | 2-chlorophenyl | imidazol-1-yl |
| 2438 | 1 | (CH₂)₂C(O)OCH₂ | 2-bromophenyl | N,N-dimethylamido |
| 2439 | 1 | (CH₂)₂C(O)OCH₂ | 2-pyridyl | morpholin-1-yl |
| 2440 | 1 | (CH₂)₂C(O)OCH₂ | 2-pyrimidinyl | 2-methylindazol-1-yl |
| 2441 | 1 | (CH₂)₂C(O)OCH₂ | 2-fluorophenyl | N,N-dimethylsulfamido |
| 2442 | 1 | (CH₂)₂C(O)NHCH₂ | 2-chlorophenyl | pyridin-3-yl |
| 2443 | 1 | (CH₂)₂C(O)NHCH₂ | 2-bromophenyl | 2-((5'-trifluormethyl)tetrazol-1'-yl)phenyl |
| 2444 | 1 | (CH₂)₂C(O)NHCH₂ | 2-pyridyl | pyrazol-l-yl |
| 2445 | 1 | (CH₂)₂C(O)NHCH₂ | 2-pyrimidinyl | cyclohexyl |
| 2446 | 1 | (CH₂)₂NHC(O)NHCH₂ | 2-fluorophenyl | imidazol-1-yl |
| 2447 | 1 | (CH₂)₂NHC(O)NHCH₂ | 2-chlorophenyl | N,N-dimethylamido |
| 2448 | 1 | (CH₂)₂NHC(O)NHCH₂ | 2-bromophenyl | morpholin-l-yl |
| 2449 | 1 | (CH₂)₂NHC(O)NHCH₂ | 2-pyridyl | 2-methylindazol-l-yl |
| 2450 | 1 | (CH₂)₂NHC(O)NHCH₂ | 2-fluorophenyl | N,N-dimethylsulfamido |
| 2451 | 1 | (CH₂)₂S(O)₂NHCH₂ | 2-chlorophenyl | pyridin-3-yl |
| 2452 | 1 | (CH₂)₂S(O)₂NHCH₂ | 2-bromophenyl | 2-((5'-trifluormethyl)tetrazol-1'-yl)phenyl |
| 2453 | 1 | (CH₂)₂S(O)₂NHCH₂ | 2-pyridyl | pyrazol-l-yl |
| 2454 | 1 | (CH₂)₂S(O)₂NHCH₂ | 2-pyrimidinyl | cyclohexyl |

*B is substituted para to Z on A.

TABLE 24

| Ex. | n | Z | A* | B* |
|---|---|---|---|---|
| 2501 | 2 | (CH$_2$)$_2$O | 2-fluorophenyl | imidazol-1-yl |
| 2502 | 2 | (CH$_2$)$_2$O | 2-chlorophenyl | N,N-dimethylamido |
| 2503 | 2 | (CH$_2$)$_2$O | 2-bromophenyl | morpholin-1-yl |
| 2504 | 2 | (CH$_2$)$_2$O | 2-pyridyl | 2-methylindazol-l-yl |
| 2505 | 2 | (CH$_2$)$_2$O | 2-pyrimidinyl | N,N-dimethylsulfamido |
| 2506 | 2 | (CH$_2$)$_2$C(O) | 2-fluorophenyl | pyridin-3-yl |
| 2507 | 2 | (CH$_2$)$_2$C(O) | 2-chlorophenyl | 2-((5'-trifluormethyl) tetrazol-1'-yl) phenyl |
| 2508 | 2 | (CH$_2$)$_2$C(O) | 2-bromophenyl | pyrazol-1-yl |
| 2509 | 2 | (CH$_2$)$_2$C(O) | 2-pyridyl | cyclohexyl |
| 2510 | 2 | (CH$_2$)$_2$C(O)O | 2-pyrimidinyl | imidazol-1-yl |
| 2511 | 2 | (CH$_2$)$_2$C(O)O | 2-fluorophenyl | N,N-dimethylamido |
| 2512 | 2 | (CH$_2$)$_2$C(O)O | 2-chlorophenyl | morpholin-l-yl |
| 2513 | 2 | (CH$_2$)$_2$C(O)O | 2-bromophenyl | 2-methylindazol-l-yl |
| 2514 | 2 | (CH$_2$)$_2$C(O)NH | 2-pyridyl | N,N-dimethylsulfamido |
| 2515 | 2 | (CH$_2$)$_2$C(O)NH | 2-pyrimidinyl | pyridin-3-yl |
| 2516 | 2 | (CH$_2$)$_2$C(O)NH | 2-fluorophenyl | 2-((5'-trifluormethyl) tetrazol-1'-yl) phenyl |
| 2517 | 2 | (CH$_2$)$_2$C(O)NH | 2-chlorophenyl | pyrazol-1-yl |
| 2518 | 2 | (CH$_2$)$_2$C(O)NH | 2-bromophenyl | cyclohexyl |
| 2519 | 2 | (CH$_2$)$_2$NHC(O)NH | 2-pyridyl | imidazol-1-yl |
| 2520 | 2 | (CH$_2$)$_2$NHC(O)NH | 2-pyrimidinyl | N,N-dimethylamido |
| 2521 | 2 | (CH$_2$)$_2$NHC(O)NH | 2-fluorophenyl | morpholin-1-yl |
| 2522 | 2 | (CH$_2$)$_2$NHC(O)NH | 2-chlorophenyl | 2-methylindazol-1-yl |
| 2523 | 2 | (CH$_2$)$_2$S(O)$_2$NH | 2-bromophenyl | N,N-dimethylsulfamido |
| 2524 | 2 | (CH$_2$)$_2$S(O)$_2$NH | 2-pyridyl | pyridin-3-yl |
| 2525 | 2 | (CH$_2$)$_2$S(O)$_2$NH | 2- pyrimidinyl | 2-((5'-trifluormethyl) tetrazol-1'-yl) phenyl |
| 2526 | 2 | (CH$_2$)$_2$S(O)$_2$NH | 2-fluorophenyl | pyrazol-1-yl |
| 2527 | 2 | (CH$_2$)$_2$S(O)$_2$NH | 2-chlorophenyl | cyclohexyl |
| 2528 | 2 | (CH$_2$)$_2$OCH$_2$ | 2-bromophenyl | imidazol-1-yl |
| 2529 | 2 | (CH$_2$)$_2$OCH$_2$ | 2-pyridyl | N,N-dimethylamido |
| 2530 | 2 | (CH$_2$)$_2$OCH$_2$ | 2-pyrimidinyl | morpholin-1-yl |
| 2531 | 2 | (CH$_2$)$_2$OCH$_2$ | 2-fluorophenyl | 2-methylindazol-1-yl |
| 2532 | 2 | (CH$_2$)$_2$OCH$_2$ | 2-chlorophenyl | N,N-dimethylsulfamido |
| 2533 | 2 | (CH$_2$)$_2$C(O)CH$_2$ | 2-bromophenyl | pyridin-3-yl |
| 2534 | 2 | (CH$_2$)$_2$C(O)CH$_2$ | 2-pyridyl | 2-((5'-trifluormethyl) tetrazol-1'-yl) phenyl |
| 2535 | 2 | (CH$_2$)$_2$C(O)CH$_2$ | 2-pyrimidinyl | pyrazol-1-yl |
| 2536 | 2 | (CH$_2$)$_2$C(O)CH$_2$ | 2-fluorophenyl | cyclohexyl |
| 2537 | 2 | (CH$_2$)$_2$C(O)OCH$_2$ | 2-chlorophenyl | imidazol-1-yl |
| 2538 | 2 | (CH$_2$)$_2$C(O)OCH$_2$ | 2-bromophenyl | N,N-dimethylamido |
| 2539 | 2 | (CH$_2$)$_2$C(O)OCH$_2$ | 2-pyridyl | morpholin-1-yl |
| 2540 | 2 | (CH$_2$)$_2$C(O)OCH$_2$ | 2-pyrimidinyl | 2-methylindazol-l-yl |
| 2541 | 2 | (CH$_2$)$_2$C(O)OCH$_2$ | 2-fluorophenyl | N,N-dimethylsulfamido |
| 2542 | 2 | (CH$_2$)$_2$C(O)NHCH$_2$ | 2-chlorophenyl | pyridin-3-yl |
| 2543 | 2 | (CH$_2$)$_2$C(O)NHCH$_2$ | 2-bromophenyl | 2-((5'-trifluormethyl) tetrazol-1'yl)phenyl |
| 2544 | 2 | (CH$_2$)$_2$C(O)NHCH$_2$ | 2-pyridyl | pyrazol-1-yl cyclohexyl |
| 2545 | 2 | (CH$_2$)$_2$C(O)NHCH$_2$ | 2-pyrimidinyl | imidazol-1-yl |
| 2546 | 2 | (CH$_2$)$_2$NHC(O)NHCH$_2$ | 2-fluorophenyl | |
| 2547 | 2 | (CH$_2$)$_2$NHC(O)NHCH$_2$ | 2-chlorophenyl | N,N-dimethylamido |
| 2548 | 2 | (CH$_2$)$_2$NHC(O)NHCH$_2$ | 2-bromophenyl | morpholin-1-yl |
| 2549 | 2 | (CH$_2$)$_2$NHC(O)NHCH$_2$ | 2-pyridyl | 2-methylindazol-1-yl |
| 2550 | 2 | (CH$_2$)$_2$NHC(O)NHCH$_2$ | 2-fluorophenyl | N,N-dimethylsulfamido |
| 2551 | 2 | (CH$_2$)$_2$S(O)$_2$NHCH$_2$ | 2-chlorophenyl | pyridin-3-yl |
| 2552 | 2 | (CH$_2$)$_2$S(O)$_2$NHCH$_2$ | 2-bromophenyl | 2-((5'-trifluormethyl) tetrazol-1'-yl)phenyl |
| 2553 | 2 | (CH$_2$)$_2$S(O)$_2$NHCH$_2$ | 2-pyridyl | pyrazol-1-yl |
| 2554 | 2 | (CH$_2$)$_2$S(O)$_2$NHCH$_2$ | 2-pyrimidinyl | cyclohexyl |

*B is substituted para to Z on A.

TABLE 25*
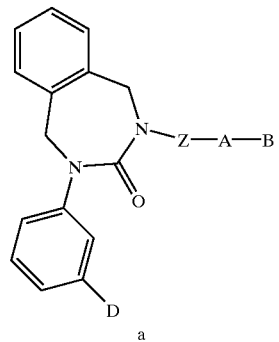
a
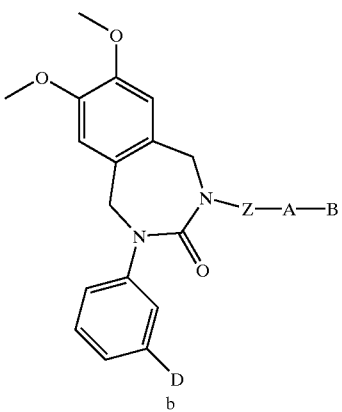
b
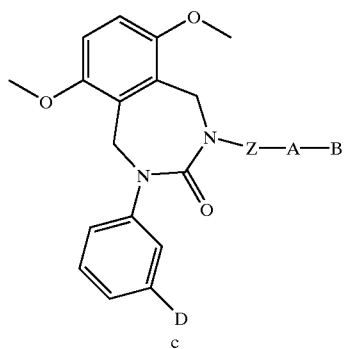
c
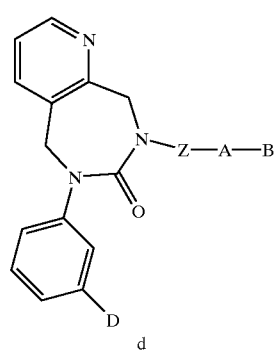
d
TABLE 25*-continued
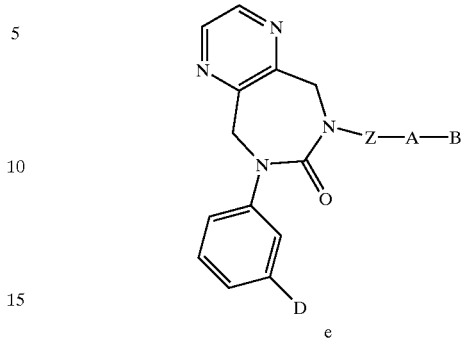
e
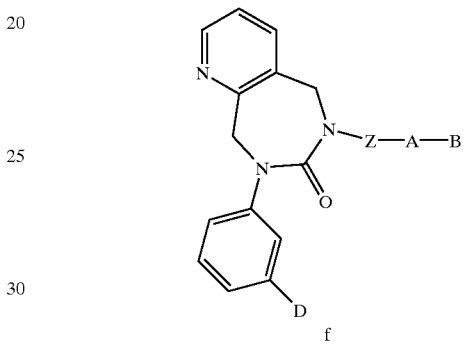
f
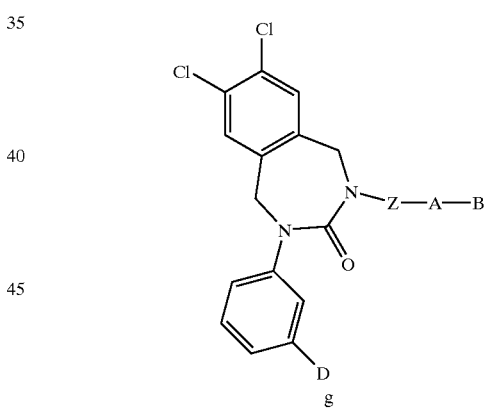
g
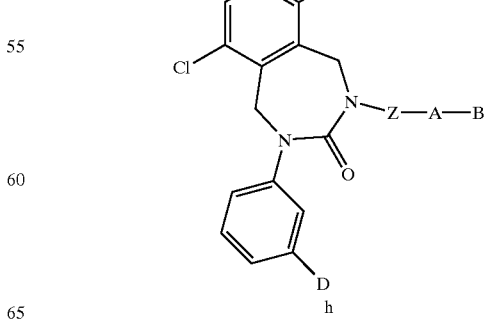
h TABLE 25*-continued Structures:

i: 1,3-dihydro-2H-benzimidazol-2-one with N1-phenyl(D) and N3-Z-A-B j: 3,4-dihydroquinazolin-2(1H)-one with N1-phenyl(D) and N3-Z-A-N k: 3,4-dihydroquinazolin-2(1H)-one with N3-phenyl(D) and N1-B-A-Z l: 1,3,4,5-tetrahydro-2H-1-benzazepin-2-one analog with N-Z-A-B and phenyl(D) substituent m: 1,3,4,5-tetrahydro-2H-benzo-diazepin-2-one with N3-phenyl(D) and N1-B-A-Z

| Ex. | D | Z | A¹ | A² | B |
|---|---|---|---|---|---|
| 2601 | C(=NH)NH₂ | bond | CH | CH | amino |
| 2602 | C(=NH)NH₂ | bond | CH | CH | amidino |
| 2603 | C(=NH)NH₂ | bond | CH | CH | guanidino |
| 2604 | C(=NH)NH₂ | bond | CH | CH | 2-sulfamidophenyl |
| 2605 | C(=NH)NH₂ | bond | CH | CH | 2-trifluoromethylphenyl |
| 2606 | C(=NH)NH₂ | CH₂ | CH | CH | amino |
| 2607 | C(=NH)NH₂ | CH₂ | CH | CH | amidino |
| 2608 | C(=NH)NH₂ | CH₂ | CH | CH | guanidino |
| 2609 | C(=NH)NH₂ | CH₂ | CH | CH | 2-sulfamidophenyl |
| 2610 | C(=NH)NH₂ | CH₂ | CH | CH | 2-trifluoromethylphenyl |
| 2611 | C(=NH)NH₂ | bond | N | CH | amino |
| 2612 | C(=NH)NH₂ | bond | N | CH | amidino |
| 2613 | C(=NH)NH₂ | bond | N | CH | guanidino |
| 2614 | C(=NH)NH₂ | bond | N | CH | 2-sulfamidophenyl |
| 2615 | C(=NH)NH₂ | bond | N | CH | 2-trifluoromethylphenyl |
| 2616 | C(=NH)NH₂ | CH₂ | N | CH | amino |
| 2617 | C(=NH)NH₂ | CH₂ | N | CH | amidino |
| 2618 | C(=NH)NH₂ | CH₂ | N | CH | guanidino |
| 2619 | C(=NH)NH₂ | CH₂ | N | CH | 2-sulfamidophenyl |
| 2620 | C(=NH)NH₂ | CH₂ | N | CH | 2-trifluoromethylphenyl |
| 2621 | C(=NH)NH₂ | bond | N | N | amino |
| 2622 | C(=NH)NH₂ | bond | N | N | amidino |
| 2623 | C(=NH)NH₂ | bond | N | N | guanidino |
| 2624 | C(=NH)NH₂ | bond | N | N | 2-sulfamidophenyl |
| 2625 | C(=NH)NH₂ | bond | N | N | 2-trifluoromethylphenyl |
| 2626 | C(=NH)NH₂ | CH₂ | N | N | amino |
| 2627 | C(=NH)NH₂ | CH₂ | N | N | amidino |
| 2628 | C(=NH)NH₂ | CH₂ | N | N | guanidino |
| 2629 | C(=NH)NH₂ | CH₂ | N | N | 2-sulfamidophenyl |
| 2630 | C(=NH)NH₂ | CH₂ | N | N | 2-trifluoromethylphenyl |
| 2631 | C(=NH)NH₂ | bond | CH | CH | imidazol-1-yl |
| 2632 | C(=NH)NH₂ | bond | CH | CH | morpholin-1-yl |
| 2633 | C(=NH)NH₂ | bond | CH | CH | 2-methylimidazol-1-yl |
| 2634 | C(=NH)NH₂ | bond | CH | CH | pyridin-3-yl |
| 2635 | C(=NH)NH₂ | bond | CH | CH | 2-(5'-trifluoromethyl)tetrazol-1'-yl |
| 2636 | C(=NH)NH₂ | bond | CH | CH | pyrazol-1-yl |
| 2637 | C(=NH)NH₂ | bond | CH | CH | phenyl |
| 2638 | C(=NH)NH₂ | bond | CH | CH | cyclohexyl |
| 2639 | C(=NH)NH₂ | bond | CH | CH | N,N-dimethylsulfamido |
| 2640 | C(=NH)NH₂ | bond | CH | CH | N,N-dimethylamido |
| 2641 | C(=NH)NH₂ | bond | N | CH | imidazol-1-yl |
| 2642 | C(=NH)NH₂ | bond | N | CH | morpholin-1-yl |
| 2643 | C(=NH)NH₂ | bond | N | CH | 2-methylimidazol-1-yl |
| 2644 | C(=NH)NH₂ | bond | N | CH | pyridin-3-yl |
| 2645 | C(=NH)NH₂ | bond | N | CH | 2-(5'-trifluoromethyl)tetrazol-1'-yl |
| 2646 | C(=NH)NH₂ | bond | N | CH | pyrazol-1-yl |
| 2647 | C(=NH)NH₂ | bond | N | CH | phenyl |
| 2648 | C(=NH)NH₂ | bond | N | CH | cyclohexyl |
| 2649 | C(=NH)NH₂ | bond | N | CH | N,N-dimethylsulfamido |
| 2650 | C(=NH)NH₂ | bond | N | CH | N,N-dimethylamido |
| 2651 | C(=NH)NH₂ | bond | N | N | imidazol-1-yl |
| 2652 | C(=NH)NH₂ | bond | N | N | morpholin-1-yl |
| 2653 | C(=NH)NH₂ | bond | N | N | 2-methylimidazol-1-yl |
| 2654 | C(=NH)NH₂ | bond | N | N | pyridin-3-yl |
| 2655 | C(=NH)NH₂ | bond | N | N | 2-(5'-trifluoromethyl)tetrazol-1'-yl |
| 2656 | C(=NH)NH₂ | bond | N | N | pyrazol-1-yl |
| 2657 | C(=NH)NH₂ | bond | N | N | phenyl |
| 2658 | C(=NH)NH₂ | bond | N | N | cyclohexyl |
| 2659 | C(=NH)NH₂ | bond | N | N | N,N-dimethylsulfamido |
| 2660 | C(=NH)NH₂ | bond | N | N | N,N-dimethylamido |
| 2661 | C(=NH)NH₂ | bond | F | CH | imidazol-1-yl |
| 2662 | C(=NH)NH₂ | bond | F | CH | morpholin-1-yl |
| 2663 | C(=NH)NH₂ | bond | F | CH | 2-methylimidazol-1-yl |
| 2664 | C(=NH)NH₂ | bond | F | CH | pyridin-3-yl |
| 2665 | C(=NH)NH₂ | bond | F | CH | 2-(5'-trifluoromethyl)tetrazol-1'-yl |
| 2666 | C(=NH)NH₂ | bond | F | CH | pyrazol-1-yl |
| 2667 | C(=NH)NH₂ | bond | F | CH | phenyl |
| 2668 | C(=NH)NH₂ | bond | F | CH | cyclohexyl |
| 2669 | C(=NH)NH₂ | bond | F | CH | N,N-dimethylsulfamido |
| 2670 | C(=NH)NH₂ | bond | F | CH | N,N-dimethylamido |
| 2671 | C(=NH)NH₂ | bond | Cl | CH | imidazol-1-yl |
| 2672 | C(=NH)NH₂ | bond | Cl | CH | morpholin-1-yl |
| 2673 | C(=NH)NH₂ | bond | Cl | CH | 2-methylimidazol-1-yl |
| 2674 | C(=NH)NH₂ | bond | Cl | CH | pyridin-3-yl |
| 2675 | C(=NH)NH₂ | bond | Cl | CH | 2-(5'-trifluoromethyl)tetrazol-1'-yl |
| 2676 | C(=NH)NH₂ | bond | Cl | CH | pyrazol-1-yl |
| 2677 | C(=NH)NH₂ | bond | Cl | CH | phenyl |
| 2678 | C(=NH)NH₂ | bond | Cl | CH | cyclohexyl |
| 2679 | C(=NH)NH₂ | bond | Cl | CH | N,N-dimethylsulfamido |
| 2680 | C(=NH)NH₂ | bond | Cl | CH | N,N-dimethylamido |
| 2681 | C(=NH)NH₂ | bond | Br | CH | imidazol-1-yl |
| 2682 | C(=NH)NH₂ | bond | Br | CH | morpholin-1-yl |
| 2683 | C(=NH)NH₂ | bond | Br | CH | 2-methylimidazol-1-yl |
| 2684 | C(=NH)NH₂ | bond | Br | CH | pyridin-3-yl |
| 2685 | C(=NH)NH₂ | bond | Br | CH | 2-(5'-trifluoromethyl)tetrazol-1'-yl |

TABLE 25*-continued

| | | | | | |
|---|---|---|---|---|---|
| 2686 | C(=NH)NH$_2$ | bond | Br | CH | pyrazol-1-yl |
| 2687 | C(=NH)NH$_2$ | bond | Br | CH | phenyl |
| 2688 | C(=NH)NH$_2$ | bond | Br | CH | cyclohexyl |
| 2689 | C(=NH)NH$_2$ | bond | Br | CH | N,N-dimethylsulfamido |
| 2690 | C(=NH)NH$_2$ | bond | Br | CH | N,N-dimethylamido |
| 2691 | C(=NH)NH$_2$ | CH$_2$ | CH | CH | imidazol-1-yl |
| 2692 | C(=NH)NH$_2$ | CH$_2$ | CH | CH | morpholin-1-yl |
| 2693 | C(=NH)NH$_2$ | CH$_2$ | CH | CH | 2-methylimidazol-1-yl |
| 2694 | C(=NH)NH$_2$ | CH$_2$ | CH | CH | pyridin-3-yl |
| 2695 | C(=NH)NH$_2$ | CH$_2$ | CH | CH | 2-(5'-trifluoromethyl)tetrazol-1'-yl |
| 2696 | C(=NH)NH$_2$ | CH$_2$ | CH | CH | pyrazol-1-yl |
| 2697 | C(=NH)NH$_2$ | CH$_2$ | CH | CH | phenyl |
| 2698 | C(=NH)NH$_2$ | CH$_2$ | CH | CH | cyclohexyl |
| 2699 | C(=NH)NH$_2$ | CH$_2$ | CH | CH | N,N-dimethylsulfamido |
| 2700 | C(=NH)NH$_2$ | CH$_2$ | CH | CH | N,N-dimethylamido |
| 2701 | C(=NH)NH$_2$ | CH$_2$ | N | CH | imidazol-1-yl |
| 2702 | C(=NH)NH$_2$ | CH$_2$ | N | CH | morpholin-1-yl |
| 2703 | C(=NH)NH$_2$ | CH$_2$ | N | CH | 2-methylimidazol-1-yl |
| 2704 | C(=NH)NH$_2$ | CH$_2$ | N | CH | pyridin-3-yl |
| 2705 | C(=NH)NH$_2$ | CH$_2$ | N | CH | 2-(5'-trifluoromethyl)tetrazol-1'-yl |
| 2706 | C(=NH)NH$_2$ | CH$_2$ | N | CH | pyrazol-1-yl |
| 2707 | C(=NH)NH$_2$ | CH$_2$ | N | CH | phenyl |
| 2708 | C(=NH)NH$_2$ | CH$_2$ | N | CH | cyclohexyl |
| 2709 | C(=NH)NH$_2$ | CH$_2$ | N | CH | N,N-dimethylsulfamido |
| 2710 | C(=NH)NH$_2$ | CH$_2$ | N | CH | N,N-dimethylamido |
| 2711 | C(=NH)NH$_2$ | CH$_2$ | N | N | imidazol-1-yl |
| 2712 | C(=NH)NH$_2$ | CH$_2$ | N | N | morpholin-1-yl |
| 2713 | C(=NH)NH$_2$ | CH$_2$ | N | N | 2-methylimidazol-1-yl |
| 2714 | C(=NH)NH$_2$ | CH$_2$ | N | N | pyridin-3-yl |
| 2715 | C(=NH)NH$_2$ | CH$_2$ | N | N | 2-(5'-trifluoromethyl)tetrazol-1'-yl |
| 2716 | C(=NH)NH$_2$ | CH$_2$ | N | N | pyrazol-1-yl |
| 2717 | C(=NH)NH$_2$ | CH$_2$ | N | N | phenyl |
| 2718 | C(=NH)NH$_2$ | CH$_2$ | N | N | cyclohexyl |
| 2719 | C(=NH)NH$_2$ | CH$_2$ | N | N | N,N-dimethylsulfamido |
| 2720 | C(=NH)NH$_2$ | CH$_2$ | N | N | N,N-dimethylamido |
| 2721 | C(=NH)NH$_2$ | CH$_2$ | F | CH | imidazol-1-yl |
| 2722 | C(=NH)NH$_2$ | CH$_2$ | F | CH | morpholin-1-yl |
| 2723 | C(=NH)NH$_2$ | CH$_2$ | F | CH | 2-methylimidazol-1-yl |
| 2724 | C(=NH)NH$_2$ | CH$_2$ | F | CH | pyridin-3-yl |
| 2725 | C(=NH)NH$_2$ | CH$_2$ | F | CH | 2-(5'-trifluoromethyl)tetrazol-1'-yl |
| 2726 | C(=NH)NH$_2$ | CH$_2$ | F | CH | pyrazol-1-yl |
| 2727 | C(=NH)NH$_2$ | CH$_2$ | F | CH | phenyl |
| 2728 | C(=NH)NH$_2$ | CH$_2$ | F | CH | cyclohexyl |
| 2729 | C(=NH)NH$_2$ | CH$_2$ | F | CH | N,N-dimethylsulfamido |
| 2730 | C(=NH)NH$_2$ | CH$_2$ | F | CH | N,N-dimethylamido |
| 2731 | C(=NH)NH$_2$ | CH$_2$ | Cl | CH | imidazol-1-yl |
| 2732 | C(=NH)NH$_2$ | CH$_2$ | Cl | CH | morpholin-1-yl |
| 2733 | C(=NH)NH$_2$ | CH$_2$ | Cl | CH | 2-methylimidazol-1-yl |
| 2734 | C(=NH)NH$_2$ | CH$_2$ | Cl | CH | pyridin-3-yl |
| 2735 | C(=NH)NH$_2$ | CH$_2$ | Cl | CH | 2-(5'-trifluoromethyl)tetrazol-1'-yl |
| 2736 | C(=NH)NH$_2$ | CH$_2$ | Cl | CH | pyrazol-1-yl |
| 2737 | C(=NH)NH$_2$ | CH$_2$ | Cl | CH | phenyl |
| 2738 | C(=NH)NH$_2$ | CH$_2$ | Cl | CH | cyclohexyl |
| 2739 | C(=NH)NH$_2$ | CH$_2$ | Cl | CH | N,N-dimethylsulfamido |
| 2740 | C(=NH)NH$_2$ | CH$_2$ | Cl | CH | N,N-dimethylamido |
| 2741 | C(=NH)NH$_2$ | CH$_2$ | Br | CH | imidazol-1-yl |
| 2742 | C(=NH)NH$_2$ | CH$_2$ | Br | CH | morpholin-1-yl |
| 2743 | C(=NH)NH$_2$ | CH$_2$ | Br | CH | 2-methylimidazol-1-yl |
| 2744 | C(=NH)NH$_2$ | CH$_2$ | Br | CH | pyridin-3-yl |
| 2745 | C(=NH)NH$_2$ | CH$_2$ | Br | CH | 2-(5'-trifluoromethyl)tetrazol-1'-yl |
| 2746 | C(=NH)NH$_2$ | CH$_2$ | Br | CH | pyrazol-1-yl |
| 2747 | C(=NH)NH$_2$ | CH$_2$ | Br | CH | phenyl |
| 2748 | C(=NH)NH$_2$ | CH$_2$ | Br | CH | cyclohexyl |
| 2749 | C(=NH)NH$_2$ | CH$_2$ | Br | CH | N,N-dimethylsulfamido |
| 2750 | C(=NH)NH$_2$ | CH$_2$ | Br | CH | N,N-dimethylamido |

*Each entry in Table 25 is intended to correspond individually to each of formulae a–m.

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms.

The anticoagulant effect of compounds of the present invention is believed to be due to inhibition of factor Xa. The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s = I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 1$ μm, thereby confirming the utility of the compounds of the present invention as effective Xa inhibitors.

The antithrombotic effect of the compounds of the present invention can be demonstrated in a rat vena cava thrombosis model. In this model Male Sprague-Dawley rats weighing 350–450 grams anesthetized with a mixture of xylazine (10 mg/kg i.m.) and ketamine (110 mg/kg i.m.) are used. A carotid artery, a jugular vein and a femoral vein are cannulated for blood sampling, drug infusion and hypotonic saline injection, respectively. The abdominal vena cava is isolated and all its side-branches are ligated beneath the left renal vein. Thrombus formation is induced by rapid injection of 1 ml hypotonic saline (0.225%) into the vena cava. This is followed 15 seconds later by a 15-minute stasis of an isolated segment (about 1 cm) of the vena cava. The formed thrombus in the vena cava is removed and immediately weighed.

Test compounds or vehicle are given as continuous intravenous infusions or orally starting 1 hour before the injection of hypotonic saline. Arterial blood samples (1.5 ml) for the determination of clotting times are collected before and 1 hour after the infusion or oral dosing of test compounds or vehicle. The percentage inhibition of thrombus formation is determined for each treatment group. The ID50 values (dose which produces 50% inhibition of thrombus formation) are estimated by linear regression.

The compounds of formula (I) are also considered to be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nm in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 5 μm, thereby confirming the utility of the compounds of the invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. of the NSAIDS, aspirin (acetylsalicyclic acid or ASA), and piroxicam are preferred. other suitable anti-platelet agents include ticlopidine, including pharmaceutically acceptable salts or prodrugs thereof. Ticlopidine is also a preferred compound since it is known to be gentle on the gastrointestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/ or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin CaDsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

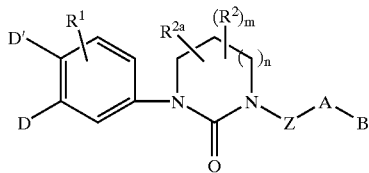

or stereoisomer or pharmaceutically acceptable salt form thereof, wherein;

one of D and D' is selected from CN, $C(=NR^{11})NR^{12}R^{13}$, $NHC(=NR^{11})NR^{12}R^{13}$, $NR^{12}CH(=NR^{11})$ $C(O)NR^{12}R^{13}$, and $CH_2NR^{12}R^{13}$ and the other is H;

$R^1$ is selected from H, $(CH_2)_rOR^3$, halo, $C_{1-4}$ alkyl, $(CH_2)_rNR^4R^{4'}$, $(CH_2)_rCO_2H$, $(CH_2)_rC(=O)R^4$, $(CH_2)_r NR^4C(=O)R^4$, $(CH_2)_rSO_2R^5$, and $(CH_2)_rNR^4SO_2R^5$;

$R^2$ is selected from H, =O, $C_{1-4}$ alkyl substituted with 0, 1, or 2 $R^7$, $C_{2-6}$ alkenyl substituted with 0, 1, or 2 $R^7$, $(CH_2)_rOR^3$, $(CH_2)_rC(O)R^4$, $(CH_2)_rOC(O)R^4$, $(CH_2)_r NR^3R^{3'}$, $(CH_2)_rNR^3C(O)R^4$, $(CH_2)_rSO_2R^5$, $(CH_2)_r NR^3SO_2R^5$, $C_{3-10}$ carbocyclic residue substituted with 0–2 $R^6$; and, 5–10 membered heterocyclic system containing from 1–3 heteroatoms selected from the group consisting of N, O, and S substituted with 0–2 $R^6$;

$R^{2a}$ is absent;

$R^3$ and $R^{3'}$ are independently selected from H, $C_{1-4}$ alkyl, benzyl and phenyl;

$R^3$ and $R^{3'}$ may be taken together to form a 5 or 6 membered ring substituted with 0–2 $R^6$;

$R^4$ and $R^{4'}$ are independently selected from H, $OR^3$, $C_{1-4}$ alkyl, phenyl and $NR^3R^{3'}$;

$R^5$ is selected from $C_{1-4}$ alkyl, phenyl and $NR^3R^{3'}$;

Z is selected from a bond, $C_{1-4}$ alkylene, $(CH_2)_rO(CH_2)_r$, $(CH_2)_2NR^3(CH_2)_r$, $(CH_2)_rC(O)(CH_2)_r$, $(CH_2)_rC(O)O(CH_2)_r$, $(CH_2)_2OC(O)(CH_2)_r$, $(CH_2)_rC(O)NR^3(CH_2)_r$, $(CH_2)_2NR^3C(O)(CH_2)_r$, $(CH_2)_2OC(O)O(CH_2)_r$, $(CH_2)_2OC(O)NR^3(CH_2)_r$, $(CH_2)_2NR^3C(O)O(CH_2)_r$, $(CH_2)_2NR^3C(O)NR^3(CH_2)_r$, $(CH_2)_rS(O)_p(CH_2)_r$, $(CH_2)_rSO_2NR^3(CH_2)_r$, $(CH_2)_2NR^3SO_2(CH_2)_r$, and $(CH_2)_2NR^3SO_2NR^3(CH_2)_r$;

A is selected from:
  $C_{3-10}$ carbocyclic residue substituted with 0–2 $R^6$, and
  5–10 membered heterocyclic system containing from 1–3 heteroatoms selected from the group consisting of N, O, and S substituted with 0–2 $R^6$;

B is selected from:
  X—Y, $NR^3R^{3'}$, $C(O)NR^3R^{3'}$, $SO_2NR^3R^{3'}$,
  benzyl substituted with 0–2 $R^6$,
  $C_{3-10}$ carbocyclic residue substituted with 0–2 $R^6$, and
  5–10 membered heterocyclic system containing from 1–3 heteroatoms selected from the group consisting of N, O, and S substituted with 0–2 $R^6$;

X is selected from $C_{1-4}$ alkylene, —C(O)—, —C(O)$CR^3R^{3'}$—, —$CR^3R^{3'}$C(O)—, —C(O)O—, —C(O)$OCR^3R^{3'}$, —$CR^3R^{3'}$C(O)O—, —OC(O)—, —OC(O)$CR^3R^{3'}$—, —$CR^3R^{3'}$OC(O)—, —S(O)$_p$—, —S(O)$_p CR^3R^{3'}$—, —$CR^3R^{3'}$S(O)$_p$—, —S(O)$_2 NR^3$—, —$NR^3 S$(O)$_2$—, —$NR^3 S$(O)$_2 CR^3R^{3'}$—, —$CR^3R^{3'}$S(O)$_2 NR^3$—, —$NR^3 S$(O)$_2 NR^3$—, —C(O)$NR^3$—, —$NR^3 C$(O)—, —C(O)$NR^3 CR^3R^{3'}$—, —$NR^3 C$(O)$CR^3R^{3'}$—, —$CR^3R^{3'}$C(O)$NR^3$—, —$CR^3R^{3'}$NR^3 C(O)—, —$NR^3 C(O)O$—, —OC(O)$NR^3$—, —$NR^3 C$(O)$NR^3$—, —$NR^3$—, —$NR^3 CR^3R^{3'}$—, —$CR^3R^{3'}NR^3$—, O, —$CR^3R^{3'}O$—, —$OCR^3R^{3'}$—, S, —$CR^3R^{3'}S$—, and —$SCR^3R^{3'}$—;

Y is selected from:
  $C_{1-4}$ alkyl substituted with 0–2 $R^6$
  $C_{3-10}$ carbocyclic residue substituted with 0–2 $R^6$, and
  5–10 membered heterocyclic system containing from 1–3 heteroatoms selected from the group consisting of N, O, and S substituted with 0–2 $R^6$;

$R^6$ is selected from H, OH, $CF_3$, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $NR^3SO_2NR^3R^{3'}$, $NR^3SO_2$—$C_{1-4}$ alkyl, $SO_2$-phenyl, and $NR^3SO_2R^8$;

$R^7$ is selected from:
  $C_{3-10}$ carbocyclic residue substituted with 0–2 $R^6$; and,
  5–10 membered heterocyclic system containing from 1–3 heteroatoms selected from the group consisting of N, O, and S substituted with 0–2 $R^6$;

$R^8$ is selected from:
  $C_{3-10}$ carbocyclic residue substituted with 0–2 $R^9$; and,
  5–10 membered heterocyclic system containing from 1–3 heteroatoms selected from the group consisting of N, O, and S substituted with 0–2 $R^9$;

$R^9$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $NR^3SO_2NR^3R^{3'}$, and $NR^3SO_2$—$C_{1-4}$ alkyl;

$R^{10}$ is selected from H, $OR^3$, halo, $C_{1-4}$ alkyl, CN, $NO_2$, $NR^3R^{3'}$, $NR^3C(O)R^{3'}$, $NR^3C(O)OR^{3'}$, $NR^3SO_2$-phenyl, and $NR^3SO_2$—$C_{1-4}$ alkyl;

$R^{10a}$ if a substituent on nitrogen is selected from H and $C_{1-4}$ alkyl;

$R^{10a}$ if a substituent on carbon is selected from H, $C_{1-4}$ alkyl, $NR^3R^{3'}$, $NR^3C(O)R^{3'}$, $NR^3C(O)OR^{3'}$, $NR^3SO_2$-phenyl, and $NR^3SO_2$—$C_{1-4}$ alkyl;

$R^{11}$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^{12}$ is selected from H, $C_{1-6}$ alkyl and $(CH_2)_n$-phenyl;

$R^{13}$ is selected from H, $C_{1-6}$ alkyl and $(CH_2)_n$-phenyl;

n is 2;

m is selected from 0 and 1;

p is selected from 0, 1, and 2;

q is selected from 1, 2, 3, 4, and 5; and, r is selected from 0, 1, and 2.

2. A compound according to claim 1, wherein:

D is $C(=NH)NH_2$;

D' is H;

$R^1$ is selected from H, $(CH_2)_rOR^3$, halo, $(CH_2)_rNR^4R^{4'}$, $(CH_2)_rCO_2H$, $(CH_2)_rC(=O)R^4$, $(CH_2)_rNR^4C(=O)R^4$, $(CH_2)_rSO_2R^5$, and $(CH_2)_rNHSO_2R^5$;

$R^2$ is selected from H, =O, $(CH_2)_rOR^3$, $(CH_2)_rC(O)R^4$, $(CH_2)_rOC(O)R^4$, $(CH_2)_rNR^3R^{3'}$, $(CH_2)_rNR^3C(O)R^4$, $(CH_2)_rSO_2R^5$, $(CH_2)_rNR^3SO_2R^5$, $C_{3-10}$ carbocyclic residue substituted with 0–2 $R^6$; and, 5–10 membered heterocyclic system containing from 1–3 heteroatoms selected from the group consisting of N, O, and S substituted with 0–2 $R^6$;

$R^4$ and $R^{4'}$ are independently selected from H, $OR^3$, $C_{1-4}$ alkyl, and $NR^3R^{3'}$;

$R^5$ is selected from $C_{1-4}$ alkyl and $NR^3R^{3'}$;

Z is selected from a bond, $C_{1-4}$ alkylene, $(CH_2)_rC(O)(CH_2)_r$, $(CH_2)_rC(O)NR^3(CH_2)_r$, $(CH_2)_2NR^3C(O)(CH_2)_r$, $(CH_2)_2OC(O)NR^3(CH_2)_r$, $(CH_2)_2NR^3C(O)O(CH_2)_r$, $(CH_2)_2NR^3C(O)NR^3(CH_2)_r$, $(CH_2)_rS(O)_p(CH_2)_r$, $(CH_2)_rSO_2NR^3(CH_2)_r$, $(CH_2)_2NR^3SO_2(CH_2)_r$, and $(CH_2)_2NR^3SO_2NR^3(CH_2)_r$; and, X is selected from $C_{1-4}$ alkylene, —$CH_2$—, —C(O)—, —C(O)$CR^3R^{3'}$—, —$CR^3R^{3'}$C(O)—, —C(O)O—, —C(O)$OCR^3R^{3'}$—, —$CR^3R^{3'}$C(O)O—, —OC(O)—, —OC(O)$CR^3R^{3'}$—, —$CR^3R^{3'}$OC(O)—, —S(O)$_p$—, —S(O)$_p$$CR^3R^{3'}$—, —$CR^3R^{3'}$S(O)$_p$—, —S(O)$_2$$NR^3$—, —C(O)$NR^3$—, —$NR^3$C(O)—, —$NR^3$C(O)O—, —OC(O)$NR^3$—, —$NR^3$C(O)$NR^3$—, —$NR^3$—, —$NR^3$$CR^3R^{3'}$—, —$CR^3R^{3'}$$NR^3$—, O, —$CR^3R^{3'}$O—, and —$OCR^3R^{3'}$—.

3. A compound according to claim 2, wherein:

$R^1$ is selected from H, $OR^3$, $(CH_2)OR^3$, halo, $NR^4R^{4'}$, $(CH_2)NR^4R^{4'}$, $C(=O)R^4$, $(CH_2)C(=O)R^4$, $NHC(=O)R^4$, $(CH_2)NHC(=O)R^4$, $SO_2R^5$, $(CH_2)SO_2R^5$, $NHSO_2R^5$, and $(CH_2)NHSO_2R^5$;

is selected from H, =O, $OR^3$, $C(O)R^4$, $(CH_2)C(O)R^4$, $OC(O)R^4$, $NR^4R^{4'}$, $NR^3C(O)R^4$, and $NR^4SO_2R^5$;

A is selected from:
$C_{5-6}$ carbocyclic residue substituted with 0–1 $R^6$, and 5–6 membered heterocyclic system containing from 1–2 heteroatoms selected from the group consisting of N and O substituted with 0–1 $R^6$;

B is selected from: Y, X—Y, and $NR^2R^{2a}$;

Y is selected from one of the following carbocyclic and heterocyclic systems which are substituted with 0–2 $R^{4a}$;
phenyl, piperidinyl, piperazinyl, pyridyl, pyrimidyl, furanyl, thiophenyl, pyrrolyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzoxazole, benzthiazole, indazole, benzisoxazole, benzisothiazole, isoindazole, and benzothiadiazole;

Y may also be selected from the following bicyclic heteroaryl ring systems:

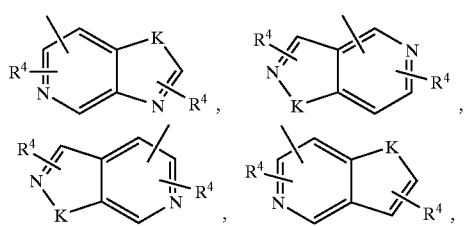

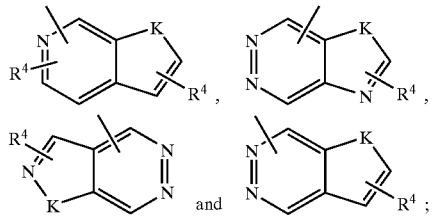

K is selected from O, S, NH, and N;

X is selected from —$CH_2$—, —C(O)—, —C(O)$CHR^3$—, —$CHR^3$C(O)—, —S(O)$_p$—, —S(O)$_p$$CR^3R^{3'}$—, —$CHR^3$S(O)$_p$—, —S(O)$_2$$NR^3$—, —C(O)$NR^3$—, —$NR^3$C(O)—, —$NR^3$—, —$NR^3$$CHR^3$—, and —$CHR^3$$NR^3$—;

$R^6$ is selected from H, OH, $CF_3$, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $SO_2NR^3R^{3'}$, $SO_2$-phenyl, $NR^3SO_2$—$C_{1-4}$ alkyl, and $NR^3SO_2R^8$;

$R^8$ is selected from:
$C_{5-6}$ carbocyclic residue substituted with 0–2 $R^9$; and, 5–6 membered heterocyclic system containing from 1–3 heteroatoms selected from the group consisting of N, O, and S substituted with 0–2 $R^9$;

$R^9$ is selected from H, OH, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $NR^3C(O)NR^3R^{3'}$, $SO_2NR^3R^{3'}$, $NR^3SO_2NR^3R^{3'}$, and $NR^3SO_2$—$C_{1-4}$ alkyl; and, p is 2.

4. A compound according to claim 3, wherein:

Z is selected from a bond, $C_{1-4}$ alkylene, $(CH_2)_rC(O)(CH_2)_r$, $(CH_2)_rC(O)NR^3(CH_2)_r$, $(CH_2)_2NR^3C(O)(CH_2)_r$, $(CH_2)_2NR^3C(O)NR^3(CH_2)_r$, and $(CH_2)_rS(CH_2)_r$;

X is selected from —$CH_2$—, —C(O)—, —C(O)$CHR^3$—, —$CHR^3$C(O)—, —S(O)$_p$—, —S(O)$_p$$CR^3R^{3'}$—, —$CHR^3$S(O)$_p$—, —S(O)$_2$$NR^3$—, —C(O)$NR^3$—, and —$NR^3$C(O)—;

$R^6$ is selected from H, OH, $CF_3$, $(CH_2)_nOR^3$, halo, $C_{1-4}$ alkyl, CN, $NO_2$, $(CH_2)_rNR^3R^{3'}$, $(CH_2)_rC(O)R^3$, $NR^3C(O)R^{3'}$, $SO_2NR^3R^{3'}$, $SO_2$-phenyl, and $NR^3SO_2$—$C_{1-4}$ alkyl;

m is 1; and, r is selected from 0 and 1.

5. A compound according to claim 4, wherein:

$R^3$ and $R^{3'}$ are independently selected from H and $C_{1-4}$ alkyl;

Z is selected from a bond, $C_{1-4}$ alkylene, $(CH_2)_rC(O)NR^3(CH_2)_r$, $(CH_2)_2NR^3C(O)(CH_2)_r$, and $(CH_2)_2NR^3C(O)NR^3(CH_2)_r$;

A is selected from phenyl substituted with 0–1 $R^6$ and a 6 membered heterocyclic system containing 1 N and 0–1 O atoms and substituted with 0–1 $R^6$;

X is selected from —$CH_2$—, —S(O)$_p$—, —S(O)$_p$$CR^3R^{3'}$—, —S(O)$_2$$NR^3$—, and —C(O)$NR^3$—;

Y is selected from phenyl, quinolynyl, thiadizolyl, benzothiadiazolyl, thiophenyl, pyridyl, and naphthyl, each of which is substituted with 0–2 $R^6$.

6. A compound according to claim 5, wherein:

$R^3$ and $R^{3'}$ are independently selected from H and methyl;

Z is selected from a bond, $CH_2$, —$CH_2CH_2$—, —$CH_2CH_2CH_2$— and —$CH_2CH_2CH_2CH_2$—;

A is selected from phenyl substituted with 0–1 $R^6$, and piperidinyl substituted with 0–1 $R^6$.

7. A compound according to claim 6, wherein the compound is selected from:

N-(3-amidinophenyl)-N'-((4-((2-sulphonamido)phenyl)phenyl)methyl)cycloheptylurea;
N-(3-amidinophenyl)-N'-(1-benzylpiperidin-4-yl)cycloheptylurea;
N-(3-amidinophenyl)-N'-(1-(picolin-2-yl)piperidin-4-yl)cycloheptylurea;
N-(3-amidinophenyl)-N'-(1-(picolin-3-yl)piperidin-4-yl)cycloheptylurea;
N-(3-amidinophenyl)-N'-(1-(picolin-4-yl)piperidin-4-yl)cycloheptylurea;
N-(3-amidinophenyl)-N'-(1-(a-phenethyl)piperidin-4-yl)cycloheptylurea;
N-(3-amidinophenyl)-N'-(1-((phenyl)methane)sulfonyl)-piperidin-4-yl)cycloheptylurea;
N-(3-amidinophenyl)-N'-(1-(phenyl)sulfonylpiperidin-4-yl)cycloheptylurea;
N-(3-amidinophenyl)-N'-(1-(quinolin-8-yl)sulfonylpiperidin-4-yl)cycloheptylurea;
N-(3-amidinophenyl)-N'-(1-(2-fluorophenyl)sulfonylpiperidin-4-yl)cycloheptylurea;
N-(3-amidinophenyl)-N'-(1-(4-acetamidophenyl)sulfonylpiperidin-4-yl)cycloheptylurea;
N-(3-amidinophenyl)-N'-(1-(2-aminophenyl)sulfonylpiperidin-4-yl)cycloheptylurea;
N-(3-amidinophenyl)-N'-(1-(3-aminophenyl)sulfonylpiperidin-4-yl)cycloheptylurea;
N-(3-amidinophenyl)-N'-(1-(4-aminophenyl)sulfonylpiperidin-4-yl)cycloheptylurea;
N-(3-amidinophenyl)-N'-(1-((2-aminophenyl)methane)sulfonyl)piperidin-4-yl)cycloheptylurea;
N-(3-amidinophenyl)-N'-(1-((2-acetamido-phenyl)methane)sulfonylpiperidin-4-yl)cycloheptylurea;
N-(3-amidinophenyl)-N'-(1-((thiophen-2-yl)sulfonyl)piperidin-4-yl)cycloheptylurea;
N-(3-amidinophenyl)-N'-(1-((5-chlorothiophen-2-yl)sulfonyl)piperidin-4-yl)cycloheptylurea;
N-(3-amidinophenyl)-N'-(1-((5-carbomethoxythiophen-2-yl)sulfonyl)piperidin-4-yl)cycloheptylurea;
N-(3-amidinophenyl)-N'-(1-((benzo-2,1,3-thiadiazo-4-yl)sulfonyl)piperidin-4-yl)cycloheptylurea;
N-(3-amidinophenyl)-N'-(1-((cyclohexyl)sulfamido)piperidin-4-yl)cycloheptylurea;
N-(3-amidinophenyl)-N'-(1-((isopropyl)sulfamido)piperidin-4-yl)cycloheptylurea;
N-(3-amidinophenyl)-N'-(1-((phenyl)sulfamido)piperidin-4-yl)cycloheptylurea;
N-(3-amidinophenyl)-N'-(1-((isopropyl)sulfonyl)piperidin-4-yl)cycloheptylurea;
N-(3-amidinophenyl)-N'-(1-((5-amino-4-methylthiazol-2-yl)sulfonyl)piperidin-4-yl)cycloheptylurea;
N-(3-amidinophenyl)-N'-(1-((5-acetamido-4-methylthiazol-2-yl)sulfonyl)piperidin-4-yl)cycloheptylurea;
N-(3-amidinophenyl)-N'-(1-(6-carbomethoxyphenyl-sulfonyl)piperidin-4-yl)cycloheptylurea;
N-(3-amidinophenyl)-N'-(2-pyridylmethyl) piperidin-4-yl)cycloheptylurea;
N-(3-amidinophenyl)-N'-(3-pyridylmethyl)piperidin-4-yl)cycloheptylurea;
N-(3-amidinophenyl)-N'-(4-pyridylmethyl)piperidin-4-yl)cycloheptylurea;
N-(3-amidinophenyl)-N'-(phenyl-N''-methylsulfamido)piperidin-4-yl)cycloheptylurea;
N-(3-amidinophenyl)-N'-((4-phenylsulfonylthiophen-2-yl)sulfonyl)-piperidin-4-yl)cycloheptylurea;
N-(3-amidinophenyl)-N'-(4-pyridylmethylsulfonyl)piperidin-4-yl)cycloheptylurea;
N-(3-amidinophenyl)-N'-(thiophen-2-ylsulfonyl)piperidin-4-yl)cycloheptylurea;
N-(3-amidinophenyl)-N'-(4-fluorobenzylsulfonyl)piperidin-4-yl) cycloheptylurea;
N-(3-amidinophenyl)-N'-(2-pyridylsulfonyl)piperidin-4-yl)cycloheptylurea;
N-(3-amidinophenyl)-N'-(2-trifluormethylphenylsulfonyl)piperidin-4-yl)cycloheptylurea;
N-(3-amidinophenyl)-N'-(2-phenylisopropylsulfonyl)piperidin-4-yl)cycloheptylurea;
N-(3-amidinophenyl)-N'-((1-((phenyl)-1,1-dimethyl)methane)sulfonyl)-piperidin-4-yl)cycloheptylurea;
(3-amidinophenyl)-N'-(methyl((phenylmethane)carbamide)morpholin-3-yl))cycloheptylurea;
N-(3-amidinophenyl)-N'-(methyl((thiophen-2-yl)sulfonyl)morpholin-3-yl))cycloheptylurea;
N-(3-amidinophenyl)-N'-(methyl((phenylmethane)sulfonyl)morpholin-3-yl))cycloheptylurea;
N-(3-amidinophenyl)-N'-((N-benzyl)piperidin-3-yl)cycloheptylurea;
N-(3-amidinophenyl)-N'-((N-(benzyl)sulfonyl)-piperidin-3-yl)cycloheptylurea;
N-(3-amidinophenyl)-N'-((N-(thiophen-2-yl)sulfonyl)piperidin-3-yl)cycloheptylurea;
N-(3-amidinophenyl)-N'-(4-(2-sulfonamidophenyl)phenyl)cycloheptylurea;
N-(3-amidinophenyl)-N'-(5-(2-sulfonamido-phenyl)pyridin-2-yl)cycloheptylurea; and,
N-(3-amidinophenyl)-N'-(methyl(4-(2-sulfonamidophenyl)phenyl))cycloheptylurea;

or stereoisomers or pharmaceutically acceptable salt forms thereof.

8. A compound according to claim 5, wherein:
A is phenyl substituted with 0–1 $R^6$.
9. A compound according to claim 5, wherein:
A is pyridyl substituted with 0–1 $R^6$.
10. A compound according to claim 5, wherein:
A is piperidinyl substituted with 0–1 $R^6$.
11. A compound according to claim 1, wherein:
D is C(=NH)NH$_2$ or CH$_2$NR$^{12}$R$^{13}$;
$R^1$ is selected from H, (CH$_2$)$_r$OR$^3$, halo, (CH$_2$)$_r$NR$^4$R$^{4'}$, (CH$_2$)$_r$CO$_2$H, (CH$_2$)$_r$C(=O)R$^4$, (CH$_2$)$_r$NR$^4$C(=O)R$^4$, (CH$_2$)$_r$SO$_2$R$^5$, and (CH$_2$)$_r$NHSO$_2$R$^5$;
$R^4$ and $R^{4'}$ are independently selected from H, OR$^3$, C$_{1-4}$ alkyl, and NR$^3$R$^{3'}$;
$R^5$ is selected from C$_{1-4}$ alkyl and NR$^3$R$^{3'}$;
Z is selected from a bond, C$_{1-4}$ alkylene, (CH$_2$)$_r$C(O)(CH$_2$)$_r$, (CH$_2$)$_r$C(O)NR$^3$(CH$_2$)$_r$, (CH$_2$)$_2$NR$^3$C(O)(CH$_2$)$_r$, and (CH$_2$)$_r$S(O)$_p$(CH$_2$)$_r$; and,
X is selected from C$_{1-4}$ alkylene, —C(O)—, —C(O)CR$^3$R$^{3'}$—, —CR$^3$R$^{3'}$C(O)—, —S(O)$_p$—, —S(O)$_p$CR$^3$R$^{3'}$—, —CR$^3$R$^{3'}$S(O)$_p$—, —C(O)NR$^3$—, and —NR$^3$C(O)—.

12. A compound according to claim 11, wherein:
Z is selected from a bond, C$_{1-4}$ alkylene, C(O)(CH$_2$)$_r$, C(O)NR$^3$(CH$_2$)$_r$, S(O)$_2$, and S(O)$_2$CH$_2$; and,
X is selected from C$_{1-4}$ alkylene, —C(O)—, —C(O)CR$^3$R$^{3'}$—, —CR$^3$R$^{3'}$C(O)—, —S(O)$_p$—, —S(O)$_p$CR$^3$R$^{3'}$—, and —C(O)NR$^3$—.

13. A pharmaceutical composition, comprising: a pharmaceutically acceptable carrier and a therapeutically effective amount of a compound according to claim 1 or a pharmaceutically acceptable salt thereof.

14. A pharmaceutical composition, comprising: a pharmaceutically acceptable carrier and a therapeutically effective amount of a compound according to claim 2 or a pharmaceutically acceptable salt thereof.

15. A pharmaceutical composition, comprising: a pharmaceutically acceptable carrier and a therapeutically effective amount of a compound according to claim 3 or a pharmaceutically acceptable salt thereof.

16. A pharmaceutical composition, comprising: a pharmaceutically acceptable carrier and a therapeutically effective amount of a compound according to claim 4 or a pharmaceutically acceptable salt thereof.

17. A pharmaceutical composition, comprising: a pharmaceutically acceptable carrier and a therapeutically effective amount of a compound according to claim 5 or a pharmaceutically acceptable salt thereof.

18. A pharmaceutical composition, comprising: a pharmaceutically acceptable carrier and a therapeutically effective amount of a compound according to claim 6 or a pharmaceutically acceptable salt thereof.

19. A pharmaceutical composition, comprising: a pharmaceutically acceptable carrier and a therapeutically effective amount of a compound according to claim 7 or a pharmaceutically acceptable salt thereof.

20. A pharmaceutical composition, comprising: a pharmaceutically acceptable carrier and a therapeutically effective amount of a compound according to claim 8 or a pharmaceutically acceptable salt thereof.

21. A pharmaceutical composition, comprising: a pharmaceutically acceptable carrier and a therapeutically effective amount of a compound according to claim 9 or a pharmaceutically acceptable salt thereof.

22. A pharmaceutical composition, comprising: a pharmaceutically acceptable carrier and a therapeutically effective amount of a compound according to claim 10 or a pharmaceutically acceptable salt thereof.

23. A pharmaceutical composition, comprising: a pharmaceutically acceptable carrier and a therapeutically effective amount of a compound according to claim 11 or a pharmaceutically acceptable salt thereof.

24. A pharmaceutical composition, comprising: a pharmaceutically acceptable carrier and a therapeutically effective amount of a compound according to claim 12 or a pharmaceutically acceptable salt thereof.

25. A method for treating a thromboembolic disorder, comprising: administering to a patient in need thereof a therapeutically effective amount of a compound according to claim 1 or a pharmaceutically acceptable salt thereof.

26. A method for treating a thromboembolic disorder, comprising: administering to a patient in need thereof a therapeutically effective amount of a compound according to claim 2 or a pharmaceutically acceptable salt thereof.

27. A method for treating a thromboembolic disorder, comprising: administering to a patient in need thereof a therapeutically effective amount of a compound according to claim 3 or a pharmaceutically acceptable salt thereof.

28. A method for treating a thromboembolic disorder, comprising: administering to a patient in need thereof a therapeutically effective amount of a compound according to claim 4 or a pharmaceutically acceptable salt thereof.

29. A method for treating a thromboembolic disorder, comprising: administering to a patient in need thereof a therapeutically effective amount of a compound according to claim 5 or a pharmaceutically acceptable salt thereof.

30. A method for treating a thromboembolic disorder, comprising: administering to a patient in need thereof a therapeutically effective amount of a compound according to claim 6 or a pharmaceutically acceptable salt thereof.

31. A method for treating a thromboembolic disorder, comprising: administering to a patient in need thereof a therapeutically effective amount of a compound according to claim 7 or a pharmaceutically acceptable salt thereof.

32. A method for treating a thromboembolic disorder, comprising: administering to a patient in need thereof a therapeutically effective amount of a compound according to claim 8 or a pharmaceutically acceptable salt thereof.

33. A method for treating a thromboembolic disorder, comprising: administering to a patient in need thereof a therapeutically effective amount of a compound according to claim 9 or a pharmaceutically acceptable salt thereof.

34. A method for treating a thromboembolic disorder, comprising: administering to a patient in need thereof a therapeutically effective amount of a compound according to claim 10 or a pharmaceutically acceptable salt thereof.

35. A method for treating a thromboembolic disorder, comprising: administering to a patient in need thereof a therapeutically effective amount of a compound according to claim 11 or a pharmaceutically acceptable salt thereof.

36. A method for treating a thromboembolic disorder, comprising: administering to a patient in need thereof a therapeutically effective amount of a compound according to claim 12 or a pharmaceutically acceptable salt thereof.

37. A method according to claim 25, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

38. A method according to claim 26, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

39. A method according to claim 27, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

40. A method according to claim 28, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

41. A method according to claim 29, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

42. A method according to claim 30, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

43. A method according to claim 31, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

44. A method according to claim 32, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

45. A method according to claim 33, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

46. A method according to claim 34, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

47. A method according to claim 35, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

48. A method according to claim 36, wherein the thromboembolic disorder is selected from the group consisting of arterial cardiovascular thromboembolic disorders, venous cardiovascular thromboembolic disorders, aterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

* * * * *